(12) United States Patent
Krishnan et al.

(10) Patent No.: US 11,918,660 B2
(45) Date of Patent: **\*Mar. 5, 2024**

(54) VIRAL VECTORS FOR CANCER THERAPY

(71) Applicant: Krystal Biotech, Inc., Pittsburgh, PA (US)

(72) Inventors: Suma Krishnan, Pittsburgh, PA (US); Trevor Parry, San Diego, CA (US); Dana Michelle Previte, Sewickley, PA (US); Mary Jane Duermeyer, Glenshaw, PA (US)

(73) Assignee: Krystal Biotech, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/180,791

(22) Filed: Mar. 8, 2023

(65) Prior Publication Data

US 2023/0241251 A1 Aug. 3, 2023

Related U.S. Application Data

(63) Continuation of application No. 17/711,947, filed on Apr. 1, 2022, now Pat. No. 11,779,660.

(60) Provisional application No. 63/170,103, filed on Apr. 2, 2021.

(51) Int. Cl.
| | |
|---|---|
| *C12N 15/869* | (2006.01) |
| *A61K 35/763* | (2015.01) |
| *A61K 38/19* | (2006.01) |
| *A61K 38/20* | (2006.01) |
| *A61K 48/00* | (2006.01) |
| *A61P 35/00* | (2006.01) |
| *C12N 7/00* | (2006.01) |
| *C12N 15/24* | (2006.01) |
| *C12N 15/26* | (2006.01) |
| *C12N 15/86* | (2006.01) |

(52) U.S. Cl.
CPC ........ *A61K 48/0066* (2013.01); *A61K 38/193* (2013.01); *A61K 38/2013* (2013.01); *A61K 38/208* (2013.01); *A61P 35/00* (2018.01); *C12N 7/00* (2013.01); *C12N 15/86* (2013.01); *C12N 2710/16622* (2013.01); *C12N 2710/16633* (2013.01); *C12N 2710/16643* (2013.01); *C12N 2710/16662* (2013.01); *C12N 2710/16671* (2013.01)

(58) Field of Classification Search
None
See application file for complete search history.

(56) References Cited

U.S. PATENT DOCUMENTS

| | | | |
|---|---|---|---|
| 5,658,724 A | 8/1997 | Deluca et al. | |
| 5,672,344 A | 9/1997 | Kelley et al. | |
| 5,753,234 A | 5/1998 | Lee et al. | |
| 5,998,174 A | 12/1999 | Glorioso et al. | |
| 6,106,826 A | 8/2000 | Brandt et al. | |
| 6,719,982 B1 | 4/2004 | Coffin et al. | |
| 6,846,670 B2 | 1/2005 | Schwartz et al. | |
| 6,887,490 B1 | 5/2005 | Jahoda et al. | |
| 7,081,483 B2 | 7/2006 | Cahiko | |
| 7,531,167 B2 | 5/2009 | Glorioso et al. | |
| 9,314,505 B2 | 4/2016 | Wise et al. | |
| 9,877,990 B2 * | 1/2018 | Krishnan | C12N 9/0071 |
| 10,155,016 B2 * | 12/2018 | Krishnan | C12N 9/0071 |
| 10,174,341 B2 | 1/2019 | Glorioso et al. | |
| 10,441,614 B2 * | 10/2019 | Krishnan | A61K 35/763 |
| 10,525,090 B2 | 1/2020 | Krishnan et al. | |
| 10,786,438 B2 * | 9/2020 | Krishnan | A61K 8/99 |
| 10,829,529 B2 * | 11/2020 | Parry | A61K 9/0073 |
| 11,185,564 B2 * | 11/2021 | Krishnan | A61K 48/005 |
| 11,642,384 B2 * | 5/2023 | Agarwal | C07K 14/4703 424/93.2 |
| 2003/0082142 A1 | 5/2003 | Coffin et al. | |
| 2004/0253606 A1 | 12/2004 | Aziz et al. | |
| 2006/0246139 A1 | 11/2006 | Miyaji et al. | |
| 2007/0066552 A1 | 3/2007 | Clarke et al. | |
| 2007/0092575 A1 | 4/2007 | Balaban et al. | |
| 2007/0148074 A1 | 6/2007 | Sadoqi et al. | |
| 2008/0260851 A1 | 10/2008 | Somasundaran et al. | |
| 2008/0299182 A1 | 12/2008 | Zhang | |

(Continued)

FOREIGN PATENT DOCUMENTS

| | | |
|---|---|---|
| CN | 102 212 559 | 4/2014 |
| EP | 3211000 | 8/2017 |

(Continued)

OTHER PUBLICATIONS

Onsorio and Ghiasi, Recombinant Herpes Simplex Virus Type 1 (HSV-1) Codelivering Interleukin-12p35 as a Molecular Adjuvant Enhances the Protective Immune Response against Ocular HSV-1 Challenge, Journal of Virology, Mar. 2005, p. 3297-3308.*
Tanaka et al., Induction of antitumor immunity by combined immunogene therapy using IL-2 and IL-12 in low antigenic Lewis lung carcinoma, Cancer Gene Therapy, 2000, pp. 1481-1490.*
WO 2021175293 english translation, published Sep. 2021, pp. 1-10.*
Sabater et al., "Topical beremagene geperpavec (B-VEC) for the treatment of recurrent cicatrizing conjunctivitis in a patient with dystrophic epidermolysis bullosa," ARVO Annual Meeting, New Orleans, LA, USA, Apr. 23-27, 2023. (2023).
Acland et al., "Gene therapy restores vision in a canine model of childhood blindness," Nat Genet. (2001) 28(1):92-5.

(Continued)

*Primary Examiner* — Maria Marvich
(74) *Attorney, Agent, or Firm* — The Webb Law Firm

(57) ABSTRACT

The present disclosure provides recombinant nucleic acids comprising one or more polynucleotides encoding an immunomodulatory polypeptide (e.g., a pro-inflammatory cytokine such as a human IL-2 or IL-12 polypeptide); viruses comprising the recombinant nucleic acids; compositions and formulations comprising the recombinant nucleic acids and/or viruses; methods of their use (e.g., for the treatment of cancer, such as lung cancer); and articles of manufacture or kits thereof.

23 Claims, 26 Drawing Sheets

Specification includes a Sequence Listing.

(56) References Cited

U.S. PATENT DOCUMENTS

| | | | |
|---|---|---|---|
| 2009/0136917 A1* | 5/2009 | Szalay | A61K 38/45 435/235.1 |
| 2010/0081707 A1 | 4/2010 | Ali et al. | |
| 2011/0212530 A1 | 9/2011 | Baltimore et al. | |
| 2013/0280224 A1 | 10/2013 | Monsonego | |
| 2013/0295076 A1 | 11/2013 | Kolattukudy et al. | |
| 2013/0331547 A1 | 12/2013 | Hall et al. | |
| 2014/0256798 A1 | 9/2014 | Osborn et al. | |
| 2014/0288155 A1 | 9/2014 | Hovnanian et al. | |
| 2014/0341877 A1 | 11/2014 | Kolattukudy | |
| 2015/0038556 A1 | 2/2015 | Heartlein et al. | |
| 2015/0352191 A1 | 12/2015 | South et al. | |
| 2016/0153000 A1 | 6/2016 | Glorioso et al. | |
| 2016/0250267 A1 | 9/2016 | Uchida et al. | |
| 2016/0324934 A1 | 11/2016 | Angel et al. | |
| 2017/0096684 A1 | 4/2017 | Alton et al. | |
| 2017/0290866 A1 | 10/2017 | Krishnan et al. | |
| 2017/0319693 A1 | 11/2017 | Koizumi et al. | |
| 2018/0177893 A1* | 6/2018 | Angel | A61P 35/00 |
| 2018/0353614 A1 | 12/2018 | Peters | |
| 2019/0160122 A1 | 5/2019 | Krishnan et al. | |
| 2019/0270817 A1* | 9/2019 | Ali | A61P 35/00 |
| 2019/0276845 A1 | 9/2019 | Glorioso et al. | |
| 2020/0009203 A1 | 1/2020 | Sobol et al. | |
| 2020/0061209 A1 | 2/2020 | Bennett et al. | |
| 2020/0093874 A1 | 3/2020 | Agarwal et al. | |
| 2020/0101123 A1 | 4/2020 | Krishnan et al. | |
| 2020/0149067 A1* | 5/2020 | Li | C12N 15/86 |
| 2020/0197456 A1 | 6/2020 | Krishnan et al. | |
| 2020/0199618 A1 | 6/2020 | Krisky et al. | |
| 2021/0040172 A1 | 2/2021 | Cascio et al. | |
| 2021/0045988 A1 | 2/2021 | Krishnan et al. | |
| 2021/0087245 A1 | 3/2021 | Parry et al. | |
| 2021/0189427 A1 | 6/2021 | Krishnan et al. | |
| 2021/0261649 A1 | 8/2021 | Parry et al. | |
| 2021/0395775 A1 | 12/2021 | Parry et al. | |
| 2022/0016191 A1 | 1/2022 | Weiss et al. | |
| 2022/0273737 A1 | 9/2022 | Krishnan et al. | |
| 2023/0149486 A1 | 5/2023 | Krishnan | |

FOREIGN PATENT DOCUMENTS

| | | | |
|---|---|---|---|
| EP | 3377637 | | 9/2018 |
| EP | 3640327 | | 4/2020 |
| WO | WO 99/07394 | * | 2/1999 |
| WO | WO 9960135 | * | 11/1999 |
| WO | WO 1999/064094 | | 12/1999 |
| WO | WO 2000/040734 | | 7/2000 |
| WO | WO 2005/092374 | | 10/2005 |
| WO | WO 2005092374 | * | 10/2005 |
| WO | WO 2013/121202 | | 8/2013 |
| WO | WO 2015/009952 | | 1/2015 |
| WO | WO 2016/191684 | | 12/2016 |
| WO | WO 2017/165806 | | 9/2017 |
| WO | WO 2017/165813 | | 9/2017 |
| WO | WO 2017/176336 | | 10/2017 |
| WO | WO 2017/189754 | | 11/2017 |
| WO | WO 2019191070 | * | 1/2021 |
| WO | WO 2021/046131 | | 3/2021 |
| WO | WO 2021175293 | * | 9/2021 |
| WO | WO 2022/165340 | | 8/2022 |
| WO | WO 2022/212896 | | 10/2022 |

OTHER PUBLICATIONS

Aldawsari et al., "Progress in Topical siRNA Delivery Approaches for Skin Disorders," Curr Pharm Des. (2015) 21(31): 4594-4605.

Ali et al., "Gene therapy for inherited retinal degeneration," Br J Ophthalmol. (1997) 81(9):795-801.

Andtbacka et al., "Talimogene Laherparepvec Improves Durable Response Rate in Patients With Advanced Melanoma," J Clin Oncol. (2015) 33(25): 2780-2788.

Armstrong, M. "Krystal gets more skin in the epidermolysis bullosa game." Vantage. Mar. 5, 2019.

Armstrong, M. "Krystal gets a flying start in epidermolysis bullosa gene therapy" Vantage. Oct. 17, 2018.

Arndt et al., "Inhaled granulocyte-macrophage colony stimulating factor for first pulmonary recurrence of osteosarcoma: Effects on disease-free survival and immunomodulation. A report from the Children's Oncology Group," Clinical Cancer Research. (2010) 16: 4024-4030.

Arndt et al., "Common musculoskeletal tumors of childhood and adolescence," Mayo Clinic proceedings. (2012) 87: 475-87.

Assier et al. "NK cells and polymorphonuclear neutrophils are both critical for IL-2-induced pulmonary vascular leak syndrome," Journal of immunology. (2004) 172:7661-7668.

Bastian et al., "Herpes simplex virus type 1 immediate-early protein ICP22 is required for VICE domain formation during productive viral infection." J Viral. Mar. 2010;84(5):2384-94. doi: 10.1128/JVI.01686-09. Epub Dec. 23, 2009.

Baxevanis et al., "Granulocyte-macrophage colony-stimulating factor improves immunological parameters in patients with refractory solid tumours receiving second-line chemotherapy: correlation with clinical responses," European Journal of Cancer. (1997) 33(8): 1202-1208.

Becher et al., "GM-CSF: From Growth Factor to Central Mediator of Tissue Inflammation," Immunity. (2016) 45: 963-973.

Berkers et al., "Rectal Organoids Enable Personalized Treatment of Cystic Fibrosis," Cell Rep (2019) 26(7): 1701-1708.e3.

Birket et al., "Development of an airway mucus defect in the cystic fibrosis rat," JCI Insight (2018) 3(1): e97199.

Boehmer et al., "Herpes Virus Replication," IUBMB Life (2003) 55(1):13-22.

Bowen et al., Comparison of Herpes Simplex Virus 1 Strains Circulating in Finland Demonstrates the Uncoupling of Whole-Genome Relatedness and Phenotypic Outcomes of Viral Infection, J Virol. (2019) 93(8):e01824-18.

Brehm et al., "Immunogenicity of herpes simplex virus type 1 mutants containing deletions in one or more alpha-genes: ICP4, ICP27, ICP22, and ICP0," Virology (1999) 256(2): 258-69.

Burton et al., "Gene delivery using herpes simplex virus vectors." DNA Cell Biol. Dec. 2002;21(12):915-936.

Carew et al., "A novel approach to cancer therapy using an oncolytic herpes virus to package amplicons containing cytokine genes," Mol Ther. (2001) 4(3): 250-6. doi: 10.1006/mthe.2001.0448. PMID: 11545616.

Carvalho et al., "The function and performance of aqueous devices for inhalation therapy," Journal of Pharmacy and Pharmacology. (2016) 68: 556-578.

Chamorro et al., "Gene Editing for the Efficient Correction of a Recurrent COL7A1 Mutation in Recessive Dystrophic Epidermolysis Bullosa Keratinocytes", Molecular Therapy—Nucleic Acids, vol. 5, 2016, pp. 1-13.

Choate et al., "Transglutaminase 1 delivery to lamellar ichthyosis keratinocytes," Human Gene Therapy (1996) 7:2247-2253.

Christiano AM. Collagen, type VII, alpha 1 (epidermolysis bullosa, dystrophic, dominant and recessive) [Homo sapiens]. NCBI Reference Sequence: NP_000085.1. Dep. Mar. 19, 1999.

Clancy et al., "Personalized Medicine in Cystic Fibrosis: Dawning of a New Era," Am J Respir Crit Care Med (2012) 186(7): 593-597.

Clancy et al., "CFTR Modulator Theratyping: Current Status, Gaps and Future Directions," J Cyst Fibros (2019) 18(1): 22-34.

Clinicaltrials.gov. NCT03536143: Topical Bercolagene Telserpavec (KB103) Gene Therapy to Restore Functional Collagen VII for the Treatment of Dystrophic Epidermolysis Bullosa (GEM-1). May 24, 2018.

Clinicaltrials.gov. NCT04047732: Topical KB105 Gene Therapy for the Treatment of TGM1-deficient Autosomal Recessive Congenital Ichthyosis (ARCI). Aug. 7, 2019.

Clinicaltrials.gov. NCT04214002: The Natural History of Wounds in Patients with Dystrophic Epidermolysis Bullosa (DEB). Dec. 30, 2019.

Collawn et al., "CFTR and Lung Homeostasis," Am J Physiol Lung Cell Mol Physiol (2014) 307(12): L917-923.

(56) References Cited

OTHER PUBLICATIONS

Cooney et al., "Cystic Fibrosis Gene Therapy: Looking Back, Looking Forward," Genes (Basel) (2018) 9(11): 538.
Cutting, G. "Cystic Fibrosis Genetics: From Molecular Understanding to Clinical Application," Nat Rev Genet (2015) 16(1): 45-56.
Dekkers et al., "A Functional CFTR Assay Using Primary Cystic Fibrosis Intestinal Organoids," Nat Med (2013) 19(7): 939-945.
Deluca et al., "Isolation and Characterization of Deletion Mutants of Herpes Simplex Virus Type 1 in the Gene Encoding Immediate-Early Regulatory Protein ICP4", Journal of Virology, (1985) 56(2): 558-570.
Derichs et al., "Hyperviscous Airway Periciliary and Mucous Liquid Layers in Cystic Fibrosis Measured by Confocal Fluorescence Photobleaching," FASEB J (2011) 25(7): 2325-2332.
Di et al., "Phase I study protocol for ex vivo lentiviral gene therapy for the inherited skin disease, Netherton syndrome," Hum Gene Ther Clin Dev. (2013) 24(4):182-190.
Dingwell et al., "The Herpes Simplex Virus gE-gI Complex Facilitates Cell-to-Cell Spread and Binds to Components of Cell Junctions," J Virol. (1998) 72(11): 8933-8942.
Eming SA, Krieg T, Davidson JM. Gene therapy and wound healing. Clin Dermatol. Jan.-Feb. 2007;25(1):79-92.
Eming et al., "Gene transfer in tissue repair: status, challenges and future directions," Exp Opin Biol Ther (2004) 4(9):1373-1386.
Estrada-Veras et al., "Palliative Care for Patients With Cystic Fibrosis #265," J Palliat Med (2013) 16(4): 446-447.
Farasat et al., "Novel transglutaminase-1 mutations and genotype-phenotype investigations of 104 patients with autosomal recessive congenital ichthyosis in the USA," J Med Genet (2009) 46(2):103-111.
Fath et al., "Multiparameter RNA and codon optimization: a standardized tool to assess and enhance autologous mammalian gene expression," PLoS One. (2011) 6(3): e17596.
Fink et al., "Gene therapy for pain: Results of a Phase I clinical trial," Ann Neurol (2011) 70(2):207-212.
Fraefel et al., "In vivo gene transfer to the rat retina using herpes simplex virus type 1 (HSV-1)-based amplicon vectors," Gene Ther. (2005) 12(16):1283-8.
Gallotta et al., "Inhaled TLR9 Agonist Renders Lung Tumors Permissive to PD-1 Blockade by Promoting Optimal CD4+ and CD8+ T-cell Interplay" Cancer Res. (2018) 78(17) :4943-4956. doi: 10.1158/0008-5472.CAN-18-0729. Epub Jun. 26, 2018. PMID: 29945961.
Gardenhire et al. A Guide to Aerosol Delivery Devices for Respiratory Therapists, 4th Edition, American Association for Respiratory Care, 2017.
Geller et al., "An efficient deletion mutant packaging system for defective herpes simplex virus vectors: potential applications to human gene therapy and neuronal physiology," Proc Natl Acad Sci U S A. (1990) 87(22): 8950-8954.
Georgiadis et al., "Lentiviral Engineered Fibroblasts Expressing Codon- Optimized COL7A1 Restore Anchoring Fibrils in RDEB", Journal of Investigative Dermatology, (2016) 136: 284-292.
Ghimessy et al., "KRAS Mutations Predict Response and Outcome in Advanced Lung Adenocarcinoma Patients Receiving First-Line Bevacizumab and Platinum-Based Chemotherapy," Cancers. (2019) 11(10):1514. doi: 10.3390/cancers11101514. PMID: 31600989; Pmcid: PMC6827133.
Ghouse et al., "Oncolytic Herpes Simplex Virus Encoding IL12 Controls Triple-Negative Breast Cancer Growth and Metastasis," Front Oncol. (2020) 10: 384. doi: 10.3389/fonc.2020.00384. PMID: 32266155; Pmcid: PMC7105799.
Gill et al., "Delivery of Genes Into the CF Airway," Thorax (2014) 69(10): 962-964.
Glorioso JC. "Herpes simplex viral vectors: late bloomers with big potential." Hum Gene Ther. (2014) 25(2): 83-91.
Goins et al. "Engineering HSV-1 Vectors for Gene Therapy," Methods Mol Biol (2014) 1144: 63-79.
Goins et al. "Generation of replication-competent and -defective HSV vectors," Cold Spring Harb Protoc. May 1, 2011;2011(5): 512; pdb.prot5615.
Goldsmith et al., "Infected cell protein (ICP)47 enhances herpes simplex virus neurovirulence by blocking the CD8+ T cell response," J Exp Med. (1998) 187(3): 341-348.
Gorell et al., "Gene therapy for skin diseases," Cold Spring Harb Perspect Med (2014) 4:a015149.
Goto et al., "Fibroblasts Show More Potential as Target Cells than Keratinocytes in COL7A1 Gene Therapy of Dystrophic Epidermolysis Bullosa", Journal of Investigative Dermatology, (2006) 126: 766-772.
Grant, Kyle, "Production and Purification of Highly Replication Defective Hsv- 1 Based Gene Therapy Vectors", Doctoral Dissertation, University of Pittsburgh, 2008, 137 pages.
Grisez et al., "Highly metastatic K7M2 cell line: A novel murine model capable of in vivo imaging via luciferase vector transfection," Journal of Orthopaedic Research. (2018) 36: 2296-2304.
Guma et al., "Natural killer cell therapy and aerosol interleukin-2 for the treatment of osteosarcoma lung metastasis," Pediatric Blood Cancer (2014) 61(4): 618.
Gurevich et al. 759 "Successful in vivo COL7A1 gene delivery and correction of recessive dystrophic epidermolysis bullosa (RDEB) skin using an off the shelf HSV-1 vector (KB103)." J Invest Derm. Vol. 138, Iss. 5 Supp. May 2018, p. S129. Available online Apr. 19, 2018.
Heikkinen et al., "Diremerization of human lysyl hydroxylase 3 (LH3) is mediated by the amino acids 541 547," Matrix Biology (2010) 30(1):27-33.
Hennig et al., "HEK293-based production platform for y-retroviral (self-inactivating) vectors: application for safe and efficient transfer of COL7A1 cDNA". Hum Gene Ther Clin Dev. Dec. 2014;25(4):218-28.
Herve et al., "VEGF neutralizing aerosol therapy in primary pulmonary adenocarcinoma with K-ras activating-mutations," MAbs. (2014); 6(6):1638-48. doi: 10.4161/mabs.34454. PMID: 25484066; PMCID: PMC4623465.
Hill et al., "Herpes simplex virus turns off the TAP to evade host immunity," Nature. (1995) 375(6530): 411-415.
Hyde et al., "Repeat Administration of DNA/liposomes to the Nasal Epithelium of Patients With Cystic Fibrosis," Gene Ther (2000) 7(13): 1156-1165.
IMLYGIC Prescribing Information, revised 2021.
Isakoff et al., Osteosarcoma: Current Treatment and a Collaborative Pathway to Success. Journal of clinical oncology : official journal of the American Society of Clinical Oncology. (2015) 33(27): 3029-35.
Jia et al., "Aerosol Gene Therapy with PEI:IL-12 Eradicates Osteosarcoma Lung Metastases1," Clin. Cancer Res. (2003) 9: 3462-3468.
Jia et al., "Eradication of osteosarcoma lung metastases following intranasal interleukin-12 gene therapy using a nonviral polyethylenimine vector," Cancer Gene Therapy. (2002) 9; 260-266.
Jiang et al., "Role of IL-2 in cancer immunotherapy," Oncolmmunology. (2016) 5(6) e1163462.
Jorgovanovic et al., "Roles of IFN-γ in tumor progression and regression: A review," Biomarker Research. (2020) 8:49.
Kaste et al., "Metastases detected at the time of diagnosis of primary pediatric extremity osteosarcoma at diagnosis: imaging features," Cancer. (1999) 86(8); 1602-8.
Kell et al., "Preclinical development of the TLR9 agonist DV281 as an inhaled aerosolized immunotherapeutic for lung cancer: Pharmacological profile in mice, non-human primates, and human primary cells," Int Immunopharmacol. (2019) 66:296-308.
Kerem et al., "Identification of the Cystic Fibrosis Gene: Genetic Analysis," Science (1989) 245(4922):1073-1080.
Kim et al., "Microneedles for Drug and Vaccine Delivery", Advanced Drug Delivery Reviews, vol. 64, 2012, pp. 1547-1568.
Kim et al., "Barriers to Inhaled Gene Therapy of Obstructive Lung Diseases: A Review," J Control Release (2016) 240: 465-488.
Knowles et al., "A Controlled Study of Adenoviral-Vector-Mediated Gene Transfer in the Nasal Epithelium of Patients With Cystic Fibrosis," N Engl J Med (1995) 333(13): 823-831.

(56) References Cited

OTHER PUBLICATIONS

Kohlhapp et al., Molecular Pathways: Mechanism of Action for Talimogene Laherparepvec, a New Oncolytic Virus Immunotherapy, Clinical Cancer Research (2015) 22(5):1048-1054.

Kopecki et al., "Commentary: New advances in the development of therapies for treating inherited skin fragility disorders," Wound Practice and Research (2015) 23(4): 184, Dec. 5, 2015.

Krisky et al., "Deletion of multiple immediate-early genes from herpes simplex virus reduces cytotoxicity and permits long-term gene expression in neurons," Gene Ther. (1998) 5(12):1593-603.

Krisky et al., "Development of herpes simplex virus replication-defective multigene vectors for combination gene therapy applications," Gene Ther (1998) 5(110):1517-1530.

Krystal Biotech, Inc. "Krystal Biotech Announces Settlement with PeriphaGen, Inc." Mar. 15, 2022, https://ir.krystalbio.com/node/8481/pdf. (Year: 2022).

Lachmann, R. "Herpes simplex virus-based vectors," Int J Exp Pathol. (2004) 85(4): 177-190.

Lasek et al., "Interleukin 12: still a promising candidate for tumor immunotherapy?" Cancer immunol Immunother. (2014) 63: 419-35.

Laurent et al., "Cetuxiimab administered through pulmonary route in a mice model of lung tumor," European Respiratory Society Annual Congress 2013, Abstract 401.

Leonard et al., "Effects of single-dose interleukin-12 exposure on interleukin-12 associated toxicity and interferon-γ production," Blood. (1997) 90(7): 2541-2548.

Lewin et al., "Gene therapy for autosomal dominant disorders of keratin," J Investig Dermatol Symp Proc. (2005) 10(1): 47-61.

Liou et al., "Year-to-year Changes in Lung Function in Individuals With Cystic Fibrosis," J Cyst Fibros (2010) 9(4): 250-256.

Liu et al., "An inhalable nanoparticulate STING agonist synergizes with radiotherapy to confer long-term control of lung metastases," Nat Commun. (2019) 10(1):5108. doi: 10.1038/s41467-019-13094-5. PMID: 31704921; PMCID: PMC6841721.

Liu et al., "Herpes simplex virus mediated gene transfer to primate ocular tissues," Exp Eye Res. (1999) 69(4):385-95.

Lommatzsch et al., "The Combination of Tezacaftor and Ivacaftor in the Treatment of Patients With Cystic Fibrosis: Clinical Evidence and Future Prospects in Cystic Fibrosis Therapy," Ther Adv Respir Dis (2019) 13: 1-13. https://doi.org/10.1177/1753466619844424.

Lu et al., "Topical Application of Viral Vectors for Epidermal Gene Transfer", J Invest Dermatol. (1997) 108(5): 803-808.

Ma et al., "Efficacy of Herpes Simplex Virus Vector Encoding V the Human Preproenkephalin Gene for Treatment of Facial Pain in Mice," J aral Facial Pain Headachce (2016) 30(1):42-50.

Marconi et al., "HSV as a Vector in Vaccine Development and Gene Therapy." In: Madame Curie Bioscience Database [Internet]. Austin (TX): Landes Bioscience; 2000- 2013. 30 pages.

Marconi et al., "Replication-defective herpes simplex virus vectors for gene transfer in vivo," Proc Natl Acad Sci USA (1996) 93:11319-11320.

Marx et al. Intranasal Drug Administration—An Attractive Delivery Route for Some Drugs, 2015.

Mayr et al., "Gene Therapy for the COL7A1 Gene", Chapter 23, Intech, 2013, pp. 561-589.

McGowan et al., "Keratin 17 null mice exhibit age- and strain-dependent alopecia," Genes & Dev (2002) 16:1412-1422.

Messmer et al., "Ocular manifestations of keratitis-ichthyosis-deafness (KID) syndrome," Ophthalmology. (2005) 112(2):e1-6.

Miezeiewski et al., "Role of adherens junction proteins in differential herpes simplex virus type 2 infectivity in communication-competent and -deficient cell lines," Intervirology. (2012) 55(6):465-474.

Mirabello et al., "International osteosarcoma incidence patterns in children and adolescents, middle ages and elderly persons," Int J Cancer. (2009) 125(1): 229-234.

Misaghi et al., "Osteosarcoma: a comprehensive review," SICOT-J. (2018) 4, 12.

Miyagawa et al., "Herpes simplex viral-vector design for efficient transduction of nonneuronal cells without cytotoxcity," Proc Natl Acad Sci USA (2015) 112(13):E1632-E1641.

Miyagawa et al., "Deletion of the Virion Host Shut-off Gene Enhances Neuronal-Selective Transgene Expression from an HSV Vector Lacking Functional IE Genes," Mol Ther Methods Clin Dev. (2017) 6: 79-90.

Morales-Nebreda et al., "Intratracheal administration of influenza virus is superior to intranasal administration as a model of acute lung injury," Journal of Virological Methods. (2014) 209: 116-120.

Ng et al., "Fibroblast-Derived Dermal Matrix Drives Development of Aggressive Cutaneous Squamous Cell Carcinoma in Patients with Recessive Dystrophic Epidermolysis Bullosa", Cancer Research, vol. 72, No. 14, Jul. 15, 2012, pp. 3522-3534.

Nguyen et al., "Oncolytic Virus Encoding a Master Pro-Inflammatory Cytokine Interleukin 12 in Cancer Immunotherapy," Cells. (2020) 9(2):400. doi: 10.3390/cells9020400. PMID: 32050597; PMCID: PMC7072539.

Nguyen et al., "Localized Interleukin-12 for Cancer Immunotherapy," Frontiers in Immunology. (2020) 11: 575597.

Ortiz-Urda et al., "Injection of Genetically Engineered Fibroblasts Corrects Regenerated Human Epidermolysis Bullosa Skin Tissue", The Journal of Clinical Investigation, vol. 111, No. 2, Jan. 2003, pp. 251-255.

Parker et al., "Engineered herpes simplex virus expressing IL-12 in the treatment of experimental murine brain tumors," Proc Natl Acad Sci USA. (2000) 97(5): 2208-13. doi: 10.1073/pnas.040557897. PMID: 10681459; PMCID: PMC15779.

Patil et al., "Pulmonary Drug Delivery Strategies: A Concise, Systematic Review," Lung India (2012) 29(1): 44-49.

Peace et al., "Toxicity and therapeutic efficacy of high-dose interleukin 2. In vivo infusion of antibody to NK-1.1 attenuates toxicity without compromising efficacy against murine leukemia," J. Exp. Med. (1989) 169: 161.

Peek et al., "Herpes simplex virus infection of the human eye induces a compartmentalized virus-specific B cell response," J Infect Dis. (2002) 186(11):1539-46.

Pepose et al., "Herpes simplex viral vectors for therapeutic gene delivery to ocular tissues. Recent breakthroughs in the molecular genetics of ocular diseases," Invest Ophthalmol Vis Sci. (1994) 35(6):2662-6.

Periphagen, Krystal Biotech Inc., Answer and Counterclaim in *PeriphaGen* v. *Krystal Biotech*, Filed Jun. 6, 2020 in the Western District of Pennsylvania (60 pgs).

Rahn et al., "Invasion of Herpes Simplex Virus Type 1 into Murine Epidermis: An Ex Vivo Infection Study," J Invest Dermatol. (2015) 135(12): 3009-3016.

Salam A. "Krystal's KB103 splits experts' thoughts on potential for HSV-1 risk in dystrophic epidermolysis bullosa patients, but final Phase I/II efficacy assured." Nov. 7, 2018. Biopharm Insight.

Salameh et al., "Early events in herpes simplex virus lifecycle with implications for an infection of lifetime," Open Virol J. (2012) 6:1-6.

Salmon-Ehr et al., "Implication of Interleukin-4 in Wound Healing", Laboratory Investigation, vol. 80, No. 8, Aug. 2000, pp. 1337-1343.

Samaniego et al., "Persistence and Expression of the Herpes Simplex Virus Genome in the Absence of Immediate-Early Proteins", Journal of Virology, (1998) 72(4): 3307-3320.

Samaniego et al., "The herpes simplex virus immediate-early protein ICP0 affects transcription from the viral genome and infected-cell survival in the absence of ICP4 and ICP27," J Virol. (1997) 71(6): 4614-4625.

Sankar et al., "A novel role for keratin 17 in coordinating oncogenic transformation and cellular adhesion in ewing sarcoma," Molecular and Cellular Biology (2013) 33(22):4448- 4460.

Sapalidis et al., "Inhaled Immunotherapy Administration for Lung Cancer; Efficient? Certainly Possible? J Cancer. (2018) 9(6):1121-1126. doi: 10.7150/jca.24397. PMID: 29581792; PMCID: PMC5868180.

Shen et al., "Herpes simplex virus 1 (HSV-1) for cancer treatment," Cancer Gene Therapy (2006) 13: 975-992.

Silva et al., "Herpes Virus Amplicon Vectors", Viruses, vol. 1, 2009, pp. 594-629.

(56) References Cited

OTHER PUBLICATIONS

Siprashvili et al., "Long-term type VII collagen restoration to human epidermolysis bullosa skin tissue," Hum Gene Ther. Oct. 2010;21(10):1299-310.
Spencer et al., "HSV-1 vector-delivered FGF2 to the retina is neuroprotective but does not preserve functional responses," Mol Ther. (2001) 3(5 Pt 1):746-56.
Stow et al., Isolation and characterization of a herpes simplex virus type 1 mutant containing a deletion within the gene encoding the immediate early polypeptide Vmw110. J Gen Viral. Dec. 1986;67 ( Pt 12):2571-85.
Sufiawati et al., "HIV-associated disruption of tight and adherens junctions of oral epithelial cells facilitates HSV-1 infection and spread," PLoS One. (2014) 9(2): e88803.
Sufiawati et al., "HIV-induced matrix metalloproteinase-9 activation through mitogen-activated protein kinase signalling promotes HSV-1 cell-to-cell spread in oral epithelial cells," J Gen Virol. (2018) 99(7): 937-947.
Theopold et al., "A novel replication-defective HSV-1 vector for regulatable gene delivery to wounds," Journal of the American College of Surgeons (2004) 199(3):57-58.
Uitto et al., "Progress toward Treatment and Cure of Epidermolysis Bullosa: Summary of the DEBRA International Research Symposium EB2015", Journal of Investigative Dermatology, vol. 136, 2016, pp. 352-358.
Vauthier et al., "Poly(alkylcyanoacrylates) as biodegradable materials for biomedical applications," Adv Drug Del Rev. (2003) 55: 519-48.
Wang et al., "Comparative Effectiveness of Antinociceptive Gene Therapies in Animal Models of Diabetic Neuropathic Pain", Gene Therapy, vol. 20, 2013, pp. 742-750.
Wang et al., "Updates on Gene Therapy for Diabetic Retinopathy," Curr Diab Rep. (2020) 20(7):22.
Watanabe et al., "Properties of a Herpes Simplex Virus Multiple Immediate- early Gene-Deleted Recombinant as a Vaccine Vector", Virology, vol. 357, 2007, pp. 186-198.
Watt et al., "Lysyl Hydroxylase 3 Localizes to Epidermal Basement Membrane and Is Reduced in Patients with Recessive Dystrophic Epidermolysis Bullosa", Plos One, (2015) 10(9): e0137639.
Watts et al., "Current therapies and technological advances in aqueous aerosol drug delivery," Drug Dev Ind Pharm. (2008) 34(9): 913-22.
Wei et al., "Pharmacokinetics of combined gene therapy expressing constitutive human GM-CSF and hyperthermia-regulated human IL-12," J Exp Clin Cancer Res. (2013) 32(1):5.
Weiss et al., "The Role of Interleukin 10 in the Pathogenesis and Potential Treatment of Skin Diseases", Journal of the American Academy of Dermatology, vol. 50, No. 5, May 2004, pp. 657-675.
White et al., "Evaluation and optimization of the administration of a selectively replicating herpes simplex viral vector to the brain by convection-enhanced delivery," Cancer Gene Ther. May 2011;18(5):358-69. doi: 10.1038/ cgt.2011.2. Epub Mar. 4, 2011.
Wolfe et al., "Engineering Herpes Simplex Viral Vectors for Therapeutic Gene Transfer", Chapter 6, Gene and Cell Therapy, 2004, pp. 103-129.
Woodley et al., "Normal and Gene-Corrected Dystrophic Epidermolysis Bullosa Fibroblasts Alone Can Produce Type VII Collagen at the Basement Membrane Zone", The Journal of Investigative Dermatology, vol. 121, No. 5, Nov. 2003, pp. 1021-1028.
Woodley, et al., "Intradermal Injection of Lentiviral Vectors Corrects Regenerated Human Dystrophic Epidermolysis Bullosa Skin Tissue in Vivo", Molecular Therapy, vol. 10, No. 2, Aug. 2004, pp. 318-326.
Wu et al., "Prolonged gene expression and cell survival after infection by a herpes simplex virus mutant defective in the immediate-early genes encoding ICP4, ICP27, and ICP22," J Virol. (1996) 70(9): 6358-6369.
Yu et al., Evaluation of effectiveness of granulocyte-macrophage colony-stimulating factor therapy to cancer patients after chemotherapy: a meta-analysis. Oncotarget. (2018) 9(46): 28226-28239. doi: 10.18632/oncotarget.24890. PMID: 29963274; PMCID: PMC6021338.
Zhao et al., "Osteosarcoma: a review of current and future therapeutic approaches," BioMed Eng Online. (2021) 20: 24.
Conlon et al., "Cytokines in the Treatment of Cancer", Journal of Interferon & Cytokin Research, 2019, pp. 6-21, vol. 39, No. 1.
Propper et al., "Harnessing cytokines and chemokines for cancer therapy", Clinical Oncology, 2022, pp. 237-253, vol. 19.
Tang et al., "The Dilemma of HSV-1 Oncolytic Virus Delivery: The Method Choice and Hurdles", International Journal of Molecular Sciences, 2023, pp. 1-18, vol. 24.

* cited by examiner

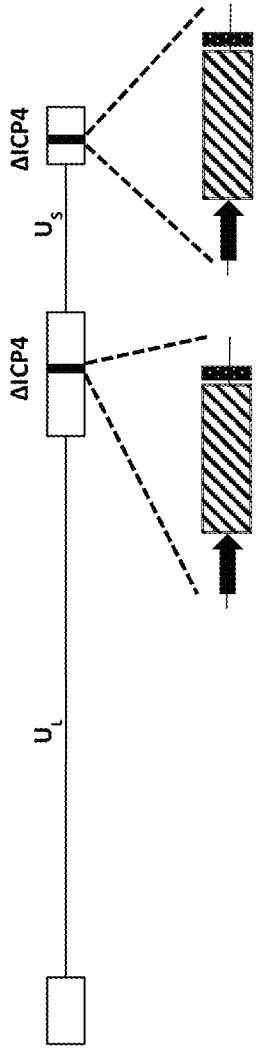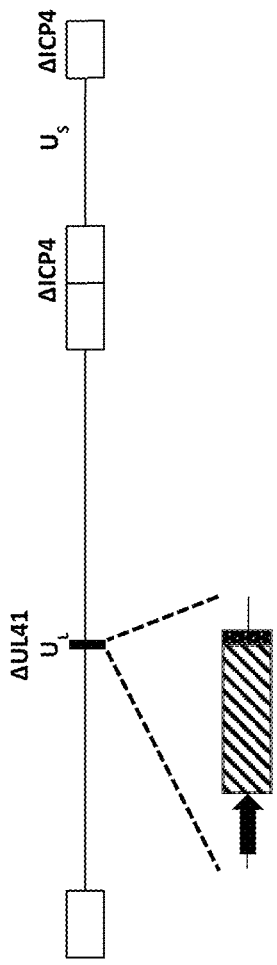

- High dose - 9.5E8 pfu
- Mid dose - 1.9E8 pfu
- Low dose - 3.8E7 pfu
- rIL-12 s.c. - 0.5 μg
- Vehicle control

BALF

BAL cell counts

BAL cell viability body weight

*Il2* genomes

*Il2* transcripts

- Vehicle
- High dose - 2.1E8 pfu
- Mid dose - 4.2E7 pfu
- Low dose - 8.4E6 pfu
- IV rIL-2 - 48 ng serum

BALF

Lung homogenate

- Vehicle
- High dose - 2.1E8 pfu
- Mid dose - 4.2E7 pfu
- Low dose - 8.4E6 pfu
- IV rIL-2 - 48 ng

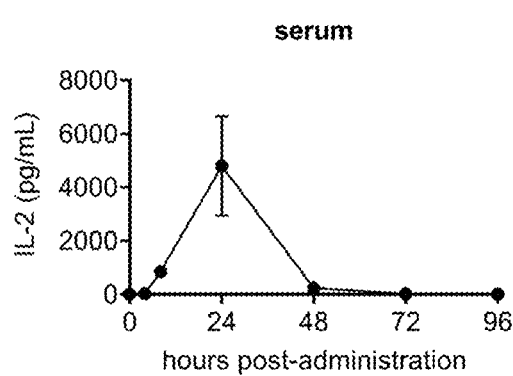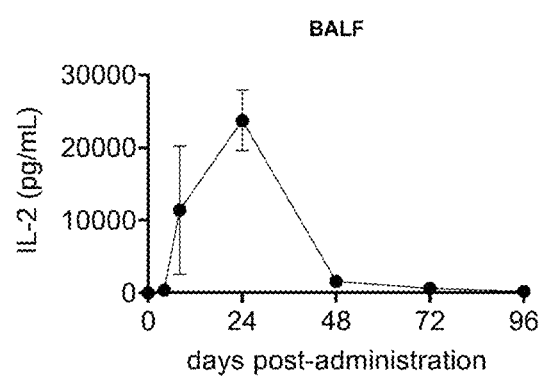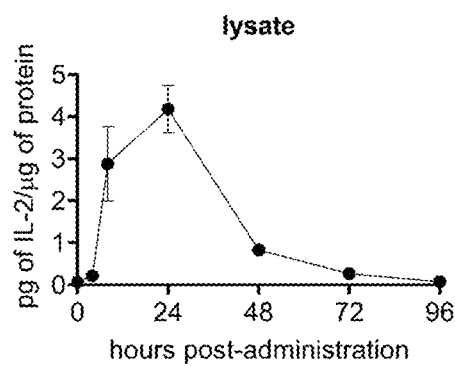

body weight

*Gmcsf* genomes

*Gmcsf* transcripts

- ● Vehicle
- ☐ High dose - 4.88E8 pfu
- ▲ Mid dose - 9.75E7 pfu
- ▽ Low dose - 1.95E7 pfu
- ◆ rGM-CSF - 0.6 μg serum

BALF lung homogenates

- ● Vehicle
- ☐ High dose - 4.88E8 pfu
- ▲ Mid dose - 9.75E7 pfu
- ▽ Low dose - 1.95E7 pfu
- ◆ rGM-CSF - 0.6 µg serum

BALF lung homogenates

BALF

BALF 3 weeks post-inoculation 6 weeks post-inoculation

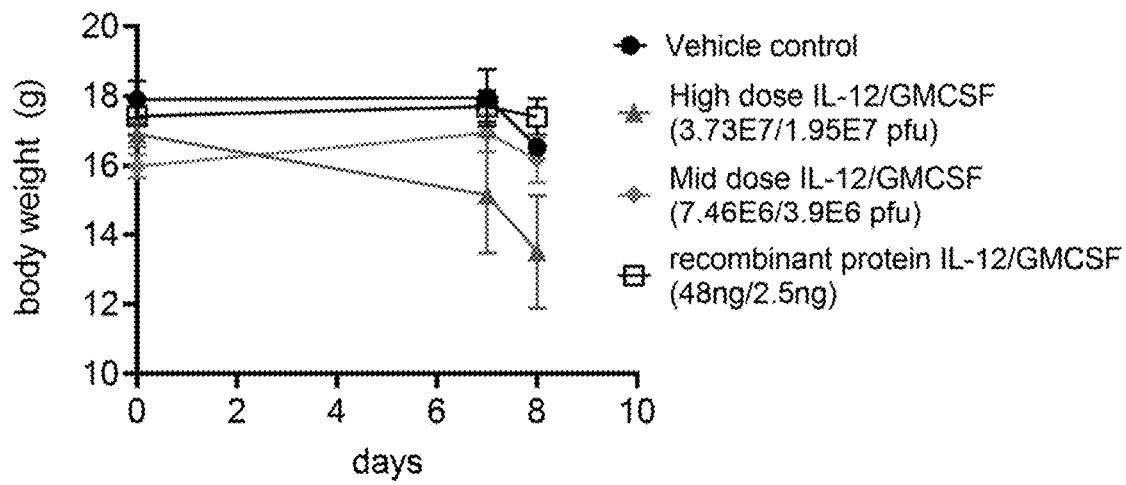
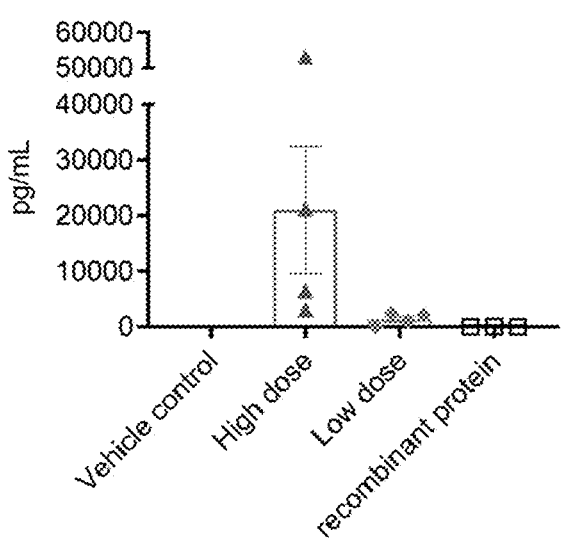 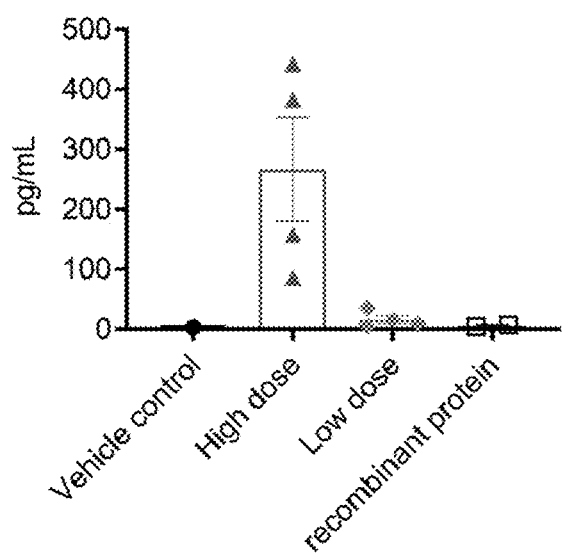

VIRAL VECTORS FOR CANCER THERAPY

CROSS REFERENCE TO RELATED APPLICATIONS

This application is a continuation of U.S. application Ser. No. 17/711,947, filed Apr. 1, 2022, which claims the priority benefit of U.S. Provisional Application Ser. No. 63/170,103, filed Apr. 2, 2021, which applications are incorporated herein by reference in their entireties.

REFERENCE TO AN ELECTRONIC SEQUENCE LISTING

The contents of the electronic sequence listing (761342001501seqlist.xml; Size: 109,194 bytes; and Date of Creation: Mar. 8, 2023) is herein incorporated by reference in its entirety.

FIELD OF THE INVENTION

The present disclosure relates, in part, to recombinant nucleic acids comprising one or more polynucleotides encoding an immunomodulatory polypeptide, viruses comprising the same, pharmaceutical compositions and formulations thereof, and methods of their use (e.g., for treating cancer, such as lung cancer).

BACKGROUND

Cancer is among the leading causes of death worldwide. Despite significant advances in clinical care and treatment methods, more effective cancer treatment options are still needed to prolong survival and decrease cancer death rates.

All references cited herein, including patent applications, patent publications, non-patent literature, and NCBI/UniProtKB/Swiss-Prot Accession numbers are herein incorporated by reference in their entirety, as if each individual reference were specifically and individually indicated to be incorporated by reference.

BRIEF SUMMARY

In order to meet these and other needs, provided herein are recombinant nucleic acids (e.g., recombinant herpes virus genomes) encoding one or more polypeptides (e.g., one or more immunomodulatory polypeptides such as cytokines and chemokines) for use in viruses (e.g., herpes viruses), pharmaceutical compositions and formulations, medicaments, and/or methods useful for treating cancer in a subject in need thereof.

Accordingly, certain aspects of the present disclosure relate to a recombinant herpes virus genome comprising one or more polynucleotides encoding an immunomodulatory polypeptide. In some embodiments, the recombinant herpes virus genome comprises two or more polynucleotides encoding an immunomodulatory polypeptide. In some embodiments, the recombinant herpes virus genome is replication competent. In some embodiments, the recombinant herpes virus genome is replication defective. In some embodiments that may be combined with any of the preceding embodiments, the recombinant herpes virus genome comprises the one or more polynucleotides encoding the immunomodulatory polypeptide within one or more viral gene loci. In some embodiments that may be combined with any of the preceding embodiments, the recombinant herpes virus genome is selected from a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, an Epstein-Barr virus genome, a recombinant Kaposi's sarcoma-associated herpesvirus genome, and any combinations or derivatives thereof.

In some embodiments that may be combined with any of the preceding embodiments, the recombinant herpes virus genome is a recombinant herpes simplex virus genome. In some embodiments, the recombinant herpes simplex virus genome is a recombinant type 1 herpes simplex virus (HSV-1) genome, a recombinant type 2 herpes simplex virus (HSV-2) genome, or any combinations or derivatives thereof. In some embodiments, the recombinant herpes simplex virus genome is a recombinant HSV-1 genome.

In some embodiments that may be combined with any of the preceding embodiments, the recombinant herpes simplex virus genome has been engineered to reduce or eliminate expression of one or more herpes simplex virus genes (e.g., one or more toxic herpes simplex virus genes). In some embodiments that may be combined with any of the preceding embodiments, the recombinant herpes simplex virus genome comprises an inactivating mutation. In some embodiments, the inactivating mutation is in a herpes simplex virus gene. In some embodiments, the inactivating mutation is a deletion of the coding sequence of the herpes simplex virus gene. In some embodiments, the herpes simplex virus gene is selected from Infected Cell Protein (ICP) 0 (one or both copies), ICP4 (one or both copies), ICP22, ICP27, ICP47, thymidine kinase (tk), Long Unique Region (UL) 41, and UL55. In some embodiments that may be combined with any of the preceding embodiments, the recombinant herpes simplex virus genome comprises an inactivating mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivating mutation in the UL41 gene. In some embodiments that may be combined with any of the preceding embodiments, the recombinant herpes simplex virus genome comprises an inactivating mutation in one or both copies of the ICP0 gene. In some embodiments that may be combined with any of the preceding embodiments, the recombinant herpes simplex virus genome comprises an inactivating mutation in the ICP27 gene. In some embodiments that may be combined with any of the preceding embodiments, the recombinant herpes simplex virus genome comprises an inactivating mutation in the UL55 gene. In some embodiments that may be combined with any of the preceding embodiments, the recombinant herpes simplex virus genome does not comprise an inactivating mutation in the ICP47 gene. In some embodiments, the recombinant herpes simplex virus genome does not comprise an inactivating mutation in one or both copies of the ICP34.5 gene. In some embodiments that may be combined with any of the preceding embodiments, the recombinant herpes simplex virus genome does not comprise an inactivating mutation in the UL36 gene.

In some embodiments that may be combined with any of the preceding embodiments, the recombinant herpes simplex virus genome comprises the one or more polynucleotides encoding the immunomodulatory polypeptide within one or more viral gene loci. In some embodiments that may be combined with any of the preceding embodiments, the recombinant herpes simplex virus genome comprises the one or more polynucleotides encoding the immunomodulatory polypeptide within one or both of the ICP4 viral gene loci. In some embodiments that may be combined with any of the preceding embodiments, the recombinant herpes simplex virus genome comprises the one or more polynucleotides encoding the immunomodulatory polypeptide within the ICP22 viral gene locus. In some embodiments that may be combined with any of the preceding embodiments, the recombinant herpes simplex virus genome comprises the one or more polynucleotides encoding the immunomodulatory polypeptide within the UL41 viral gene locus. In some embodiments that may be combined with any of the preceding embodiments, the recombinant herpes simplex virus genome comprises the one or more polynucleotides encoding the immunomodulatory polypeptide within one or both of the ICP0 viral gene loci. In some embodiments that may be combined with any of the preceding embodiments, the recombinant herpes simplex virus genome comprises the one or more polynucleotides encoding the immunomodulatory polypeptide within the ICP27 viral gene locus. In some embodiments that may be combined with any of the preceding embodiments, the recombinant herpes simplex virus genome comprises the one or more polynucleotides encoding the immunomodulatory polypeptide within the UL55 viral gene locus.

In some embodiments that may be combined with any of the preceding embodiments, the immunomodulatory polypeptide is a human immunomodulatory polypeptide. In some embodiments that may be combined with any of the preceding embodiments, the immunomodulatory polypeptide is a secreted immunomodulatory polypeptide. In some embodiments that may be combined with any of the preceding embodiments, the immunomodulatory polypeptide is a cytokine or chemokine. In some embodiments that may be combined with any of the preceding embodiments, the cytokine is a pro-inflammatory cytokine. In some embodiments that may be combined with any of the preceding embodiments, the cytokine is selected from Interleukin-1 (IL-1), Interleukin-2 (IL-2), Interleukin-7 (IL-7), Interleukin-12 (IL-12), Interleukin-13 (IL-13), Interleukin-15 (IL-15), Interleukin-17 (IL-17), Interleukin-18 (IL-18), Interleukin-28 (IL-28), Interleukin-32 (IL-32), Interleukin-33 (IL-33), Interleukin-34 (IL-34), Tumor Necrosis Factor alpha (TNFα), Interferon gamma (IFNγ), Granulocyte Colony-Stimulating Factor (G-CSF), and Granulocyte-Macrophage Colony-Stimulating Factor (GM-CSF). In some embodiments that may be combined with any of the preceding embodiments, the cytokine is IL-2. In some embodiments that may be combined with any of the preceding embodiments, the cytokine is IL-12. In some embodiments that may be combined with any of the preceding embodiments, the cytokine is not GM-CSF. In some embodiments that may be combined with any of the preceding embodiments, the chemokine is a pro-inflammatory chemokine. In some embodiments that may be combined with any of the preceding embodiments, the chemokine is selected from Chemokine (C-X-C motif) Ligand 1 (CXCL1), Chemokine (C-X-C motif) Ligand 2 (CSCL2), Chemokine (C-X-C motif) Ligand 8 (CXCL8), Chemokine (C-X-C motif) Ligand 9 (CXCL9), Chemokine (C-X-C motif) Ligand 11 (CXCL11), Chemokine (C-X-C motif) Ligand 16 (CXCL16), C-C Motif Chemokine Ligand 2 (CCL2), C-C Motif Chemokine Ligand 3 (CCL3), C-C Motif Chemokine Ligand 4 (CCL4), C-C Motif Chemokine Ligand 5 (CCL5), and C-C Motif Chemokine Ligand 11 (CCL11). In some embodiments that may be combined with any of the preceding embodiments, the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 1-30. In some embodiments, the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 1-19. In some embodiments, the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 20-30. In some embodiments, the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 3. In some embodiments, the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 5-6.

In some embodiments that may be combined with any of the preceding embodiments, the recombinant herpes virus genome has reduced cytotoxicity when introduced into a target cell as compared to a corresponding wild-type herpes virus genome. In some embodiments, the target cell is a human cell. In some embodiments, the target cell is a cell of the respiratory tract. In some embodiments, the target cell is an airway epithelial cell.

Other aspects of the present disclosure relate to a herpes virus comprising any of the recombinant herpes virus genomes described herein. In some embodiments, the herpes virus is replication competent. In some embodiments, the herpes virus is replication defective. In some embodiments that may be combined with any of the preceding embodiments, the herpes virus is not oncolytic. In some embodiments that may be combined with any of the preceding embodiments, the herpes virus is a pseudotyped virus. In some embodiments that may be combined with any of the preceding embodiments, the herpes virus is not a pseudotyped virus. In some embodiments that may be combined with any of the preceding embodiments, the herpes virus is not a pseudotyped oncolytic virus. In some embodiments that may be combined with any of the preceding embodiments, the herpes virus has reduced cytotoxicity as compared to a corresponding wild-type herpes virus. In some embodiments that may be combined with any of the preceding embodiments, the herpes virus is selected from a herpes simplex virus, a varicella zoster virus, a human cytomegalovirus, a herpesvirus 6A, a herpesvirus 6B, a herpesvirus 7, an Epstein-Barr virus, a Kaposi's sarcoma-associated herpesvirus, and any combinations or derivatives thereof. In some embodiments that may be combined with any of the preceding embodiments, the herpes virus is a herpes simplex virus. In some embodiments, the herpes simplex virus is not oncolytic. In some embodiments, the herpes simplex virus is an HSV-1, an HSV-2, or any combinations or derivatives thereof. In some embodiments, the herpes simplex virus is an HSV-1. In some embodiments, the HSV-1 is not oncolytic.

Other aspects of the present disclosure relate to a pharmaceutical composition comprising any of the recombinant herpes virus genomes and/or any of the recombinant herpes viruses described herein and a pharmaceutically acceptable carrier or excipient. In some embodiments that may be combined with any of the preceding embodiments, the pharmaceutical composition is suitable for topical, transdermal, subcutaneous, intradermal, oral, intranasal, intratracheal, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration. In some embodiments that may be combined with any of the preceding embodiments, the pharmaceutical composition is suitable for oral, intranasal, intratracheal, or inhaled administration. In some embodiments, the pharmaceutical composition is suitable for intranasal or inhaled administration. In some embodiments, the pharmaceutical composition is suitable for inhaled administration. In some embodiments that may be combined with any of the preceding embodiments, the pharmaceutical composition is suitable for use in a dry powder inhaler, a pressurized metered dose inhaler, a soft mist inhaler, a nebulizer, an electrohydrodynamic aerosol device, or any combinations thereof. In some embodiments that may be combined with any of the preceding embodiments, the pharmaceutical composition is suitable for use in a nebulizer. In some embodiments, the nebulizer is a vibrating mesh nebulizer. In some embodiments that may be combined with any of the preceding embodiments, the pharmaceutical composition comprises a phosphate buffer. In some embodiments that may be combined with any of the preceding embodiments, the pharmaceutical composition comprises glycerol. In some embodiments that may be combined with any of the preceding embodiments, the pharmaceutical composition comprises a lipid carrier. In some embodiments that may be combined with any of the preceding embodiments, the pharmaceutical composition comprises a nanoparticle carrier.

Other aspects of the present disclosure relate to the use of any of the recombinant nucleic acids (e.g., recombinant herpes virus genomes), recombinant viruses (e.g., recombinant herpes viruses), and/or pharmaceutical compositions described herein as a medicament.

Other aspects of the present disclosure relate to the use of any of the recombinant nucleic acids (e.g., recombinant herpes virus genomes), recombinant viruses (e.g., recombinant herpes viruses), and/or pharmaceutical compositions described herein in a therapy.

Other aspects of the present disclosure relate to the use of any of the recombinant nucleic acids (e.g., recombinant herpes virus genomes), recombinant viruses (e.g., recombinant herpes viruses), and/or pharmaceutical compositions described herein in the preparation of a medicament for treating cancer (e.g., lung cancer).

Other aspects of the present disclosure relate to a method of expressing, enhancing, increasing, augmenting, and/or supplementing the levels of an immunomodulatory polypeptide in one or more cells of a subject comprising administering to the subject an effective amount of any of the recombinant herpes viruses and/or pharmaceutical compositions described herein. In some embodiments, the one or more cells are one or more cells of the respiratory tract, airway epithelial, and/or lung. In some embodiments that may be combined with any of the preceding embodiments, the subject is a human. In some embodiments that may be combined with any of the preceding embodiments, the herpes virus or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, peri-articularly, intratumorally, locally, or via inhalation to the subject. In some embodiments that may be combined with any of the preceding embodiments, the herpes virus or pharmaceutical composition is administered orally, intranasally, intratracheally, or via inhalation to the subject. In some embodiments, the herpes virus or pharmaceutical composition is administered intranasally or via inhalation to the subject. In some embodiments, the herpes virus or pharmaceutical composition is administered via inhalation to the subject. In some embodiments, the herpes virus or pharmaceutical composition is administered using a dry powder inhaler, a pressurized metered dose inhaler, a soft mist inhaler, a nebulizer, or an electrohydrodynamic aerosol device. In some embodiments, the herpes virus or pharmaceutical composition is administered using a nebulizer. In some embodiments, the nebulizer is a vibrating mesh nebulizer.

Other aspects of the present disclosure relate to a method of providing prophylactic, palliative, or therapeutic relief of one or more signs or symptoms of cancer in a subject in need thereof comprising administering to the subject an effective amount of any of the recombinant herpes viruses and/or pharmaceutical compositions described herein. In some embodiments, the cancer is selected from a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, skin cancer, stomach cancer, thymic epithelial cancer, and thyroid cancer. In some embodiments, the cancer is small-cell lung cancer, non-small cell lung cancer, adenocarcinoma of the lung, or squamous carcinoma of the lung. In some embodiments, the cancer is non-small cell lung cancer. In some embodiments, the cancer is osteosarcoma. In some embodiments that may be combined with any of the preceding embodiments, the subject is a human. In some embodiments that may be combined with any of the preceding embodiments, the herpes virus or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, peri-articularly, intratumorally, locally, or via inhalation to the subject. In some embodiments that may be combined with any of the preceding embodiments, the herpes virus or pharmaceutical composition is administered orally, intranasally, intratracheally, or via inhalation to the subject. In some embodiments that may be combined with any of the preceding embodiments, the herpes virus or pharmaceutical composition is administered orally, intranasally, intratracheally, or via inhalation to the subject. In some embodiments, the herpes virus or pharmaceutical composition is administered intranasally or via inhalation to the subject. In some embodiments, the herpes virus or pharmaceutical composition is administered via inhalation to the subject. In some embodiments, the herpes virus or pharmaceutical composition is administered using a dry powder inhaler, a pressurized metered dose inhaler, a soft mist inhaler, a nebulizer, or an electrohydrodynamic aerosol device. In some embodiments, the herpes virus or pharmaceutical composition is administered using a nebulizer. In some embodiments, the nebulizer is a vibrating mesh nebulizer.

Other aspects of the present disclosure relate to a method of treating cancer in a subject in need thereof comprising administering to the subject an effective amount of any of the recombinant herpes viruses and/or pharmaceutical compositions described herein. In some embodiments, the cancer is selected from carcinoma, lymphoma, blastoma, sarcoma, a neuroendocrine tumor, mesothelioma, schwannoma, meningioma, adenocarcinoma, melanoma, leukemia, and lymphoid malignancy. In some embodiments, the cancer is selected from a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, skin cancer, stomach cancer, thymic epithelial cancer, and thyroid cancer. In some embodiments, the cancer is small-cell lung cancer, non-small cell lung cancer, adenocarcinoma of the lung, or squamous carcinoma of the lung. In some embodiments, the cancer is non-small cell lung cancer. In some embodiments, the cancer is osteosarcoma. In some embodiments that may be combined with any of the preceding embodiments, the subject is a human. In some embodiments that may be combined with any of the preceding embodiments, the herpes virus or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, peri-articularly, intratumorally, locally, or via inhalation to the subject. In some embodiments that may be combined with any of the preceding embodiments, the herpes virus or pharmaceutical composition is administered orally, intranasally, intratracheally, or via inhalation to the subject. In some embodiments, the herpes virus or pharmaceutical composition is administered intranasally or via inhalation to the subject. In some embodiments, the herpes virus or pharmaceutical composition is administered via inhalation to the subject. In some embodiments, the herpes virus or pharmaceutical composition is administered using a dry powder inhaler, a pressurized metered dose inhaler, a soft mist inhaler, a nebulizer, or an electrohydrodynamic aerosol device. In some embodiments, the herpes virus or pharmaceutical composition is administered using a nebulizer. In some embodiments, the nebulizer is a vibrating mesh nebulizer.

Other aspects of the present disclosure relate to a method of delivering a polypeptide (e.g., an immune modulator polypeptide) to one or more cells of the respiratory tract of a subject comprising administering to the subject a pharmaceutical composition comprising (a) a herpes virus comprising a recombinant herpes virus genome, wherein the recombinant herpes virus genome comprises one or more polynucleotides encoding the polypeptide, and (b) a pharmaceutically acceptable carrier. In some embodiments, the subject suffers from a disease or condition affecting one or more cells of the respiratory tract, such as a cancer or neoplasm affecting the airways and/or lungs which has either originated from the respiratory tract or metastasized from other tissues or organs. In some embodiments, the subject does not suffer from a genetic pulmonary disease. In some embodiments, the subject does not suffer from a disease selected from alpha-1-antitrypsin deficiency, pulmonary alveolar microlithiasis, primary ciliary dyskinesia, congenital pulmonary alveolar proteinosis, pulmonary arterial hypertension, and pulmonary fibrosis. In some embodiments, the lack or a reduced level of expression and/or activity of the polypeptide in the subject is not associated with a genetic pulmonary disease. In some embodiments, the lack or a reduced level of expression and/or activity of the polypeptide in the subject is not associated with a disease selected from alpha-1-antitrypsin deficiency, pulmonary alveolar microlithiasis, primary ciliary dyskinesia, congenital pulmonary alveolar proteinosis, pulmonary arterial hypertension, and pulmonary fibrosis.

In some embodiments that may be combined with any of the preceding embodiments, the herpes virus is a pseudotyped virus. In some embodiments that may be combined with any of the preceding embodiments, the herpes virus is not a pseudotyped virus. In some embodiments that may be combined with any of the preceding embodiments, the herpes virus is not a pseudotyped oncolytic virus.

Other aspects of the present disclosure relate to an article of manufacture or kit comprising any of the recombinant nucleic acids, viruses, medicaments, and/or pharmaceutical compositions or formulations described herein and instructions for administration thereof.

BRIEF DESCRIPTION OF THE DRAWINGS

FIGS. 1A-1I show schematics of wild-type and modified herpes simplex virus genomes. FIG. 1A shows a wild-type herpes simplex virus genome. FIG. 1B shows a modified herpes simplex virus genome comprising deletions of the coding sequence of ICP4 (both copies), with an expression cassette containing a nucleic acid encoding an immunomodulatory polypeptide integrated at each of the ICP4 loci. FIG. 1C shows a modified herpes simplex virus genome comprising deletions of the coding sequences of ICP4 (both copies) and UL41, with an expression cassette containing a nucleic acid encoding an immunomodulatory polypeptide integrated at each of the ICP4 loci. FIG. 1D shows a modified herpes simplex virus genome comprising deletions of the coding sequences of ICP4 (both copies) and UL41, with an expression cassette containing a nucleic acid encoding an immunomodulatory polypeptide integrated at the UL41 locus. FIG. 1E shows a modified herpes simplex virus genome comprising deletions of the coding sequences of ICP4 (both copies) and ICP22, with an expression cassette containing a nucleic acid encoding an immunomodulatory polypeptide integrated at each of the ICP4 loci. FIG. 1F shows a modified herpes simplex virus genome comprising deletions of the coding sequences of ICP4 (both copies) and ICP22, with an expression cassette containing a nucleic acid encoding an immunomodulatory polypeptide integrated at the ICP22 locus. FIG. 1G shows a modified herpes simplex virus genome comprising deletions of the coding sequences of ICP4 (both copies), UL41, and ICP22, with an expression cassette containing a nucleic acid encoding an immunomodulatory polypeptide integrated at each of the ICP4 loci. FIG. 1H shows a modified herpes simplex virus genome comprising deletions of the coding sequences of ICP4 (both copies), UL41, and ICP22, with an expression cassette containing a nucleic acid encoding an immunomodulatory polypeptide integrated at the UL41 locus. FIG. 1I shows a modified herpes simplex virus genome comprising deletions of the coding sequences of ICP4 (both copies), UL41, and ICP22, with an expression cassette containing a nucleic acid encoding an immunomodulatory polypeptide integrated at the ICP22 locus.

FIG. 2A: lane 1 ladder; lane 2 recombinant IL-12; lanes 3-6 HSV-IL12; lane 7 mock. FIG. 2B: lane 1 ladder; lane 2 recombinant IL-2; lanes 3-5 HSV-IL2; lane 6 mock.

FIG. 4A depicts animal weights following HSV-IL12 intratracheal administration. Data are presented as mean±standard error of the mean (SEM); n=2-3 animals per group per time point. FIGS. 4B-4C show genome (FIG. 4B) and transcript (FIG. 4C) levels in lungs of BALB/c animals post-intratracheal administration of HSV-IL12. qPCR (FIG. 4B) and qRT-PCR (FIG. 4C) were performed to measure il12 genomes and transcripts; respectively. Data are indicative of samples run in duplicate, and displayed as mean±SEM of n=2-3 animals per group. FIGS. 4D-4E show IL-12 protein concentrations in serum (FIG. 4D) and bronchoalveolar lavage fluid (BALF; FIG. 4E) analyzed by ELISA. Serum samples are shown as mean±SD of one animal sample assayed in duplicate. BALF data are shown as mean±SEM of n=2-3 animals per group. FIG. 4F depicts IL-12 concentration in lung homogenates following HSV-IL12 intratracheal administration. Biopsies were cut from frozen lung tissue, homogenized, and assayed by ELISA in duplicate. Protein concentrations of homogenates were determined by BCA assay, and IL-12 concentrations were normalized to total protein. Data are displayed as mean±SEM of n=2-3 animals per group. FIG. 4G depicts animal weights following once weekly HSV-IL12 intratracheal administration. Animals were weighed prior to HSV-IL12 administration at the indicated time points. Data are presented as mean±SEM; n=4-6 animals per group. FIGS. 4H-4I depict il12 genome (FIG. 4H) and transcript (FIG. 4I) levels in lungs of BALB/c animals following once weekly treatment for three consecutive weeks. Data are indicative of samples run in duplicate. Values from individual animals are displayed in conjunction with the mean±SEM of n=2-3 animals per group. FIGS. 4J-4K depict IL-12 protein concentrations in BALF and lung homogenates. BALF (FIG. 4J) and lung homogenates (FIG. 4K) were analyzed by ELISA for mIL-12 protein concentration. All samples were assayed in duplicate. Values from individual animals are shown in conjunction with the mean±SEM of n=2-3 animals per group. FIGS. 4L-4M depict analysis of BALF cells as a measure of inflammation. Biopsies were cut from frozen lung tissue, homogenized, and assayed by ELISA in duplicate. Data are displayed as mean±SEM of n=2-3 animals per group.

FIGS. 5A-5I show the in vivo evaluation of HSV-IL2 in healthy mice. FIG. 5A depicts animal weights following HSV-IL2 intratracheal administration. Data are presented as mean±SEM; n=2-3 animals per group per time point. FIGS. 5B-5C show il2 genome (FIG. 5B) and transcript (FIG. 5C) levels in lungs of BALB/c animals post-intratracheal administration of HSV-IL2. Data are indicative of samples run in duplicate and displayed as mean±SEM of n=2-3 animals per group. FIGS. 5D-5E show IL-2 protein concentrations in serum (FIG. 5D) and bronchoalveolar lavage fluid (BALF; FIG. 5E) analyzed by ELISA. Serum samples are shown as mean±SEM of 2-3 animals per group with samples assayed in duplicate. BALF data are shown as mean±SEM of n=2-3 animals per group. FIG. 5F depicts IL-2 concentration in lung homogenates following HSV-IL2 intratracheal administration. Biopsies were cut from frozen lung tissue, homogenized, and assayed by ELISA in duplicate. Protein concentrations of homogenates were determined by BCA assay, and IL-2 concentrations were normalized to total protein. Data are displayed as mean±SEM of n=2-3 animals per group. FIGS. 5G-5I depict IL-2 pharmacokinetics in serum (FIG. 5G), bronchoalveolar lavage fluid (BALF; FIG. 5H), and lysate (FIG. 5I). Data are displayed as mean±SEM of n=2-3 animals per group.

FIG. 6A depicts animal weights following HSV-GMCSF intratracheal administration. Data are presented as mean±SEM; n=2-3 animals per group per time point. FIG. 6E) analyzed by ELISA. Serum and BALF data are shown as mean±SEM of n=2-3 animals per group. FIGS. 6M-6N depict analysis of BALF cells as a measure of inflammation. Cells isolated from BALF were enumerated using a hemocytometer, and viability was determined based on Trypan blue exclusion. Data are displayed as mean±SEM of n=2-3 animals per group.

FIG. 7A shows body weights in control (vehicle) versus K7M2 (murine tumor cell line) infused mice. Data are presented as mean±SEM; n=2-5 animals per group per time point. FIGS. 7B-7C depict lung weights in control vs. tumor cell line-exposed mice at three weeks (FIG. 7B) or six weeks (FIG. 7C) post-inoculation of the K7M2 cells. Values from individual animals are shown in conjunction with the mean±SEM of n=2-5 animals per group. FIGS. 7D-7F depict hematoxylin and eosin (H&E) histological staining of lung sections 6-weeks post inoculation of the K7M2 cells. Magnification is 2.5× (FIG. 7D), 20× (FIG. 7E), 10× (FIG. 7F), and 20× (FIG. 7G).

FIG. 8A shows body weights in control versus HSV-IL12 dosed mice. Data are presented as mean±SEM; n=5 animals per group per time point. FIG. 8B depicts lung weights in control versus HSV-IL12 dosed mice. Values from individual animals are shown in conjunction with the mean±SEM; n=3-5 animals per group.

FIGS. 9A-9F show the in vivo evaluation of once weekly combinatorial HSV-IL12/GMCSF intratracheal administration in healthy mice. FIG. 9A depicts animal weights following once weekly HSV-IL12/GMCSF combinatorial intratracheal administration. Animals were weighed prior to HSV-IL12/GMCSF administration on days 0 and 7 and at sacrifice on day 8. Data are presented as mean±SEM; n=3-4 animals per group. FIGS. 9B-9E depict IL-12 and GMCSF protein concentrations in BALF and lung homogenates. BALF (FIGS. 9B-9C) and lung homogenates (FIGS. 9D-9E) were analyzed by ELISA for mIL-12 and mGM-CSF protein concentration. All samples were assayed in duplicate. Values from individual animals are shown in conjunction with the mean±SEM of n=3-4 animals per group. FIG. 9F depicts analysis of BALF cells as a measure of inflammation. Cells isolated from BALF were enumerated using a hemocytometer, and viability was determined based on Trypan blue exclusion. Data are displayed as mean±SEM of n=3-4 animals per group.

FIG. 10A shows body weight in control versus HSV-IL12 alone, HSV-GMCSF alone, and combinatorial HSV-IL12 and HSV-GMCSF dosed mice. Data are presented as mean±SEM; n=2-5 animals per group per time point. FIG. 10B depicts survival curves in control versus HSV-IL12 alone, HSV-GMCSF alone, and combinatorial HSV-IL12 and HSV-GMCSF dosed mice. Data are presented as mean±SEM; n=5 animals per group.

DETAILED DESCRIPTION

Figure 1A:
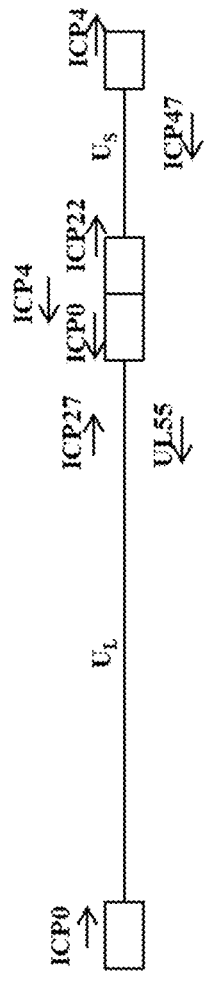

The following description sets forth exemplary methods, parameters, and the like. It should be recognized, however, that such a description is not intended as a limitation on the scope of the present disclosure but is instead provided as a description of exemplary embodiments.

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Gene Transfer Vectors for Mammalian Cells* (J. M. Miller and M. P. Calos, eds., 1987); *PCR: The Polymerase Chain Reaction*, (Mullis et al., eds., 1994); *Short Protocols in Molecular Biology* (Wiley and Sons, 1999).

II. Definitions

Before describing the present disclosure in detail, it is to be understood that the present disclosure is not limited to particular compositions or biological systems, which can, of course, vary. It is also to be understood that the terminology used herein is for the purpose of describing particular embodiments only and is not intended to be limiting.

As used herein, the singular forms "a", "an" and "the" include plural referents unless the content clearly dictates otherwise. Thus, for example, reference to "a molecule" optionally includes a combination of two or more such molecules, and the like.

As used herein, the term "and/or" may include any and all combinations of one or more of the associated listed items. For example, the term "a and/or b" may refer to "a alone", "b alone", "a or b", or "a and b"; the term "a, b, and/or c" may refer to "a alone", "b alone", "c alone", "a or b", "a or c", "b or c", "a, b, or c", "a and b", "a and c", "b and c", or "a, b, and c"; etc.

As used herein, the term "about" refers to the usual error range for the respective value readily known to the skilled person in this technical field. Reference to "about" a value or parameter herein includes (and describes) embodiments that are directed to that value or parameter per se.

It is understood that aspects and embodiments of the present disclosure include "comprising", "consisting", and "consisting essentially of" aspects and embodiments.

As used herein, the terms "polynucleotide", "nucleic acid sequence", "nucleic acid", and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications.

As used herein, a nucleic acid is "operatively linked" or "operably linked" when it is placed into a functional relationship with another nucleic acid sequence. For example, a promoter or enhancer is operably linked to a coding sequence if it affects the transcription of the sequence, or a ribosome binding site is operably linked to a coding sequence if it is positioned so as to facilitate translation. Generally, "operatively linked" or "operably linked" means that the DNA or RNA sequences being linked are contiguous.

As used herein, the term "vector" refers to discrete elements that are used to introduce heterologous nucleic acids into cells for either expression or replication thereof. An expression vector includes vectors capable of expressing nucleic acids that are operatively linked with regulatory sequences, such as promoter regions, that are capable of effecting expression of such nucleic acids. Thus, an expression vector may refer to a DNA or RNA construct, such as a plasmid, a phage, recombinant virus, or other vector that, upon introduction into an appropriate host cell, results in expression of the nucleic acids. Appropriate expression vectors are well known to those of skill in the art and include those that are replicable in eukaryotic cells and those that remain episomal or those which integrate into the host cell genome.

As used herein, an "open reading frame" or "ORF" refers to a continuous stretch of nucleic acids, either DNA or RNA, that encode a protein or polypeptide. Typically, the nucleic acids comprise a translation start signal or initiation codon, such as ATG or AUG, and a termination codon.

As used herein, an "untranslated region" or "UTR" refers to untranslated nucleic acids at the 5' and/or 3' ends of an open reading frame. The inclusion of one or more UTRs in a polynucleotide may affect post-transcriptional regulation, mRNA stability, and/or translation of the polynucleotide.

As used herein, the term "transgene" refers to a polynucleotide that is capable of being transcribed into RNA and translated and/or expressed under appropriate conditions after being introduced into a cell. In some aspects, it confers a desired property to a cell into which it was introduced, or otherwise leads to a desired therapeutic or diagnostic outcome.

As used herein, the terms "polypeptide," "protein," and "peptide" are used interchangeably and may refer to a polymer of two or more amino acids.

As used herein, a "subject", "host", or an "individual" refers to any animal classified as a mammal, including humans, domestic and farm animals, and zoo, sports, or pet animals, such as dogs, horses, cats, cows, as well as animals used in research, such as mice, rats, hamsters, rabbits, and non-human primates, etc. In some embodiments, the mammal is human.

As used herein, the terms "pharmaceutical formulation" or "pharmaceutical composition" refer to a preparation which is in such a form as to permit the biological activity of the active ingredient(s) to be effective, and which contains no additional components which are unacceptably toxic to a subject to which the composition or formulation would be administered. "Pharmaceutically acceptable" excipients (e.g., vehicles, additives) are those which can reasonably be administered to a subject mammal to provide an effective dose of the active ingredient(s) employed.

As used herein, an "effective amount" is at least the minimum amount required to affect a measurable improvement or prevention of one or more symptoms of a particular disorder. An "effective amount" may vary according to factors such as the disease state, age, sex, and weight of the patient. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications used to treat symptoms of the disease, delaying the progression of the disease, and/or prolonging survival. An effective amount can be administered in one or more administrations. For purposes of the present disclosure, an effective amount of a recombinant nucleic acid, virus, and/or pharmaceutical composition is an amount sufficient to accomplish prophylactic or therapeutic treatment either directly or indirectly. As is understood in the clinical context, an effective amount of a recombinant nucleic acid, virus, and/or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "treatment" refers to clinical intervention designed to alter the natural course of the individual or cell being treated during the course of clinical pathology. Desirable effects of treatment include decreasing the rate of disease/disorder/defect progression, ameliorating, or palliating the disease/disorder/defect state, and remission or improved prognosis.

As used herein, the term "delaying progression of" a disease/disorder/defect refers to deferring, hindering, slowing, retarding, stabilizing, and/or postponing development of the disease/disorder/defect. This delay can be of varying lengths or time, depending on the history of the disease/disorder/defect and/or the individual being treated. As is evident to one of ordinary skill in the art, a sufficient or significant delay can, in effect, encompass prevention, in that the individual does not develop the disease.

Throughout the present disclosure, various aspects are presented in a range format. It should be understood that the description in range format is merely for convenience and brevity and should not be construed as an inflexible limitation on the scope of the present disclosure. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the present disclosure. The upper and lower limits of these smaller ranges may independently be comprised in the smaller ranges, and are also encompassed within the present disclosure, subject to any specifically excluded limit in the stated range. Where the stated range comprises one or both of the limits, ranges excluding either or both of those comprised limits are also comprised in the present disclosure. This applies regardless of the breadth of the range.

III. Recombinant Nucleic Acids

Certain aspects of the present disclosure relate to recombinant nucleic acids (e.g., isolated recombinant nucleic acids) comprising one or more (e.g., one or more, two or more, three or more, four or more, five or more, ten or more, etc.) polynucleotides encoding an immunomodulatory polypeptide. In some embodiments, the recombinant nucleic acid comprises one polynucleotide encoding an immunomodulatory polypeptide. In some embodiments, the recombinant nucleic acid comprises two polynucleotides encoding an immunomodulatory polypeptide. In some embodiments, the recombinant nucleic acid comprises three or more polynucleotides encoding an immunomodulatory polypeptide. In some embodiments, the recombinant nucleic acid comprises one or more polynucleotides encoding two or more immunomodulatory polypeptides. In some embodiments, the recombinant nucleic acid comprises two or more polynucleotides encoding two or more immunomodulatory polypeptides. In some embodiments, the two or more immunomodulatory polypeptides are identical. In some embodiments, the two or more immunomodulatory polypeptides are different.

In some embodiments, the present disclosure relates to recombinant nucleic acids comprising a polynucleotide encoding a chimeric polypeptide comprising: a first immunomodulatory polypeptide, a linker polypeptide, and a second immunomodulatory polypeptide. In some embodiments, the first and second immunomodulatory polypeptides are the same. In some embodiments, the first and second immunomodulatory polypeptides are different. In some embodiments, the linker polypeptide is a cleavable linker polypeptide. In some embodiments, the linker polypeptide is a non-cleavable linker polypeptide.

In some embodiments, the recombinant nucleic acid is a vector. In some embodiments, the recombinant nucleic acid is a viral vector. In some embodiments, the recombinant nucleic acid is a herpes viral vector. In some embodiments, the recombinant nucleic acid is a herpes simplex virus amplicon. In some embodiments, the recombinant nucleic acid is a recombinant herpes virus genome. In some embodiments, the recombinant herpes virus genome is a recombinant herpes simplex virus genome. In some embodiments, the recombinant herpes simplex virus genome is a recombinant herpes simplex virus type 1 (HSV-1) genome.

Polynucleotides Encoding Immunomodulatory Polypeptides

In some embodiments, the present disclosure relates to recombinant nucleic acids comprising one or more polynucleotides encoding one or more immunomodulatory polypeptides (e.g., one or more human immunomodulatory polypeptides). Any suitable immunomodulatory polypeptide described herein or known in the art may be encoded by a polynucleotide of the present disclosure, including, for example, human cytokines and chemokines, such as human pro-inflammatory cytokines and chemokines.

In some embodiments, a polynucleotide of the present disclosure comprises the wild-type coding sequence of any immunomodulatory gene described herein or known in the art (including any isoform thereof). In some embodiments, a polynucleotide of the present disclosure comprises a codon-optimized variant of the wild-type coding sequence of any immunomodulatory gene described herein or known in the art. In some embodiments, use of a codon-optimized variant of the coding sequence of a gene increases stability and/or yield of heterologous expression (RNA and/or protein) of the encoded polypeptide in a target cell, as compared to the stability and/or yield of heterologous expression of a corresponding, non-codon-optimized, wild-type sequence. Any suitable method known in the art for performing codon optimization of a sequence for expression in one or more target cells (e.g., one or more human cells) may be used, including, for example, by the methods described by Fath et al. (PLoS One. 2011 Mar. 3; 6(3): e17596).

In some embodiments, the present disclosure relates to a recombinant nucleic acid comprising one or more polynucleotides comprising the coding sequence of a human cytokine. Any suitable human cytokine gene (including any isoform thereof) known in the art may be encoded by a polynucleotide of the present disclosure, including, for example, an IL1A gene (see e.g., NCBI Gene ID: 3552; SEQ ID NO: 31), an IL1B gene (see e.g., NCBI Gene ID: 3553; SEQ ID NO: 32), an 1L2 gene (see e.g., NCBI Gene ID: 3558; SEQ ID NO: 33), an IL3 gene (see e.g., NCBI Gene ID: 3562), an IL4 gene (see e.g., NCBI Gene ID: 3565), an IL5 gene (see e.g., NCBI Gene ID: 3567), an IL6 gene (see e.g., NCBI Gene ID: 3569), an IL7 gene (see e.g., NCBI Gene ID: 3574; SEQ ID NO: 34), an IL9 gene (see e.g., NCBI Gene ID: 3578), and IL10 gene (see e.g., NCBI Gene ID: 3586), an IL11 gene (see e.g., NCBI Gene ID: 3589), an IL12A gene (see e.g., NCBI Gene ID: 3592; SEQ ID NO: 35), an IL12B gene (see e.g., NCBI Gene ID: 3593; SEQ ID NO: 36), an IL13 gene (see e.g., NCBI Gene ID: 3596; SEQ ID NO: 317), an IL15 gene (see e.g., NCBI Gene ID: 3600; SEQ ID NO: 38), an IL17A gene (see e.g., NCBI Gene ID: 3605; SEQ ID NO: 39), an IL17B gene (see e.g., NCBI Gene ID: 27190), an IL17C gene (see e.g., NCBI Gene ID: 27189), an IL17D gene (see e.g., NCBI Gene ID: 53342), an IL25 gene (see e.g., NCBI Gene ID: 64806), an IL17F gene (see e.g., NCBI Gene ID: 1127, an IL18 gene (see e.g., NCBI Gene ID: 3606; SEQ ID NO: 40), an IFNL2 gene (see e.g., NCBI Gene ID: 282616; SEQ ID NO: 41), an IFNL3 gene (see e.g., NCBI Gene ID: 282617; SEQ ID NO: 42), an IFNL1 gene (see e.g., NCBI Gene ID: 282618), an IL32 gene (see e.g., NCBI Gene ID: 9235; SEQ ID NO: 43), an IL33 gene (see e.g., NCBI Gene ID: 90865; SEQ ID NO: 44), an IL34 gene (see e.g., NCBI Gene ID: 146433; SEQ ID NO: 45), an IL36A gene (see e.g., NCBI Gene ID: 27179), an IL36B gene (see e.g., NCBI Gene ID: 27177), an IL36G gene (see e.g., NCBI Gene ID: 56300), an IFNA1 gene (see e.g., NCBI Gene ID: 3439), an IFNA13 gene (see e.g., NCBI Gene ID: 3447), an IFNA2 gene (see e.g., NCBI Gene ID: 3440), an IFNA4 gene (see e.g., NCBI Gene ID: 3441), an IFNA5 gene (see e.g., NCBI Gene ID: 3442), an IFNA6 gene (see e.g., NCBI Gene ID: 3443), an IFNA7 gene (see e.g., NCBI Gene ID: 3444), an IFNA8 gene (see e.g., NCBI Gene ID: 3445), an IFNA10 gene (see e.g., NCBI Gene ID: 3446), an IFNA14 gene (see e.g., NCBI Gene ID: 3448), IFNA16 gene (see e.g., NCBI Gene ID: 3449), IFNA17 gene (see e.g., NCBI Gene ID: 3451), an IFNA21 gene (see e.g., NCBI Gene ID: 3452), an IFNB1 gene (see e.g., NCBI Gene ID: 3456), an IFNB3 gene (see e.g., NCBI Gene ID: 618946), an IFNG gene (see e.g., NCBI Gene ID: 3458; SEQ ID NO: 46), a TNF gene (see e.g., NCBI Gene ID: 7124; SEQ ID NO: 47), a LTA gene (see e.g., NCBI Gene ID: 4049), a CSF3 gene (see e.g., NCBI Gene ID: 1440; SEQ ID NO: 48), a CSF2 gene (see e.g., NCBI Gene ID: 1437; SEQ ID NO: 49), a CSF1 gene (see e.g., NCBI Gene ID: 1435), etc. In some embodiments, a polynucleotide of the present disclosure does not comprise a sequence encoding an IL4 gene. In some embodiments, a polynucleotide of the present disclosure does not comprise a sequence encoding an IL10 gene. In some embodiments, a polynucleotide of the present disclosure does not comprise a sequence encoding an GM-CSF gene. In some embodiments, a polynucleotide of the present disclosure does not comprise a sequence encoding an IL4, IL10, and/or GM-CSF gene. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the human cytokine genes (and/or coding sequences thereof) described herein or known in the art. In some embodiments, the cytokine is a pro-inflammatory cytokine. In some embodiments, the cytokine is selected from human IL-1, IL-2, IL-7, IL-12, IL-13, IL-15, IL-17, IL-18, IL-28 (e.g., IL-28a and/or IL-28(3), IL-32, IL-33, IL-34, TNFα, IFNγ, G-CSF, and/or GM-CSF.

In some embodiments, a polynucleotide of the present disclosure encodes an IL-1a polypeptide. In some embodiments, the IL-1a polypeptide is a human IL-1a polypeptide (see e.g., UniProt accession number: P01583). In some embodiments, the polynucleotide comprises the coding sequence of a wild-type ILIA gene (see e.g., NCBI Gene ID: 3552, SEQ ID NO: 31), or a codon-optimized variant thereof. In some embodiments, a polynucleotide encoding an IL-1a polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 1. In some embodiments, a polynucleotide encoding an IL-1a polypeptide is a polynucleotide that encodes a polypeptide comprising the amino acid sequence of SEQ ID NO: 1.

In some embodiments, a polynucleotide encoding an IL-1a polypeptide is a polynucleotide that encodes an N-terminal truncation, a C-terminal truncation, or a fragment of the amino acid sequence of SEQ ID NO: 1. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 271, consecutive amino acids of SEQ ID NO: 1.

In some embodiments, a polynucleotide of the present disclosure encodes an IL-1β polypeptide. In some embodiments, the IL-1β polypeptide is a human IL-1β polypeptide (see e.g., UniProt accession number: P01584). In some embodiments, the polynucleotide comprises the coding sequence of a wild-type IL1B gene (see e.g., NCBI Gene ID: 3553, SEQ ID NO: 32), or a codon-optimized variant thereof. In some embodiments, a polynucleotide encoding an IL-1β polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 2. In some embodiments, a polynucleotide encoding an IL-1β polypeptide is a polynucleotide that encodes a polypeptide comprising the amino acid sequence of SEQ ID NO: 2.

In some embodiments, a polynucleotide encoding an IL-1β polypeptide is a polynucleotide that encodes an N-terminal truncation, a C-terminal truncation, or a fragment of the amino acid sequence of SEQ ID NO: 2. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 269, consecutive amino acids of SEQ ID NO: 2.

In some embodiments, a polynucleotide of the present disclosure encodes an IL-2 polypeptide. In some embodiments, the IL-2 polypeptide is a human IL-2 polypeptide (see e.g., UniProt accession number: P60568). In some embodiments, the polynucleotide comprises the coding sequence of a wild-type IL2 gene (see e.g., NCBI Gene ID: 3558, SEQ ID NO: 33), or a codon-optimized variant thereof (see e.g., SEQ ID NO: 61). In some embodiments, a polynucleotide encoding an IL-2 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 3. In some embodiments, a polynucleotide encoding an IL-2 polypeptide is a polynucleotide that encodes a polypeptide comprising the amino acid sequence of SEQ ID NO: 3.

In some embodiments, a polynucleotide encoding an IL-2 polypeptide is a polynucleotide that encodes an N-terminal truncation, a C-terminal truncation, or a fragment of the amino acid sequence of SEQ ID NO: 3. N-terminal truncations, C-terminal truncations, or fragments may comprise at least 10, at least 12, at least 14, at least 16, at least 18, at least 20, at least 30, at least 40, at least 50, at least 75, at least 100, but fewer than 153, consecutive amino acids of SEQ ID NO: 3.

In some embodiments, a polynucleotide of the present disclosure encodes an IL-7 polypeptide. In some embodiments, the IL-7 polypeptide is a human IL-7 polypeptide (see e.g., UniProt accession number: P13232). In some embodiments, the polynucleotide comprises the coding sequence of a wild-type IL7 gene (see e.g., NCBI Gene ID: 3574, SEQ ID NO: 34), or a codon-optimized variant thereof. In some embodiments, a polynucleotide encoding an IL-7 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 4. In some embodiments, a polynucleotide encoding an IL-7 polypeptide is a polynucleotide that encodes a polypeptide comprising the amino acid sequence of SEQ ID NO: 4.

In some embodiments, a polynucleotide encoding an IL-7 polypeptide is a polynucleotide that encodes an N-terminal truncation, a C-terminal truncation, or a fragment of the amino acid sequence of SEQ ID NO: 4. N-terminal truncations, C-terminal truncations, or fragments may comprise at least 10, at least 12, at least 14, at least 16, at least 18, at least 20, at least 30, at least 40, at least 50, at least 75, at least 100, but fewer than 177, consecutive amino acids of SEQ ID NO: 4.

In some embodiments, a polynucleotide of the present disclosure encodes an IL-12 subunit α polypeptide. In some embodiments, the IL-12 subunit α polypeptide is a human IL-12 subunit α polypeptide (see e.g., UniProt accession number: P29459). In some embodiments, the polynucleotide comprises the coding sequence of a wild-type IL12A gene (see e.g., NCBI Gene ID: 3592, SEQ ID NO: 35), or a codon-optimized variant thereof (see e.g., SEQ ID NO: 62). In some embodiments, a polynucleotide encoding an IL-12 subunit a polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 5. In some embodiments, a polynucleotide encoding an IL-12 subunit α polypeptide is a polynucleotide that encodes a polypeptide comprising the amino acid sequence of SEQ ID NO: 5.

In some embodiments, a polynucleotide encoding an IL-12 subunit α polypeptide is a polynucleotide that encodes an N-terminal truncation, a C-terminal truncation, or a fragment of the amino acid sequence of SEQ ID NO: 5. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 219, consecutive amino acids of SEQ ID NO: 5.

In some embodiments, a polynucleotide of the present disclosure encodes an IL-12 subunit β polypeptide. In some embodiments, the IL-12 subunit β polypeptide is a human IL-12 subunit β polypeptide (see e.g., UniProt accession number: P29460). In some embodiments, the polynucleotide comprises the coding sequence of a wild-type IL12B gene (see e.g., NCBI Gene ID: 3593, SEQ ID NO: 36), or a codon-optimized variant thereof (see e.g., SEQ ID NO: 63). In some embodiments, a polynucleotide encoding an IL-12 subunit β polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 6. In some embodiments, a polynucleotide encoding an IL-12 subunit β polypeptide is a polynucleotide that encodes a polypeptide comprising the amino acid sequence of SEQ ID NO: 6.

In some embodiments, a polynucleotide encoding an IL-12 subunit 13 polypeptide is a polynucleotide that encodes an N-terminal truncation, a C-terminal truncation, or a fragment of the amino acid sequence of SEQ ID NO: 6. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, but fewer than 328, consecutive amino acids of SEQ ID NO: 6.

In some embodiments, a polynucleotide of the present disclosure encodes an IL-13 polypeptide. In some embodiments, the IL-13 polypeptide is a human IL-13 polypeptide (see e.g., UniProt accession number: P35225). In some embodiments, the polynucleotide comprises the coding sequence of a wild-type IL13 gene (see e.g., NCBI Gene ID: 3596, SEQ ID NO: 37), or a codon-optimized variant thereof. In some embodiments, a polynucleotide encoding an IL-13 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 7. In some embodiments, a polynucleotide encoding an IL-13 polypeptide is a polynucleotide that encodes a polypeptide comprising the amino acid sequence of SEQ ID NO: 7.

In some embodiments, a polynucleotide encoding an IL-13 polypeptide is a polynucleotide that encodes an N-terminal truncation, a C-terminal truncation, or a fragment of the amino acid sequence of SEQ ID NO: 7. N-terminal truncations, C-terminal truncations, or fragments may comprise at least 10, at least 12, at least 14, at least 16, at least 18, at least 20, at least 30, at least 40, at least 50, at least 75, at least 100, but fewer than 146, consecutive amino acids of SEQ ID NO: 7.

In some embodiments, a polynucleotide of the present disclosure encodes an IL-15 polypeptide. In some embodiments, the IL-15 polypeptide is a human IL-15 polypeptide (see e.g., UniProt accession number: P40933). In some embodiments, the polynucleotide comprises the coding sequence of a wild-type IL15 gene (see e.g., NCBI Gene ID: 3600, SEQ ID NO: 38), or a codon-optimized variant thereof. In some embodiments, a polynucleotide encoding an IL-15 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 8. In some embodiments, a polynucleotide encoding an IL-15 polypeptide is a polynucleotide that encodes a polypeptide comprising the amino acid sequence of SEQ ID NO: 8.

In some embodiments, a polynucleotide encoding an IL-15 polypeptide is a polynucleotide that encodes an N-terminal truncation, a C-terminal truncation, or a fragment of the amino acid sequence of SEQ ID NO: 8. N-terminal truncations, C-terminal truncations, or fragments may comprise at least 10, at least 12, at least 14, at least 16, at least 18, at least 20, at least 30, at least 40, at least 50, at least 75, at least 100, but fewer than 162, consecutive amino acids of SEQ ID NO: 8.

In some embodiments, a polynucleotide of the present disclosure encodes an IL-17A polypeptide. In some embodiments, the IL-17A polypeptide is a human IL-17A polypeptide (see e.g., UniProt accession number: O16552). In some embodiments, the polynucleotide comprises the coding sequence of a wild-type IL17A gene (see e.g., NCBI Gene ID: 3605, SEQ ID NO: 39), or a codon-optimized variant thereof. In some embodiments, a polynucleotide encoding an IL-17A polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 9. In some embodiments, a polynucleotide encoding an IL-17A polypeptide is a polynucleotide that encodes a polypeptide comprising the amino acid sequence of SEQ ID NO: 9.

In some embodiments, a polynucleotide encoding an IL-17A polypeptide is a polynucleotide that encodes an N-terminal truncation, a C-terminal truncation, or a fragment of the amino acid sequence of SEQ ID NO: 9. N-terminal truncations, C-terminal truncations, or fragments may comprise at least 10, at least 12, at least 14, at least 16, at least 18, at least 20, at least 30, at least 40, at least 50, at least 75, at least 100, but fewer than 155, consecutive amino acids of SEQ ID NO: 9.

In some embodiments, a polynucleotide of the present disclosure encodes an IL-18 polypeptide. In some embodiments, the IL-18 polypeptide is a human IL-18 polypeptide (see e.g., UniProt accession number: Q14116). In some embodiments, the polynucleotide comprises the coding sequence of a wild-type IL18 gene (see e.g., NCBI Gene ID: 3606, SEQ ID NO: 40), or a codon-optimized variant thereof. In some embodiments, a polynucleotide encoding an IL-18 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 10. In some embodiments, a polynucleotide encoding an IL-18 polypeptide is a polynucleotide that encodes a polypeptide comprising the amino acid sequence of SEQ ID NO: 10.

In some embodiments, a polynucleotide encoding an IL-18 polypeptide is a polynucleotide that encodes an N-terminal truncation, a C-terminal truncation, or a fragment of the amino acid sequence of SEQ ID NO: 10. N-terminal truncations, C-terminal truncations, or fragments may comprise at least 10, at least 12, at least 14, at least 16, at least 18, at least 20, at least 30, at least 40, at least 50, at least 75, at least 100, at least 150, but fewer than 193, consecutive amino acids of SEQ ID NO: 10.

In some embodiments, a polynucleotide of the present disclosure encodes an IL-28A polypeptide. In some embodiments, the IL-28A polypeptide is a human IL-28A polypeptide (see e.g., UniProt accession number: Q8IZJ0). In some embodiments, the polynucleotide comprises the coding sequence of a wild-type IFNL2 gene (see e.g., NCBI Gene ID: 282616, SEQ ID NO: 41), or a codon-optimized variant thereof. In some embodiments, a polynucleotide encoding an IL-28A polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 11. In some embodiments, a polynucleotide encoding an IL-28A polypeptide is a polynucleotide that encodes a polypeptide comprising the amino acid sequence of SEQ ID NO: 11.

In some embodiments, a polynucleotide encoding an IL-28A polypeptide is a polynucleotide that encodes an N-terminal truncation, a C-terminal truncation, or a fragment of the amino acid sequence of SEQ ID NO: 11. N-terminal truncations, C-terminal truncations, or fragments may comprise at least 10, at least 12, at least 14, at least 16, at least 18, at least 20, at least 30, at least 40, at least 50, at least 75, at least 100, at least 150, but fewer than 200, consecutive amino acids of SEQ ID NO: 11.

In some embodiments, a polynucleotide of the present disclosure encodes an IL-28B polypeptide. In some embodiments, the IL-28B polypeptide is a human IL-28B polypeptide (see e.g., UniProt accession number: Q8IZI9). In some embodiments, the polynucleotide comprises the coding sequence of a wild-type IFNL3 gene (see e.g., NCBI Gene ID: 282617, SEQ ID NO: 42), or a codon-optimized variant thereof. In some embodiments, a polynucleotide encoding an IL-28B polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 12. In some embodiments, a polynucleotide encoding an IL-28B polypeptide is a polynucleotide that encodes a polypeptide comprising the amino acid sequence of SEQ ID NO: 12.

In some embodiments, a polynucleotide encoding an IL-28B polypeptide is a polynucleotide that encodes an N-terminal truncation, a C-terminal truncation, or a fragment of the amino acid sequence of SEQ ID NO: 12. N-terminal truncations, C-terminal truncations, or fragments may comprise at least 10, at least 12, at least 14, at least 16, at least 18, at least 20, at least 30, at least 40, at least 50, at least 75, at least 100, but fewer than 196, consecutive amino acids of SEQ ID NO: 12.

In some embodiments, a polynucleotide of the present disclosure encodes an IL-32 polypeptide. In some embodiments, the IL-32 polypeptide is a human IL-32 polypeptide (see e.g., UniProt accession number: P24001). In some embodiments, the polynucleotide comprises the coding sequence of a wild-type IL32 gene (see e.g., NCBI Gene ID: 9235, SEQ ID NO: 43), or a codon-optimized variant thereof. In some embodiments, a polynucleotide encoding an IL-32 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 13. In some embodiments, a polynucleotide encoding an IL-32 polypeptide is a polynucleotide that encodes a polypeptide comprising the amino acid sequence of SEQ ID NO: 13.

In some embodiments, a polynucleotide encoding an IL-32 polypeptide is a polynucleotide that encodes an N-terminal truncation, a C-terminal truncation, or a fragment of the amino acid sequence of SEQ ID NO: 13. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 234, consecutive amino acids of SEQ ID NO: 13.

In some embodiments, a polynucleotide of the present disclosure encodes an IL-33 polypeptide. In some embodiments, the IL-33 polypeptide is a human IL-33 polypeptide (see e.g., UniProt accession number: 095760). In some embodiments, the polynucleotide comprises the coding sequence of a wild-type IL33 gene (see e.g., NCBI Gene ID: 90865, SEQ ID NO: 44), or a codon-optimized variant thereof. In some embodiments, a polynucleotide encoding an IL-33 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 14. In some embodiments, a polynucleotide encoding an IL-33 polypeptide is a polynucleotide that encodes a polypeptide comprising the amino acid sequence of SEQ ID NO: 14.

In some embodiments, a polynucleotide encoding an IL-33 polypeptide is a polynucleotide that encodes an N-terminal truncation, a C-terminal truncation, or a fragment of the amino acid sequence of SEQ ID NO: 14. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 270, consecutive amino acids of SEQ ID NO: 14.

In some embodiments, a polynucleotide of the present disclosure encodes an IL-34 polypeptide. In some embodiments, the IL-34 polypeptide is a human IL-34 polypeptide (see e.g., UniProt accession number: Q6ZMJ4). In some embodiments, the polynucleotide comprises the coding sequence of a wild-type IL34 gene (see e.g., NCBI Gene ID: 146433, SEQ ID NO: 45), or a codon-optimized variant thereof. In some embodiments, a polynucleotide encoding an IL-34 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 15. In some embodiments, a polynucleotide encoding an IL-34 polypeptide is a polynucleotide that encodes a polypeptide comprising the amino acid sequence of SEQ ID NO: 15.

In some embodiments, a polynucleotide encoding an IL-34 polypeptide is a polynucleotide that encodes an N-terminal truncation, a C-terminal truncation, or a fragment of the amino acid sequence of SEQ ID NO: 15. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 242, consecutive amino acids of SEQ ID NO: 15.

In some embodiments, a polynucleotide of the present disclosure encodes a TNFα polypeptide. In some embodiments, the TNFα polypeptide is a human TNFα polypeptide (see e.g., UniProt accession number: P01375). In some embodiments, the polynucleotide comprises the coding sequence of a wild-type TNF gene (see e.g., NCBI Gene ID: 7124, SEQ ID NO: 46), or a codon-optimized variant thereof. In some embodiments, a polynucleotide encoding a TNFα polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 16. In some embodiments, a polynucleotide encoding a TNFα polypeptide is a polynucleotide that encodes a polypeptide comprising the amino acid sequence of SEQ ID NO: 16.

In some embodiments, a polynucleotide encoding a TNFα polypeptide is a polynucleotide that encodes an N-terminal truncation, a C-terminal truncation, or a fragment of the amino acid sequence of SEQ ID NO: 16. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 233, consecutive amino acids of SEQ ID NO: 16.

In some embodiments, a polynucleotide of the present disclosure encodes an IFNγ polypeptide. In some embodiments, the IFNγ polypeptide is a human IFNγ polypeptide (see e.g., UniProt accession number: P01579). In some embodiments, the polynucleotide comprises the coding sequence of a wild-type IFNG gene (see e.g., NCBI Gene ID: 3458, SEQ ID NO: 47), or a codon-optimized variant thereof. In some embodiments, a polynucleotide encoding a IFNγ polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 17. In some embodiments, a polynucleotide encoding a IFNγ polypeptide is a polynucleotide that encodes a polypeptide comprising the amino acid sequence of SEQ ID NO: 17.

In some embodiments, a polynucleotide encoding an IFNγ polypeptide is a polynucleotide that encodes an N-terminal truncation, a C-terminal truncation, or a fragment of the amino acid sequence of SEQ ID NO: 17. N-terminal truncations, C-terminal truncations, or fragments may comprise at least 10, at least 12, at least 14, at least 16, at least 18, at least 20, at least 30, at least 40, at least 50, at least 75, at least 100, but fewer than 166, consecutive amino acids of SEQ ID NO: 17.

In some embodiments, a polynucleotide of the present disclosure encodes a G-CSF polypeptide. In some embodiments, the G-CSF polypeptide is a human G-CSF polypeptide (see e.g., UniProt accession number: P09919). In some embodiments, the polynucleotide comprises the coding sequence of a wild-type CSF3 gene (see e.g., NCBI Gene ID: 1440, SEQ ID NO: 48), or a codon-optimized variant thereof. In some embodiments, a polynucleotide encoding a G-CSF polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 18. In some embodiments, a polynucleotide encoding a G-CSF polypeptide is a polynucleotide that encodes a polypeptide comprising the amino acid sequence of SEQ ID NO: 18.

In some embodiments, a polynucleotide encoding a G-CSF polypeptide is a polynucleotide that encodes an N-terminal truncation, a C-terminal truncation, or a fragment of the amino acid sequence of SEQ ID NO: 18. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 207, consecutive amino acids of SEQ ID NO: 18.

In some embodiments, a polynucleotide of the present disclosure encodes a GM-CSF polypeptide. In some embodiments, the GM-CSF polypeptide is a human GM-CSF polypeptide (see e.g., UniProt accession number: P04141). In some embodiments, the polynucleotide comprises the coding sequence of a wild-type CSF2 gene (see e.g., NCBI Gene ID: 1437, SEQ ID NO: 49), or a codon-optimized variant thereof. In some embodiments, a polynucleotide encoding a GM-CSF polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 19. In some embodiments, a polynucleotide encoding a GM-CSF polypeptide is a polynucleotide that encodes a polypeptide comprising the amino acid sequence of SEQ ID NO: 19.

In some embodiments, a polynucleotide encoding a GM-CSF polypeptide is a polynucleotide that encodes an N-terminal truncation, a C-terminal truncation, or a fragment of the amino acid sequence of SEQ ID NO: 19. N-terminal truncations, C-terminal truncations, or fragments may comprise at least 10, at least 12, at least 14, at least 16, at least 18, at least 20, at least 30, at least 40, at least 50, at least 75, at least 100, but fewer than 144, consecutive amino acids of SEQ ID NO: 19.

In some embodiments, the present disclosure relates to a recombinant nucleic acid comprising one or more polynucleotides comprising the coding sequence of a human chemokine. Any suitable human chemokine gene (including any isoform thereof) known in the art may be encoded by a polynucleotide of the present disclosure, including, for example, a CCL1 gene (see e.g., NCBI Gene ID: 6346), a CCL2 gene (see e.g., NCBI Gene ID: 6347; SEQ ID NO: 56), a CCL3 gene (see e.g., NCBI Gene ID: 6348; SEQ ID NO: 57), a CCL4 gene (see e.g., NCBI Gene ID: 6351; SEQ ID NO: 58), a CCL5 gene (see e.g., NCBI Gene ID: 6352; SEQ ID NO: 59, a CCL7 gene (see e.g., NCBI Gene ID: 6354), a CCL8 gene (see e.g., NCBI Gene ID: 6355), a CCL11 gene (see e.g., NCBI Gene ID: 6356; SEQ ID NO: 60), a CCL13 gene (see e.g., NCBI Gene ID: (33:57), a CCL14 gene (see e.g., NCBI Gene ID: 6358), a CCL15 gene (see e.g., NCBI Gene ID: 6359), a CCL16 gene (see e.g., NCBI Gene ID: 6360), a CCL17 gene (see e.g., NCBI Gene ID: 6361), a CCL18 gene (see e.g., NCBI Gene ID: 6362), a CCL19 gene (see e.g., NCBI Gene ID: 6363), a CCL20 gene (see e.g., NCBI Gene ID: 6364), a CCL21 gene (see e.g., NCBI Gene ID: 6366), a CCL22 gene (see e.g., NCBI Gene ID: 6367), a CCL23 gene (see e.g., NCBI Gene ID:

6368), a CCL24 gene (see e.g., NCBI Gene ID: 6369), a CCL25 gene (see e.g., NCBI Gene ID: 6370), a CCL26 gene (see e.g., NCBI Gene ID: 10344), a CCL27 gene (see e.g., NCBI Gene ID: 108.50), a CCL28 gene (see e.g., NCBI Gene ID: 56477), a CXCL1 gene (see e.g., NCBI Gene ID: 2919; SEQ ID NO: 50), a CXCL2 gene (see e.g., NCBI Gene ID: 2920; SEQ ID NO: 51), a CXCL3 gene (see e.g., NCBI Gene ID: 2921), a CXCL4 gene (see e.g., NCBI Gene ID: 5196), a CXCL5 gene (see e.g., NCBI Gene ID: 6374), a CXCL6 gene (see e.g., NCBI Gene ID: 6372), a PPBP gene (also known as CXCL7 gene, see e.g., NCBI Gene ID: 5473), a CXCL8 gene (see e.g., NCBI Gene ID: 3576; SEQ ID NO: 52), a CXCL9 gene (see e.g., NCBI Gene ID: 4283; SEQ ID NO: 53), a CXCL10 gene (see e.g., NCBI Gene ID: 3627), a CXCL11 gene (see e.g., NCBI Gene ID: 6373; SEQ ID NO: 54), a CXCL12 gene (see e.g., NCBI Gene ID: 6387), a CXCL13 gene (see e.g., NCBI Gene ID: 10563), a CXCL14 gene (see e.g., NCBI Gene ID: 9547), a CXCL16 gene (see e.g., NCBI Gene ID: 58191; SEQ ID NO: 55), a CXCL17 gene (see e.g., NCBI Gene ID: 284340), a XCL1 gene (see e.g., NCBI Gene ID: 6375), a XCL2 gene (see e.g., NCBI Gene ID: 6846), a CX3CL1 gene (see e.g., NCBI Gene ID: 6376), etc. In some embodiments, a polynucleotide (e.g., one or more first polynucleotides and/or one or more second polynucleotides) of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the human chemokine genes (and/or coding sequences thereof) described herein or known in the art. In some embodiments, the chemokine is a pro-inflammatory chemokine. In some embodiments, the chemokine is selected from human CXCL1, CXCL2, CXCL8, CXCL9, CXCL11, CXCL16, CCL2, CCL3, CCL4, CCL5, and/or CCL11.

In some embodiments, a polynucleotide of the present disclosure encodes a CXCL1 polypeptide. In some embodiments, the CXCL1 polypeptide is a human CXCL1 polypeptide (see e.g., UniProt accession number: P09341). In some embodiments, the polynucleotide comprises the coding sequence of a wild-type CXCL1 gene (see e.g., NCBI Gene ID: 2919, SEQ ID NO: 50), or a codon-optimized variant thereof. In some embodiments, a polynucleotide encoding a CXCL1 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 20. In some embodiments, a polynucleotide encoding a CXCL1 polypeptide is a polynucleotide that encodes a polypeptide comprising the amino acid sequence of SEQ ID NO: 20.

In some embodiments, a polynucleotide encoding a CXCL1 polypeptide is a polynucleotide that encodes an N-terminal truncation, a C-terminal truncation, or a fragment of the amino acid sequence of SEQ ID NO: 20. N-terminal truncations, C-terminal truncations, or fragments may comprise at least 10, at least 12, at least 14, at least 16, at least 18, at least 20, at least 30, at least 40, at least 50, at least 75, at least 100, but fewer than 107, consecutive amino acids of SEQ ID NO: 20.

In some embodiments, a polynucleotide of the present disclosure encodes a CXCL2 polypeptide. In some embodiments, the CXCL2 polypeptide is a human CXCL2 polypeptide (see e.g., UniProt accession number: P19875). In some embodiments, the polynucleotide comprises the coding sequence of a wild-type CXCL2 gene (see e.g., NCBI Gene ID: 2920, SEQ ID NO: 51), or a codon-optimized variant thereof. In some embodiments, a polynucleotide encoding a CXCL2 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 21. In some embodiments, a polynucleotide encoding a CXCL2 polypeptide is a polynucleotide that encodes a polypeptide comprising the amino acid sequence of SEQ ID NO: 21.

In some embodiments, a polynucleotide encoding a CXCL2 polypeptide is a polynucleotide that encodes an N-terminal truncation, a C-terminal truncation, or a fragment of the amino acid sequence of SEQ ID NO: 21. N-terminal truncations, C-terminal truncations, or fragments may comprise at least 10, at least 12, at least 14, at least 16, at least 18, at least 20, at least 30, at least 40, at least 50, at least 75, at least 100, but fewer than 107, consecutive amino acids of SEQ ID NO: 21.

In some embodiments, a polynucleotide of the present disclosure encodes a CXCL8 polypeptide. In some embodiments, the CXCL8 polypeptide is a human CXCL8 polypeptide (see e.g., UniProt accession number: P10145). In some embodiments, the polynucleotide comprises the coding sequence of a wild-type CXCL8 gene (see e.g., NCBI Gene ID: 3576, SEQ ID NO: 52), or a codon-optimized variant thereof. In some embodiments, a polynucleotide encoding a CXCL8 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 22. In some embodiments, a polynucleotide encoding a CXCL8 polypeptide is a polynucleotide that encodes a polypeptide comprising the amino acid sequence of SEQ ID NO: 22.

In some embodiments, a polynucleotide encoding a CXCL8 polypeptide is a polynucleotide that encodes an N-terminal truncation, a C-terminal truncation, or a fragment of the amino acid sequence of SEQ ID NO: 22. N-terminal truncations, C-terminal truncations, or fragments may comprise at least 10, at least 12, at least 14, at least 16, at least 18, at least 20, at least 30, at least 40, at least 50, at least 75, but fewer than 99, consecutive amino acids of SEQ ID NO: 22.

In some embodiments, a polynucleotide of the present disclosure encodes a CXCL9 polypeptide. In some embodiments, the CXCL9 polypeptide is a human CXCL9 polypeptide (see e.g., UniProt accession number: Q07325). In some embodiments, the polynucleotide comprises the coding sequence of a wild-type CXCL9 gene (see e.g., NCBI Gene ID: 4283, SEQ ID NO: 53), or a codon-optimized variant thereof. In some embodiments, a polynucleotide encoding a CXCL9 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 23. In some embodiments, a polynucleotide encoding a CXCL9 polypeptide is a polynucleotide that encodes a polypeptide comprising the amino acid sequence of SEQ ID NO: 23.

In some embodiments, a polynucleotide encoding a CXCL9 polypeptide is a polynucleotide that encodes an N-terminal truncation, a C-terminal truncation, or a fragment of the amino acid sequence of SEQ ID NO: 23. N-terminal truncations, C-terminal truncations, or fragments may comprise at least 10, at least 12, at least 14, at least 16, at least 18, at least 20, at least 30, at least 40, at least 50, at least 75, at least 100, but fewer than 125, consecutive amino acids of SEQ ID NO: 23.

In some embodiments, a polynucleotide of the present disclosure encodes a CXCL11 polypeptide. In some embodiments, the CXCL11 polypeptide is a human CXCL11 polypeptide (see e.g., UniProt accession number: O14625). In some embodiments, the polynucleotide comprises the coding sequence of a wild-type CXCL11 gene (see e.g., NCBI Gene ID: 6373, SEQ ID NO: 54), or a codon-optimized variant thereof. In some embodiments, a polynucleotide encoding a CXCL11 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 24. In some embodiments, a polynucleotide encoding a CXCL11 polypeptide is a polynucleotide that encodes a polypeptide comprising the amino acid sequence of SEQ ID NO: 24.

In some embodiments, a polynucleotide encoding a CXCL11 polypeptide is a polynucleotide that encodes an N-terminal truncation, a C-terminal truncation, or a fragment of the amino acid sequence of SEQ ID NO: 24. N-terminal truncations, C-terminal truncations, or fragments may comprise at least 10, at least 12, at least 14, at least 16, at least 18, at least 20, at least 30, at least 40, at least 50, at least 75, but fewer than 94, consecutive amino acids of SEQ ID NO: 24.

In some embodiments, a polynucleotide of the present disclosure encodes a CXCL16 polypeptide. In some embodiments, the CXCL16 polypeptide is a human CXCL16 polypeptide (see e.g., UniProt accession number: Q9H2A7). In some embodiments, the polynucleotide comprises the coding sequence of a wild-type CXCL16 gene (see e.g., NCBI Gene ID: 58191, SEQ ID NO: 55), or a codon-optimized variant thereof. In some embodiments, a polynucleotide encoding a CXCL16 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 25. In some embodiments, a polynucleotide encoding a CXCL16 polypeptide is a polynucleotide that encodes a polypeptide comprising the amino acid sequence of SEQ ID NO: 25.

In some embodiments, a polynucleotide encoding a CXCL16 polypeptide is a polynucleotide that encodes an N-terminal truncation, a C-terminal truncation, or a fragment of the amino acid sequence of SEQ ID NO: 25. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 254, consecutive amino acids of SEQ ID NO: 25.

In some embodiments, a polynucleotide of the present disclosure encodes a CCL2 polypeptide. In some embodiments, the CCL2 polypeptide is a human CCL2 polypeptide (see e.g., UniProt accession number: P13500). In some embodiments, the polynucleotide comprises the coding sequence of a wild-type CCL2 gene (see e.g., NCBI Gene ID: 6347, SEQ ID NO: 56), or a codon-optimized variant thereof. In some embodiments, a polynucleotide encoding a CCL2 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 26. In some embodiments, a polynucleotide encoding a CCL2 polypeptide is a polynucleotide that encodes a polypeptide comprising the amino acid sequence of SEQ ID NO: 26.

In some embodiments, a polynucleotide encoding a CCL2 polypeptide is a polynucleotide that encodes an N-terminal truncation, a C-terminal truncation, or a fragment of the amino acid sequence of SEQ ID NO: 26. N-terminal truncations, C-terminal truncations, or fragments may comprise at least 10, at least 12, at least 14, at least 16, at least 18, at least 20, at least 30, at least 40, at least 50, at least 75, but fewer than 99, consecutive amino acids of SEQ ID NO: 26.

In some embodiments, a polynucleotide of the present disclosure encodes a CCL3 polypeptide. In some embodiments, the CCL3 polypeptide is a human CCL3 polypeptide (see e.g., UniProt accession number: P10147). In some embodiments, the polynucleotide comprises the coding sequence of a wild-type CCL3 gene (see e.g., NCBI Gene ID: 6348, SEQ ID NO: 57), or a codon-optimized variant thereof. In some embodiments, a polynucleotide encoding a CCL3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 27. In some embodiments, a polynucleotide encoding a CCL3 polypeptide is a polynucleotide that encodes a polypeptide comprising the amino acid sequence of SEQ ID NO: 27.

In some embodiments, a polynucleotide encoding a CCL3 polypeptide is a polynucleotide that encodes an N-terminal truncation, a C-terminal truncation, or a fragment of the amino acid sequence of SEQ ID NO: 27. N-terminal truncations, C-terminal truncations, or fragments may comprise at least 10, at least 12, at least 14, at least 16, at least 18, at least 20, at least 30, at least 40, at least 50, at least 75, but fewer than 92, consecutive amino acids of SEQ ID NO: 27.

In some embodiments, a polynucleotide of the present disclosure encodes a CCL4 polypeptide. In some embodiments, the CCL4 polypeptide is a human CCL4 polypeptide (see e.g., UniProt accession number: P13236). In some embodiments, the polynucleotide comprises the coding sequence of a wild-type CCL4 gene (see e.g., NCBI Gene ID: 6351, SEQ ID NO: 58), or a codon-optimized variant thereof. In some embodiments, a polynucleotide encoding a CCL4 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 28. In some embodiments, a polynucleotide encoding a CCL4 polypeptide is a polynucleotide that encodes a polypeptide comprising the amino acid sequence of SEQ ID NO: 28.

In some embodiments, a polynucleotide encoding a CCL4 polypeptide is a polynucleotide that encodes an N-terminal truncation, a C-terminal truncation, or a fragment of the amino acid sequence of SEQ ID NO: 28. N-terminal truncations, C-terminal truncations, or fragments may comprise at least 10, at least 12, at least 14, at least 16, at least 18, at least 20, at least 30, at least 40, at least 50, at least 75, but fewer than 92, consecutive amino acids of SEQ ID NO: 28.

In some embodiments, a polynucleotide of the present disclosure encodes a CCL5 polypeptide. In some embodiments, the CCL5 polypeptide is a human CCL5 polypeptide (see e.g., UniProt accession number: P13501). In some embodiments, the polynucleotide comprises the coding sequence of a wild-type CCL5 gene (see e.g., NCBI Gene ID: 6352, SEQ ID NO: 59), or a codon-optimized variant thereof. In some embodiments, a polynucleotide encoding a CCL5 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 29. In some embodiments, a polynucleotide encoding a CCL5 polypeptide is a polynucleotide that encodes a polypeptide comprising the amino acid sequence of SEQ ID NO: 29.

In some embodiments, a polynucleotide encoding a CCL5 polypeptide is a polynucleotide that encodes an N-terminal truncation, a C-terminal truncation, or a fragment of the amino acid sequence of SEQ ID NO: 29. N-terminal truncations, C-terminal truncations, or fragments may comprise at least 10, at least 12, at least 14, at least 16, at least 18, at least 20, at least 30, at least 40, at least 50, at least 75, but fewer than 91, consecutive amino acids of SEQ ID NO: 29.

In some embodiments, a polynucleotide of the present disclosure encodes a CCL11 polypeptide. In some embodiments, the CCL11 polypeptide is a human CCL11 polypeptide (see e.g., UniProt accession number: P51671). In some embodiments, the polynucleotide comprises the coding sequence of a wild-type CCL11 gene (see e.g., NCBI Gene ID: 6356, SEQ ID NO: 60), or a codon-optimized variant thereof. In some embodiments, a polynucleotide encoding a CCL11 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 30. In some embodiments, a polynucleotide encoding a CCL11 polypeptide is a polynucleotide that encodes a polypeptide comprising the amino acid sequence of SEQ ID NO: 30.

In some embodiments, a polynucleotide encoding a CCL11 polypeptide is a polynucleotide that encodes an N-terminal truncation, a C-terminal truncation, or a fragment of the amino acid sequence of SEQ ID NO: 30. N-terminal truncations, C-terminal truncations, or fragments may comprise at least 10, at least 12, at least 14, at least 16, at least 18, at least 20, at least 30, at least 40, at least 50, at least 75, but fewer than 97, consecutive amino acids of SEQ ID NO: 30.

In some embodiments, a polynucleotide of the present disclosure encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an amino acid sequence selected from SEQ ID NOS: 1-30. In some embodiments, a polynucleotide of the present disclosure encodes a polypeptide comprising an amino acid sequence selected from SEQ ID NOS: 1-30.

In some embodiments, a polynucleotide of the present disclosure encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an amino acid sequence selected from SEQ ID NOS: 1-19. In some embodiments, a polynucleotide of the present disclosure encodes a polypeptide comprising an amino acid sequence selected from SEQ ID NOS: 1-19.

In some embodiments, a polynucleotide of the present disclosure encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an amino acid sequence selected from SEQ ID NOS: 20-30. In some embodiments, a polynucleotide of the present disclosure encodes a polypeptide comprising an amino acid sequence selected from SEQ ID NOS: 20-30.

In some embodiments, a polynucleotide of the present disclosure encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an amino acid sequence selected from SEQ ID NOS: 3, 5 and 6. In some embodiments, a polynucleotide of the present disclosure encodes a polypeptide comprising an amino acid sequence selected from SEQ ID NOS: 3, 5 and 6.

In some embodiments, a polynucleotide of the present disclosure encodes any one or more of an Interleukin-1 alpha (IL-1a) peptide, an Interleukin-1 beta (IL-1β) peptide, an Interleukin-2 (IL-2) peptide, an Interleukin-3 (IL-3) peptide, an Interleukin-4 (IL-4) peptide, an Interleukin-5 (IL-5) peptide, an Interleukin-6 (IL-6) peptide, an Interleukin-7 (IL-7) peptide, an Interleukin-8 (IL-8) peptide, an Interleukin-9 (IL-9) peptide, an Interleukin-10 (IL-10) peptide, an Interleukin-11(IL-11) peptide, an Interleukin-12 subunit alpha (IL-12a) peptide, an Interleukin-12 subunit beta (IL-12β) peptide, an Interleukin-13 (IL-13) peptide, an Interleukin-15 (IL-15) peptide, an Interleukin-17 (IL-17) peptide, an Interleukin-17B (IL-17B) peptide, an Interleukin-17C (IL-17C) peptide, an Interleukin-17D (IL-17D) peptide, an Interleukin-25 (IL-25) peptide, an Interleukin-17F (IL-17F) peptide, an Interleukin-18 (IL-18) peptide, an Interleukin-28A (IL-28A) peptide, an Interleukin-28B (IL-28B) peptide, an Interleukin-29 (IL-29) peptide, an Interleukin-32 (IL-32) peptide, an Interleukin-33 (IL-33) peptide, an Interleukin-34 (IL-34) peptide, an Interleukin-36 alpha (IL-36α) peptide, an Interleukin-36 (IL-36β) beta peptide, an Interleukin-36 gamma (IL-36γ) peptide, an Interferon alpha-1 (IFNα-1) peptide, an Interferon alpha-2 (IFNα-2) peptide, an Interferon alpha-4 (IFNα-4) peptide, an Interferon alpha-5 (IFNα-5) peptide, an Interferon alpha-6 (IFNα-6) peptide, an Interferon alpha-7 (IFNα-7) peptide, an Interferon alpha-8 (IFNα-8) peptide, an Interferon alpha-10 (IFNα-10) peptide, an Interferon alpha-14 (IFNα-14) peptide, an Interferon alpha-16 (IFNα-16) peptide, an Interferon alpha-17 (IFNα-17) peptide, an Interferon alpha-21 (IFNα-21) peptide, an Interferon beta-1 (IFNβ-1) peptide, an Interferon beta-3 (IFNβ-3) peptide, an Interferon gamma (IFNγ) peptide, a Tumor Necrosis Factor alpha (TNFα) peptide, a Tumor Necrosis Factor beta (TNFβ) peptide, a Granulocyte Colony-Stimulating Factor (G-CSF) peptide, a Granulocyte-Macrophage Colony-Stimulating Factor (GM-CSF) peptide, a Macrophage Colony-Stimulating Factor (M-CSF) peptide, a C-C Motif Chemokine 1 (CCL1) peptide, a C-C Motif Chemokine 2 (CCL2) peptide, a C-C Motif Chemokine 3 (CCL3) peptide, a C-C Motif Chemokine 4 (CCL4) peptide, a C-C Motif Chemokine 5 (CCL5) peptide, a C-C Motif Chemokine 7 (CCL7) peptide, a C-C Motif Chemokine 8 (CCL8) peptide, a C-C Motif Chemokine 11 (CCL11) peptide, a C-C Motif Chemokine 13 (CCL13) peptide, a C-C Motif Chemokine 14 (CCL14) peptide, a C-C Motif Chemokine 15 (CCL15) peptide, a C-C Motif Chemokine 16 (CCL16) peptide, a C-C Motif Chemokine 17 (CCL17) peptide, a C-C Motif Chemokine 18 (CCL18) peptide, a C-C Motif Chemokine 19 (CCL19) peptide, a C-C Motif Chemokine 20 (CCL20) peptide, a C-C Motif Chemokine 21 (CCL21) peptide, a C-C Motif Chemokine 22 (CCL22) peptide, a C-C Motif Chemokine 23 (CCL23) peptide, a C-C Motif Chemokine 24 (CCL24) peptide, a C-C Motif Chemokine 25 (CCL25) peptide, a C-C Motif Chemokine 26 (CCL26) peptide, a C-C Motif Chemokine 27 (CCL27) peptide, a C-C Motif Chemokine 28 (CCL28) peptide, a C-X-C Motif Chemokine 1 (CXCL1) peptide, a C-X-C Motif Chemokine 2 (CXCL2) peptide, a C-X-C Motif Chemokine 3 (CXCL3) peptide, a C-X-C Motif Chemokine 4 (CXCL4) peptide, a C-X-C Motif Chemokine 5 (CXCL5) peptide, a C-X-C Motif Chemokine 6 (CXCL6) peptide, a C-X-C Motif Chemokine 7 (CXCL7) peptide, a C-X-C Motif Chemokine 9 (CXCL9) peptide, a C-X-C Motif Chemokine 10 (CXCL10) peptide, a C-X-C Motif Chemokine 11 (CXCL11) peptide, a C-X-C Motif Chemokine 12 (CXCL12) peptide, a C-X-C Motif Chemokine 13 (CXCL13) peptide, a C-X-C Motif Chemokine 14 (CXCL14) peptide, a C-X-C Motif Chemokine 16 (CXCL16) peptide, a C-X-C Motif Chemokine 17 (CXCL17) peptide, a C Motif Chemokine 1 (XCL1) peptide, a C Motif Chemokine 2 (XCL2) peptide, a C-X3-C Motif Chemokine 1 (CX3CL1) peptide, and/or any chimeric polypeptides thereof, in any suitable combination. In some embodiments, a polynucleotide of the present disclosure does not encode an Interleukin-4 (IL-4) peptide. In some embodiments, a polynucleotide of the present disclosure does not encode an Interleukin-10 (IL-10) peptide. In some embodiments, a polynucleotide of the present disclosure does not encode a Granulocyte-Macrophage Colony-Stimulating Factor (GM-CSF) peptide. In some embodiments, a polynucleotide of the present disclosure does not encode an Interleukin-4 (IL-4) peptide, an Interleukin-10 (IL-10) peptide, and/or a Granulocyte-Macrophage Colony-Stimulating Factor (GM-CSF) peptide.

A polynucleotide of the present disclosure encoding a polypeptide (e.g., an immunomodulatory polypeptide) may further encode additional coding and non-coding sequences. Examples of additional coding and non-coding sequences may include, but are not limited to, sequences encoding additional polypeptide tags (e.g., encoded in-frame with the polypeptide in order to produce a fusion protein), introns (e.g., native, modified, or heterologous introns), 5' and/or 3' UTRs (e.g., native, modified, or heterologous 5' and/or 3' UTRs), and the like. Examples of suitable polypeptide tags may include, but are not limited to, any combination of purification tags, such as his-tags, flag-tags, maltose binding protein and glutathione-S-transferase tags, detection tags, such as tags that may be detected photometrically (e.g., green fluorescent protein, red fluorescent protein, etc.) and tags that have a detectable enzymatic activity (e.g., alkaline phosphatase, etc.), tags containing secretory sequences, signal sequences, leader sequences, and/or stabilizing sequences, protease cleavage sites (e.g., furin cleavage sites, TEV cleavage sites, Thrombin cleavage sites, etc.), and the like. In some embodiments, the 5' and/or 3'UTRs increase the stability, localization, and/or translational efficiency of the polynucleotides. In some embodiments, the 5' and/or 3'UTRs improve the level and/or duration of protein expression. In some embodiments, the 5' and/or 3'UTRs include elements (e.g., one or more miRNA binding sites, etc.) that may block or reduce off-target expression (e.g., inhibiting expression in specific cell types (e.g., neuronal cells), at specific times in the cell cycle, at specific developmental stages, etc.). In some embodiments, the 5' and/or 3'UTRs include elements (e.g., one or more miRNA binding sites, etc.) that may enhance expression of the encoded polypeptide in specific cell types.

In some embodiments, a polynucleotide of the present disclosure encoding a polypeptide (e.g., an immunomodulatory polypeptide) is operably linked to one or more (e.g., one or more, two or more, three or more, four or more, five or more, ten or more, etc.) regulatory sequences. The term "regulatory sequence" may include enhancers, insulators, promoters, and other expression control elements (e.g., polyadenylation signals). Any suitable enhancer(s) known in the art may be used, including, for example, enhancer sequences from mammalian genes (such as globin, elastase, albumin, α-fetoprotein, insulin and the like), enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like), and any combinations thereof. Any suitable insulator(s) known in the art may be used, including, for example, HSV chromatin boundary (CTRL/CTCF-binding/insulator) elements CTRL1 and/or CTRL2, chicken hypersensitive site 4 insulator (cHS4), human HNRPA2B1-CBX3 ubiquitous chromatin opening element (UCOE), the scaffold/matrix attachment region (S/MAR) from the human interferon beta gene (IFNB1), and any combinations thereof. Any suitable promoter (e.g., suitable for transcription in mammalian host cells) known in the art may be used, including, for example, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), promoters from heterologous mammalian genes (such as the actin promoter (e.g., the (3-actin promoter), a ubiquitin promoter (e.g., a ubiquitin C (UbC) promoter), a phosphoglycerate kinase (PGK) promoter, an immunoglobulin promoter, from heat-shock promoters, and the like), promoters from homologous mammalian genes, synthetic promoters (such as the CAG promoter), and any combinations thereof, provided such promoters are compatible with the host cells. Regulatory sequences may include those which direct constitutive expression of a nucleic acid, as well as tissue-specific regulatory and/or inducible or repressible sequences.

In some embodiments, a polynucleotide of the present disclosure is operably linked to one or more heterologous promoters. In some embodiments, the one or more heterologous promoters are one or more of constitutive promoters, tissue-specific promoters, temporal promoters, spatial promoters, inducible promoters, and repressible promoters. In some embodiments, the one or more heterologous promoters are one or more of the human cytomegalovirus (HCMV) immediate early promoter, the human elongation factor-1 (EF1) promoter, the human β-actin promoter, the human UbC promoter, the human PGK promoter, the synthetic CAGG promoter, and any combinations thereof. In some embodiments, a polynucleotide of the present disclosure encoding a polypeptide (e.g., an immunomodulatory polypeptide) is operably linked to an HCMV promoter.

In some embodiments, a polynucleotide of the present disclosure encoding a polypeptide (e.g., an immunomodulatory polypeptide, such as IL-2 and/or IL-12) expresses the polypeptide when the polynucleotide is delivered into one or more target cells of a subject (e.g., one or more cells of the respiratory tract, airway, lungs, etc. of the subject). In some embodiments, expression of the polypeptide (e.g., an immunomodulatory polypeptide, such as IL-2 and/or IL-12) enhances, increases, augments, and/or supplements the levels, function, and/or activity of the polypeptide in one or more target cells of a subject (e.g., as compared to prior to expression of the polypeptide, as compared to levels of the endogenous polypeptide expressed in the cell, etc.). In some embodiments, expression of the polypeptide (e.g., an immunomodulatory polypeptide, such as IL-2 and/or IL-12) provides prophylactic, palliative, or therapeutic relief of one or more signs or symptoms of cancer (e.g., solid tumor, hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, skin cancer, stomach cancer, thymic epithelial cancer, thyroid cancer, etc.) in a subject (e.g., as compared to prior to expression of the polypeptide).

Chimeric Polypeptides

In some embodiments, a polynucleotide of the present disclosure encodes a chimeric polypeptide comprising a first immunomodulatory polypeptide and a second immunomodulatory polypeptide. In some embodiments, the first and second immunomodulatory polypeptides are the same. In some embodiments, the first and second immunomodulatory polypeptides are different. In some embodiments, the chimeric polypeptide further comprises a linker polypeptide linking the first and second immunomodulatory polypeptides. In some embodiments, the chimeric polypeptide comprises, from N-terminus to C-terminus, the first immunomodulatory polypeptide-the linker polypeptide-the second immunomodulatory polypeptide. The first and/or second immunomodulatory polypeptides may be any of the immunomodulatory polypeptides described herein or known in the art.

In some embodiments, the linker polypeptide is a cleavable linker polypeptide. Any cleavable linker polypeptide known in the art may be used in the chimeric polypeptides of the present disclosure, including, for example, a T2A linker, a P2A linker, a E2A linker, and F2A linker, etc. In some embodiments, the linker polypeptide is a T2A linker polypeptide. An exemplary nucleic acid sequence encoding a T2A linker polypeptide is provided as SEQ ID NO: 64. An exemplary amino acid sequence of a T2A linker polypeptide is provided as SEQ ID NO: 68. In some embodiments, the linker polypeptide is a P2A linker polypeptide. An exemplary nucleic acid sequence encoding a P2A linker polypeptide is provided as SEQ ID NO: 65. An exemplary amino acid sequence of a P2A linker polypeptide is provided as SEQ ID NO: 69. In some embodiments, the linker polypeptide is an E2A linker polypeptide. An exemplary nucleic acid sequence encoding an E2A linker polypeptide is provided as SEQ ID NO: 66. An exemplary amino acid sequence of an E2A linker polypeptide is provided as SEQ ID NO: 70. In some embodiments, the linker polypeptide is an F2A linker polypeptide. An exemplary nucleic acid sequence encoding an F2A linker polypeptide is provided as SEQ ID NO: 67. An exemplary amino acid sequence of an F2A linker polypeptide is provided as SEQ ID NO: 71. In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 68-71. In some embodiments, the linker polypeptide comprises a sequence selected from SEQ ID NOS: 68-71.

In some embodiments, the linker polypeptide is a non-cleavable linker polypeptide. Any non-cleavable linker polypeptide known in the art may be used in the chimeric polypeptides of the present disclosure, including, for example, a GGGGSGGGGSGGGGS (SEQ ID NO: 72) linker, a GGSSRSSSSGGGGSGGGG (SEQ ID NO: 73) linker, a GGGGSGGGGSGGGGSGGGGS (SEQ ID NO: 74) linker, a CGGGSGGGGSGGGGS (SEQ ID NO: 75) linker, a SHGGHGGGGSGGGGS (SEQ ID NO: 76) linker, a MGGMSGGGGSGGGGS (SEQ ID NO: 77) linker, a YGGYSGGGGSGGGGS (SEQ ID NO: 78) linker, a WGGYSGGGGSGGGGS (SEQ ID NO: 79) linker, a SVSVGMKPSPRP (SEQ ID NO: 80) linker, a VISNHA-GSSRRL (SEQ ID NO: 81) linker, a PWIPTPRPTFTG (SEQ ID NO: 82) linker, a RGRGRGRGRGR (SEQ ID NO: 83) linker, etc. In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 72-83. In some embodiments, the linker polypeptide comprises a sequence selected from SEQ ID NOS: 72-83.

An exemplary nucleic acid sequence encoding a chimeric polypeptide comprising a first human immunomodulatory polypeptide, a linker polypeptide, and a second human immunomodulatory polypeptide is provided as SEQ ID NO: 84. An exemplary amino acid sequence of a chimeric polypeptide comprising a first human immunomodulatory polypeptide, a linker polypeptide, and a second human immunomodulatory polypeptide is provided as SEQ ID NO: 85. In some embodiments, a polynucleotide of the present disclosure encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 85. In some embodiments, a polynucleotide of the present disclosure encodes a polypeptide comprising the amino acid sequence of SEQ ID NO: 85.

In some embodiments, a polynucleotide of the present disclosure does not comprise the coding sequence of (e.g., a transgene encoding) a Collagen alpha-1 (VII) chain polypeptide (COLT). In some embodiments, a polynucleotide of the present disclosure does not comprise the coding sequence of (e.g., a transgene encoding) a Lysyl hydroxylase 3 polypeptide (LH3). In some embodiments, a polynucleotide of the present disclosure does not comprise the coding sequence of (e.g., a transgene encoding) a Keratin type I cytoskeletal 17 polypeptide (KRT17). In some embodiments, a polynucleotide of the present disclosure does not comprise the coding sequence of (e.g., a transgene encoding) a transglutaminase (TGM) polypeptide (e.g., a human transglutaminase polypeptide such as a human TGM1 polypeptide and/or a human TGMS polypeptide). In some embodiments, a polynucleotide of the present disclosure does not comprise the coding sequence of (e.g., a transgene encoding) a cosmetic protein (e.g., collagen proteins, fibronectins, elastins, lumicans, vitronectins/vitronectin receptors, laminins, neuromodulators, fibrillins, additional dermal extracellular matrix proteins, etc.). In some embodiments, a polynucleotide of the present disclosure does not comprise the coding sequence of (e.g., a transgene encoding) an antibody (e.g., a full-length antibody, an antibody fragment, etc.). In some embodiments, a polynucleotide of the present disclosure does not comprise the coding sequence of (e.g., a transgene encoding) a Serine Protease Inhibitor Kazal-type (SPINK) polypeptide (e.g., a human SPINK polypeptide, such as a SPINK5 polypeptide). In some embodiments, a polynucleotide of the present disclosure does not comprise the coding sequence of (e.g., a transgene encoding) a filaggrin or filaggrin 2 polypeptide (e.g., a human filaggrin or filaggrin 2 polypeptide). In some embodiments, a polynucleotide of the present disclosure does not comprise the coding sequence of (e.g., a transgene encoding) a Cystic Fibrosis Transmembrane Conductance Regulator (CFTR) polypeptide (e.g., a human CFTR polypeptide). In some embodiments, a polynucleotide of the present disclosure does not comprise the coding sequence of (e.g., a transgene encoding) an ichthyosis-associated polypeptide (e.g., an ATP-binding cassette sub-family A member 12 polypeptide, a 1-acylglycerol-3-phosphate O-acyltransferase ABHD5 polypeptide, an Aldehyde dehydrogenase family 3 member A2 polypeptide, an Arachidonate 12-lipoxygenase 12R-type polypeptide, a Hydroperoxide isomerase ALOXE3 polypeptide, an AP-1 complex subunit sigma-1A polypeptide, an Arylsulfatase E polypeptide, a Caspase-14 polypeptide, a Corneodesmosin polypeptide, a Ceramide synthase 3 polypeptide, a Carbohydrate sulfotransferase 8 polypeptide, a Claudin-1 polypeptide, a Cystatin-A polypeptide, a Cytochrome P450 4F22 polypeptide, a 3-beta-hydroxysteroid-Delta(8), Delta(7)-isomerase polypeptide, an Elongation of very long chain fatty acids protein 4 polypeptide, a Filaggrin polypeptide, a Filaggrin 2 polypeptide, a Gap junction beta-2 polypeptide, a Gap junction beta-3 polypeptide, a Gap junction beta-4 polypeptide, a Gap junction beta-6 polypeptide, a 3-ketodihydrosphingosine reductase polypeptide, a Keratin, type II cytoskeletal 1 polypeptide, a Keratin, type II cytoskeletal 2 epidermal polypeptide, a Keratin, type I cytoskeletal 9 polypeptide, a Keratin, type I cytoskeletal 10 polypeptide, a Lipase member N polypeptide, a Loricrin polypeptide, a Membrane-bound transcription factor site-2 protease polypeptide, a Magnesium transporter NIPA4 polypeptide, a Sterol-4-alpha-carboxylate 3-dehydrogenase, decarboxylating polypeptide, a Peroxisomal targeting signal 2 receptor polypeptide, a D-3-phosphoglycerate dehydrogenase polypeptide, a Phytanoyl-CoA dioxygenase, peroxisomal polypeptide, Patatin-like phospholipase domain-containing protein 1 polypeptide, a Proteasome maturation protein polypeptide, a Phosphoserine aminotransferase polypeptide, a Short-chain dehydrogenase/reductase family 9C member 7 polypeptide, a Serpin B8 polypeptide, a Long-chain fatty acid transport protein 4 polypeptide, a Synaptosomal-associated protein 29 polypeptide, a Suppressor of tumorigenicity 14 protein polypeptide, a Steryl-sulfatase polypeptide, a Vacuolar protein sorting-associated protein 33B polypeptide, and a CAAX prenyl protease 1 homolog polypeptide). In some embodiments, a polynucleotide of the present disclosure does not comprise the coding sequence of (e.g., a transgene encoding) a Collagen alpha-1 (VII) chain polypeptide, a Lysyl hydroxylase 3 polypeptide, a Keratin type I cytoskeletal 17 polypeptide, and/or any chimeric polypeptides thereof. In some embodiments, a polynucleotide of the present disclosure does not comprise the coding sequence of (e.g., a transgene encoding) a Collagen alpha-1 (VII) chain polypeptide, a Lysyl hydroxylase 3 polypeptide, a Keratin type I cytoskeletal 17 polypeptide, a transglutaminase (TGM) polypeptide, a filaggrin polypeptide, a cosmetic protein, an antibody, a SPINK polypeptide, a CFTR polypeptide, an ichthyosis-associated polypeptide, an Alpha-1-antitrypsin polypeptide, a Sodium-dependent phosphate transport protein 2B polypeptide, a Dynein heavy chain 5 axonemal polypeptide, a Dynein heavy chain 11 axonemal polypeptide, a Coiled-coil domain-containing protein 39 polypeptide, a Dynein intermediate chain 1 axonemal polypeptide, a Coiled-coil domain-containing protein 40 polypeptide, a Coiled-coil domain containing protein 103 polypeptide, a Sperm-associated antigen 1 polypeptide, a Zinc finger MYND domain-containing protein 10 polypeptide, an Armadillo repeat containing protein 4 polypeptide, a Coiled-coil domain-containing protein 151 polypeptide, a Dynein intermediate chain 2 axonemal polypeptide, a Radial spoke head 1 homolog polypeptide, a Coiled-coil domain-containing protein 114 polypeptide, a Radial spoke head protein 4 homolog A polypeptide, a Dynein assembly factor 1 axonemal polypeptide, a Dynein assembly factor 2 axonemal polypeptide, a Leucine-rich repeat-containing protein 6 polypeptide, a Pulmonary surfactant-associated protein B polypeptide, a Pulmonary surfactant-associated protein C polypeptide, a Homeobox protein Nkx-2.1 polypeptide, an ATP-binding cassette sub-family A member 3 polypeptide, a Cytokine receptor common subunit beta polypeptide, a Granulocyte-macrophage colony-stimulating factor receptor subunit alpha polypeptide, a Bone morphogenetic protein receptor type-2 polypeptide, a Sarcoplasmic/endoplasmic reticulum calcium ATPase 2 polypeptide, a serine/threonine-protein kinase receptor R3 polypeptide, an Endoglin polypeptide, a Mothers against decapentaplegic homolog 9 polypeptide, a Caveolin-1 polypeptide, a Potassium channel subfamily K member 3 polypeptide, an eIF-2-alpha kinase GCN2 polypeptide, a Pulmonary surfactant-associated protein A2 polypeptide, a Telomerase reverse transcriptase polypeptide, a Dyskerin polypeptide, a Regulator of telomere elongation helicase 1 polypeptide, a Poly(A)-specific ribonuclease PARN polypeptide, a TERF1-interacting nuclear factor 2 polypeptide, an H/ACA ribonucleoprotein complex non-core subunit NAF1 polypeptide, a Mucin-5B polypeptide, a Desmoplakin polypeptide, a CST complex subunit STN1 polypeptide, a Dipeptidyl peptidase 9 polypeptide, and/or any chimeric polypeptides thereof.

Recombinant Nucleic Acids

In some embodiments, the present disclosure relates to recombinant nucleic acids comprising any one or more of the polynucleotides described herein. In some embodiments, the recombinant nucleic acid is a vector (e.g., an expression vector, a display vector, etc.). In some embodiments, the vector is a DNA vector or an RNA vector. Generally, vectors suitable to maintain, propagate, and/or express polynucleotides to produce one or more polypeptides in a subject may be used. Examples of suitable vectors may include, for example, plasmids, cosmids, episomes, transposons, and viral vectors (e.g., adenoviral vectors, adeno-associated viral vectors, vaccinia viral vectors, Sindbis-viral vectors, measles vectors, herpes viral vectors, lentiviral vectors, retroviral vectors, etc.). In some embodiments, the vector is a herpes viral vector. In some embodiments, the vector is capable of autonomous replication in a host cell. In some embodiments, the vector is incapable of autonomous replication in a host cell. In some embodiments, the vector can integrate into a host DNA. In some embodiments, the vector cannot integrate into a host DNA (e.g., is episomal). Methods of making vectors containing one or more polynucleotides of interest are well known to one of ordinary skill in the art, including, for example, by chemical synthesis or by artificial manipulation of isolated segments of nucleic acids (e.g., by genetic engineering techniques).

In some embodiments, a recombinant nucleic acid of the present disclosure is a herpes simplex virus (HSV) amplicon. Herpes virus amplicons, including the structural features and methods of making the same, are generally known to one of ordinary skill in the art (see e.g., de Silva S. and Bowers W. "Herpes Virus Amplicon Vectors". Viruses 2009, 1, 594-629). In some embodiments, the herpes simplex virus amplicon is an HSV-1 amplicon. In some embodiments, the herpes simplex virus amplicon is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and/or HSV/Sleeping Beauty hybrid amplicons. In some embodiments, the amplicon is an HSV/AAV hybrid amplicon. In some embodiments, the amplicon is an HSV/Sleeping Beauty hybrid amplicon.

In some embodiments, a recombinant nucleic acid of the present disclosure is a recombinant herpes virus genome. The recombinant herpes virus genome may be a recombinant genome from any member of the Herpesviridae family of DNA viruses known in the art, including, for example, a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Epstein-Barr virus genome, a recombinant Kaposi's sarcoma-associated herpesvirus genome, and any combinations or derivatives thereof. In some embodiments, the recombinant herpes virus genome comprises one or more (e.g., one or more, two or more, three or more, four or more, five or more, six or more, seven or more, eight or more, nine or more, ten or more, etc.) inactivating mutations. As used herein, an "inactivating mutation" may refer to any mutation that results in a gene or regulon product (RNA or protein) having reduced, undetectable, or eliminated quantity and/or function (e.g., as compared to a corresponding sequence lacking the inactivating mutation). Examples of inactivating mutations may include, but are not limited to, deletions, insertions, point mutations, and rearrangements in transcriptional control sequences (promoters, enhancers, insulators, etc.) and/or coding sequences of a given gene or regulon. Any suitable method of measuring the quantity of a gene or regulon product known in the art may be used, including, for example, qPCR, Northern blots, RNAseq, western blots, ELISAs, etc. In some embodiments, the one or more inactivating mutations are in one or more (e.g., one or more, two or more, three or more, four or more, five or more, six or more, seven or more, eight or more, nine or more, ten or more, etc.) herpes virus genes. In some embodiments, the recombinant herpes virus genome is attenuated (e.g., as compared to a corresponding, wild-type herpes virus genome). In some embodiments, the recombinant herpes virus genome is replication competent. In some embodiments, the recombinant herpes virus genome is replication defective. In some embodiments, the recombinant herpes virus genome is not oncolytic.

In some embodiments, the recombinant nucleic acid is a recombinant herpes simplex virus (HSV) genome. In some embodiments, the recombinant herpes simplex virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes simplex virus genes. In some embodiments, the recombinant herpes simplex virus genome is attenuated (e.g., as compared to a corresponding, wild-type herpes simplex virus genome). In some embodiments, the recombinant herpes simplex virus genome is replication competent. In some embodiments, the recombinant herpes simplex virus genome is replication defective. In some embodiments, the recombinant herpes simplex virus genome is not oncolytic.

In some embodiments, the recombinant herpes virus genome is a recombinant herpes simplex virus type 1 (HSV-1) genome, a recombinant herpes simplex virus type 2 (HSV-2) genome, or any derivatives thereof. In some embodiments, the recombinant herpes simplex virus genome is a recombinant HSV-1 genome. In some embodiments, the recombinant HSV-1 genome may be from any HSV-1 strain known in the art, including, for example, strains 17, Ty25, R62, S25, Ku86, S23, R11, Ty148, Ku47, H166$_{syn}$, 1319-2005, F-13, M-12, 90237, F-17, KOS, 3083-2008, F12g, L2, CD38, H193, M-15, India 2011, 0116209, F-11I, 66-207, 2762, 369-2007, 3355, MacIntyre, McKrae, 7862, 7-hse, HF10, 1394, 2005, 270-2007, OD4, SC16, M-19, 4J1037, 5J1060, J1060, KOS79, 132-1988, 160-1982, H166, 2158-2007, RE, 78326, F18g, F11, 172-2010, H129, F, E4, CJ994, F14g, E03, E22, E10, E06, E11, E25, E23, E35, E15, E07, E12, E14, E08, E19, E13, ATCC 2011, etc. (see e.g., Bowen et al. J Virol. 2019 Apr. 3; 93(8)). In some embodiments, the recombinant HSV-1 genome is from the KOS strain. In some embodiments, the recombinant HSV-1 genome is not from the McKrae strain. In some embodiments, the recombinant HSV-1 genome is attenuated (e.g., as compared to a corresponding, wild-type HSV-1 genome). In some embodiments, the recombinant HSV-1 genome is replication competent. In some embodiments, the recombinant HSV-1 genome is replication defective. In some embodiments, the recombinant HSV-1 genome is not oncolytic.

In some embodiments, the recombinant herpes simplex virus genome comprises an inactivating mutation in at least one, at least two, at least three, at least four, at least five, at least six, at least seven, or all eight of the Infected Cell Protein (or Infected Cell Polypeptide) (ICP) 0, ICP4, ICP22, ICP27, ICP47, thymidine kinase (tk), Long Unique Region (UL) 41 and/or UL55 herpes simplex virus genes. In some embodiments, the recombinant herpes simplex virus genome does not comprise an inactivating mutation in the ICP34.5 (one or both copies) and/or ICP47 herpes simplex virus genes (e.g., to avoid production of an immune-stimulating virus). In some embodiments, the recombinant herpes simplex virus genome does not comprise an inactivating mutation in the ICP34.5 (one or both copies) herpes simplex virus gene. In some embodiments, the recombinant herpes simplex virus genome does not comprise an inactivating mutation in the ICP47 herpes simplex virus gene. In some embodiments, the recombinant herpes simplex virus genome does not comprise an inactivating mutation in the ICP34.5 (one or both copies) and ICP47 herpes simplex virus genes. In some embodiments, the recombinant herpes simplex virus genome is not oncolytic. In some embodiments, the recombinant herpes simplex virus genome is not conditionally replication competent. In some embodiments, the recombinant herpes simplex virus genome is not conditionally replication competent in a cancerous cell.

In some embodiments, the recombinant herpes simplex virus genome comprises an inactivating mutation in the ICP0 gene (one or both copies). In some embodiments, the recombinant herpes simplex virus genome comprises an inactivating mutation in the ICP0 gene (one or both copies), and further comprises an inactivating mutation in the ICP4 (one or both copies), ICP22, ICP27, ICP47, UL41, and/or UL55 genes. In some embodiments, the recombinant herpes simplex virus genome comprises an inactivating mutation in the ICP0 gene (one or both copies), and an inactivating mutation in the ICP4 gene (one or both copies). In some embodiments, the recombinant herpes simplex virus genome comprises an inactivating mutation in the ICP0 gene (one or both copies), and an inactivating mutation in the ICP22 gene. In some embodiments, the recombinant herpes simplex virus genome comprises an inactivating mutation in the ICP0 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), and an inactivating mutation in the ICP22 gene. In some embodiments, the recombinant herpes simplex virus genome comprises an inactivating mutation in the ICP0 gene (one or both copies), an inactivating mutation in the ICP4 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP22 gene, and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP0 (one or both copies), ICP4 (one or both copies), ICP22, and/or UL41 genes. In some embodiments, the recombinant herpes simplex virus genome further comprises an inactivating mutation in the ICP27, ICP47, and/or UL55 genes.

In some embodiments, the recombinant herpes simplex virus genome comprises an inactivating mutation in the ICP4 gene (one or both copies). In some embodiments, the recombinant herpes simplex virus genome comprises an inactivating mutation in the ICP4 gene (one or both copies), and further comprises an inactivating mutation in the ICP0 (one or both copies), ICP22, ICP27, ICP47, UL41, and/or UL55 genes. In some embodiments, the recombinant herpes simplex virus genome comprises an inactivating mutation in the ICP4 gene (one or both copies), and an inactivating mutation in the ICP22 gene. In some embodiments, the recombinant herpes simplex virus genome comprises an inactivating mutation in the ICP4 gene (one or both copies), and an inactivating mutation in the UL41 gene. In some embodiments, the recombinant herpes simplex virus genome comprises an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP4 (one or both copies), ICP22, and/or UL41 genes. In some embodiments, the recombinant herpes simplex virus genome further comprises an inactivating mutation in the ICP0 (one or both copies), ICP27, ICP47, and/or UL55 genes.

In some embodiments, the recombinant herpes simplex virus genome comprises an inactivating mutation in the ICP22 gene. In some embodiments, the recombinant herpes simplex virus genome comprises an inactivating mutation in the ICP22 gene, and further comprises an inactivating mutation in the ICP0 (one or both copies), ICP4 (one or both copies), ICP27, ICP47, UL41, and/or UL55 genes. In some embodiments, the recombinant herpes simplex virus genome comprises an inactivating mutation in the ICP22 gene, and an inactivating mutation UL41 gene. In some embodiments, the inactivating mutation is a deletion of the coding sequence of the ICP22 and/or UL41 genes. In some embodiments, the recombinant herpes simplex virus genome further comprises an inactivating mutation in the ICP0 (one or both copies), ICP4 (one or both copies), ICP27, ICP47, and/or UL55 genes.

In some embodiments, the recombinant herpes simplex virus genome comprises an inactivating mutation in the ICP27 gene. In some embodiments, the recombinant herpes simplex virus genome comprises an inactivating mutation in the ICP27 gene, and further comprises an inactivating mutation in the ICP0 (one or both copies), ICP4 (one or both copies), ICP22, ICP47, UL41, and/or UL55 genes. In some embodiments, the inactivating mutation is a deletion of the coding sequence of the ICP27 gene.

In some embodiments, the recombinant herpes simplex virus genome comprises an inactivating mutation in the ICP47 gene. In some embodiments, the recombinant herpes simplex virus genome comprises an inactivating mutation in the ICP47 gene, and further comprises an inactivating mutation in the ICP0 (one or both copies), ICP4 (one or both copies), ICP22, ICP27, UL41, and/or UL55 genes. In some embodiments, the inactivating mutation is a deletion of the coding sequence of the ICP47 gene.

In some embodiments, the recombinant herpes simplex virus genome comprises an inactivating mutation in the UL41 gene. In some embodiments, the recombinant herpes simplex virus genome comprises an inactivating mutation in the UL41 gene, and further comprises an inactivating mutation in the ICP0 (one or both copies), ICP4 (one or both copies), ICP22, ICP27, ICP47, and/or UL55 genes. In some embodiments, the inactivating mutation is a deletion of the coding sequence of the UL41 gene.

In some embodiments, the recombinant herpes simplex virus genome comprises an inactivating mutation in the UL55 gene. In some embodiments, the recombinant herpes simplex virus genome comprises an inactivating mutation in the UL55 gene, and further comprises an inactivating mutation in the ICP0 (one or both copies), ICP4 (one or both copies), ICP22, ICP27, ICP47, and/or UL41 genes. In some embodiments, the inactivating mutation is a deletion of the coding sequence of the UL55 gene.

In some embodiments, the recombinant herpes simplex virus genome comprises an inactivating mutation in (e.g., a deletion of) the internal repeat (Joint) region comprising the internal repeat long (IRL) and internal repeat short (IRs) regions. In some embodiments, inactivation (e.g., deletion) of the Joint region eliminates one copy each of the ICP4 and ICP0 genes. In some embodiments, inactivation (e.g., deletion) of the Joint region further inactivates (e.g., deletes) the promoter for the ICP22 and ICP47 genes. If desired, expression of one or both of these genes can be restored by insertion of an immediate early promoter into the recombinant herpes simplex virus genome (see e.g., Hill et al. (1995). Nature 375(6530): 411-415; Goldsmith et al. (1998). J Exp Med 187(3): 341-348). Without wishing to be bound by theory, it is believed that inactivating (e.g., deleting) the Joint region may contribute to the stability of the recombinant herpes simplex virus genome and/or allow for the recombinant herpes simplex virus genome to accommodate more and/or larger transgenes.

In some embodiments, the recombinant herpes simplex virus genome comprises an inactivating mutation in the ICP4 (one or both copies), ICP22, and ICP27 genes. In some embodiments, the recombinant herpes simplex virus genome comprises an inactivating mutation in the ICP4 (one or both copies), ICP27, and UL55 genes. In some embodiments, the recombinant herpes simplex virus genome comprises an inactivating mutation in the ICP4 (one or both copies), ICP22, ICP27, ICP47, and UL55 genes. In some embodiments, the inactivating mutation in the ICP4 (one or both copies), ICP27, and/or UL55 genes is a deletion of the coding sequence of the ICP4 (one or both copies), ICP27, and/or UL55 genes. In some embodiments, the inactivating mutation in the ICP22 and ICP47 genes is a deletion in the promoter region of the ICP22 and ICP47 genes (e.g., the ICP22 and ICP47 coding sequences are intact but are not transcriptionally active). In some embodiments, the recombinant herpes simplex virus genome comprises a deletion in the coding sequence of the ICP4 (one or both copies), ICP27, and UL55 genes, and a deletion in the promoter region of the ICP22 and ICP47 genes. In some embodiments, the recombinant herpes simplex virus genome further comprises an inactivating mutation in the ICP0 (one or both copies) and/or UL41 genes.

In some embodiments, the recombinant herpes simplex virus genome comprises an inactivating mutation in the ICP0 (one or both copies) gene. In some embodiments, the recombinant herpes simplex virus genome comprises an inactivating mutation in the ICP0 (one or both copies) and ICP4 (one or both copies) genes. In some embodiments, the recombinant herpes simplex virus genome comprises an inactivating mutation in the ICP0 (one or both copies), ICP4 (one or both copies), and ICP22 genes. In some embodiments, the recombinant herpes simplex virus genome comprises an inactivating mutation in the ICP0 (one or both copies), ICP4 (one or both copies), ICP22, and ICP27 genes. In some embodiments, the recombinant herpes simplex virus genome comprises an inactivating mutation in the ICP0 (one or both copies), ICP4 (one or both copies), ICP22, ICP27 and UL55 genes. In some embodiments, the inactivating mutation in the ICP0 (one or both copies), ICP4 (one or both copies), ICP22, ICP27 and/or UL55 genes comprises a deletion of the coding sequence of the ICP0 (one or both copies), ICP4 (one or both copies), ICP22, ICP27 and/or UL55 genes. In some embodiments, the recombinant herpes simplex virus genome further comprises an inactivating mutation in the ICP47 and/or the UL41 genes.

In some embodiments, a recombinant herpes simplex virus genome comprises one or more polynucleotides of the present disclosure within one, two, three, four, five, six, seven or more viral gene loci. Examples of suitable viral loci may include, without limitation, the ICP0 (one or both copies), ICP4 (one or both copies), ICP22, ICP27, ICP47, tk, UL41 and UL55 herpes simplex viral gene loci. In some embodiments, a recombinant herpes simplex virus genome comprises one or more polynucleotides of the present disclosure within one or both of the viral ICP4 gene loci (e.g., a recombinant virus comprising a polynucleotide encoding a polypeptide (such as an immunomodulatory polypeptide) in one or both of the ICP4 loci). In some embodiments, a recombinant herpes simplex virus genome comprises one or more polynucleotides of the present disclosure within the viral ICP22 gene locus (e.g., a recombinant virus comprising a polynucleotide encoding a polypeptide (such as an immunomodulatory polypeptide) in the ICP22 locus). In some embodiments, a recombinant herpes simplex virus genome comprises one or more polynucleotides of the present disclosure within the viral UL41 gene locus (e.g., a recombinant virus comprising a polynucleotide encoding a polypeptide (such as an immunomodulatory polypeptide) in the UL41 locus). In some embodiments, a recombinant herpes simplex virus genome comprises one or more polynucleotides of the present disclosure within the viral ICP27 gene locus (e.g., a recombinant virus comprising a polynucleotide encoding a polypeptide (such as an immunomodulatory polypeptide) in the ICP27 locus). In some embodiments, a recombinant herpes simplex virus genome comprises one or more polynucleotides of the present disclosure within the viral ICP47 gene locus (e.g., a recombinant virus comprising a polynucleotide encoding a polypeptide (such as an immunomodulatory polypeptide) in the ICP47 locus). In some embodiments, a recombinant herpes simplex virus genome comprises one or more polynucleotides of the present disclosure within the viral UL55 gene locus (e.g., a recombinant virus comprising a polynucleotide encoding a polypeptide (such as an immunomodulatory polypeptide) in the UL55 locus). In some embodiments, a recombinant herpes simplex virus genome comprises one or more polynucleotides of the present disclosure within the viral tk gene locus (e.g., a recombinant virus comprising a polynucleotide encoding a polypeptide (such as an immunomodulatory polypeptide) in the tk locus).

In some embodiments, a recombinant herpes simplex virus genome comprises one or more polynucleotides of the present disclosure within one or both of the viral ICP4 gene loci, and one or more polynucleotides of the present disclosure within the viral ICP22 gene locus (e.g., a recombinant virus comprising a polynucleotide encoding an immunomodulatory polypeptide (such as a human IL-12 polypeptide) in one or both of the ICP4 loci, and a polynucleotide encoding an immunomodulatory polypeptide (such as a human GM-CSF polypeptide) in the ICP22 locus). In some embodiments, a recombinant herpes simplex virus genome comprises one or more polynucleotides of the present disclosure within one or both of the viral ICP4 gene loci, and one or more polynucleotides of the present disclosure within the viral UL41 gene locus (e.g., a recombinant virus comprising a polynucleotide encoding an immunomodulatory polypeptide (such as a human IL-12 polypeptide) in one or both of the ICP4 loci, and a polynucleotide encoding an immunomodulatory polypeptide (such as a human GM-CSF polypeptide) in the UL41 locus). In some embodiments, a recombinant herpes simplex virus genome comprises one or more polynucleotides of the present disclosure within the viral ICP22 gene locus, and one or more polynucleotides of the present disclosure within the viral UL41 gene locus (e.g., a recombinant virus comprising a polynucleotide encoding an immunomodulatory polypeptide (such as a human IL-12 polypeptide) in the ICP22 locus, and a polynucleotide encoding an immunomodulatory polypeptide (such as a human GM-CSF polypeptide) in the UL41 locus). In some embodiments, a recombinant herpes simplex virus genome comprises one or more polynucleotides of the present disclosure within one or both of the viral ICP4 gene loci, one or more polynucleotides of the present disclosure within the viral ICP22 gene locus, and one or more polynucleotides of the present disclosure within the viral UL41 gene locus (e.g., a recombinant virus comprising a polynucleotide encoding an immunomodulatory polypeptide (such as a human IL-12 polypeptide) in one or both of the ICP4 loci, a polynucleotide encoding an immunomodulatory polypeptide (such as a human GM-CSF polypeptide) in the ICP22 locus, and a polynucleotide encoding an immunomodulatory polypeptide (such as a human IL-2 polypeptide) in the UL41 locus). In some embodiments, a recombinant herpes simplex virus genome comprises one or more polynucleotides of the present disclosure within one or both of the viral ICP4 gene loci, one or more polynucleotides of the present disclosure within the viral ICP22 gene locus, one or more polynucleotides of the present disclosure within the viral UL41 gene locus, one or more polynucleotides of the present disclosure within the viral ICP27 gene locus, one or more polynucleotides of the present disclosure within the viral ICP47 gene locus, one or more polynucleotides of the present disclosure within the viral tk gene locus, and/or one or more polynucleotides of the present disclosure within the viral UL55 gene locus.

In some embodiments, the recombinant herpes virus genome (e.g., a recombinant herpes simplex virus genome) has been engineered to decrease or eliminate expression of one or more herpes virus genes (e.g., one or more toxic herpes virus genes), such as one or both copies of the HSV ICP0 gene, one or both copies of the HSV ICP4 gene, the HSV ICP22 gene, the HSV UL41 gene, the HSV ICP27 gene, the HSV ICP47 gene, the HSV tk gene, the HSV UL55 gene, etc. In some embodiments, the recombinant herpes virus genome (e.g., a recombinant herpes simplex virus genome) has been engineered to reduce cytotoxicity of the recombinant genome (e.g., when introduced into a target cell), as compared to a corresponding wild-type herpes virus genome (e.g., a wild-type herpes simplex virus genome). In some embodiments, the target cell is a human cell (primary cells or a cell line derived therefrom). In some embodiments, the target cell is a cell of the respiratory tract (primary cells or a cell line derived therefrom). In some embodiments, the target cell is an airway epithelial cell (primary cells or a cell line derived therefrom). In some embodiments, the target cell is a cell of the lung (primary cells or a cell line derived therefrom). In some embodiments, cytotoxicity (e.g., in a target cell) of the recombinant genome (e.g., a recombinant herpes simplex virus genome) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% as compared to a corresponding wild-type herpes virus genome (e.g., measuring the relative cytotoxicity of a recombinant ΔICP4 (one or both copies) herpes simplex virus genome vs. a wild-type herpes simplex virus genome in a target cell; measuring the relative cytotoxicity of a recombinant ΔICP4 (one or both copies)/ΔICP22 herpes simplex virus genome vs. a wild-type herpes simplex virus genome in a target cell, etc.). In some embodiments, cytotoxicity (e.g., in a target cell) of the recombinant herpes genome (e.g., a recombinant herpes simplex virus genome) is reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more as compared to a corresponding wild-type herpes virus genome (e.g., measuring the relative cytotoxicity of a recombinant ΔICP4 (one or both copies) herpes simplex virus genome vs. a wild-type herpes simplex virus genome in a target cell; measuring the relative cytotoxicity of a recombinant ΔICP4 (one or both copies)/ΔICP22 herpes simplex virus genome vs. a wild-type herpes simplex virus genome in a target cell, etc.). Methods of measuring cytotoxicity are known to one of ordinary skill in the art, including, for example, through the use of vital dyes (formazan dyes), protease biomarkers, an MTT assay (or an assay using related tetrazolium salts such as XTT, MTS, water-soluble tetrazolium salts, etc.), measuring ATP content, etc.

In some embodiments, the recombinant genome (e.g., a recombinant herpes simplex virus genome) has been engineered to reduce its impact on target cell proliferation after exposure of a target cell to the recombinant genome, as compared to a corresponding wild-type genome (e.g., a wild-type herpes simplex virus genome). In some embodiments, the target cell is a human cell (primary cells or a cell line derived therefrom). In some embodiments, the target cell is a cell of the respiratory tract (primary cells or a cell line derived therefrom). In some embodiments, the target cell is an airway epithelial cell (primary cells or a cell line derived therefrom). In some embodiments, the target cell is a cell of the lung (primary cells or a cell line derived therefrom). In some embodiments, target cell proliferation after exposure to the recombinant genome is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% faster as compared to target cell proliferation after exposure to a corresponding wild-type genome (e.g., measuring the relative cellular proliferation after exposure to a recombinant ΔICP4 (one or both copies) herpes simplex virus genome vs. cellular proliferation after exposure to a wild-type herpes simplex virus genome in target cells; measuring the relative cellular proliferation after exposure to a recombinant ΔICP4 (one or both copies)/ΔICP22 herpes simplex virus genome vs. cellular proliferation after exposure to a wild-type herpes simplex virus genome in target cells, etc.). In some embodiments, target cell proliferation after exposure to the recombinant genome is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, or at least about 1000-fold faster as compared to target cell proliferation after exposure to a corresponding wild-type genome (e.g., measuring the relative cellular proliferation after exposure to a recombinant ΔICP4 (one or both copies) herpes simplex virus genome vs. cellular proliferation after exposure to a wild-type herpes simplex virus genome in target cells; measuring the relative cellular proliferation after exposure to a recombinant ΔICP4 (one or both copies)/ΔICP22 herpes simplex virus genome vs. cellular proliferation after exposure to a wild-type herpes simplex virus genome in target cells, etc.). Methods of measuring cellular proliferation are known to one of ordinary skill in the art, including, e.g., through the use of a Ki67 cell proliferation assay, a BrdU cell proliferation assay, etc.

A vector (e.g., herpes viral vector) may include one or more polynucleotides of the present disclosure in a form suitable for expression of the polynucleotide in a host cell. Vectors may include one or more regulatory sequences operatively linked to the polynucleotide to be expressed (e.g., as described above).

In some embodiments, the present disclosure relates to one or more heterologous polynucleotides (e.g., a bacterial artificial chromosome (BAC)) comprising any of the recombinant nucleic acids described herein.

In some embodiments, a recombinant nucleic acid (e.g., a recombinant herpes simplex virus genome) of the present disclosure comprises one or more of the polynucleotides described herein inserted in any orientation in the recombinant nucleic acid. If the recombinant nucleic acid comprises two or more polynucleotides described herein (e.g., two or more, three or more, etc.), the polynucleotides may be inserted in the same orientation or opposite orientations to one another. Without wishing to be bound be theory, incorporating two polynucleotides (e.g., two transgenes) into a recombinant nucleic acid (e.g., a vector) in an antisense orientation may help to avoid read-through and ensure proper expression of each polynucleotide.

In some embodiments, a recombinant nucleic of the present disclosure does not comprise a polynucleotide encoding a Collagen alpha-1 (VII) chain polypeptide (COLT). In some embodiments, a recombinant nucleic of the present disclosure does not comprise a polynucleotide encoding a Lysyl hydroxylase 3 polypeptide (LH3). In some embodiments, a recombinant nucleic of the present disclosure does not comprise a polynucleotide encoding a Keratin type I cytoskeletal 17 polypeptide (KRT17). In some embodiments, a recombinant nucleic of the present disclosure does not comprise a polynucleotide encoding a transglutaminase (TGM) polypeptide (e.g., a human transglutaminase polypeptide such as a human TGM1 polypeptide and/or a human TGMS polypeptide). In some embodiments, a recombinant nucleic of the present disclosure does not comprise a polynucleotide encoding a cosmetic protein (e.g., collagen proteins, fibronectins, elastins, lumicans, vitronectins/vitronectin receptors, laminins, neuromodulators, fibrillins, additional dermal extracellular matrix proteins, etc.). In some embodiments, a recombinant nucleic of the present disclosure does not comprise a polynucleotide encoding an antibody (e.g., a full-length antibody, an antibody fragment, etc.). In some embodiments, a recombinant nucleic of the present disclosure does not comprise a polynucleotide encoding a Serine Protease Inhibitor Kazal-type (SPINK) polypeptide (e.g., a human SPINK polypeptide, such as a SPINK5 polypeptide). In some embodiments, a recombinant nucleic of the present disclosure does not comprise a polynucleotide encoding a filaggrin or filaggrin 2 polypeptide (e.g., a human filaggrin or filaggrin 2 polypeptide). In some embodiments, a recombinant nucleic of the present disclosure does not comprise a polynucleotide encoding a Cystic Fibrosis Transmembrane Conductance Regulator (CFTR) polypeptide (e.g., a human CFTR polypeptide). In some embodiments, a recombinant nucleic of the present disclosure does not comprise a polynucleotide encoding an ichthyosis-associated polypeptide (e.g., an ATP-binding cassette sub-family A member 12 polypeptide, a 1-acylglycerol-3-phosphate O-acyltransferase ABHD5 polypeptide, an Aldehyde dehydrogenase family 3 member A2 polypeptide, an Arachidonate 12-lipoxygenase 12R-type polypeptide, a Hydroperoxide isomerase ALOXE3 polypeptide, an AP-1 complex subunit sigma-1A polypeptide, an Arylsulfatase E polypeptide, a Caspase-14 polypeptide, a Corneodesmosin polypeptide, a Ceramide synthase 3 polypeptide, a Carbohydrate sulfotransferase 8 polypeptide, a Claudin-1 polypeptide, a Cystatin-A polypeptide, a Cytochrome P450 4F22 polypeptide, a 3-beta-hydroxysteroid-Delta(8), Delta(7)-isomerase polypeptide, an Elongation of very long chain fatty acids protein 4 polypeptide, a Filaggrin polypeptide, a Filaggrin 2 polypeptide, a Gap junction beta-2 polypeptide, a Gap junction beta-3 polypeptide, a Gap junction beta-4 polypeptide, a Gap junction beta-6 polypeptide, a 3-ketodihydrosphingosine reductase polypeptide, a Keratin, type II cytoskeletal 1 polypeptide, a Keratin, type II cytoskeletal 2 epidermal polypeptide, a Keratin, type I cytoskeletal 9 polypeptide, a Keratin, type I cytoskeletal 10 polypeptide, a Lipase member N polypeptide, a Loricrin polypeptide, a Membrane-bound transcription factor site-2 protease polypeptide, a Magnesium transporter NIPA4 polypeptide, a Sterol-4-alpha-carboxylate 3-dehydrogenase, decarboxylating polypeptide, a Peroxisomal targeting signal 2 receptor polypeptide, a D-3-phosphoglycerate dehydrogenase polypeptide, a Phytanoyl-CoA dioxygenase, peroxisomal polypeptide, Patatin-like phospholipase domain-containing protein 1 polypeptide, a Proteasome maturation protein polypeptide, a Phosphoserine aminotransferase polypeptide, a Short-chain dehydrogenase/reductase family 9C member 7 polypeptide, a Serpin B8 polypeptide, a Long-chain fatty acid transport protein 4 polypeptide, a Synaptosomal-associated protein 29 polypeptide, a Suppressor of tumorigenicity 14 protein polypeptide, a Steryl-sulfatase polypeptide, a Vacuolar protein sorting-associated protein 33B polypeptide, and a CAAX prenyl protease 1 homolog polypeptide).

In some embodiments, a recombinant nucleic of the present disclosure does not comprise a polynucleotide encoding a Collagen alpha-1 (VII) chain polypeptide, a Lysyl hydroxylase 3 polypeptide, a Keratin type I cytoskeletal 17 polypeptide, and/or any chimeric polypeptides thereof. In some embodiments, a recombinant nucleic of the present disclosure does not comprise a polynucleotide encoding a Collagen alpha-1 (VII) chain polypeptide, a Lysyl hydroxylase 3 polypeptide, a Keratin type I cytoskeletal 17 polypeptide, a transglutaminase (TGM) polypeptide, a filaggrin polypeptide, a cosmetic protein, an antibody, a SPINK polypeptide, a CFTR polypeptide, an ichthyosis-associated polypeptide, an Alpha-1-antitrypsin polypeptide, a Sodium-dependent phosphate transport protein 2B polypeptide, a Dynein heavy chain 5 axonemal polypeptide, a Dynein heavy chain 11 axonemal polypeptide, a Coiled-coil domain-containing protein 39 polypeptide, a Dynein intermediate chain 1 axonemal polypeptide, a Coiled-coil domain-containing protein 40 polypeptide, a Coiled-coil domain containing protein 103 polypeptide, a Sperm-associated antigen 1 polypeptide, a Zinc finger MYND domain-containing protein 10 polypeptide, an Armadillo repeat containing protein 4 polypeptide, a Coiled-coil domain-containing protein 151 polypeptide, a Dynein intermediate chain 2 axonemal polypeptide, a Radial spoke head 1 homolog polypeptide, a Coiled-coil domain-containing protein 114 polypeptide, a Radial spoke head protein 4 homolog A polypeptide, a Dynein assembly factor 1 axonemal polypeptide, a Dynein assembly factor 2 axonemal polypeptide, a Leucine-rich repeat-containing protein 6 polypeptide, a Pulmonary surfactant-associated protein B polypeptide, a Pulmonary surfactant-associated protein C polypeptide, a Homeobox protein Nkx-2.1 polypeptide, an ATP-binding cassette sub-family A member 3 polypeptide, a Cytokine receptor common subunit beta polypeptide, a Granulocyte-macrophage colony-stimulating factor receptor subunit alpha polypeptide, a Bone morphogenetic protein receptor type-2 polypeptide, a Sarcoplasmic/endoplasmic reticulum calcium ATPase 2 polypeptide, a serine/threonine-protein kinase receptor R3 polypeptide, an Endoglin polypeptide, a Mothers against decapentaplegic homolog 9 polypeptide, a Caveolin-1 polypeptide, a Potassium channel subfamily K member 3 polypeptide, an eIF-2-alpha kinase GCN2 polypeptide, a Pulmonary surfactant-associated protein A2 polypeptide, a Telomerase reverse transcriptase polypeptide, a Dyskerin polypeptide, a Regulator of telomere elongation helicase 1 polypeptide, a Poly (A)-specific ribonuclease PARN polypeptide, a TERF1-interacting nuclear factor 2 polypeptide, an H/ACA ribonucleoprotein complex non-core subunit NAF1 polypeptide, a Mucin-5B polypeptide, a Desmoplakin polypeptide, a CST complex subunit STN1 polypeptide, a Dipeptidyl peptidase 9 polypeptide, and/or any chimeric polypeptides thereof.

IV. Viruses

Certain aspects of the present disclosure relate to viruses comprising any of the polynucleotides and/or recombinant nucleic acids described herein. In some embodiments, the virus is capable of infecting one or more target cells of a subject (e.g., a human). In some embodiments, the virus is suitable for delivering the polynucleotides and/or recombinant nucleic acids into one or more target cells of a subject (e.g., a human). In some embodiments, the one or more target cells are human cells. In some embodiments, the one or more target cells are one or more airway epithelial cells. In some embodiments, the one or more target cells are one or more cells of the respiratory tract (e.g., airway epithelial cells (such as goblet cells, ciliated cells, Clara cells, neuroendocrine cells, basal cells, intermediate or parabasal cells, Serous cells, brush cells, oncocytes, non-ciliated columnar cells, and/or metaplastic cells); alveolar cells (such as type 1 pneumocytes, type 2 pneumocytes, and/or cuboidal non-ciliated cells); salivary gland cells in bronchi (such as Serous cells, mucous cells, and/or ductal cells); etc.). In some embodiments, the one or more target cells are one or more cells of the lung.

Any suitable virus known in the art may be used, including, for example, adenovirus, adeno-associated virus, retrovirus, lentivirus, sendai virus, papillomavirus, herpes virus (e.g., a herpes simplex virus), vaccinia virus, and/or any hybrid or derivative viruses thereof. In some embodiments, the virus is attenuated. In some embodiments, the virus is replication competent. In some embodiments, the virus is replication defective. In some embodiments, the virus is not oncolytic. In some embodiments, the virus has been modified to alter its tissue tropism relative to the tissue tropism of a corresponding unmodified, wild-type virus. In some embodiments, the virus has reduced cytotoxicity (e.g., in a target cell) as compared to a corresponding wild-type virus. Methods of producing a virus comprising recombinant nucleic acids are well known to one of ordinary skill in the art.

In some embodiments, the virus is a member of the Herpesviridae family of DNA viruses, including, for example, a herpes simplex virus, a varicella zoster virus, a human cytomegalovirus, a herpesvirus 6A, a herpesvirus 6B, a herpesvirus 7, an Epstein-Barr virus, and a Kaposi's sarcoma-associated herpesvirus, etc. In some embodiments, the herpes virus is attenuated. In some embodiments, the herpes virus is replication defective. In some embodiments, the herpes virus is replication competent. In some embodiments, the herpes virus has been engineered to reduce or eliminate expression of one or more herpes virus genes (e.g., one or more toxic herpes virus genes). In some embodiments, the herpes virus has reduced cytotoxicity as compared to a corresponding wild-type herpes virus. In some embodiments, the herpes virus is not oncolytic.

In some embodiments, the virus is a herpes simplex virus. Herpes simplex viruses comprising recombinant nucleic acids may be produced by a process disclosed, for example, in U.S. Pat. No. 10,174,341, US 2019/0276845, U.S. Pat. Nos. 9,877,990, 10,155,016, 10,441,614, 11,185,564, US 2020/0093874, U.S. Pat. No. 10,525,090, US 2020/0197456, US 2021/0261649, US 2021/0395775, U.S. Pat. No. 10,829,529, US 2021/0087245, US 2021/0189427, U.S. Pat. No. 10,786,438, US 2021/0045988, and/or WO2021/046131, all of which are incorporated by reference herein in their entirety. In some embodiments, the herpes simplex virus is attenuated. In some embodiments, the herpes simplex virus is replication defective. In some embodiments, the herpes simplex virus is replication competent. In some embodiments, the herpes simplex virus has been engineered to reduce or eliminate expression of one or more herpes simplex virus genes (e.g., one or more toxic herpes simplex virus genes). In some embodiments, the herpes simplex virus has reduced cytotoxicity as compared to a corresponding wild-type herpes simplex virus. In some embodiments, the herpes simplex virus is not oncolytic. In some embodiments, the herpes simplex virus is an HSV-1, an HSV-2, or any derivatives thereof. In some embodiments, the herpes simplex virus is an HSV-1 virus. In some embodiments, the HSV-1 is attenuated. In some embodiments, the HSV-1 is replication defective. In some embodiments, the HSV-1 is replication competent. In some embodiments, the HSV-1 has been engineered to reduce or eliminate expression of one or more HSV-1 genes (e.g., one or more toxic HSV-1 genes). In some embodiments, the HSV-1 has reduced cytotoxicity as compared to a corresponding wild-type HSV-1. In some embodiments, the HSV-1 is not oncolytic.

In some embodiments, the herpes simplex virus has been modified to alter its tissue tropism relative to the tissue tropism of an unmodified, wild-type herpes simplex virus. In some embodiments, the herpes simplex virus comprises a modified envelope. In some embodiments, the modified envelope comprises one or more (e.g., one or more, two or more, three or more, four or more, etc.) mutant herpes simplex virus glycoproteins. Examples of herpes simplex virus glycoproteins may include, but are not limited to, the glycoproteins gB, gC, gD, gH, and gL. In some embodiments, the modified envelope alters the herpes simplex virus tissue tropism relative to a wild-type herpes simplex virus.

In some embodiments, the transduction efficiency (in vitro and/or in vivo) of a virus of the present disclosure (e.g., a herpes virus such as a herpes simplex virus) for one or more target cells (e.g., one or more cells of the respiratory tract) is at least about 25%. For example, the transduction efficiency of the virus for one or more target cells may be at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 99.5%, or more. In some embodiments, the virus is a herpes simplex virus and the transduction efficiency of the virus for one or more target cells (e.g., one or more cells of the respiratory tract) is about 85% to about 100%. In some embodiments, the virus is a herpes simplex virus and the transduction efficiency of the virus for one or more target cells (e.g., one or more cells of the respiratory tract) is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100%. Methods of measuring viral transduction efficiency in vitro or in vivo are well known to one of ordinary skill in the art, including, for example, qPCR analysis, deep sequencing, western blotting, fluorometric analysis (such as fluorescent in situ hybridization (FISH), fluorescent reporter gene expression, immunofluorescence, FACS), etc.

In some embodiments, provided herein are recombinant viruses, which may or may not be pseudotyped, that produce one or more therapeutic polypeptides for the treatment of cancer including solid tumors (e.g., advanced solid tumors) and hematologic malignancies. In some embodiments, the recombinant virus is non-oncolytic. In some embodiments, the one or more therapeutic polypeptides produced by the recombinant viruses described herein mediate or enhance an anti-tumor effect, such as by effector-cell mediated lysis of tumor cells. The present disclosure further provides therapeutic compositions comprising the recombinant viruses and methods of use in the treatment of solid tumors and hematologic malignancies.

In some embodiments, the therapeutic polypeptide is an immunomodulatory polypeptide. In some embodiments, the immunomodulatory polypeptide modulates the activity of one or more cell types, such as regulatory T cells (Tregs), myeloid-derived suppressor cells (MDSCs), dendritic cells, T cells, macrophages, neutrophils, and/or NK cells.

V. Pharmaceutical Compositions and Formulations

Certain aspects of the present disclosure relate to pharmaceutical compositions or formulations comprising any of the recombinant nucleic acids (e.g., a recombinant herpes virus genome) and/or viruses (e.g., a herpes virus comprising a recombinant genome) described herein (such as a herpes simplex virus comprising a recombinant herpes simplex virus genome), and a pharmaceutically acceptable excipient or carrier.

In some embodiments, the pharmaceutical composition or formulation comprises any one or more of the viruses (e.g., herpes viruses) described herein. In some embodiments, the pharmaceutical composition or formulation comprises from about $10^4$ to about $10^{12}$ plaque forming units (PFU)/mL of the virus. For example, the pharmaceutical composition or formulation may comprise from about $10^4$ to about $10^{12}$, about $10^5$ to about $10^{12}$, about $10^6$ to about $10^{12}$, about $10^7$ to about $10^{12}$, about $10^8$ to about $10^{12}$, about $10^9$ to about $10^{12}$, about $10^{10}$ to about $10^{12}$, about $10^{11}$ to about $10^{12}$, about $10^4$ to about $10^{11}$, about $10^5$ to about $10^{11}$, about $10^6$ to about $10^{11}$, about $10^7$ to about $10^{11}$, about $10^8$ to about $10^{11}$, about $10^9$ to about $10^{11}$, about $10^{10}$ to about $10^{11}$, about $10^4$ to about $10^{10}$, about $10^5$ to about $10^{10}$, about $10^6$ to about $10^{10}$, about $10^7$ to about $10^{10}$, about $10^8$ to about $10^{10}$, about $10^9$ to about $10^{10}$, about $10^4$ to about $10^9$, about $10^5$ to about $10^9$, about $10^6$ to about $10^9$, about $10^7$ to about $10^9$, about $10^8$ to about $10^9$, about $10^4$ to about $10^8$, about $10^5$ to about $10^8$, about $10^6$ to about $108$, about $10^7$ to about $10^8$, about $10^4$ to about $10^7$, about $10^5$ to about $10^7$, about $10^6$ to about $10^7$, about $10^4$ to about $10^6$, about $10^5$ to about $10^6$, or about $10^4$ to about $10^5$ PFU/mL of the virus. In some embodiments, the pharmaceutical composition or formulation comprises about $10^4$, about $10^5$, about $10^6$, about $10^7$, about $10^8$, about $10^9$, about $10^{10}$, about $10^{11}$, or about $10^{12}$ PFU/mL of the virus.

Pharmaceutical compositions and formulations can be prepared by mixing the active ingredient(s) (such as a recombinant nucleic acid and/or a virus) having the desired degree of purity with one or more pharmaceutically acceptable carriers or excipients. Pharmaceutically acceptable carriers or excipients are generally nontoxic to recipients at the dosages and concentrations employed, and may include, but are not limited to: buffers (such as phosphate, citrate, acetate, and other organic acids); antioxidants (such as ascorbic acid and methionine); preservatives (such as octadecyldimethylbenzyl ammonium chloride, benzalkonium chloride, benzethonium chloride, phenol, butyl or benzyl alcohol, alkyl parabens, catechol, resorcinol, cyclohexanol, 3-pentanol, and m-cresol); amino acids (such as glycine, glutamine, asparagine, histidine, arginine, or lysine); low molecular weight (less than about 10 residues) polypeptides; proteins (such as serum albumin, gelatin, or immunoglobulins); polyols (such as glycerol, e.g., formulations including 1%, 2%, 3%, 4%, 5%, 6%, 7%, 8%, 9%, 10%, 11%, 12%, 13%, 14%, 15%, etc. glycerol); hydrophilic polymers (such as polyvinylpyrrolidone); monosaccharides, disaccharides, and other carbohydrates (including glucose, mannose, or dextrins); chelating agents (such as EDTA); sugars (such as sucrose, mannitol, trehalose, or sorbitol); salt-forming counter-ions (such as sodium); metal complexes (such as Zn-protein complexes); and/or non-ionic surfactants (such as polyethylene glycol (PEG)). A thorough discussion of pharmaceutically acceptable carriers is available in REMINGTON'S PHARMACEUTICAL SCIENCES (Mack Pub. Co., N.J. 1991).

In some embodiments, the pharmaceutical composition or formulation comprises one or more lipid (e.g., cationic lipid) carriers. In some embodiments, the pharmaceutical composition or formulation comprises one or more nanoparticle carriers. Nanoparticles are submicron (less than about 1000 nm) sized drug delivery vehicles that can carry encapsulated drugs (such as synthetic small molecules, proteins, peptides, cells, viruses, and nucleic acid-based biotherapeutics) for rapid or controlled release. A variety of molecules (e.g., proteins, peptides, recombinant nucleic acids, etc.) can be efficiently encapsulated in nanoparticles using processes well known in the art. In some embodiments, a molecule "encapsulated" in a nanoparticle may refer to a molecule (such as a virus) that is contained within the nanoparticle or attached to and/or associated with the surface of the nanoparticle, or any combination thereof. Nanoparticles for use in the compositions or formulations described herein may be any type of biocompatible nanoparticle known in the art, including, for example, nanoparticles comprising poly(lactic acid), poly(glycolic acid), PLGA, PLA, PGA, and any combinations thereof (see e.g., Vauthier et al. Adv Drug Del Rev. (2003) 55: 519-48; US 2007/0148074; US 2007/0092575; US 2006/0246139; U.S. Pat. Nos. 5,753,234; 7,081,483; and US 2008/0260851, all of which are incorporated by reference herein in their entirety).

In some embodiments, the pharmaceutically acceptable carrier or excipient may be adapted for or suitable for any administration route known in the art, including, for example, intravenous, intramuscular, subcutaneous, cutaneous, oral, intranasal, intratracheal, sublingual, buccal, topical, transdermal, intradermal, intraperitoneal, intraorbital, intravitreal, subretinal, transmucosal, intraarticular, by implantation, by inhalation, intrathecal, intraventricular, and/or intranasal administration. In some embodiments, the pharmaceutically acceptable carrier or excipient is adapted for or suitable for oral, intranasal, intratracheal, and/or inhaled administration. In some embodiments, the pharmaceutically acceptable carrier or excipient is adapted for or suitable for intranasal and/or inhaled administration. In some embodiments, the pharmaceutically acceptable carrier or excipient is adapted for or suitable for inhaled administration.

In some embodiments, the pharmaceutical composition or formulation is adapted for or suitable for any administration route known in the art, including, for example, intravenous, intramuscular, subcutaneous, cutaneous, oral, intranasal, intratracheal, sublingual, buccal, topical, transdermal, intradermal, intraperitoneal, intraorbital, intravitreal, subretinal, transmucosal, intraarticular, by implantation, by inhalation, intrathecal, intraventricular, or intranasal administration. In some embodiments, the pharmaceutical composition or formulation is adapted for or suitable for oral, intranasal, intratracheal, and/or inhaled administration. In some embodiments, the pharmaceutical composition or formulation is adapted for or suitable for intranasal and/or inhaled administration. In some embodiments, the pharmaceutical composition or formulation is adapted for or suitable for inhaled administration.

In some embodiments, the pharmaceutical composition or formulation further comprises one or more additional components. Examples of additional components may include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; hydroxymethylcellulose; polyvinylpyrrolidone; sweetenings; flavorings; perfuming agents; colorants; moisturizers; sunscreens; antibacterial agents; agents able to stabilize polynucleotides or prevent their degradation, and the like. In some embodiments, the pharmaceutical composition or formulation comprises a methylcellulose gel (e.g., hydroxypropyl methylcellulose, carboxy methylcellulose, etc.). In some embodiments, the pharmaceutical composition or formulation comprises a phosphate buffer. In some embodiments, the pharmaceutical composition or formulation comprises glycerol (e.g., at about 1%, about 2%, about 3%, about 4%, about 5%, about 6%, about 7%, about 8%, about 9%, about 10%, about 11%, about 12%, about 13%, about 14%, about 15%, etc.). In some embodiments, the pharmaceutical composition or formulation comprises a phosphate buffer and glycerol.

Pharmaceutical compositions and formulations to be used for in vivo administration are generally sterile. Sterility may be readily accomplished, e.g., by filtration through sterile filtration membranes.

In some embodiments, any of the recombinant nucleic acids, viruses, and/or pharmaceutical compositions or formulations described herein may be used to deliver one or more polynucleotides encoding a polypeptide (e.g., an immunomodulatory polypeptide such as an IL-2 or IL-12 polypeptide) into one or more cells of a subject (e.g., one or more cells of the respiratory tract of the subject). In some embodiments, the subject suffers from cancer. In some embodiments, any of the recombinant nucleic acids, viruses, and/or pharmaceutical compositions or formulations described herein may be used in the treatment of cancer. In some embodiments, any of the recombinant nucleic acids, viruses, and/or pharmaceutical compositions or formulations described herein may be used in the treatment of carcinoma. In some embodiments, any of the recombinant nucleic acids, viruses, and/or pharmaceutical compositions or formulations described herein may be used in the treatment of lymphoma. In some embodiments, any of the recombinant nucleic acids, viruses, and/or pharmaceutical compositions or formulations described herein may be used in the treatment of blastoma. In some embodiments, any of the recombinant nucleic acids, viruses, and/or pharmaceutical compositions or formulations described herein may be used in the treatment of sarcoma. In some embodiments, any of the recombinant nucleic acids, viruses, and/or pharmaceutical compositions or formulations described herein may be used in the treatment of a neuroendocrine tumor. In some embodiments, any of the recombinant nucleic acids, viruses, and/or pharmaceutical compositions or formulations described herein may be used in the treatment of mesothelioma. In some embodiments, any of the recombinant nucleic acids, viruses, and/or pharmaceutical compositions or formulations described herein may be used in the treatment of schwannoma. In some embodiments, any of the recombinant nucleic acids, viruses, and/or pharmaceutical compositions or formulations described herein may be used in the treatment of meningioma. In some embodiments, any of the recombinant nucleic acids, viruses, and/or pharmaceutical compositions or formulations described herein may be used in the treatment of adenocarcinoma. In some embodiments, any of the recombinant nucleic acids, viruses, and/or pharmaceutical compositions or formulations described herein may be used in the treatment of melanoma. In some embodiments, any of the recombinant nucleic acids, viruses, and/or pharmaceutical compositions or formulations described herein may be used in the treatment of leukemia. In some embodiments, any of the recombinant nucleic acids, viruses, and/or pharmaceutical compositions or formulations described herein may be used in the treatment of lymphoid malignancy.

In some embodiments, any of the recombinant nucleic acids, viruses, and/or pharmaceutical compositions or formulations described herein may be used to deliver one or more polynucleotides encoding a polypeptide (e.g., an immunomodulatory polypeptide such as an IL-2 or IL-12 polypeptide) into one or more cells of a subject (e.g., one or more cells of the respiratory tract of the subject). In some embodiments, the subject suffers from cancer. In some embodiments, any of the recombinant nucleic acids, viruses, and/or pharmaceutical compositions or formulations described herein may be used in the treatment of a solid tumor. In some embodiments, any of the recombinant nucleic acids, viruses, and/or pharmaceutical compositions or formulations described herein may be used in the treatment of a hematologic cancer. In some embodiments, any of the recombinant nucleic acids, viruses, and/or pharmaceutical compositions or formulations described herein may be used in the treatment of bladder cancer. In some embodiments, any of the recombinant nucleic acids, viruses, and/or pharmaceutical compositions or formulations described herein may be used in the treatment of brain cancer. In some embodiments, any of the recombinant nucleic acids, viruses, and/or pharmaceutical compositions or formulations described herein may be used in the treatment of breast cancer. In some embodiments, any of the recombinant nucleic acids, viruses, and/or pharmaceutical compositions or formulations described herein may be used in the treatment of colon cancer. In some embodiments, any of the recombinant nucleic acids, viruses, and/or pharmaceutical compositions or formulations described herein may be used in the treatment of gastric cancer. In some embodiments, any of the recombinant nucleic acids, viruses, and/or pharmaceutical compositions or formulations described herein may be used in the treatment of glioma. In some embodiments, any of the recombinant nucleic acids, viruses, and/or pharmaceutical compositions or formulations described herein may be used in the treatment of head cancer. In some embodiments, any of the recombinant nucleic acids, viruses, and/or pharmaceutical compositions or formulations described herein may be used in the treatment of leukemia. In some embodiments, any of the recombinant nucleic acids, viruses, and/or pharmaceutical compositions or formulations described herein may be used in the treatment of liver cancer. In some embodiments, any of the recombinant nucleic acids, viruses, and/or pharmaceutical compositions or formulations described herein may be used in the treatment of lung cancer. In some embodiments, any of the recombinant nucleic acids, viruses, and/or pharmaceutical compositions or formulations described herein may be used in the treatment of lymphoma. In some embodiments, any of the recombinant nucleic acids, viruses, and/or pharmaceutical compositions or formulations described herein may be used in the treatment of myeloma. In some embodiments, any of the recombinant nucleic acids, viruses, and/or pharmaceutical compositions or formulations described herein may be used in the treatment of neck cancer. In some embodiments, any of the recombinant nucleic acids, viruses, and/or pharmaceutical compositions or formulations described herein may be used in the treatment of ovarian cancer. In some embodiments, any of the recombinant nucleic acids, viruses, and/or pharmaceutical compositions or formulations described herein may be used in the treatment of melanoma. In some embodiments, any of the recombinant nucleic acids, viruses, and/or pharmaceutical compositions or formulations described herein may be used in the treatment of pancreatic cancer. In some embodiments, any of the recombinant nucleic acids, viruses, and/or pharmaceutical compositions or formulations described herein may be used in the treatment of renal cancer. In some embodiments, any of the recombinant nucleic acids, viruses, and/or pharmaceutical compositions or formulations described herein may be used in the treatment of salivary cancer. In some embodiments, any of the recombinant nucleic acids, viruses, and/or pharmaceutical compositions or formulations described herein may be used in the treatment of skin cancer (e.g., melanoma, basal cell carcinoma, squamous cell carcinoma, actinic keratosis, an atypical mole, and/or Merkel cell carcinoma). In some embodiments, any of the recombinant nucleic acids, viruses, and/or pharmaceutical compositions or formulations described herein may be used in the treatment of stomach cancer. In some embodiments, any of the recombinant nucleic acids, viruses, and/or pharmaceutical compositions or formulations described herein may be used in the treatment of thymic epithelial cancer. In some embodiments, any of the recombinant nucleic acids, viruses, and/or pharmaceutical compositions or formulations described herein may be used in the treatment of thyroid cancer. In some embodiments, any of the recombinant nucleic acids, viruses, and/or pharmaceutical compositions or formulations described herein may be used in the treatment of osteosarcoma.

In some embodiments, any of the recombinant nucleic acids, viruses, and/or pharmaceutical compositions or formulations described herein may be used to deliver one or more polynucleotides encoding a polypeptide (e.g., an immunomodulatory polypeptide such as an IL-2 or IL-12 polypeptide) into one or more cells of a subject (e.g., one or more cells of the respiratory tract of the subject). In some embodiments, the subject suffers from lung cancer. Lung cancers are often divided into the broad categories of small-cell lung cancer (SCLC), also called oat cell cancer, and non-small-cell lung cancer (NSCLC). NSCLC is further divided into three major types, squamous, cell carcinoma (SCC), adenocarcinoma and large cell carcinomas. In some embodiments, any of the recombinant nucleic acids, viruses, and/or pharmaceutical compositions or formulations described herein may be used in the treatment of small-cell lung cancer. In some embodiments, any of the recombinant nucleic acids, viruses, and/or pharmaceutical compositions or formulations described herein may be used in the treatment of adenocarcinoma of the lung. In some embodiments, any of the recombinant nucleic acids, viruses, and/or pharmaceutical compositions or formulations described herein may be used in the treatment of squamous carcinoma of the lung. In some embodiments, any of the recombinant nucleic acids, viruses, and/or pharmaceutical compositions or formulations described herein may be used in the treatment of non-small cell lung cancer.

VI. Methods

Certain aspects of the present disclosure relate to a method of delivering an immunomodulatory polypeptide to one or more cells of a subject (e.g., one or more cells of the respiratory tract, such as airway epithelial cells (goblet cells, ciliated cells, Clara cells, neuroendocrine cells, basal cells, intermediate or parabasal cells, Serous cells, brush cells, oncocytes, non-ciliated columnar cells, and/or metaplastic cells); alveolar cells (type 1 pneumocytes, type 2 pneumocytes, and/or cuboidal non-ciliated cells); salivary gland cells in bronchi (Serous cells, mucous cells, and/or ductal cells); etc.) comprising administering to the subject a pharmaceutical composition comprising any of the viruses described herein (e.g., a herpes simplex virus, such as an HSV-1) comprising any of the recombinant nucleic acids described herein (e.g., a recombinant herpes simplex virus genome, such as a recombinant HSV-1 genome) comprising one or more polynucleotides encoding the immunomodulatory polypeptide, and a pharmaceutically acceptable carrier. In some embodiments, the pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, intratumorally, locally, or via inhalation to the subject. In some embodiments, the pharmaceutical composition is administered orally, intranasally, intratracheally, or via inhalation to the subject. In some embodiments, the pharmaceutical composition is administered intranasally or via inhalation to the subject. In some embodiments, the pharmaceutical composition is administered via inhalation to the subject. In some embodiments, the herpes virus or pharmaceutical composition is administered using a dry powder inhaler, a pressurized metered dose inhaler, a soft mist inhaler, a nebulizer, or an electrohydrodynamic aerosol device. In some embodiments, the herpes virus or pharmaceutical composition is administered using a nebulizer. In some embodiments, the nebulizer is a vibrating mesh nebulizer. In some embodiments, the herpes virus (e.g., the herpes simplex virus) is replication competent. In some embodiments, the herpes virus (e.g., the herpes simplex virus) is not conditionally replication competent. In some embodiments, the herpes virus (e.g., the herpes simplex virus) does not replicate in cancerous cells. In some embodiments, the herpes virus (e.g., the herpes simplex virus) is replication defective. In some embodiments, the herpes virus (e.g., the herpes simplex virus) is not oncolytic.

In some embodiments, the subject is a human. In some embodiments, the subject suffers from a cancer. In some embodiments, the cancer is selected from acute myeloid leukemia (LAML or AML), acute lymphoblastic leukemia (ALL), adrenocortical carcinoma (ACC), bladder urothelial cancer (BLCA), brain stem glioma, brain lower grade glioma (LGG), brain tumor, breast cancer (BRCA), bronchial tumors, Burkitt lymphoma, cancer of unknown primary site, carcinoid tumor, carcinoma of unknown primary site, central nervous system atypical teratoid/rhabdoid tumor, central nervous system embryonal tumors, cervical squamous cell carcinoma, endocervical adenocarcinoma (CESC) cancer, childhood cancers, cholangiocarcinoma (CHOL), chordoma, chronic lymphocytic leukemia, chronic myelogenous leukemia, chronic myeloproliferative disorders, colon (adenocarcinoma) cancer (COAD), colorectal cancer, craniopharyngioma, cutaneous T-cell lymphoma, endocrine pancreas islet cell tumors, endometrial cancer, ependymoblastoma, ependymoma, esophageal cancer (ESCA), esthesioneuroblastoma, Ewing sarcoma, extracranial germ cell tumor, extragonadal germ cell tumor, extrahepatic bile duct cancer, gallbladder cancer, gastric (stomach) cancer, gastrointestinal carcinoid tumor, gastrointestinal stromal cell tumor, gastrointestinal stromal tumor (GIST), gestational trophoblastic tumor, glioblastoma multiforme glioma GBM), hairy cell leukemia, head and neck cancer (HNSD), heart cancer, Hodgkin lymphoma, hypopharyngeal cancer, intraocular melanoma, islet cell tumors, Kaposi sarcoma, kidney cancer, Langerhans cell histiocytosis, laryngeal cancer, lip cancer, liver cancer, Lymphoid Neoplasm Diffuse Large B-cell Lymphoma [DLBCL], malignant fibrous histiocytoma bone cancer, medulloblastoma, medulloepithelioma, melanoma, Merkel cell carcinoma, Merkel cell skin carcinoma, mesothelioma (MESO), metastatic squamous neck cancer with occult primary, mouth cancer, multiple endocrine neoplasia syndromes, multiple myeloma, multiple myeloma/plasma cell neoplasm, mycosis fungoides, myelodysplastic syndromes, myeloproliferative neoplasms, nasal cavity cancer, nasopharyngeal cancer, neuroblastoma, Non-Hodgkin lymphoma, nonmelanoma skin cancer, non-small cell lung cancer, oral cancer, oral cavity cancer, oropharyngeal cancer, osteosarcoma, other brain and spinal cord tumors, ovarian cancer, ovarian epithelial cancer, ovarian germ cell tumor, ovarian low malignant potential tumor, pancreatic cancer, papillomatosis, paranasal sinus cancer, parathyroid cancer, pelvic cancer, penile cancer, pharyngeal cancer, pheochromocytoma and paraganglioma (PCPG), pineal parenchymal tumors of intermediate differentiation, pineoblastoma, pituitary tumor, plasma cell neoplasm/multiple myeloma, pleuropulmonary blastoma, primary central nervous system (CNS) lymphoma, primary hepatocellular liver cancer, prostate cancer such as prostate adenocarcinoma (PRAD), rectal cancer, renal cancer, renal cell (kidney) cancer, renal cell cancer, respiratory tract cancer, retinoblastoma, rhabdomyosarcoma, salivary gland cancer, sarcoma (SARC), Sezary syndrome, skin cutaneous melanoma (SKCM), small cell lung cancer, small intestine cancer, soft tissue sarcoma, squamous cell carcinoma, squamous neck cancer, stomach (gastric) cancer, supratentorial primitive neuroectodermal tumors, T-cell lymphoma, testicular cancer testicular germ cell tumors (TGCT), throat cancer, thymic carcinoma, thymoma (THYM), thyroid cancer (THCA), transitional cell cancer, transitional cell cancer of the renal pelvis and ureter, trophoblastic tumor, ureter cancer, urethral cancer, uterine cancer, uterine cancer, uveal melanoma (UVM), vaginal cancer, vulvar cancer, Waldenstrom macroglobulinemia, and/or Wilms' tumor. In some embodiments, the cancer is a virus-associated cancer. In some embodiments, the cancer is a human papilloma virus (HPV)-associated cancer (e.g., an HPV-associated cancer of the back of the throat, cervix, anus, vulva, penis, and/or vagina). In some embodiments, the cancer is not skin cancer (e.g., melanoma, basal cell carcinoma, squamous cell carcinoma, actinic keratosis, an atypical mole, and/or Merkel cell carcinoma). In some embodiments, the cancer is not melanoma. In some embodiments, the subject suffers from one or more of carcinoma, lymphoma, blastoma, sarcoma, a neuroendocrine tumor, mesothelioma, schwannoma, meningioma, adenocarcinoma, melanoma, leukemia, and lymphoid malignancy. In some embodiments, the subject suffers from one or more of a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, skin cancer, stomach cancer, thymic epithelial cancer, and thyroid cancer. In some embodiments, the subject suffers from one or more of small-cell lung cancer, non-small cell lung cancer, adenocarcinoma of the lung, or squamous carcinoma of the lung. In some embodiments, the subject suffers from osteosarcoma.

In some embodiments, administration of the recombinant nucleic acid, virus, medicament, and/or pharmaceutical composition or formulation to the subject increases the immunomodulatory polypeptide levels (transcript or protein levels) by at least about 2-fold in one or more contacted or treated cells of the subject, as compared to the endogenous levels of the polypeptide in one or more corresponding untreated cells in the subject. For example, administration of the recombinant nucleic acid, virus, medicament, and/or pharmaceutical composition or formulation may increase the immunomodulatory polypeptide levels (transcript or protein levels) by at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more in one or more contacted or treated cells of the subject, as compared to the endogenous levels of the polypeptide in one or more corresponding untreated cells in the subject. In some embodiments, the one or more contacted or treated cells are one or more cells of the respiratory tract (e.g., one or more cells of the airway epithelia). Methods of measuring transcript or protein levels from a sample are well known to one of ordinary skill in the art, including, for example, qPCR, western blot, mass spectrometry, etc.

Other aspects of the present disclosure relate to a method of providing prophylactic, palliative, or therapeutic relief to one or more signs or symptoms of cancer in a subject in need thereof comprising administering to the subject an effective amount of any of the recombinant nucleic acids, viruses, medicaments, and/or pharmaceutical compositions or formulations described herein. In some embodiments, the subject is a human. In some embodiments, the subject suffers from a cancer. In some embodiments, the cancer is selected from acute myeloid leukemia (LAML or AML), acute lymphoblastic leukemia (ALL), adrenocortical carcinoma (ACC), bladder urothelial cancer (BLCA), brain stem glioma, brain lower grade glioma (LGG), brain tumor, breast cancer (BRCA), bronchial tumors, Burkitt lymphoma, cancer of unknown primary site, carcinoid tumor, carcinoma of unknown primary site, central nervous system atypical teratoid/rhabdoid tumor, central nervous system embryonal tumors, cervical squamous cell carcinoma, endocervical adenocarcinoma (CESC) cancer, childhood cancers, cholangiocarcinoma (CHOL), chordoma, chronic lymphocytic leukemia, chronic myelogenous leukemia, chronic myeloproliferative disorders, colon (adenocarcinoma) cancer (COAD), colorectal cancer, craniopharyngioma, cutaneous T-cell lymphoma, endocrine pancreas islet cell tumors, endometrial cancer, ependymoblastoma, ependymoma, esophageal cancer (ESCA), esthesioneuroblastoma, Ewing sarcoma, extracranial germ cell tumor, extragonadal germ cell tumor, extrahepatic bile duct cancer, gallbladder cancer, gastric (stomach) cancer, gastrointestinal carcinoid tumor, gastrointestinal stromal cell tumor, gastrointestinal stromal tumor (GIST), gestational trophoblastic tumor, glioblastoma multiforme glioma GBM), hairy cell leukemia, head and neck cancer (HNSD), heart cancer, Hodgkin lymphoma, hypopharyngeal cancer, intraocular melanoma, islet cell tumors, Kaposi sarcoma, kidney cancer, Langerhans cell histiocytosis, laryngeal cancer, lip cancer, liver cancer, Lymphoid Neoplasm Diffuse Large B-cell Lymphoma [DLBCL], malignant fibrous histiocytoma bone cancer, medulloblastoma, medulloepithelioma, melanoma, Merkel cell carcinoma, Merkel cell skin carcinoma, mesothelioma (MESO), metastatic squamous neck cancer with occult primary, mouth cancer, multiple endocrine neoplasia syndromes, multiple myeloma, multiple myeloma/plasma cell neoplasm, mycosis fungoides, myelodysplastic syndromes, myeloproliferative neoplasms, nasal cavity cancer, nasopharyngeal cancer, neuroblastoma, Non-Hodgkin lymphoma, nonmelanoma skin cancer, non-small cell lung cancer, oral cancer, oral cavity cancer, oropharyngeal cancer, osteosarcoma, other brain and spinal cord tumors, ovarian cancer, ovarian epithelial cancer, ovarian germ cell tumor, ovarian low malignant potential tumor, pancreatic cancer, papillomatosis, paranasal sinus cancer, parathyroid cancer, pelvic cancer, penile cancer, pharyngeal cancer, pheochromocytoma and paraganglioma (PCPG), pineal parenchymal tumors of intermediate differentiation, pineoblastoma, pituitary tumor, plasma cell neoplasm/multiple myeloma, pleuropulmonary blastoma, primary central nervous system (CNS) lymphoma, primary hepatocellular liver cancer, prostate cancer such as prostate adenocarcinoma (PRAD), rectal cancer, renal cancer, renal cell (kidney) cancer, renal cell cancer, respiratory tract cancer, retinoblastoma, rhabdomyosarcoma, salivary gland cancer, sarcoma (SARC), Sezary syndrome, skin cutaneous melanoma (SKCM), small cell lung cancer, small intestine cancer, soft tissue sarcoma, squamous cell carcinoma, squamous neck cancer, stomach (gastric) cancer, supratentorial primitive neuroectodermal tumors, T-cell lymphoma, testicular cancer testicular germ cell tumors (TGCT), throat cancer, thymic carcinoma, thymoma (THYM), thyroid cancer (THCA), transitional cell cancer, transitional cell cancer of the renal pelvis and ureter, trophoblastic tumor, ureter cancer, urethral cancer, uterine cancer, uterine cancer, uveal melanoma (UVM), vaginal cancer, vulvar cancer, Waldenstrom macroglobulinemia, and/or Wilms' tumor. In some embodiments, the cancer is a virus-associated cancer. In some embodiments, the cancer is a human papilloma virus (HPV)-associated cancer (e.g., an HPV-associated cancer of the back of the throat, cervix, anus, vulva, penis, and/or vagina). In some embodiments, the cancer is not skin cancer (e.g., melanoma, basal cell carcinoma, squamous cell carcinoma, actinic keratosis, an atypical mole, and/or Merkel cell carcinoma). In some embodiments, the cancer is not melanoma. In some embodiments, the subject suffers from one or more of carcinoma, lymphoma, blastoma, sarcoma, a neuroendocrine tumor, mesothelioma, schwannoma, meningioma, adenocarcinoma, melanoma, leukemia, and lymphoid malignancy. In some embodiments, the subject suffers from one or more of a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, and thyroid cancer. In some embodiments, the subject suffers from one or more of small-cell lung cancer, non-small cell lung cancer, adenocarcinoma of the lung, or squamous carcinoma of the lung. In some embodiments, the subject suffers from osteosarcoma.

The recombinant nucleic acids, viruses, medicaments, and/or pharmaceutical compositions or formulations described herein may be administered by any suitable method or route known in the art, including, without limitation, orally, intranasally, intratracheally, sublingually, buccally, topically, rectally, via inhalation, transdermally, subcutaneously, intradermally, intravenously, intraarterially, intramuscularly, intracardially, intraosseously, intraperitoneally, transmucosally, vaginally, intravitreally, intraorbitally, subretinally, intraarticularly, peri-articularly, locally, epicutaneously, or any combinations thereof. The present disclosure thus encompasses methods of delivering any of the recombinant nucleic acids, viruses, medicaments, or pharmaceutical compositions or formulations described herein to an individual (e.g., an individual having cancer). In some embodiments, the recombinant nucleic acids, viruses, medicaments, and/or pharmaceutical compositions or formulations described herein are administered orally, intranasally, intratracheally, and/or via inhalation. In some embodiments, the recombinant nucleic acids, viruses, medicaments, and/or pharmaceutical compositions or formulations described herein are administered intranasally or via inhalation. In some embodiments, the recombinant nucleic acids, viruses, medicaments, and/or pharmaceutical compositions or formulations described herein are administered via inhalation. In some embodiments, the recombinant nucleic acids, viruses, medicaments, and/or pharmaceutical compositions or formulations described herein are administered using a dry powder inhaler, a pressurized metered dose inhaler, a soft mist inhaler, a nebulizer, or an electrohydrodynamic aerosol device. In some embodiments, the recombinant nucleic acids, viruses, medicaments, and/or pharmaceutical compositions or formulations described herein are administered using a nebulizer. In some embodiments, the nebulizer is a vibrating mesh nebulizer.

Methods of delivering drugs to the airways and/or lungs via oral, intranasal, intratracheal, and or inhaled routes of administration are generally known to one of ordinary skill in the art (see e.g., Gardenhire et al. A Guide to Aerosol Delivery Devices for Respiratory Therapists, 4th Edition, American Association for Respiratory care, 2017; Patil et al. Pulmonary Drug Delivery Strategies: A Concise, Systematic Review, Lung India. 2012. 29(1):44-9; Marx et al. Intranasal Drug Administration—An Attractive Delivery Route for Some Drugs, 2015).

In some embodiments, the recombinant nucleic acids, viruses, medicaments, and/or compositions or formulations are delivered to the lungs by inhalation of an aerosolized formulation. In some embodiments, the recombinant nucleic acids, viruses, medicaments, and/or compositions or formulations are delivered to the lungs by inhalation of an aerosolized formulation after lung tumor resection. Inhalation may occur through the nose and/or the mouth of the subject. Exemplary devices for delivering the recombinant nucleic acids, viruses, medicaments, and/or pharmaceutical compositions or formulations to the lung may include, without limitation, dry powder inhalers, pressurized metered dose inhalers, soft mist inhalers, nebulizers, (e.g., jet nebulizers, ultrasonic nebulizers, vibrating mesh nebulizers), colliding jets, extruded jets, surface wave microfluidic atomization, capillary aerosol generation, electrohydrodynamic aerosol devices, etc. (see e.g., Carvalho and McConville. The function and performance of aqueous devices for inhalation therapy. (2016) Journal of Pharmacy and Pharmacology).

Liquid formulations may be administered to the lungs of a subject, e.g., using a pressurized metered dose inhaler (pMDI). pMDIs generally include at least two components: a canister in which the liquid formulation is held under pressure in combination with one or more propellants, and a receptacle used to hold and actuate the canister. The canister may contain a single dose or multiple doses of the formulation. The canister may include a valve, typically a metering valve, from which the contents of the canister may be discharged. Aerosolized drug is dispensed from the pMDI by applying a force on the canister to push it into the receptacle, thereby opening the valve and causing the drug particles to be conveyed from the valve through the receptacle outlet. Upon discharge from the canister, the liquid formulation is atomized, forming an aerosol. pMDIs typically employ one or more propellants to pressurize the contents of the canister and to propel the liquid formulation out of the receptacle outlet, forming an aerosol. Any suitable propellants may be utilized, and may take a variety of forms, including, for example, a compressed gas or a liquified gas.

Liquid formulations may be administered to the lungs of a subject, e.g., using a nebulizer. Nebulizers are liquid aerosol generators that convert the liquid formulation into mists or clouds of small droplets, often having diameters less than about 5 microns mass median aerodynamic diameter, which can be inhaled into the lower respiratory tract. The droplets carry the active agent(s) into the nose, upper airways, and/or deep lungs when the aerosol cloud is inhaled. Any type of nebulizer known in the art may be used to administer the formulation to a patient, including, without limitation, pneumatic (jet) nebulizers, electromechanical nebulizers (e.g., ultrasonic nebulizers, vibrating mesh nebulizers), etc. Pneumatic (jet) nebulizers use a pressurized gas supply as a driving force for atomization of the liquid formulation. Compressed gas is delivered through a nozzle or jet to create a low-pressure field which entrains a surrounding liquid formulation and shears it into a thin film or filaments. The film or filaments are unstable and break up into small droplets that are carried by the compressed gas flow into the inspiratory breath. Baffles inserted into the droplet plume screen out the larger droplets and return them to the bulk liquid reservoir. Electromechanical nebulizers use electrically generated mechanical force to atomize liquid formulations. The electromechanical driving force can be applied, for example, by vibrating the liquid formulation at ultrasonic frequencies, or by forcing the bulk liquid through small holes in a thin film. The forces generate thin liquid films or filament streams which break up into small droplets to form a slow-moving aerosol stream which can be entrained in an inspiratory flow. In some embodiments, the nebulizer is a vibrating mesh nebulizer. Examples of vibrating mesh nebulizers include, for example, the Phillips InnoSpire, the Aerogen Solo, the PARI eFlow, etc.

Liquid formulations may be administered to the lungs of a subject, e.g., using an electrohydrodynamic (EHD) aerosol device. EHD aerosol devices use electrical energy to aerosolize liquid drug solutions or suspensions.

Dry powder formulations may be administered to the lungs of a subject, e.g., using a dry powder inhaler (DPI). DPIs typically use a mechanism such as a burst of gas to create a cloud of dry powder inside a container, which can then be inhaled by the subject. In a DPI, the dose to be administered is stored in the form of a non-pressurized dry powder and, upon actuation of the inhaler, the particles of the powder are inhaled by the subject. In some cases, a compressed gas may be used to dispense the powder, similar to pMDIs. In some cases, the DPI may be breath actuated (an aerosol is created in precise response to inspiration). Typically, dry powder inhalers administer a dose of less than a few tens of milligrams per inhalation to avoid provocation of cough. Examples of DPIs include, for example, the Turbohaler® inhaler (AstraZeneca), the Clickhaler® inhaler (Innovata), the Diskus® inhaler (Glaxo), the EasyHaler® (Orion), the Exubera® inhaler (Pfizer), etc.

In some embodiments, the recombinant nucleic acids, viruses, medicaments, and/or pharmaceutical compositions or formulations are administered once to the subject. In some embodiments, the recombinant nucleic acids, viruses, medicaments, and/or pharmaceutical compositions are administered at least twice (e.g., at least 2 times, at least 3 times, at least 4 times, at least 5 times, at least 10 times, etc.) to the subject. In some embodiments, at least about 1 hour (e.g., at least about 1 hour, at least about 6 hours, at least about 12 hours, at least about 18 hours, at least about 1 day, at least about 2 days, at least about 3 days, at least about 4 days, at least about 5 days, at least about 6 days, at least about 7 days, at least about 15 days, at least about 20 days, at least about 30 days, at least about 40 days, at least about 50 days, at least about 60 days, at least about 70 days, at least about 80 days, at least about 90 days, at least about 100 days, at least about 120 days, etc.) pass between administrations (e.g., between the first and second administrations, between the second and third administrations, etc.). In some embodiments, the recombinant nucleic acids, viruses, medicaments, and/or pharmaceutical compositions or formulations are administered one, two, three, four, five or more times per day to the subject. In some embodiments, the recombinant nucleic acids, viruses, medicaments, and/or pharmaceutical compositions or formulations are administered one, two, three, four, five or more times per month to the subject.

VII. Host Cells

Certain aspects of the present disclosure relate to one or more host cells comprising any of the recombinant nucleic acids described herein. Any suitable host cell (prokaryotic or eukaryotic) known in the art may be used, including, for example: prokaryotic cells including eubacteria, such as Gram-negative or Gram-positive organisms, for example Enterobacteriaceae such as *Escherichia* (e.g., *E. coli*), *Enterobacter, Erminia, Klebsiella, Proteus, Salmonella* (e.g., *S. typhimurium*), *Serratia* (e.g., *S. marcescans*), and *Shigella*, as well as Bacilli such as *B. subtilis* and *B. licheniformis*; fungal cells (e.g., *S. cerevisiae*); insect cells (e.g., S2 cells, etc.); and mammalian cells, including monkey kidney CV1 line transformed by SV40 (COS-7, ATCC CRL 1651), human embryonic kidney line (293 or 293 cells subcloned for growth in suspension culture), baby hamster kidney cells (BHK, ATCC CCL 10), mouse Sertoli cells (TM4), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TRI cells, MRC 5 cells, FS4 cells, human hepatoma line (Hep G2), Chinese hamster ovary (CHO) cells, including DHFR" CHO cells, and myeloma cell lines such as NS0 and Sp2/0. In some embodiments, the host cell is a human or non-human primate cell. In some embodiments, the host cells are cells from a cell line. Examples of suitable host cells or cell lines may include, but are not limited to, 293, HeLa, SH-Sy5y, Hep G2, CACO-2, A549, L929, 3T3, K562, CHO-K1, MDCK, HUVEC, Vero, N20, COS-7, PSN1, VCaP, CHO cells, and the like.

In some embodiments, the recombinant nucleic acid is a herpes simplex viral vector. In some embodiments, the recombinant nucleic acid is a herpes simplex virus amplicon. In some embodiments, the recombinant nucleic acid is an HSV-1 amplicon or HSV-1 hybrid amplicon. In some embodiments, a host cell comprising a helper virus is contacted with an HSV-1 amplicon or HSV-1 hybrid amplicon described herein, resulting in the production of a virus comprising one or more recombinant nucleic acids described herein. In some embodiments, the virus is collected from the supernatant of the contacted host cell. Methods of generating virus by contacting host cells comprising a helper virus with an HSV-1 amplicon or HSV-1 hybrid amplicon are known in the art.

In some embodiments, the host cell is a complementing host cell. In some embodiments, the complementing host cell expresses one or more genes that are inactivated in any of the viral vectors described herein. In some embodiments, the complementing host cell is contacted with a recombinant herpes virus genome (e.g., a recombinant herpes simplex virus genome) described herein. In some embodiments, contacting a complementing host cell with a recombinant herpes virus genome results in the production of a herpes virus comprising one or more recombinant nucleic acids described herein. In some embodiments, the virus is collected from the supernatant of the contacted host cell. Methods of generating virus by contacting complementing host cells with a recombinant herpes simplex virus are generally described in U.S. Pat. No. 10,174,341, US 2019/0276845, U.S. Pat. Nos. 9,877,990, 10,155,016, 10,441,614, 11,185,564, US 2020/0093874, U.S. Pat. No. 10,525,090, US 2020/0197456, US 2021/0261649, US 2021/0395775, U.S. Pat. No. 10,829,529, US 2021/0087245, US 2021/0189427, U.S. Pat. No. 10,786,438, US 2021/0045988, and/or WO2021/046131, all of which are incorporated by reference herein in their entirety.

VIII. Articles of Manufacture or Kits

Certain aspects of the present disclosure relate to an article of manufacture or a kit comprising any of the recombinant nucleic acids, viruses, medicaments, and/or pharmaceutical compositions or formulations described herein. In some embodiments, the article of manufacture or kit comprises a package insert comprising instructions for administering the recombinant nucleic acid, virus, medicament, and/or pharmaceutical composition or formulation.

Suitable containers for the recombinant nucleic acids, viruses, medicaments, and/or pharmaceutical compositions or formulations may include, for example, bottles, vials, bags, tubes, and syringes. The container may be formed from a variety of materials such as glass, plastic (such as polyvinyl chloride or polyolefin), or metal alloy (such as stainless steel or hastelloy). In some embodiments, the container comprises a label on, or associated with the container, wherein the label indicates directions for use. The article of manufacture or kit may further include other materials desirable from a commercial and user standpoint, including other buffers, diluents, filters, inhalers, nebulizers, intranasal administration devices, a package insert, and the like.

IX. Enumerated Embodiments

Embodiment 1: a recombinant herpes virus genome comprising one or more polynucleotides encoding an immunomodulatory polypeptide.

Embodiment 2: the recombinant herpes virus genome of embodiment 1, wherein the recombinant herpes virus genome is replication competent.

Embodiment 3: the recombinant herpes virus genome of any of embodiments 1 or 2, wherein the recombinant herpes virus genome is replication defective.

Embodiment 4: the recombinant herpes virus genome of any of embodiments 1-3, wherein the recombinant herpes virus genome is selected from the group consisting of a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Epstein-Barr virus genome, a recombinant Kaposi's sarcoma-associated herpesvirus genome, and any derivatives thereof.

Embodiment 5: the recombinant herpes virus genome of any of embodiments 1-4, wherein the recombinant herpes virus genome is a recombinant herpes simplex virus genome.

Embodiment 6: the recombinant herpes virus genome of any of embodiments 1-5, wherein the recombinant herpes simplex virus genome is a recombinant herpes simplex virus type 1 (HSV-1) genome, a recombinant herpes simplex virus type 2 (HSV-2) genome, or any derivatives thereof.

Embodiment 7: the recombinant herpes virus genome of any of embodiments 1-6, wherein the recombinant herpes simplex virus genome is a recombinant herpes simplex virus type 1 (HSV-1) genome.

Embodiment 8: the recombinant herpes virus genome of any of embodiments 1-7, wherein the recombinant herpes simplex virus genome is a recombinant herpes simplex virus type 2 (HSV-2) genome.

Embodiment 9: the recombinant herpes virus genome of any of embodiments 1-8, wherein the recombinant herpes simplex virus genome has been engineered to reduce or eliminate expression of one or more toxic herpes simplex virus genes.

Embodiment 10: the recombinant herpes virus genome of any of embodiments 1-9, wherein the recombinant herpes simplex virus genome has been engineered to reduce and eliminate expression of one or more toxic herpes simplex virus genes.

Embodiment 11: the recombinant herpes virus genome of any of embodiments 1-10, wherein the recombinant herpes simplex virus genome comprises an inactivating mutation.

Embodiment 12: the recombinant herpes virus genome of any of embodiments 1-11, wherein the inactivating mutation is in a herpes simplex virus gene.

Embodiment 13: the recombinant herpes virus genome of any of embodiments 1-12, wherein the inactivating mutation is a deletion of the coding sequence of the herpes simplex virus gene.

Embodiment 14: the recombinant herpes virus genome of any of embodiments 1-13, wherein the herpes simplex virus gene is selected from the group consisting of Infected Cell Protein (ICP) 0, ICP4, ICP22, ICP27, ICP47, thymidine kinase (tk), Long Unique Region (UL) 41, and UL55.

Embodiment 15: the recombinant herpes virus genome of any of embodiments 1-14, wherein the herpes simplex virus gene is ICP4.

Embodiment 16: the recombinant herpes virus genome of any of embodiments 1-15, wherein the herpes simplex virus gene is ICP22.

Embodiment 17: the recombinant herpes virus genome of any of embodiments 1-16, wherein the recombinant herpes simplex virus genome comprises an inactivating mutation in one or both copies of the ICP4 gene.

Embodiment 18: the recombinant herpes virus genome of any of embodiments 1-17, wherein the recombinant herpes simplex virus genome comprises an inactivating mutation in one or both copies of the ICP4 gene.

Embodiment 19: the recombinant herpes virus genome of any of embodiments 1-18, wherein the recombinant herpes simplex virus genome comprises an inactivating mutation in the UL41 gene.

Embodiment 20: the recombinant herpes virus genome of any of embodiments 1-19, wherein the recombinant herpes simplex virus genome comprises an inactivating mutation in one or both copies of the ICP0 gene.

Embodiment 21: the recombinant herpes virus genome of any of embodiments 1-20, wherein the recombinant herpes simplex virus genome comprises an inactivating mutation in one copy of the ICP0 gene.

Embodiment 22: the recombinant herpes virus genome of any of embodiments 1-21: wherein the recombinant herpes simplex virus genome comprises an inactivating mutation in both copies of the ICP0 gene.

Embodiment 23: the recombinant herpes virus genome of any of embodiments 1-22, wherein the recombinant herpes simplex virus genome comprises an inactivating mutation in the ICP27 gene.

Embodiment 24: the recombinant herpes virus genome of any of embodiments 1-23, wherein the recombinant herpes simplex virus genome comprises an inactivating mutation in the UL55 gene.

Embodiment 25: the recombinant herpes virus genome of any of embodiments 1-24, wherein the recombinant herpes simplex virus genome does not comprise an inactivating mutation in the ICP47 gene.

Embodiment 26: the recombinant herpes virus genome of any of embodiments 1-25, wherein the recombinant herpes simplex virus does not comprise an inactivating mutation in one or both copies of the ICP34.5 gene.

Embodiment 27: the recombinant herpes virus genome of any of embodiments 1-26, wherein the recombinant herpes simplex virus does not comprise an inactivating mutation in one copy of the ICP34.5 gene.

Embodiment 28: the recombinant herpes virus genome of any of embodiments 1-27, wherein the recombinant herpes simplex virus does not comprise an inactivating mutation in both copies of the ICP34.5 gene.

Embodiment 29: the recombinant herpes virus genome of any of embodiments 1-28, wherein the recombinant herpes simplex virus genome comprises the one or more polynucleotides encoding the immunomodulatory polypeptide within one or both of the ICP4 viral gene loci.

Embodiment 30: the recombinant herpes virus genome of any of embodiments 1-29, wherein the recombinant herpes simplex virus genome comprises the one or more polynucleotides encoding the immunomodulatory polypeptide within one of the ICP4 viral gene loci.

Embodiment 31: the recombinant herpes virus genome of any of embodiments 1-30, wherein the recombinant herpes simplex virus genome comprises the one or more polynucleotides encoding the immunomodulatory polypeptide within both of the ICP4 viral gene loci.

Embodiment 32: the recombinant herpes virus genome of any of embodiments 1-31: wherein the recombinant herpes simplex virus genome comprises the one or more polynucleotides encoding the immunomodulatory polypeptide within the ICP22 viral gene locus.

Embodiment 33: the recombinant herpes virus genome of any of embodiments 1-32, wherein the recombinant herpes simplex virus genome comprises the one or more polynucleotides encoding the immunomodulatory polypeptide within the UL41 viral gene locus.

Embodiment 34: the recombinant herpes virus genome of any of embodiments 1-33, wherein the recombinant herpes simplex virus genome comprises the one or more polynucleotides encoding the immunomodulatory polypeptide within one or both of the ICP0 viral gene loci.

Embodiment 35: the recombinant herpes virus genome of any of embodiments 1-34, wherein the recombinant herpes simplex virus genome comprises the one or more polynucleotides encoding the immunomodulatory polypeptide within one of the ICP0 viral gene loci.

Embodiment 36: the recombinant herpes virus genome of any of embodiments 1-35, wherein the recombinant herpes simplex virus genome comprises the one or more polynucleotides encoding the immunomodulatory polypeptide within both of the ICP0 viral gene loci.

Embodiment 37: the recombinant herpes virus genome of any of embodiments 1-36, wherein the recombinant herpes simplex virus genome comprises the one or more polynucleotides encoding the immunomodulatory polypeptide within the ICP27 viral gene locus.

Embodiment 38: the recombinant herpes virus genome of any of embodiments 1-37, wherein the recombinant herpes simplex virus genome comprises the one or more polynucleotides encoding the immunomodulatory polypeptide within the UL55 viral gene locus.

Embodiment 39: the recombinant herpes virus genome of any of embodiments 1-38, wherein the immunomodulatory polypeptide is a human immunomodulatory polypeptide.

Embodiment 40: the recombinant herpes virus genome of any of embodiments 1-39, wherein the immunomodulatory polypeptide is a cytokine or chemokine.

Embodiment 41: the recombinant herpes virus genome of any of embodiments 1-40, wherein the cytokine is a pro-inflammatory cytokine.

Embodiment 42: the recombinant herpes virus genome of any of embodiments 1-42, wherein the cytokine is selected from the group consisting of Interleukin (IL)-1, IL-2, IL-7, IL-12, IL-13, IL-15, IL-17, IL-18, IL-28, IL-32, IL-33, IL-34, Tumor Necrosis Factor alpha (TNFα), Interferon gamma (IFNγ), Granulocyte Colony-Stimulating Factor (G-CSF), and Granulocyte-Macrophage Colony-Stimulating Factor (GM-CSF).

Embodiment 43: the recombinant herpes virus genome of any of embodiments 1-42, wherein the cytokine is IL-2.

Embodiment 44: the recombinant herpes virus genome of any of embodiments 1-43, wherein the cytokine is IL-12.

Embodiment 45: the recombinant herpes virus genome of any of embodiments 1-44, wherein the cytokine is G-CSF.

Embodiment 46: the recombinant herpes virus genome of any of embodiments 1-45, wherein the cytokine is GM-CSF.

Embodiment 47: the recombinant herpes virus genome of any of embodiments 1-46, wherein the cytokine is not GM-CSF.

Embodiment 48: the recombinant herpes virus genome of any of embodiments 1-47, wherein the IL-2 comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 3.

Embodiment 49: the recombinant herpes virus genome of any of embodiments 1-48, wherein the IL-12 comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NO: 5, SEQ ID NO: 6, and SEQ ID NO: 85.

Embodiment 50: the recombinant herpes virus genome of any of embodiments 1-49, wherein the chemokine is a pro-inflammatory chemokine.

Embodiment 51: the recombinant herpes virus genome of any of embodiments 1-50, wherein the chemokine is selected from the group consisting of Chemokine (C-X-C motif) Ligand 1 (CXCL1), CXCL2, CXCL8, CXCL9, CXCL11, CXCL16, C-C Motif Chemokine Ligand 2 (CCL2), CCL3, CCL4, CCL5, and CCL11.

Embodiment 52: the recombinant herpes virus genome of any of embodiments 1-51, wherein the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs: 1-30.

Embodiment 53: the recombinant herpes virus genome of any of embodiments 1-52, wherein the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs: 1-19.

Embodiment 54: the recombinant herpes virus genome of any of embodiments 1-53, wherein the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs: 20-30.

Embodiment 55: the recombinant herpes virus genome of any of embodiments 1-54, wherein the recombinant herpes virus genome has reduced cytotoxicity when introduced into a target cell as compared to a corresponding wild-type herpes virus genome.

Embodiment 56: the recombinant herpes virus genome of any of embodiments 1-55, wherein the target cell is a human cell.

Embodiment 57: the recombinant herpes virus genome of any of embodiments 1-56, wherein the target cell is a cell of the respiratory tract.

Embodiment 58: the recombinant herpes virus genome of any of embodiments 1-57, wherein the target cell is an airway epithelial cell.

Embodiment 59: a herpes virus comprising the recombinant herpes virus genome of any of embodiments 1-58.

Embodiment 60: the herpes virus of embodiment 59, wherein the herpes virus is replication competent.

Embodiment 61: the herpes virus of embodiment 59 or 60, wherein the herpes virus is replication defective.

Embodiment 62: the herpes virus of any of embodiments 59-61, wherein the herpes virus is not oncolytic.

Embodiment 63: the herpes virus of any of embodiments 59-62, wherein the herpes virus has reduced cytotoxicity as compared to a corresponding wild-type herpes virus.

Embodiment 64: the herpes virus of any of embodiments 59-63, wherein the herpes virus is selected from the group consisting of a herpes simplex virus, a varicella zoster virus, a human cytomegalovirus, a herpesvirus 6A, a herpesvirus 6B, a herpesvirus 7, an Epstein-Barr virus, and a Kaposi's sarcoma-associated herpesvirus.

Embodiment 65: the herpes virus of any of embodiments 59-64, wherein the herpes virus is a herpes simplex virus.

Embodiment 66: the herpes virus of any of embodiments 59-65, wherein the herpes simplex virus is a herpes simplex virus type 1 (HSV-1), a herpes simplex virus type 2 (HSV-2), or any derivatives thereof.

Embodiment 67: the herpes virus of any of embodiments 59-66, wherein the herpes simplex virus is a herpes simplex virus type 1 (HSV-1).

Embodiment 68: the herpes virus of any of embodiments 59-67, wherein the herpes simplex virus is a herpes simplex virus type 2 (HSV-2).

Embodiment 69: the herpes virus of any of embodiments 59-68, wherein the herpes simplex virus is not oncolytic.

Embodiment 70: a pharmaceutical composition comprising the recombinant herpes virus genome of any of embodiments 1-58 or the herpes virus of any of embodiments 59-69 and a pharmaceutically acceptable excipient.

Embodiment 71: the pharmaceutical composition of embodiment 70, wherein the pharmaceutical composition is suitable for topical, transdermal, subcutaneous, intradermal, oral, intranasal, intratracheal, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration.

Embodiment 72: the pharmaceutical composition of embodiment 70 or 71, wherein the pharmaceutical composition is suitable for oral, intranasal, intratracheal, or inhaled administration.

Embodiment 73: the pharmaceutical composition of any of embodiments 70-72, wherein the pharmaceutical composition is suitable for intranasal or inhaled administration.

Embodiment 74: the pharmaceutical composition of any of embodiments 70-73, wherein the pharmaceutical composition is suitable for inhaled administration.

Embodiment 75: the pharmaceutical composition of any of embodiments 70-74, wherein the pharmaceutical composition is suitable for intranasal administration.

Embodiment 76: the pharmaceutical composition of any of embodiments 70-75, wherein the pharmaceutical composition is suitable for use in a dry powder inhaler, a pressurized metered dose inhaler, a soft mist inhaler, a nebulizer, an electrohydrodynamic aerosol device, or any combinations thereof.

Embodiment 77: the pharmaceutical composition of any of embodiments 70-76, wherein the pharmaceutical composition is suitable for use in a nebulizer.

Embodiment 78: the pharmaceutical composition of any of embodiments 70-77, wherein the nebulizer is a vibrating mesh nebulizer.

Embodiment 79: the herpes virus of any one of embodiments 59-69 or the pharmaceutical composition of any of embodiments 70-78 for use as a medicament.

Embodiment 80: the herpes virus of any of embodiments 59-69 or the pharmaceutical composition of any of embodiments 70-78 for use in a therapy.

Embodiment 81: use of the herpes virus of any of embodiments 59-69 or the pharmaceutical composition of any of embodiments 70-78 in the manufacture of a medicament for treating cancer.

Embodiment 82: the use of embodiment 81, wherein the cancer is selected from the group consisting of acute myeloid leukemia, acute lymphoblastic leukemia, adrenocortical carcinoma, bladder urothelial cancer, brain stem glioma, brain lower grade glioma, brain tumor, breast cancer, bronchial tumors, Burkitt lymphoma, cancer of unknown primary site, carcinoid tumor, carcinoma of unknown primary site, central nervous system atypical teratoid/rhabdoid tumor, central nervous system embryonal tumors, cervical squamous cell carcinoma, endocervical adenocarcinoma cancer, childhood cancers, cholangiocarcinoma, chordoma, chronic lymphocytic leukemia, chronic myelogenous leukemia, chronic myeloproliferative disorders, colon cancer, colorectal cancer, craniopharyngioma, cutaneous T-cell lymphoma, endocrine pancreas islet cell tumors, endometrial cancer, ependymoblastoma, ependymoma, esophageal cancer, esthesioneuroblastoma, Ewing sarcoma, extracranial germ cell tumor, extragonadal germ cell tumor, extrahepatic bile duct cancer, gallbladder cancer, gastric cancer, gastrointestinal carcinoid tumor, gastrointestinal stromal cell tumor, gastrointestinal stromal tumor, gestational trophoblastic tumor, glioblastoma multiforme glioma, hairy cell leukemia, head and neck cancer, heart cancer, Hodgkin lymphoma, hypopharyngeal cancer, intraocular melanoma, islet cell tumors, Kaposi sarcoma, kidney cancer, Langerhans cell histiocytosis, laryngeal cancer, lip cancer, liver cancer, Lymphoid Neoplasm Diffuse Large B-cell Lymphoma, malignant fibrous histiocytoma bone cancer, medulloblastoma, medulloepithelioma, melanoma, Merkel cell carcinoma, Merkel cell skin carcinoma, mesothelioma, metastatic squamous neck cancer with occult primary, mouth cancer, multiple endocrine neoplasia syndromes, multiple myeloma, multiple myeloma/plasma cell neoplasm, mycosis fungoides, myelodysplastic syndromes, myeloproliferative neoplasms, nasal cavity cancer, nasopharyngeal cancer, neuroblastoma, Non-Hodgkin lymphoma, nonmelanoma skin cancer, non-small cell lung cancer, oral cancer, oral cavity cancer, oropharyngeal cancer, osteosarcoma, other brain and spinal cord tumors, ovarian cancer, ovarian epithelial cancer, ovarian germ cell tumor, ovarian low malignant potential tumor, pancreatic cancer, papillomatosis, paranasal sinus cancer, parathyroid cancer, pelvic cancer, penile cancer, pharyngeal cancer, pheochromocytoma and paraganglioma, pineal parenchymal tumors of intermediate differentiation, pineoblastoma, pituitary tumor, plasma cell neoplasm/multiple myeloma, pleuropulmonary blastoma, primary central nervous system lymphoma, primary hepatocellular liver cancer, prostate cancer such as prostate adenocarcinoma, rectal cancer, renal cancer, renal cell cancer, renal cell cancer, respiratory tract cancer, retinoblastoma, rhabdomyosarcoma, salivary gland cancer, sarcoma, Sezary syndrome, skin cutaneous melanoma, small cell lung cancer, small intestine cancer, soft tissue sarcoma, squamous cell carcinoma, squamous neck cancer, stomach cancer, supratentorial primitive neuroectodermal tumors, T-cell lymphoma, testicular cancer testicular germ cell tumors, throat cancer, thymic carcinoma, thymoma, thyroid cancer, transitional cell cancer, transitional cell cancer of the renal pelvis and ureter, trophoblastic tumor, ureter cancer, urethral cancer, uterine cancer, uterine cancer, uveal melanoma, vaginal cancer, vulvar cancer, Waldenstrom macroglobulinemia, and Wilms' tumor.

Embodiment 83: a method of expressing, enhancing, increasing, augmenting, and/or supplementing the levels of an immunomodulatory polypeptide in one or more cells of a subject, the method comprising administering to the subject an effective amount of the herpes virus of any of embodiments 59-69 or the pharmaceutical composition of any of embodiments 70-78.

Embodiment 84: the method of embodiment 83, wherein the one or more cells are one or more cells of the respiratory tract, airway epithelial, and/or lung.

Embodiment 85: the method of any of embodiments 83 or 84, wherein the one or more cells are one or more cells of the respiratory tract.

Embodiment 86: the method of any of embodiments 83-85, wherein the one or more cells are one or more cells of the airway epithelial.

Embodiment 87: the method of any of embodiments 83-86, wherein the one or more cells are one or more cells of the lung.

Embodiment 88: a method of providing prophylactic, palliative, or therapeutic relief of one or more signs or symptoms of cancer in a subject in need thereof, the method comprising administering to the subject an effective amount of the herpes virus of any of embodiments 59-69 or the pharmaceutical composition of any of embodiments 70-78.

Embodiment 89: a method of treating cancer in a subject in need thereof, the method comprising administering to the subject an effective amount of the herpes virus of any of embodiments 59-69 or the pharmaceutical composition of any of embodiments 70-78.

Embodiment 90: the method of any of embodiments 88 or 89, wherein the cancer is selected from the group consisting of carcinoma, lymphoma, blastoma, sarcoma, a neuroendocrine tumor, mesothelioma, schwannoma, meningioma, adenocarcinoma, melanoma, leukemia, and lymphoid malignancy.

Embodiment 91: the method of any of embodiments 88-90, wherein the cancer is selected from the group consisting of a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, and thyroid cancer.

Embodiment 92: the method of any of embodiments 88-91, wherein the cancer is small-cell lung cancer, non-small cell lung cancer, adenocarcinoma of the lung, or squamous carcinoma of the lung.

Embodiment 93: the method of any of embodiments 88-92, wherein the cancer is small-cell lung cancer.

Embodiment 94: the method of any of embodiments 88-93, wherein the cancer is non-small cell lung cancer.

Embodiment 95: the method of any of embodiments 88-94, wherein the cancer is adenocarcinoma of the lung.

Embodiment 96: the method of any of embodiments 88-95, wherein the cancer is squamous carcinoma of the lung.

Embodiment 97: the method of any of embodiments 88-96, wherein the cancer is osteosarcoma.

Embodiment 98: the method of any of embodiments 88-97, wherein the subject is a human.

Embodiment 99: the method of any of embodiments 88-98, wherein the herpes virus or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, peri-articularly, intratumorally, locally, or via inhalation to the subject.

Embodiment 100: the method of any of embodiments 88-99, wherein the herpes virus or pharmaceutical composition is administered orally, intranasally, intratracheally, or via inhalation to the subject.

Embodiment 101: the method of any of embodiments 88-100, wherein the herpes virus or pharmaceutical composition is administered intranasally or via inhalation to the subject.

Embodiment 102: the method of any of embodiments 88-101, wherein the herpes virus or pharmaceutical composition is administered intranasally to the subject.

Embodiment 103: the method of any of embodiments 88-102, wherein the herpes virus or pharmaceutical composition is administered via inhalation to the subject.

Embodiment 104: the method of any of embodiments 88-103, wherein the herpes virus or pharmaceutical composition is administered using a dry powder inhaler, a pressurized metered dose inhaler, a soft mist inhaler, a nebulizer, or an electrohydrodynamic aerosol device.

Embodiment 105: the method of any of embodiments 88-104, wherein the herpes virus or pharmaceutical composition is administered using a nebulizer.

Embodiment 106: the method of any of embodiments 88-105, wherein the nebulizer is a vibrating mesh nebulizer.

The specification is considered to be sufficient to enable one skilled in the art to practice the present disclosure. Various modifications of the present disclosure in addition to those shown and described herein will become apparent to those skilled in the art from the foregoing description and fall within the scope of the appended claims.

EXAMPLES

The present disclosure will be more fully understood by reference to the following examples. It should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Figure 1B:
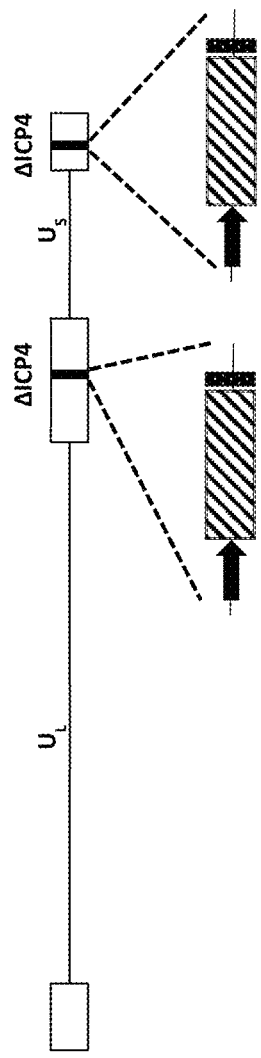
Figure 1E:
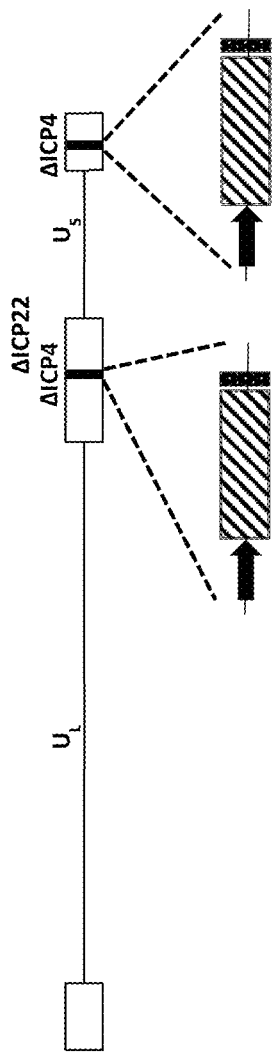
Figure 1F:
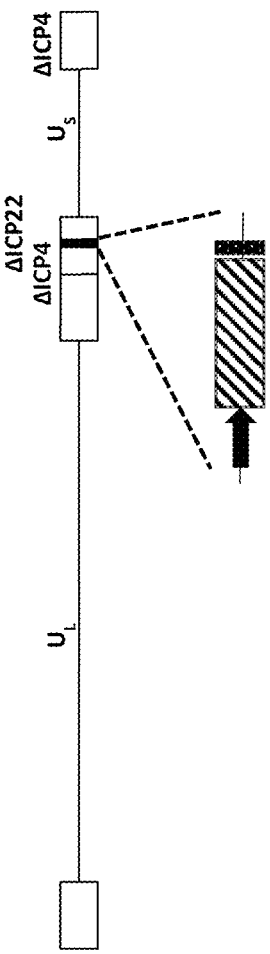
Figure 1G:
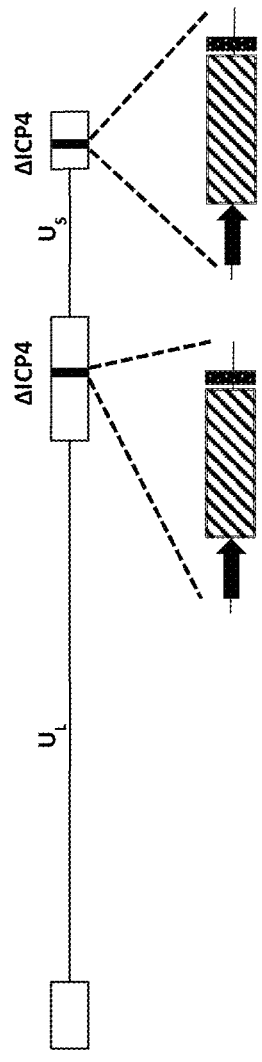
Figure 1H:
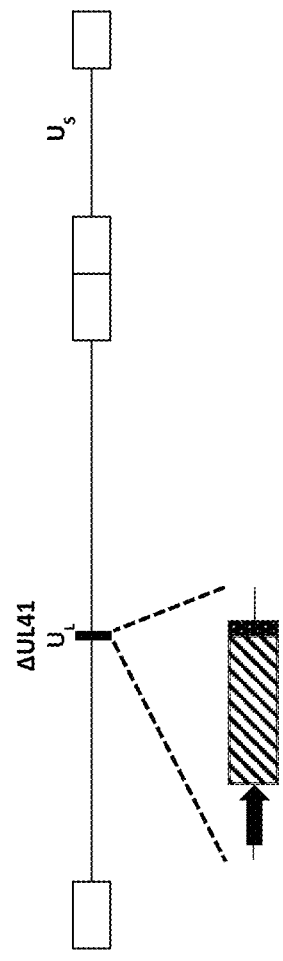
Figure 1I:
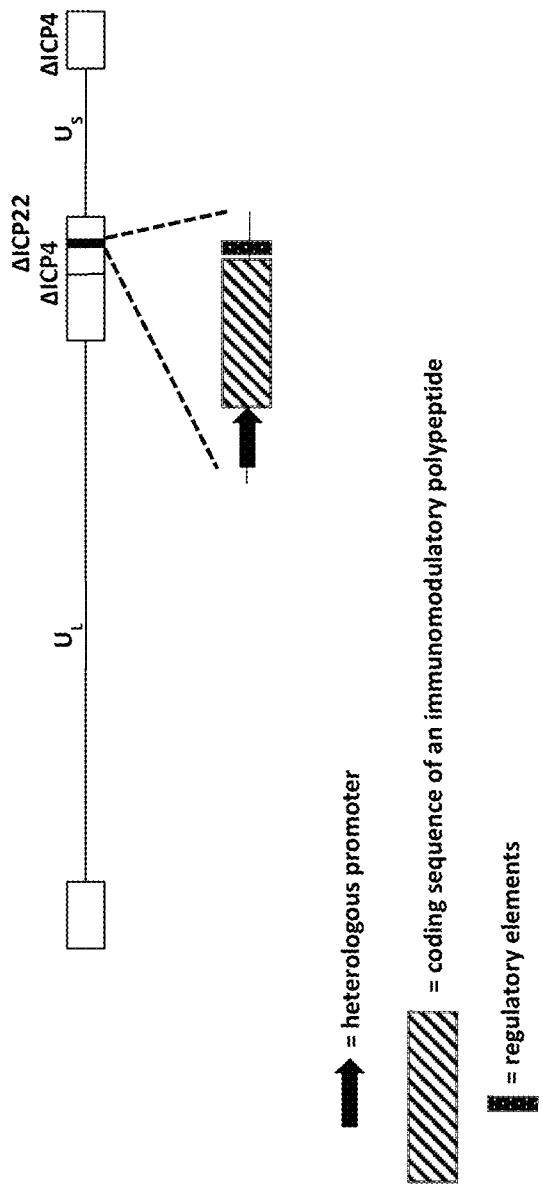

Example 1: Modified Herpes Simplex Virus Vectors Encoding an Immunomodulatory Polypeptide To make modified herpes simplex virus genome vectors capable of expressing immunomodulatory polypeptides in a target mammalian cell (such as cells of the respiratory tract), a herpes simplex virus genome (FIG. 1A) is first modified to inactivate one or more herpes simplex virus genes. Such modifications may decrease the toxicity of the genome in mammalian cells. Next, variants of these modified/attenuated recombinant viral constructs are generated such that they carry one or more polynucleotides encoding the desired immunomodulatory polypeptide. These variants include: a recombinant ΔICP4-modified HSV-1 genome comprising expression cassettes containing the coding sequence of an immunomodulatory polypeptide (e.g., SEQ ID NO: 3) under the control of a heterologous promoter integrated at each ICP4 locus (FIG. 1B); a recombinant ΔICP4/ΔUL41-modified HSV-1 genome comprising expression cassettes containing the coding sequence of an immunomodulatory polypeptide (e.g., SEQ ID NO: 3) under the control of a heterologous promoter integrated at each ICP4 locus (FIG. 1C); a recombinant ΔICP4/ΔUL41-modified HSV-1 genome comprising an expression cassette containing the coding sequence of an immunomodulatory polypeptide (e.g., SEQ ID NO: 3) under the control of a heterologous promoter integrated at the UL41 locus (FIG. 1D); a recombinant ΔICP4/ΔICP22-modified HSV-1 genome comprising expression cassettes containing the coding sequence of an immunomodulatory polypeptide (e.g., SEQ ID NO: 3) under the control of a heterologous promoter integrated at each ICP4 locus (FIG. 1E); a recombinant ΔICP4/ΔICP22-modified HSV-1 genome comprising an expression cassette containing the coding sequence of an immunomodulatory polypeptide (e.g., SEQ ID NO: 3) under the control of a heterologous promoter integrated at the ICP22 locus (FIG. 1F); a recombinant ΔICP4/ΔUL41/ΔICP22-modified HSV-1 genome comprising expression cassettes containing the coding sequence of an immunomodulatory polypeptide (e.g., SEQ ID NO: 3) under the control of a heterologous promoter integrated at each ICP4 locus (FIG. 1G); a recombinant ΔICP4/ΔUL41/ΔICP22-modified HSV-1 genome comprising an expression cassette containing the coding sequence of an immunomodulatory polypeptide (e.g., SEQ ID NO: 3) under the control of a heterologous promoter integrated at the UL41 locus (FIG. 1H); and a recombinant ΔICP4/ΔUL41/ΔICP22-modified HSV-1 genome comprising an expression cassette containing the coding sequence of an immunomodulatory polypeptide (e.g., SEQ ID NO: 3) under the control of a heterologous promoter integrated at the ICP22 locus (FIG. 1I).

These modified herpes simplex virus genome vectors are transfected into engineered cells that are modified to express one or more herpes simplex virus genes. These engineered cells secrete into the supernatant of the cell culture a replication-defective herpes simplex virus with the modified genomes packaged therein. The supernatant is then collected, concentrated, and sterile filtered.

Modified herpes simplex virus genome vectors described herein can express any one or more of the exemplary immunomodulatory polypeptides in Table 1 below, in any suitable combination.

TABLE 1

Representative Immunomodulatory Polypeptides

| Amino acid SEQ ID NO. | Protein Name | UniProt Accession No. | Nucleic acid SEQ ID NO. | Gene Name | NCBI Gene ID No. |
|---|---|---|---|---|---|
| 1 | IL-1α | P01583 | 31 | IL1A | 3552 |
| 2 | IL-1β | P01584 | 32 | Il1B | 3553 |
| 3 | IL-2 | P60568 | 33 | IL2 | 3558 |
| 4 | IL-7 | P13232 | 34 | IL7 | 3574 |
| 5 | IL-12 subunit α | P29459 | 35 | IL12A | 3592 |
| 6 | IL-12 subunit β | P29460 | 36 | IL12B | 3593 |
| 7 | IL-13 | P35225 | 37 | IL13 | 3596 |
| 8 | IL-15 | P40933 | 38 | IL15 | 3600 |
| 9 | IL-17A | Q16552 | 39 | IL17A | 3605 |
| 10 | IL-18 | Q14116 | 40 | IL18 | 3606 |
| 11 | IL-28A Interferon lambda-2 | Q8IZJ0 | 41 | IFNL2 | 282616 |
| 12 | IL-28B Interferon lambda-3 | Q8IZI9 | 42 | IFNL3 | 282617 |
| 13 | IL-32 | P24001 | 43 | IL32 | 9235 |
| 14 | IL-33 | O95760 | 44 | IL33 | 90865 |
| 15 | IL-34 | Q6ZMJ4 | 45 | IL34 | 146433 |
| 16 | TNFα | P01375 | 46 | TNF | 7124 |
| 17 | IFNγ | P01579 | 47 | IFNG | 3458 |
| 18 | Granulocyte Colony-Stimulating Factor (G-CSF) | P09919 | 48 | CSF3 | 1440 |
| 19 | Granulocyte-Macrophage Colony-Stimulating Factor (GM-CSF) | P04141 | 49 | CSF2 | 1437 |
| 20 | Chemokine (C-X-C motif) Ligand 3 (CXCL1) | P09341 | 50 | CXCL1 | 2919 |
| 21 | CXCL2 | P19875 | 51 | CXCL2 | 2920 |
| 22 | CXCL8 | P10145 | 52 | CXCL8 | 3576 |
| 23 | CXCL9 | Q07325 | 53 | CXCL9 | 4283 |
| 24 | CXCL11 | O14625 | 54 | CXCL11 | 6373 |
| 25 | CXCL16 | Q9H2A7 | 55 | CXCL16 | 58191 |
| 26 | C-C Motif Chemokine Ligand 2 (CCL2) | P13500 | 56 | CCL2 | 6347 |
| 27 | CCL3 | P10147 | 57 | CCL3 | 6348 |
| 28 | CCL4 | P13236 | 58 | CCL4 | 3883726351 |
| 29 | CCL5 | P13501 | 59 | CCL5 | 6352 |
| 30 | CCL11 | P51671 | 60 | CCL11 | 6356 |

Example 2: Construction of a Modified Herpes Simplex Virus Vector Encoding Human IL-12, IL-2, and GM-CSF The following example describes the engineering of a recombinant herpes simplex virus type 1 (HSV-1) that successfully encoded human IL-12 (see e.g. SEQ ID Nos: 35 and 36; HSV-IL12), IL-2 (see e.g. SEQ ID NO: 33; HSV-IL2), or GM-CSF (see e.g. SEQ ID NO: 49; HSV-GMCSF) and expressed full-length human IL-12 (see e.g. SEQ ID Nos: 5 and 6), IL-2 (see e.g. SEQ ID NO: 3), or GM-CSF (see e.g. SEQ ID NO: 19) protein.

A recombinant HSV-1 was engineered to incorporate a human IL-12, IL-2, or GM-CSF expression cassette containing a heterologous promoter and polyA sequence (see Example 1). Viral plaques putatively containing the human IL-12, IL-2, or GM-CSF cassette were picked and screened by infection in a complementing cell line to test for human IL-12, IL-2, and GM-CSF protein expression via western blot analysis (data not shown). High expressing clones, termed HSV-IL12, HSV-IL2, and HSV-GMCSF, were subsequently selected for additional in vitro analysis.

Figure 2A:
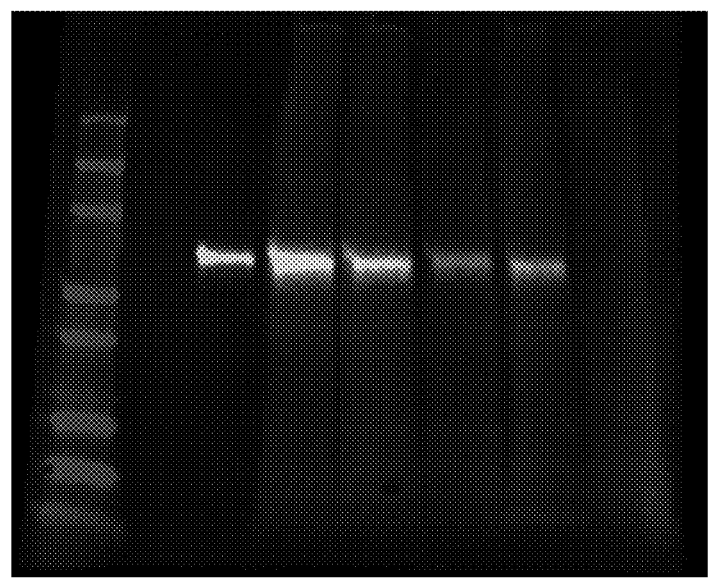
FIGS. 2A-2B depict western blot detection of human IL-12 and IL-2 in uninfected control cells (mock) or cells infected with a modified herpes simplex virus encoding human IL-12 (FIG. 2A) or IL-2 (FIG. 2B) transgene at a multiplicity of infection (MOI) of 1. Recombinant human IL-12 (FIG. 2A) or IL-2 (FIG. 2B) was used as a positive control.
Figure 2B:
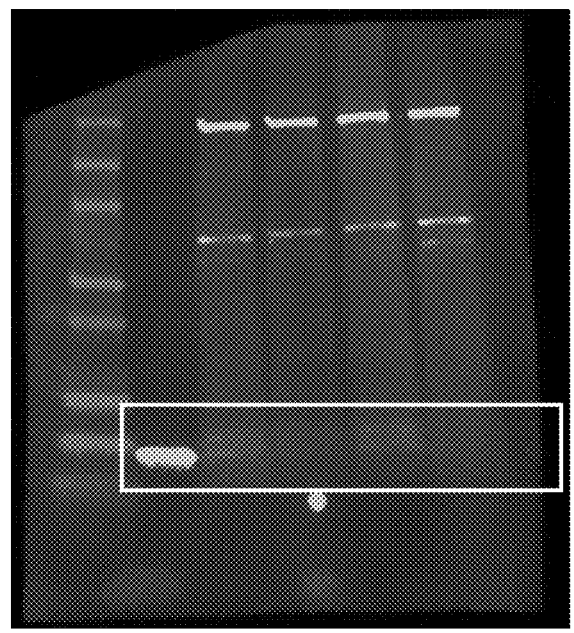

Complementing cells were mock infected with vehicle control or were infected with HSV-IL12, HSV-IL2, or HSV-GMCSF at a multiplicity of infection (MOI) of 1 in serum free cell culture medium. 24- or 48-hours post-infection, cell pellets were harvested, lysed in RIPA buffer containing protease inhibitors, and protein content was quantified via a BCA assay. 30-40 µg of each sample was loaded and run on a 4-20% acrylamide gel, and expression of the HSV-encoded human protein was assessed via western blot analysis (FIGS. 2A-2B). Recombinant human IL-12 or IL-2 was loaded on the gel as a positive control. While no human IL-12 or IL-2 was detected in the uninfected control cells, robust expression of human IL-12 (FIG. 2A) and IL-2 (FIG. 2B) was observed after infection with HSV-IL12 and HSV-IL2, respectively, in cells.

Because IL-12, IL-2, and GM-CSF are naturally secreted proteins, cell culture supernatants were also harvested and tested for the presence of the human protein by ELISA. In line with the western blot data, human IL-12 (2.01 µg/ml and 2.58 µg/ml), IL-2 (0.531 µg/ml, 0.850 µg/ml, and 1.200 µg/ml), and GM-CSF (643.427 ng/ml, 513.56 ng/ml, and 200.167 ng/ml) were detected in the supernatants of cells infected with HSV-IL12, HSV-IL2, and HSV-GMCSF, respectively, at the MOIs tested, suggesting that the full-length human protein was being properly processed/secreted after expression from the recombinant vector.

Taken together, the data presented in this example indicated that the recombinant HSV-1 vectors HSV-IL12, HSV-IL2, and HSV-GMCSF efficiently infected multiple cell types and were capable of expressing the human transgene encoded therein. Furthermore, the data indicated that the exogenous human protein was subsequently (properly) secreted from infected cells. Without wishing to be bound by theory, it is believed that this data further supports the use of engineered herpes simplex viruses as novel, targeted, broadly applicable gene therapy vectors for the treatment of various cancers (e.g. osteosarcoma).

Example 3: In Vitro Human and Mouse IL-12 Bioactivity Assay

The objective of this study was, in part, to determine if the recombinant human and/or murine IL-12 protein made from a recombinant herpes simplex virus type 1 (HSV-1) was as bioactive as commercially available recombinant IL-12 protein.

Figure 3A:
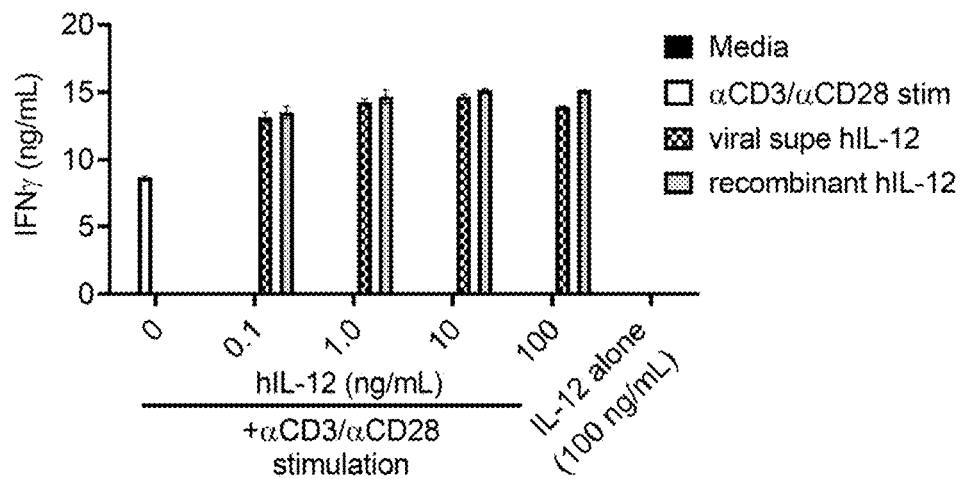
FIGS. 3A-3B depict an in vitro bioactivity assay of human (FIG. 3A) and mouse (FIG. 3B) HSV-IL12 as a function of IFNγ release from human PBMCs (FIG. 3A) or mouse splenocytes (FIG. 3B). Data indicative of cells assayed in triplicate, and data are presented as mean±standard deviation (SD), n=1.
Figure 3B:
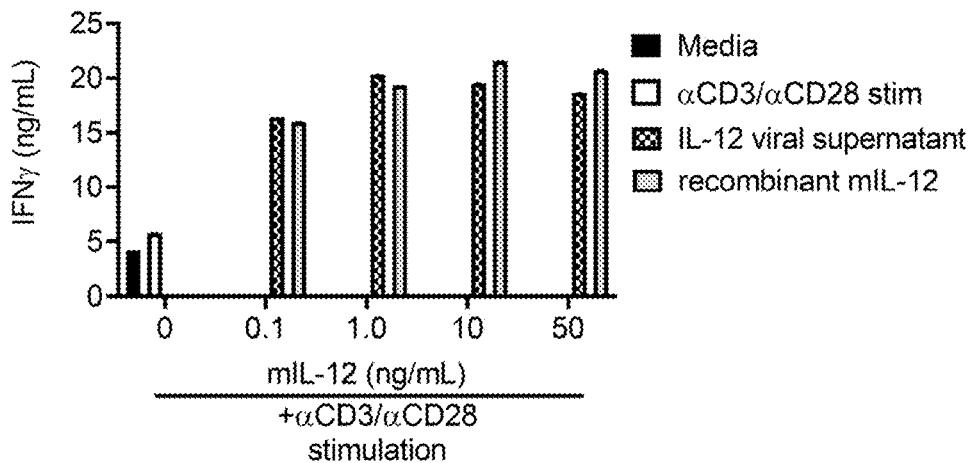

Human embryonic kidney 293 (HEK293) cells were infected at an MOI=1 with HSV-IL12 for 48 hours. IL-12 concentrations in supernatants from HEK293 infections were determined by ELISA. Human PBMCs and murine splenocytes were cultured in complete RPMI or DMEM, respectively, and maintained at 37° C. at 5% $CO_2$ in a humid environment. Commercially available human or murine αCD3/αCD28 coated beads were washed and added to PBMC or splenocyte cultures, respectively, at an amount of 2 µL per well. As indicated in FIGS. 3A-3B, serial dilutions of supernatants from HEK293 infections with human or murine HSV-IL12 were added to PBMC or splenocyte cultures in conjunction with αCD3/αCD28 coated beads. Commercially available recombinant IL-12 protein was added to some cultures at similar concentrations as a comparison. 24 hours post-stimulation, PBMC or murine splenocyte culture supernatants were harvested and assayed by ELISA for IFNγ production.

As shown in FIGS. 3A-3B, the addition of αCD3/αCD28 coated beads resulted in the release of IFNγ from both human PBMCs (FIG. 3A) and murine splenocytes (FIG. 3B). In comparison, the addition of viral supernatant from both human HSV-IL12 and murine HSV-IL12 to the αCD3/αCD28 stimulated human PBMCs (FIG. 3A) and murine splenocytes (FIG. 2B) induced greater levels of IFNγ secretion when compared to αCD3/αCD28 stimulation alone. Further, the HSV-IL12 dependent release of IFNγ was comparable to that of recombinant IL-12 (FIGS. 3A-3B).

Taken together, these results suggested the recombinant human and murine IL-12 protein made from the recombinant herpes simplex virus was as bioactive as commercially available recombinant IL-12 protein.

Example 4: Intratracheal Administration and In Vivo Evaluation of HSV-IL12 in Healthy Mice More recently in cancer treatment, immunotherapy or targeting the immune system, has shown great promise at reducing tumor burden. Specifically, administration of recombinant Interleukin(IL)-12 protein, a potent proinflammatory cytokine, has been assessed. IL-12 is a heterodimeric cytokine comprised of the p35 and p40 subunits linked by three disulfide bridges. As a proinflammatory cytokine, IL-12 is primarily produced by activated antigen presenting cells (e.g., macrophages and dendritic cells), stimulating increased Interferon-γ (IFNγ) production by T cells and Natural Killer (NK) cells. In turn, IFNγ is then capable of initiating tumor cell apoptosis, upregulating tumor cell antigen presentation, and inducing macrophage tumoricidal activity, among other effects. Research over the past few decades has indicated that IL-12 is a potent stimulator of anti-tumor immune responses, supporting its use as a cancer therapy. However, previous clinical trials have shown that systemic IL-12 treatments in cancer patients result in high levels of toxicity.

We have utilized a non-replicating HSV-1-based gene therapy vector to develop a modified vector that encodes the il12a and il12b genes (HSV-IL12) for the p35 and p40 subunits, respectively. Infection with HSV-IL12 resulted in expression of the IL-12 p70 heterodimer, with the subunits covalently linked by a G4S linker. In vitro studies comparing virally produced and recombinant IL-12 protein indicated similar efficacy at inducing IFNγ expression (see Example 3 above) during activation of murine splenic T cells.

As these studies confirmed transgene bioactivity, the next step was to test HSV-IL12 in vivo. The present study evaluated IL-12 expression, in conjunction with toxicity, following a single dose of HSV-IL12 administered intratracheally (i.t.) to young (8-10 weeks) BALB/c animals. Three different doses of HSV-IL12 were assessed for IL-12 expression by nucleic acid and protein analysis in the lung tissue, bronchoalveolar lavage fluid (BALF), and serum. Toxicity was measured by reductions in overall body weight over the course of the study (24- and 48-hours post-administration). Additionally, a group of animals received recombinant IL-12 protein systemically (subcutaneous; s.c.) as a means of comparing local HSV-IL12 delivery to previously studied administration routes.

All procedures conducted were in compliance with applicable animal welfare acts and were approved by the local Institutional Animal Care and Use Committee (IACUC). 22-28 healthy, 8-week-old female BALB/c mice were used in this study.

Mice were sedated with an intraperitoneal mix of Telazol and Dexdomitor. Sedation was determined by using the toe pinch reflex test. Eye ointment (Puralube Vet) was applied on the eyes to prevent dryness. The animals were placed on a metal tray on a supportive table for dosing.

Intratracheal (i.t.) administration was performed by thawing the viral vector on wet ice, diluting in vehicle to achieve the appropriate titers, and administering in 50 μL doses. The lower jaw and tongue were gently moved away with tweezers to expose the epiglottis and larynx. A ~4.5 cm catheter tube was inserted halfway into the trachea, and a 23G needle connected to the syringe was attached at the top of the catheter to administer the dose. Negative control mice were injected i.t. with vehicle alone. Following administration, animals were monitored during recovering from anesthesia.

Additionally, a group of animals received a subcutaneous (s.c.) injection of recombinant IL-12 protein (0.5 mg diluted in 1×PBS) as a systemic route of administration. This dose was chosen as it was demonstrated to be toxic in mice. For administration, awake animals were scruffed and the dose was administered behind the neck using a 1 mL syringe and 27G needle.

At the indicated timepoints after i.t. or s.c. administration of the above treatments, animals were euthanized by $CO_2$ asphyxiation, and a cardiac puncture was performed to collect blood in serum separator tubes (BD Biosciences). Tubes were centrifuged to pellet red blood cells and the serum was removed and snap frozen in Eppendorf tubes. Then, animals were perfused with 40 mL cold 1×PBS at a rate of 20 mL per minute. Brochoalveolar lavage (BAL) was performed using 2 mL of 1×PBS. Recovery volumes were recorded for each animal. BAL samples were centrifuged to remove cells and the BAL fluid (BALF) was collected to be assayed. 100× protease inhibitors (Fisher Scientific) were added to all BALF samples at a final concentration of 1×. Left and right lungs were then excised and snap frozen in liquid nitrogen for protein and nucleic acid analysis.

Resuspended BAL cell pellets were centrifuged at 2000 rpm for 5 minutes and supernatants removed and discarded. Residual red blood cells were lysed using 1× Red Blood Cell lysis buffer (Sigma) (incubated at room temperature for 2 minutes). 500 μL of 1×PBS was added to stop the lysis reaction and cells were centrifuged as described above. Supernatants were removed and cells were resuspended in 100-500 μL 1×PBS depending on the size of the cell pellet. An aliquot of each sample was diluted in Trypan Blue (Fisher Scientific) and cell number and viability were assessed using a hemocytometer.

Snap-frozen lungs were stored at −80° C. until processing. On the day of processing, frozen lungs were biopsied using a razor blade, quickly weighed, and returned to dry ice. Two biopsies were cut, one for RNA/DNA work and one for making homogenates for ELISA. Biopsies for nucleic acid analysis were immediately resuspended in 350 μL RLT buffer prepared with fresh DTT according to the manufacturer's protocol (Qiagen). Biopsies for protein analysis were resuspended in 3004 of Pierce's TPER reagent (Fisher Scientific) supplemented with 1× protease inhibitors (Fisher Scientific). A 5 mm metal bead was added to each tube, and samples were homogenized with a Tissue Lyser (Qiagen) at 25 Hz for 3 minutes. Nucleic acids were immediately extracted and protein homogenates were processed as follows: samples were centrifuged for 5 minutes at 10,000×g to pellet debris; supernatants were collected and aliquoted into Eppendorf tubes. Homogenates were stored at −20° C. until ELISA and BCA assay.

DNA and RNA extractions were performed using the Qiagen AllPrep DNA/RNA extraction kit according to the manufacturer's protocol. Both DNA and RNA samples were eluted in distilled deionized RNase free water. Residual genomic DNA was eliminated from RNA samples using the TURBO DNA kit (Invitrogen) using the manufacturer's instructions. All nucleic acids were quantified spectrophotometrically on a Nanodrop (BioTek). Absolute quantification of il12 DNA genomes and RNA transcripts was performed by TaqMan Real Time PCR analysis using custom, transgene-specific primer/probe pairs. A 20×il12 primer/probe mix containing 45 nmoles each of the forward and reverse primers and 12.5 nmoles of the probe were diluted to 1× in each reaction to achieve the final primer and probe concentrations. RNA was reverse transcribed into cDNA using MultiScribe Reverse Transcriptase (Applied Biosystems) prior to qRT-PCR analysis.

Taqman® Fast Advanced Master Mix (Applied Biosystems) was used for DNA (qPCR) and RNA quantification (qRT-PCR). 50 ng of DNA or cDNA were used for the qPCR and qRT-PCR assays, respectively. All samples were run in duplicate, and copy number was determined using a standard curve derived from a dilution series of gBlock standard containing a known copy number of the il12 transgene.

Prior to ELISA, protein concentration of lung homogenates was determined by BCA assay (Pierce). For ELISA, all reagents used were obtained from R&D Systems. Lung homogenates, BALF, and serum were then assayed on ELISA plates that were coated overnight with αIL-12 capture antibody according to the manufacturer's instructions. After blocking the plates with 1× reagent diluent for 1 hour at room temperature, samples and standards were diluted accordingly in reagent diluent and assayed in duplicate (50 μL per well). Samples were incubated on plates for 2 hours at room temperature with shaking. After incubation, plates were washed with 1× wash buffer 3 times with blotting between each wash.

Biotinylated detection antibody was diluted in reagent diluent to the working concentration specified in the protocol and 100 μL added to each well. Samples were incubated at room temperature for 2 hours with shaking. Following incubation, plates were washed as described above, and 40× streptavidin was diluted in reagent diluent to 1×. 100 μL was added to each well and plates were incubated at room temperature in the dark for 20 minutes. Plates were washed again and then developed using TMB substrate for 20 minutes in the dark. Reactions were quenched with 2N $H_2SO_4$. Plates were read on a SpectraMax spectrophotometer using SoftMax Pro software. All ODs had background subtracted based on the plate blank, and concentrations were determined using a 4-point standard curve.

For lung homogenates, IL-12 concentrations determined by ELISA were normalized to total protein concentrations obtained from the BCA assay and calculated as pg of IL-12 per μg of protein.

Example 4a: HSV-IL12 Single Dose

The objectives of this study were: (1) to evaluate the kinetics of HSV-IL12-mediated expression of murine IL-12 at the transcript and protein levels locally and systemically, upon intratracheal administration, to healthy BALB/c mice; (2) to assess toxicity of HSV-IL12 at various doses; and (3) to compare toxicity and IL-12 localization between HSV-IL12 administered intratracheally versus recombinant IL-12 protein administered systemically.

An in vivo study was conducted to evaluate HSV-IL12-mediated expression of murine IL-12 in healthy, immunocompetent mice upon i.t. delivery of the viral vector. A total of twenty-eight BALB/c mice were used for this study. Table 2 provides a synopsis of the experimental design. At the indicated timepoints after i.t. or s.c. administration of active or control test articles, animals were sacrificed, and lungs were snap frozen for downstream analysis.

TABLE 2

Study Design and Test Article (TA) Administration

| Grp # | Tot. Animal number | Animal # | TA name | PFU or dose | TA total volume/ animal | Route | Dosing Day | Termination |
|---|---|---|---|---|---|---|---|---|
| 1 | 2 | 1, 2 | Vehicle | — | 50 mL | i.t. | Day 0 | 24 hr post-IT |
| 2 | 2 | 3, 4 | | | | | | 48 hr post-IT |
| 3 | 3 | 5, 6, 7 | High dose | 9.5E8 pfu | 50 mL | i.t. | Day 0 | 24 hr post-IT |
| 4 | 3 | 8, 9, 10 | | | | | | 48 hr post-IT |
| 5 | 3 | 11, 12, 13 | Mid dose | 1.9E8 pfu | 50 mL | i.t. | Day 0 | 24 hr post-IT |
| 6 | 3 | 14, 15, 16 | | | | | | 48 hr post-IT |
| 7 | 3 | 17, 18, 19 | Low dose | 3.8E7 pfu | 50 mL | i.t. | Day 0 | 24 hr post-IT |
| 8 | 3 | 20, 21, 22 | | | | | | 48 hr post-IT |
| 9 | 3 | 23, 24, 25 | Recombinant mIL-12 | 0.5 mg | 50 mL | s.c. | Day 0 | 24 hr post-IT |
| 10 | 3 | 26, 27, 28 | | | | | | 48 hr post-IT | hr-hour; i.t.-intratracheal administration; s.c.-subcutaneous administration

Figure 4A:
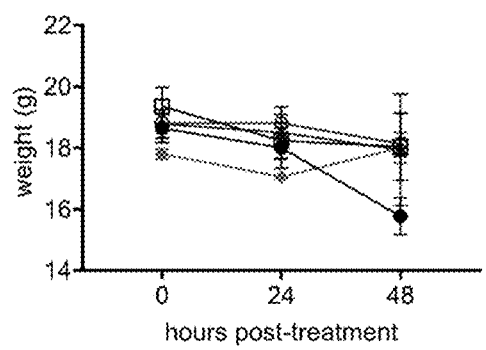
FIGS. 4A-4M show the in vivo evaluation of HSV-IL12 in healthy mice.

Prior to administration and also sacrifice, all animals were weighed to evaluate testing agent toxicity. Data indicated that the animals in the High dose group (9.5E8 pfu) demonstrated dramatic weight loss at 48 hours post-treatment (~16%), suggesting toxicity either to the virus, IL-12, or both (FIG. 4A). Animals in the other groups demonstrated no change in weight following treatment, indicating no toxic effect from dosing.

Figure 4B:
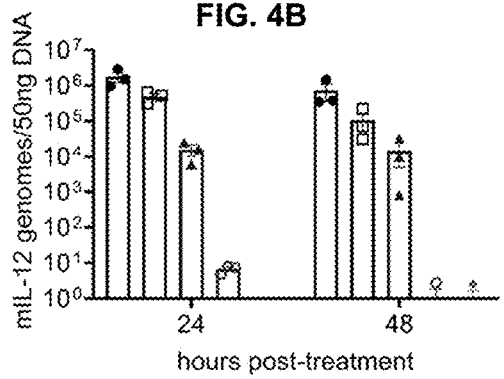
Figure 4C:
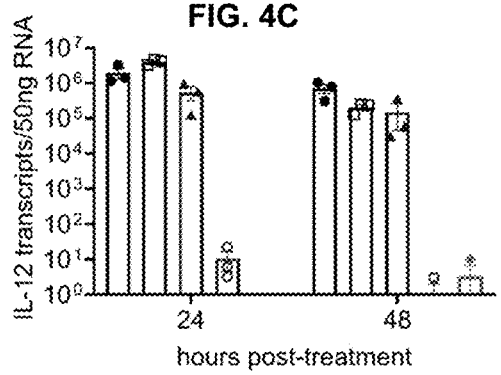
Figure 4D:
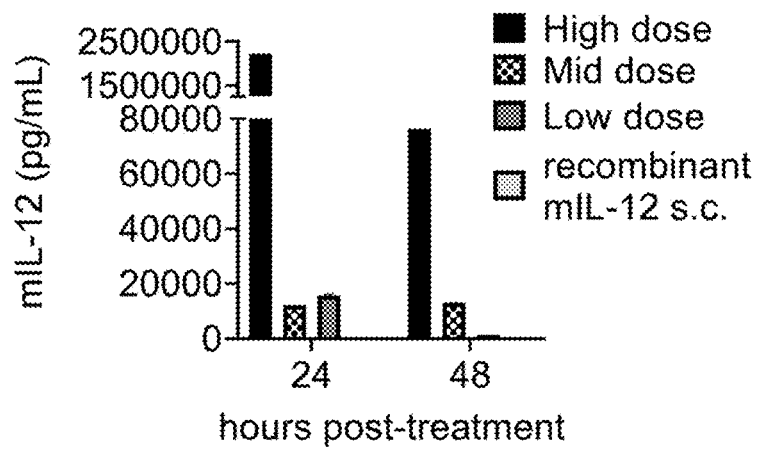
Figure 4E:
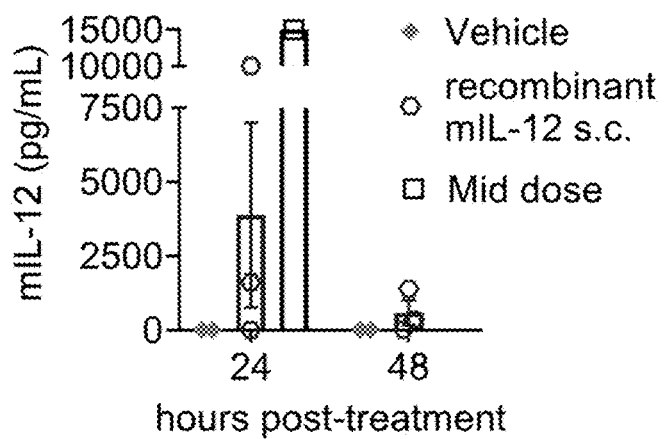

Post-sacrifice qPCR analyses of lung tissue indicated that il12 genomes demonstrated a direct relationship with administration dose at both 24- and 48-hours post-treatment (FIG. 4B). Additionally, DNA levels were relatively stable between the two time points within each dosing group. While il12 genomes differed between treatment groups, il12 transcript levels were comparable regardless of dose (FIG. 4C). These data suggest that transcript levels may plateau at a certain level of genomes in which, the presence of more genomes does not result in an increase in transcripts. This would indicate that the highest level of transgene expression (undiluted, High dose) is attainable even at a 1:25 dilution of the virus (Low dose). rIL-12 s.c. administration did not result in appreciable levels of il12 genomes or transcripts (FIGS. 4B-4C), which was expected as they received IL-12 protein, not DNA and/or RNA. Also as expected, vehicle control recipients demonstrated il12 genome/transcript levels near the limit of detection of the assays (FIGS. 4B-4C). The High dose group demonstrated >0.08 µg/mL of IL-12 protein in the serum (FIG. 4D), which was most likely a contributor to toxicity (FIG. 4A). Yet, this dramatically decreased in the mid and low dose groups (ng/mL range) (FIG. 4D). IL-12 was also detected in the BALF (FIG. 4E) in the Mid dose group. Further, considerably more IL-12 was observed in the BALF of the HSV-IL12 treated compared to the recombinant IL-12 treated group suggesting efficient local delivery of HSV-IL12.

Figure 4F:
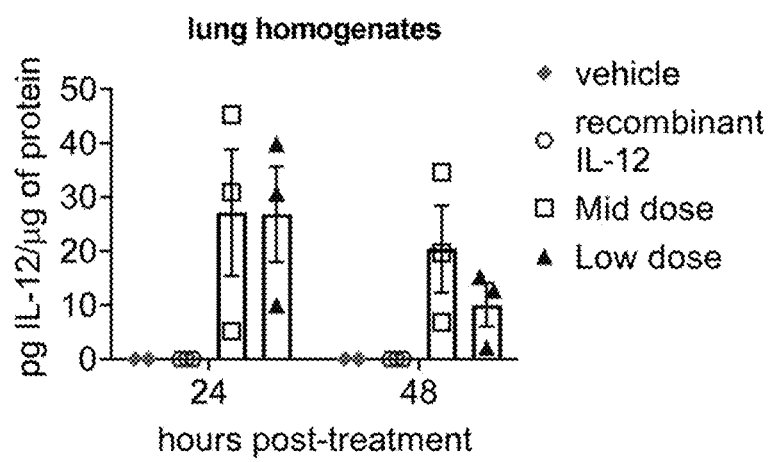

In addition to serum and BALF, lung biopsies were homogenized for IL-12 ELISA analysis. After normalizing for total protein, the results indicated that there was no significant difference in IL-12 protein concentration between vehicle and s.c. recombinant protein (FIG. 4F). Additionally, homogenates from the mid and low dose groups did contain detectable levels of IL-12 protein.

The present study evaluated: (1) the kinetics of HSV-IL12-mediated expression of murine IL-12 upon intratracheal administration to healthy BALB/c mice; (2) the toxicity of HSV-IL12 at various doses; and (3) the tolerability between HSV-IL12 compared to recombinant IL-12 protein administered systemically. Weight measurements of the mice at sacrifice indicated that the High dose (9.5E8 pfu) in this study was not tolerated well, as animals lost close to 20% of their body weight 48 hours post-administration (FIG. 4A). However, upon further investigation, it was determined that a high level of recombinant IL-12 protein was co-purified and administered i.t. with HSV-IL12, potentially contributing to the toxicity. Significant weight loss was not observed in any of the other treatment groups, indicating tolerability. While the s.c. administered rIL-12 dose was hypothesized to be somewhat toxic, animals in this study only received one dose; this is in contrast to previous studies where toxicity was observed following consecutive daily doses.

The qRT-PCR data indicated that il12 transcript levels were comparable between dosing groups at 24- and 48 hours post-treatment (FIG. 4C), even though il12 genomes decreased with test agent dosing (FIG. 4B). These results would indicate that il12 transcription may be more efficient at lower test agent doses and should be further investigated. It would also suggest lower doses of virus could be administered but would still result in high levels of transgene expression. This would be advantageous in a patient setting where HSV-IL12 is administered through nebulization.

It was observed that IL-12 protein levels in serum (FIG. 4D) and BALF (FIG. 4E) did somewhat trend with the dose of HSV-IL12 administered. IL-12 protein concentrations were quite variable in lung homogenates (FIG. 4F), indicating that further studies are necessary for understanding protein expression due to HSV-IL12 treatment.

Example 4b: HSV-IL12 Weekly Dose

The objective of this study was to, in part, evaluate HSV-IL12-mediated expression of murine IL-12 and its toxicity in healthy, immunocompetent mice. Vehicle and doses of intratracheal administered HSV-IL12, along with s.c. rIL-12, were performed once weekly for three consecutive weeks. A total of twenty-two BALB/c mice were used for this study. Table 3 provides a synopsis of the experimental design.

TABLE 3

Study Design and Test Article (TA) Administration

| Grp # | Total animals | Animal # | TA Name | PFU or dose | TA total volume/ animal | Route | Day dosing | Termination |
|---|---|---|---|---|---|---|---|---|
| 1 | 2 | 1, 2 | Vehicle | — | 50 mL | i.t. | Day 0 | Day 15 |
| 2 | 2 | 3, 4 | | | | | Day 7 | |
| 3 | 3 | 5, 6, 7 | Dose #1 | 1.9E8 | 50 mL | i.t. | Day 14 | |
| 4 | 3 | 8, 9, 10 | | | | | | |
| 5 | 3 | 11, 12, 13 | Dose #2 | 3.8E7 | 50 mL | i.t. | | |
| 6 | 3 | 14, 15, 16 | | | | | | |
| 7 | 3 | 17, 18, 19 | Dose #3 | 7.6E6 | 50 mL | i.t. | | |
| 8 | 3 | 20, 21, 22 | | | | | | |
| 9 | 3 | 23, 24, 25 | rIL-12 | 0.5 mg | 50 mL | s.c. | | |
| 10 | 3 | 26, 27, 28 | | | | | | | i.t.-Intratracheal; s.c.-subcutaneous

Prior to each administration and terminal sacrifice, animal weights were recorded. Terminal sacrifice occurred 24 hours following the last dose (day 15). BALF and associated cells, serum, and lungs were collected for downstream analysis.

Figure 4G:
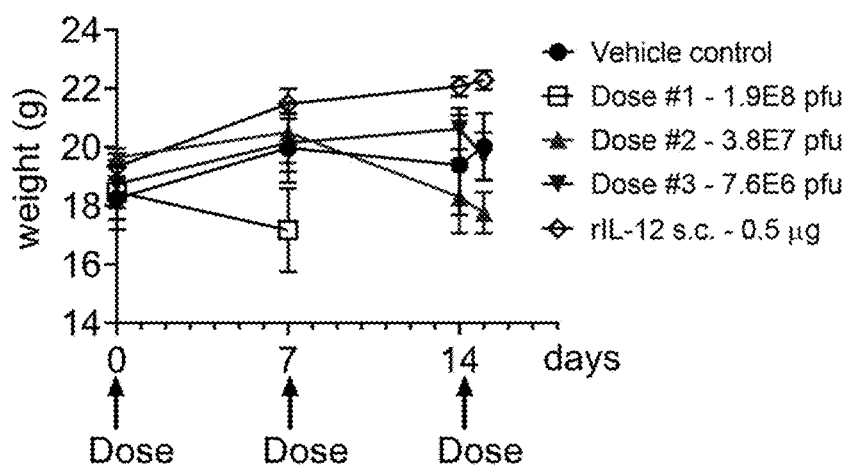
Figure 4H:
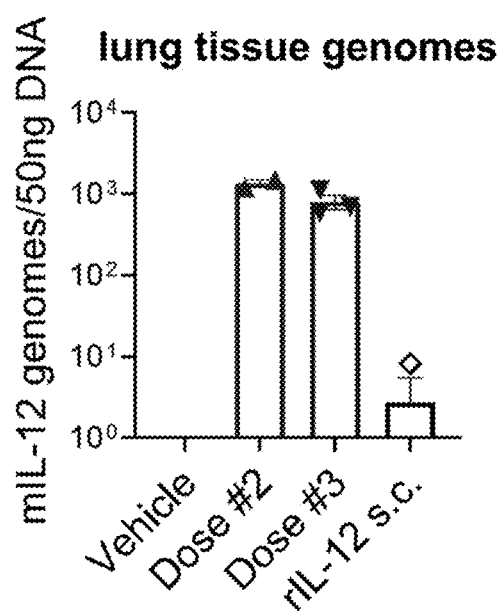
Figure 4I:
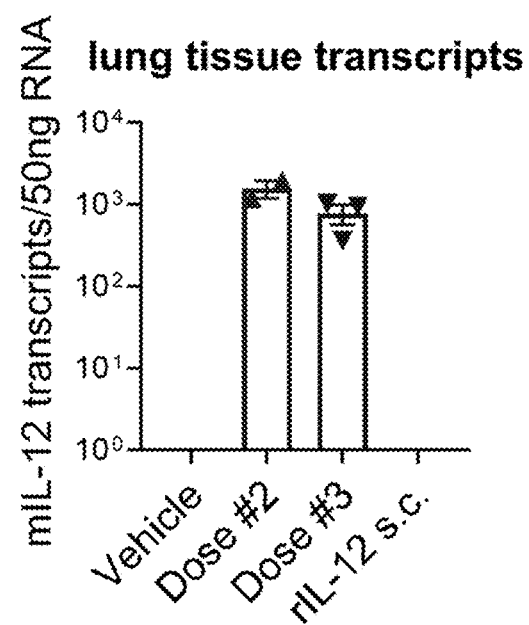

Prior to each weekly dose administration and terminal sacrifice, all animals were weighed to evaluate test agent toxicity. Following the second weekly dose administration, all animals in the highest HSV-IL12 dose group (Dose #1) died, indicating strong toxicity at this dose (FIG. 4G). Alternatively, animals in all other groups stayed relatively the same weight through the second dose. From the second to third dose however, animals in the Dose #2 group (3.8E7 pfu) lost an average of 10% of their body weight, suggesting toxicity over multiple doses. One animal from this group also died following the second administration. Animals in the Dose #3 group showed no marked signs of toxicity (weights were similar to vehicle and rIL-12 recipient groups), demonstrating that 7.6E6 pfu once weekly was the highest tolerable dose in this model.

qPCR analyses of lung tissue indicated that differences in il12 genomes between HSV-IL12 dosing groups were not statistically significant (FIG. 4H). Similar trends were observed with il12 transcripts in that animals from the Dose #2 group had slightly increased transcript copy numbers (FIG. 4I). Yet, this difference was not statistically significant from total copies in Dose #3 animals. Together, these results suggest that while there was a 5-fold decrease in administered pfu between animals in Dose #2 (3.8E7 pfu) and Dose #3 (7.6E6 pfu) groups, it did not result in higher il12 genome or transcript copies, suggesting efficient transgene expression even at lower viral doses.

Figure 4J:
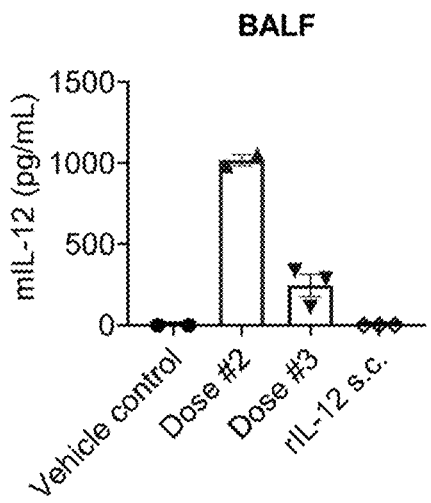
Figure 4K:
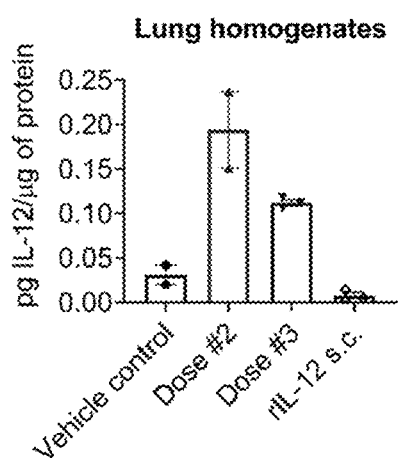
Figure 4L:
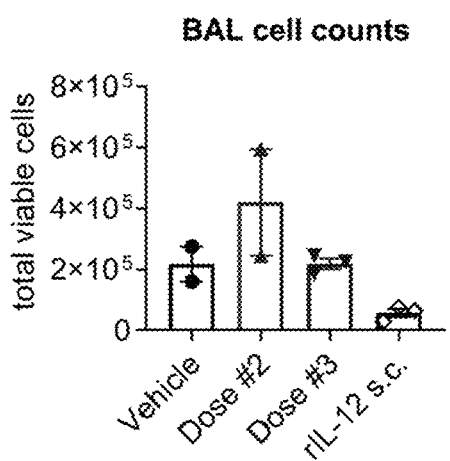
Figure 4M:
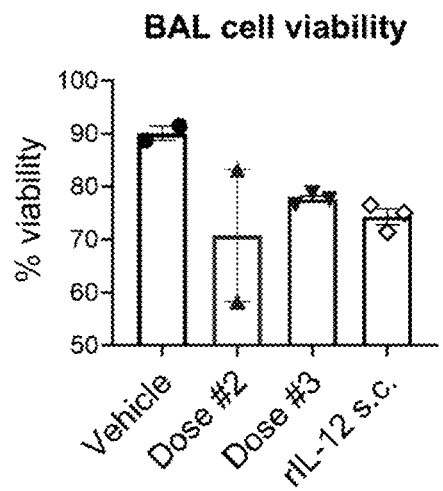

Further, and as shown in FIGS. 4J-4K, IL-12 protein levels in BALF and lung homogenates showed a direct relationship with dosing. In addition to serum and BALF, lung biopsies were homogenized for IL-12 ELISA analysis. After normalizing for total protein, the results indicated that there was no significant difference in IL-12 protein concentration between vehicle and s.c. recombinant protein (FIGS. 4L-4M). Additionally, homogenates from the mid and low dose groups did contain detectable levels of IL-12 protein.

Taken together, these data indicated intratracheal administration of low dose (7.6E6 pfu) HSV-IL12 given once weekly for three consecutive weeks was well tolerated in healthy mice.

Example 5: Intratracheal Administration and In Vivo Evaluation of HSV-IL2 in Healthy Mice Interleukin-2 (IL-2) is a monomeric cytokine that is predominantly produced by activated T cells and NK cells. For these cells, IL-2 signals, often in a paracrine manner, to stimulate cell growth and division. Specifically for T cells, IL-2 stimulation following activation is necessary for optimal clonal expansion and upregulation of anti-apoptotic signals. Research has supported the use of IL-2 as an immunotherapeutic in cancer. However, the one significant drawback to IL-2 monotherapy is its toxicity. Additionally, IL-2 has a very short serum half-life (several minutes), and therefore, must be administered systemically at extremely high doses (upwards of 600,000 IU/kg) and at high frequency (multiple times per day) to exhibit efficacy. At these doses and dose frequencies, IL-2 treatment can lead to, e.g., but not limited to, vascular leak syndrome, hypotension, and heart toxicities.

Example 5a: HSV-IL2 Single Dose

The objective of this study was, in part, to evaluate transgene expression in the lungs and serum 24-hours post intratracheal administration of HSV-IL2 compared to recombinant protein administration. Young (8-10 weeks) BALB/c animals were administered a single dose of HSV-IL2 intratracheally (i.t.). Three different doses of HSV-IL2 were assessed for IL-2 expression by nucleic acid and protein analysis in the lung tissue, bronchoalveolar lavage fluid (BALF), and serum. Additionally, a group of animals received recombinant IL-2 protein as a means of comparing local HSV-IL2 delivery to previously studied administration routes. All procedures have been described above (e.g. see Example 4 above). Table 4 provides a synopsis of the experimental design.

TABLE 4

| | | | | | | | | |
|---|---|---|---|---|---|---|---|---|
| Grp # | Tot. Animal No. | Animal # | TA name | PFU or dose | TA total volume/ animal | Route | Dosing Day | Termination | Readout |
| 1 | 3 | 1, 2, 3 | Vehicle | — | 50 mL | IT | Day 0 | Day 1 (24 hours post-treatment) | qPCR, qRT-PCR, ELISA |
| 2 | 3 | 4, 5, 6 | High dose | 2.1E8 pfu | 50 mL | IT | | | |
| 3 | 3 | 7, 8, 9 | Mid dose | 4.2E7 pfu | 50 mL | IT | | | |
| 4 | 3 | 10, 11, 12 | Low dose | 8.4E6 pfu | 50 mL | IT | | | |
| 5 | 3 | 13, 14, 15 | IT rIL-2 | 48 ng | 50 mL | IT | | | |
| 6 | 3 | 16, 17, 18 | IV rIL-2 | 48 ng | 100 mL | IV | | | |

IT-Intratracheal administration; IV-Intravenous administration

Figure 5A:
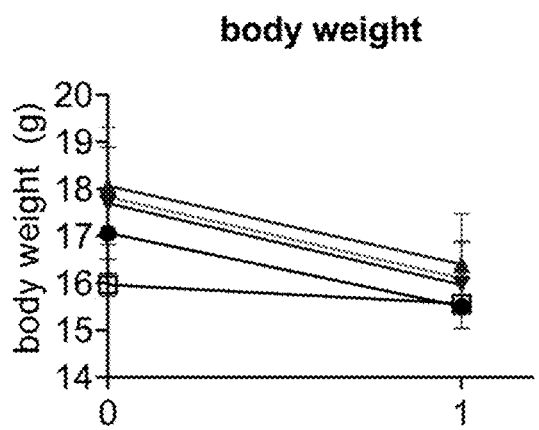
Figure 5B:
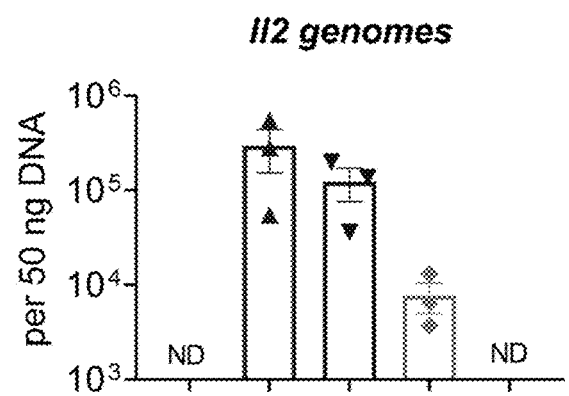
Figure 5C:
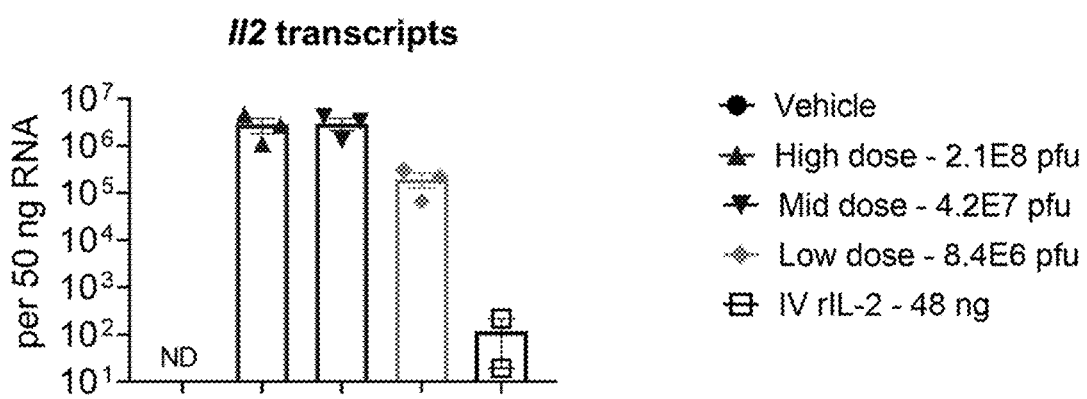
Figure 5D:
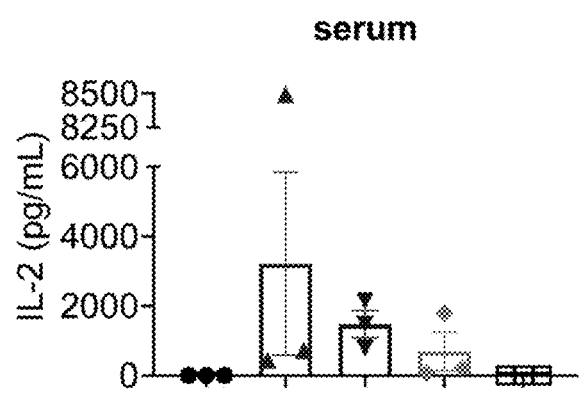
Figure 5E:
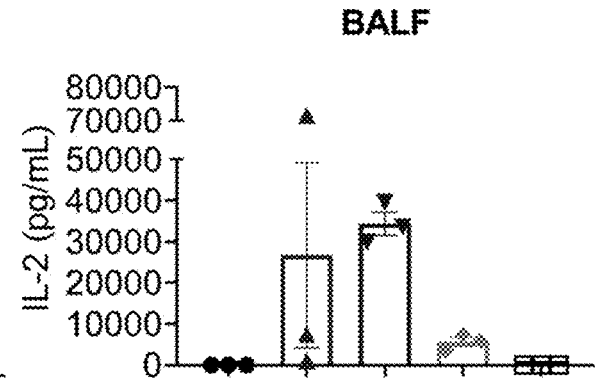
Figure 5F:
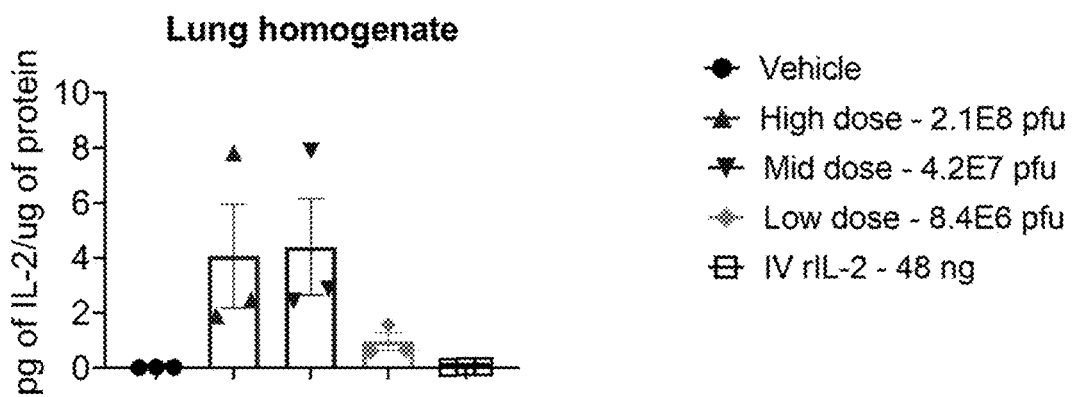

Results from this study suggest no differences in bodyweights were noted between groups (FIG. 5A). Post-sacrifice qPCR analyses of lung tissue indicated that il2 genomes demonstrated a direct relationship with administration dose at 24-hours post-treatment (FIG. 5B). While il2 genomes differed between treatment groups, il2 transcript levels were comparable regardless of dose (FIG. 5C). These results were similar to what was observed with single dose HSV-IL12 in healthy mice (FIG. 4B-4C), demonstrating consistency of the vector independent of the inserted transgene. With regards to protein levels, while IL-2 was detected in the serum (FIG. 5D), the levels in the lung as measured in the BALF (FIG. 5E) were more than 10-fold higher, indicating more significant expression in the target tissue, with limited systemic exposure. While IL-2 protein levels in lung homogenates demonstrated some variability between animals, levels were detectable and relatively high compared to recombinant protein treated animals (FIG. 5F). Further, IL-2 protein levels were undetectable in lung homogenates at 24 hours post IV injection of recombinant IL-2, most likely due to its short half-life. These data suggest prolonged effector exposure from HSV-IL2 compared to recombinant protein therapy.

Taken together, these data indicated that infection with HSV-IL2 resulted in expression of full-length, functional murine IL-2. Moreover, i.t. administration of HSV-IL2 resulted in high levels of IL-2 protein in the target organ (lung), with limited systemic exposure (as measured in the serum).

Example 5b: HSV-IL2 Pharmacokinetics

The objective of this study was, in part, to quantitatively measure the kinetics of vector transduction and IL-2 expression in lung tissues and fluids harvested from healthy mice following a single dose of HSV-IL2 administered intratracheally (i.t.).

All procedures have been described above (e.g. see Example 4 above). Table 5 provides a synopsis of the experimental design.

TABLE 5

Study Design and Test Article (TA) Administration

| Grp # | Tot. Animal number | Animal # | TA name | pfu | TA total volume/ animal | Route | Dosing Day | Termination | Readout |
|---|---|---|---|---|---|---|---|---|---|
| 1 | 3 | 1, 2, 3 | Vehicle | — | 50 μL | i.t. | Day 0 | 48 h.p. i.t. (Day 2) | qPCR/ RT-qPCR, ELISA |
| 2 | 3 | 4, 5, 6 | HSV-IL2 | 4.2E7 pfu | 50 μL | i.t. | Day 0 | 4 h.p. i.t. (Day 0) | qPCR/ RT-qPCR, ELISA |
| 3 | 3 | 7, 8, 9 | | | | | | 8 h.p. i.t. (Day 0) | |
| 4 | 3 | 10, 11, 12 | | | | | | 24 h.p. i.t. (Day 1) | |
| 5 | 3 | 13, 14, 15 | | | | | | 48 h.p. i.t. (Day 2) | |
| 6 | 3 | 16, 17, 18 | | | | | | 72 h.p. i.t. (Day 3) | |
| 7 | 3 | 19, 20, 21 | | | | | | 96 h.p. i.t. (Day 4) | | i.t: intratracheal administration; h. p. i.t: hours post-intratracheal administration Results from this study are shown in FIGS. 5G-5I and demonstrate the pharmacokinetics of IL-2 expression in the serum (FIG. 5G), BALF (FIG. 5H), and lysate (FIG. 5I) following the single-dose intratracheal administration of HSV-IL2. Overall, these results indicated that IL-2 protein levels peak at 24-hours post-i.t. administration of HSV-IL2, and decrease between 24- and 48-hours post-administration, which could be due to reductions in transgene translation, the short half-life of IL-2, or a combination thereof. However, IL2 protein exposure in these animals was significantly prolonged when expressed from the vector as compared to recombinant protein therapy.

Example 6: Intratracheal Administration and In Vivo Evaluation of HSV-GMCSF in Healthy Mice Granulocyte-macrophage colony-stimulating factor (GM-CSF) is a monomeric cytokine that plays a critical role in the activation and migration of myeloid cells to sites of inflammation. With respect to cancer therapy, GM-CSF has been shown to effectively activate anti-tumor immune responses, especially in instances of chemotherapy resistance, in addition to enhancing neutrophil recovery following chemotherapy. With regards to OS lung metastasis, a clinical trial examining inhaled GM-CSF therapy determined that multiple daily doses in patients were feasible with limited toxicity.

Example 6a: HSV-GMCSF Single Dose

The objective of this study was, in part, to evaluate transgene expression of GM-CSF at 24- and 48-hours post HSV-GMCSF intratracheal administration compared to recombinant protein to determine the optimal dose for limited toxicity and robust GM-CSF expression.

Young (8-10 weeks) BALB/c animals were administered a single dose of HSV-GM-CSF intratracheally (i.t.). Three different doses of HSV-GMCSF were assessed for GM-CSF expression by nucleic acid and protein analysis in the lung tissue, bronchoalveolar lavage fluid (BALF), and serum. Additionally, a group of animals received recombinant GM-CSF protein as a means of comparing local HSV-GMCSF delivery to previously studied administration routes.

All procedures have been described above (e.g. see Example 4 above). Table 6 provides a synopsis of the experimental design.

TABLE 6

Study Design and Test Article (TA) Administration

| Grp # | Tot. Animal number | Animal # | TA name | PFU or dose | TA total volume/ animal | Route | Dosing Day | Termination | Readout |
|---|---|---|---|---|---|---|---|---|---|
| 1 | 2 | 1, 2 | Vehicle | — | 50 μL | IT | Day 0 | 24 hr post-IT | qPCR, qRT-PCR, ELISA |
| 2 | 2 | 3, 4 | | | | | | 48 hr post-IT | |
| 3 | 3 | 5, 6, 7 | High dose | 4.88E8 pfu | 50 μL | IT | Day 0 | 24 hr post-IT | |
| 4 | 3 | 8, 9, 10 | | | | | | 48 hr post-IT | |
| 5 | 3 | 11, 12, 13 | Mid dose | 9.75E7 pfu | 50 μL | IT | Day 0 | 24 hr post-IT | |
| 6 | 3 | 14, 15, 16 | | | | | | 48 hr post-IT | |
| 7 | 3 | 17, 18, 19 | Low dose | 1.95E7 pfu | 50 μL | IT | Day 0 | 24 hr post-IT | |
| 8 | 3 | 20, 21, 22 | | | | | | 48 hr post-IT | |

TABLE 6-continued

Study Design and Test Article (TA) Administration

| Grp # | Tot. Animal number | Animal # | TA name | PFU or dose | TA total volume/ animal | Route | Dosing Day | Termination | Readout |
|---|---|---|---|---|---|---|---|---|---|
| 9 | 3 | 23, 24, 25 | rGM-CSF | 0.6 mg | 50 μL | IT | Day 0 | 24 hr post-IT | |
| 10 | 3 | 26, 27, 28 | | | | | | 48 hr post-IT | | hr-hours; IT-Intratracheal administration

Figure 6A:
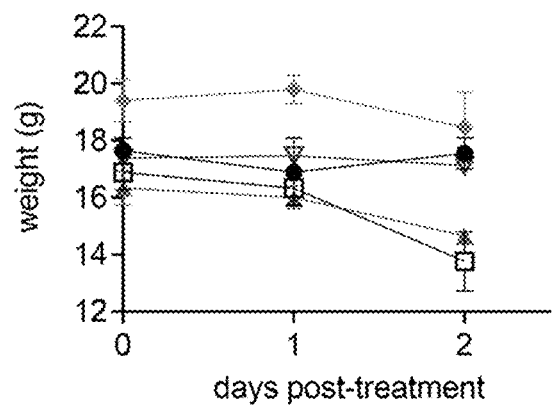
FIGS. 6A-6N show the in vivo evaluation of HSV-GMCSF in healthy mice.
Figure 6B:
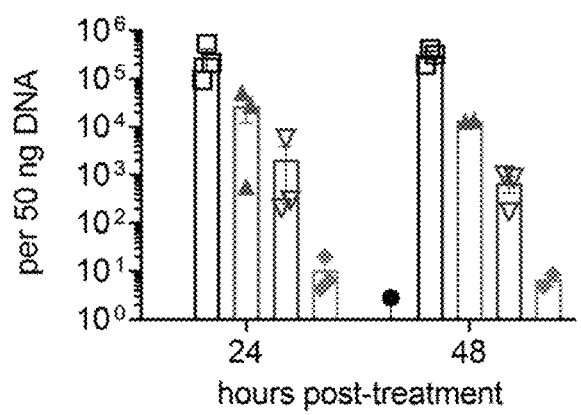
FIGS. 6B-6C show gmcsf genome (FIG. 6B) and transcript (FIG. 6C) levels in lungs of BALB/c animals post-intratracheal administration of HSV-GMCSF. qPCR (FIG. 6B) and qRT-PCR (FIG. 6C) was performed to measure gmcsf genomes and transcripts; respectively. Data are indicative of samples run in duplicate and displayed as mean±SEM of n=2-3 animals per group.
Figure 6C:
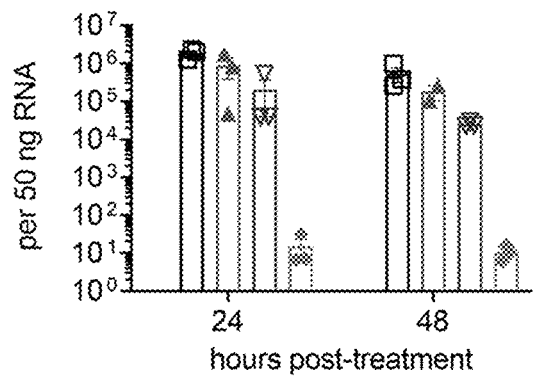
Figure 6D:
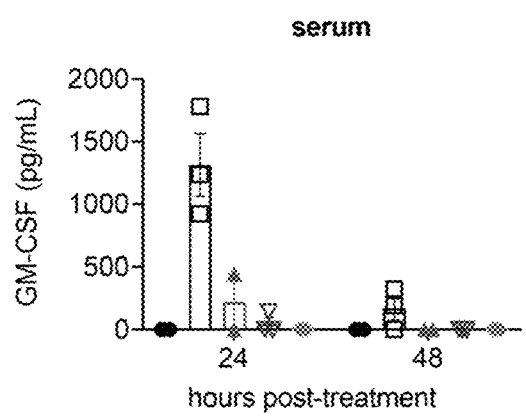
FIGS. 6D-6E show GM-CSF protein concentrations in serum (FIG. 6D) and bronchoalveolar lavage fluid (BALF.
Figure 6E:
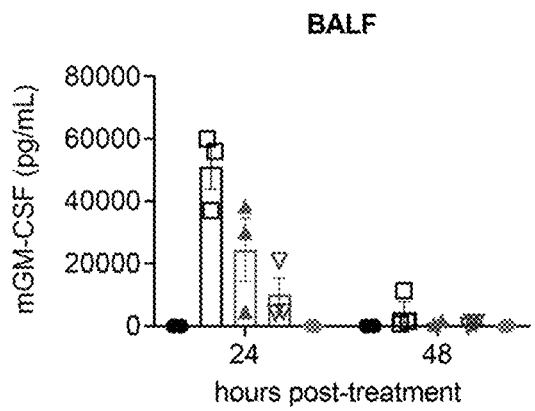
Figure 6F:
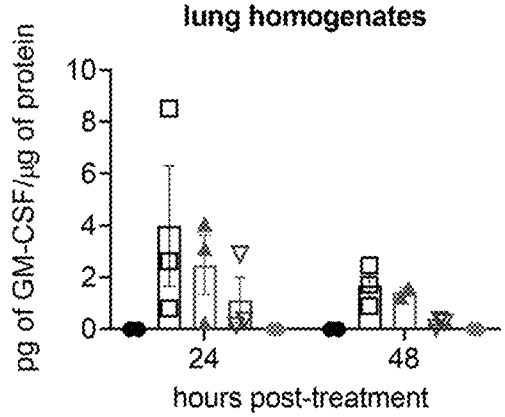
FIG. 6F depicts GM-CSF concentration in lung homogenates following HSV-GMCSF intratracheal administration.

Results from this study indicated that the animals in the high (4.88E8 pfu) and mid (9.75E7 pfu) dose groups demonstrated weight loss at 48 hours post-treatment (FIG. 6A), suggesting toxicity. Animals in the other groups demonstrated no change in weight following treatment, indicating no toxic effect from dosing. Post-sacrifice qPCR analyses of lung tissue indicated that gmcsf genomes demonstrated a direct relationship with administration dose at both 24- and 48-hours post-treatment (FIG. 6B). While gmcsf genomes differed between treatment groups, gmcsf transcript levels were comparable regardless of dose (FIG. 6C). Further, low levels of GM-CSF were detected in the serum (FIG. 6D) of HSV-GMCSF treated animals; however, these levels were approximately 40-fold lower than those in the BALF (FIG. 6E), again demonstrating limited systemic exposure. Lung homogenate analysis revealed detectable GM-CSF levels at both 24- and 48-hours post-administration, with a reduction between the two time points (FIG. 6F).

Taken together, these data indicated that infection with HSV-GMCSF resulted in expression of full-length murine GM-CSF.

Example 6b: HSV-GMCSF Weekly Dose

The objective of this study was, in part, to evaluate the toxicity of once weekly intratracheal administration of HSV-GMCSF compared to recombinant GM-CSF protein over the course of three weeks. All procedures have been described above (e.g. see Example 4 above). Table 7 provides a synopsis of the experimental design.

Prior to each administration and terminal sacrifice, animal weights were recorded. Terminal sacrifice occurred 24 hours following the last dose (day 15). BALF and associated cells, serum, and lungs were collected for downstream analysis.

TABLE 7

Study Design and Test Article (TA) Administration

| Grp # | Total animals | Animal # | TA Name | PFU or dose | TA total volume/ animal | Route | Day dosing | Termination | Readout |
|---|---|---|---|---|---|---|---|---|---|
| 1 | 2 | 1, 2 | Vehicle | — | 50 mL | IT | Day 0 Day 7 Day 14 | Day 15 | BAL, ELISA, qPCR/qRT-PCR |
| 2 | 2 | 3, 4 | | | | | | | histology |
| 3 | 3 | 5, 6, 7 | Dose # 1 | 1.95E7 | 50 mL | IT | | | BAL, ELISA, qPCR/qRT-PCR |
| 4 | 3 | 8, 9, 10 | | | | | | | histology |
| 5 | 3 | 11, 12, 13 | Dose # 2 | 3.9E6 | 50 mL | IT | | | BAL, ELISA, qPCR/qRT-PCR |
| 6 | 3 | 14, 15, 16 | | | | | | | histology |
| 7 | 3 | 17, 18, 19 | rGM-CSF suspension | 0.6 mg | 50 mL | IT | | | BAL, ELISA, qPCR/qRT-PCR |
| 8 | 3 | 20, 21, 22 | | | | | | | histology |

IT-Intratracheal

Figure 6G:
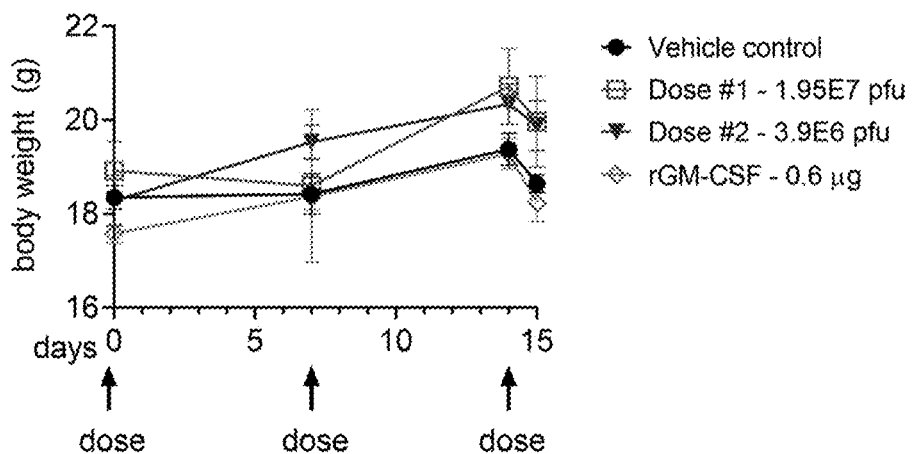
FIG. 6G depicts animal weights following once weekly HSV-GMCSF intratracheal administration. Animals were weighed prior to HSV-GMCSF administration at the indicated time points. Data are presented as mean±SEM; n=2-3 animals per group.
Figure 6H:
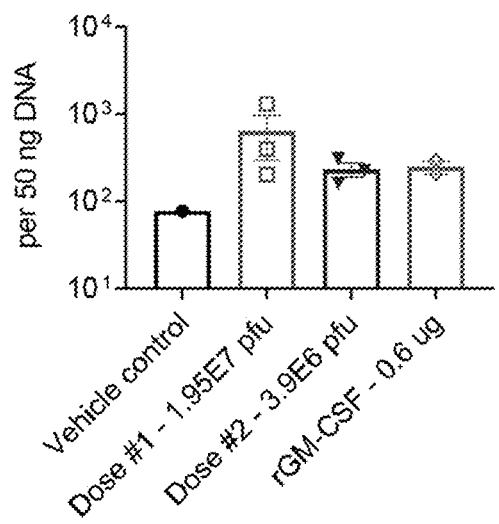
FIGS. 6H-6I depict gmcsf genome (FIG. 6H) and transcript (FIG. 6I) levels in lungs of BALB/c animals following once weekly treatment for three consecutive weeks. Data are indicative of samples run in duplicate. Values from individual animals are displayed in conjunction with the mean±SEM of n=2-3 animals per group.
Figure 6I:
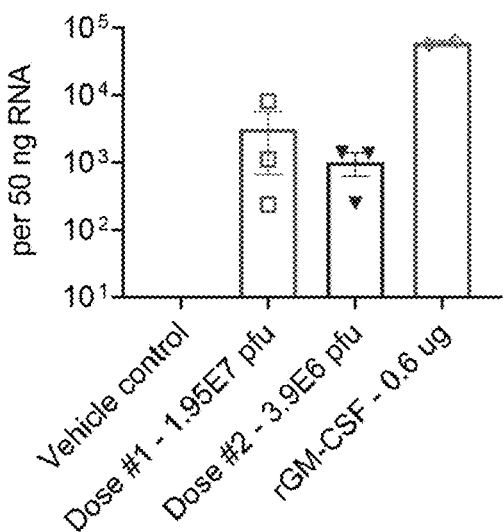

As shown in FIG. 6G, animals in either the Dose #1 or Dose #2 stayed relatively the same weight throughout the course of the study indicating both Dose #1 and Dose #2 were well tolerated. qPCR analyses of lung tissue indicated that differences in gmcsf genomes and transcripts between HSV-GMCSF dosing groups were not statistically significant (FIGS. 6H-6/). Together, these results suggest efficient transgene expression at both of the administered doses.

Figure 6J:
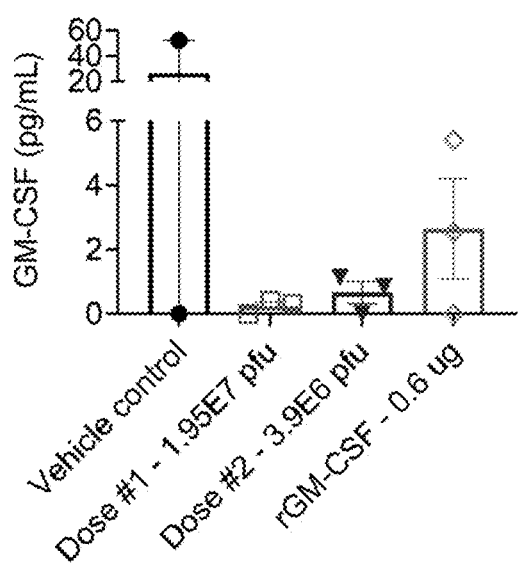
FIGS. 6J-6L depict GMCSF protein concentrations in serum (FIG. 6J), BALF (FIG. 6K), and lung homogenates (FIG. 6L). All samples were assayed in duplicate. Values from individual animals are shown in conjunction with the mean±SEM of n=2-3 animals per group.
Figure 6K:
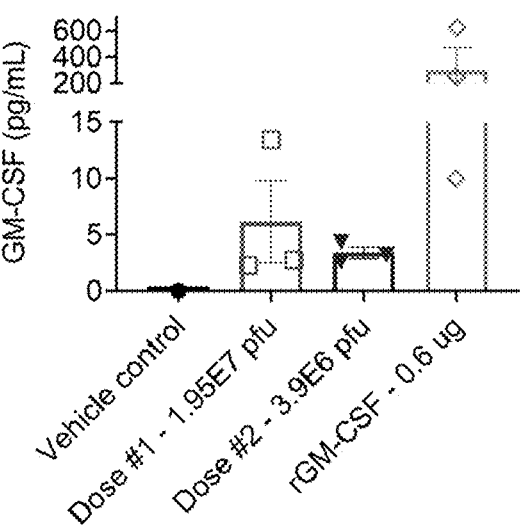
Figure 6L:
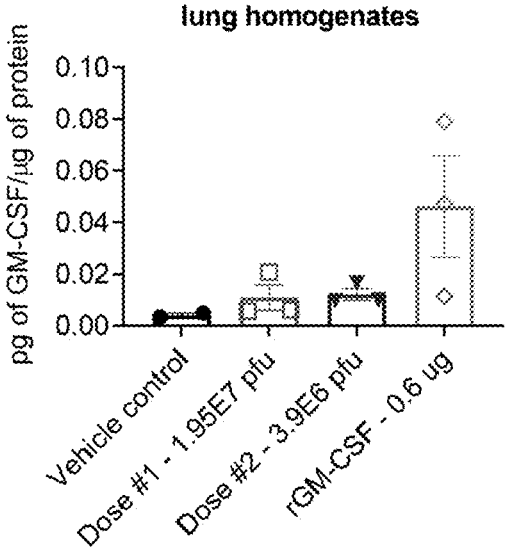
Figure 6M:
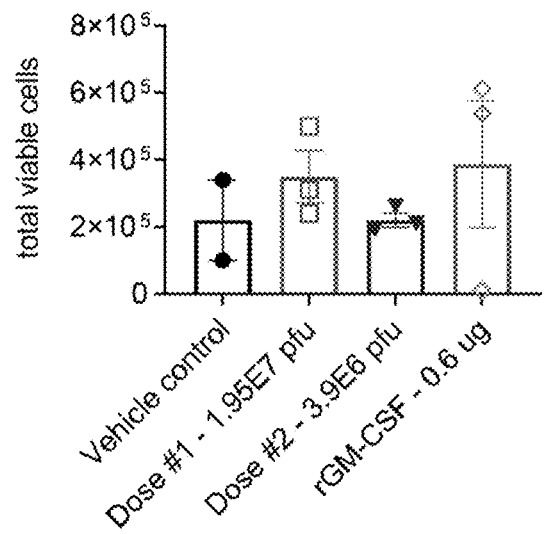
Figure 6N:
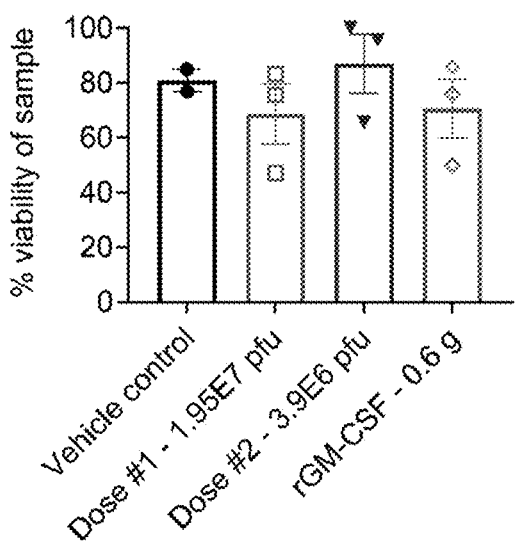

In assessing GM-CSF protein levels, it was again determined that while there was some systemic exposure to GM-CSF from the HSV-GMCSF treatment (serum levels; FIG. 6J), it was minimal compared to local expression/exposure (BALF; FIG. 6K).

Taken together, these data suggested HSV-GMCSF was well tolerated following once weekly intratracheal administration at the indicated doses.

Example 7: Establishment of In Vivo Murine Model of Osteosarcoma

Osteosarcoma (OS) is the most common type of bone cancer diagnosed in the clinic, primarily occurring in children and young adults. In terms of incidence, 3.4 cases per million people are diagnosed each year, making OS a relatively rare malignancy. Yet, with an incidence of 5.6 cases per million children (<15 years of age), it is the third most common cancer in adolescents.

OS is derived from malignant spindle-shaped stromal cells, capable of producing bone-like tissues. It is usually subdivided into one of three groups, osteoblastic, chondroblastic, or fibroblastic, based on the characteristics of the predominant cell type of the tumor. 80% of cases originate in the metaphysis (location of the growth plate) of long bones including the proximal tibia, proximal humerus and the distal femur. Although rare, cases have also been observed in the spine and pelvis.

The main site of OS metastasis is the lung, which it is estimated that 20% of OS patients have metastatic disease at the time of diagnosis. Unfortunately, the presence of lung metastases dramatically impacts the 5-year survival rate of patients, reducing it from 70% in non-metastatic patients to 30%. The standard treatment for OS pulmonary metastasis is lung resection; however, clinical trials are investigating the use of other singular and combinatorial therapies.

Several preclinical animal models have been developed to study OS tumor progression and treatment efficacy, including the K7M2 tumor-BALB/c murine model. K7M2 cells are a derivative of a BALB/c spontaneously occurring murine osteosarcoma; however, it differs from its parent line in that inoculation results in lethal lung metastasis in >90% of inoculated animals. Being a syngeneic tumor, its inoculation into immunocompetent BALB/c animals also allows for studying tumor growth and regression in the presence of a fully intact immune system. Together, these characteristics make it a suitable model for human osteosarcoma lung metastasis and preliminary studies of drug developing in this indication.

The goal of this study was to establish the previously described K7M2 BALB/c model of osteosarcoma lung metastasis following intravenous administration of α7M2 cells, and to elucidate the kinetics of tumor metastasis. All procedures have been described above (e.g. see Example 4 above). Table 8 provides a synopsis of the experimental design.

TABLE 8

Study Design and Test Article (TA) Administration

| Grp # | Total # of animals | Animal # | TA name | TA dosing | TA total volume per animal | Route | Dosing Day | Termination | Readouts |
|---|---|---|---|---|---|---|---|---|---|
| 1 | 2 | 1, 2 | Vehicle | — | 100 μL | IV | Day 0 | 3 weeks | Lung weight |
| 2 | 2 | 3, 4 | | | | | | | histology |
| 3 | 2 | 5, 6 | | | | | | 6 weeks | Lung weight |
| 4 | 2 | 7, 8 | | | | | | | histology |
| 5 | 5 | 9, 10, 11, 12, 13 | K7M2 | 1E6 total cells | 100 μL | IV | Day 0 | 3 weeks | Lung weight |
| 6 | 2 | 14, 15 | | | | | | | histology |
| 7 | 5 | 16, 17, 18, 19, 20 | | | | | | 6 weeks | Lung weight |
| 8 | 2 | 21, 22 | | | | | | | histology |

Figure 7A:
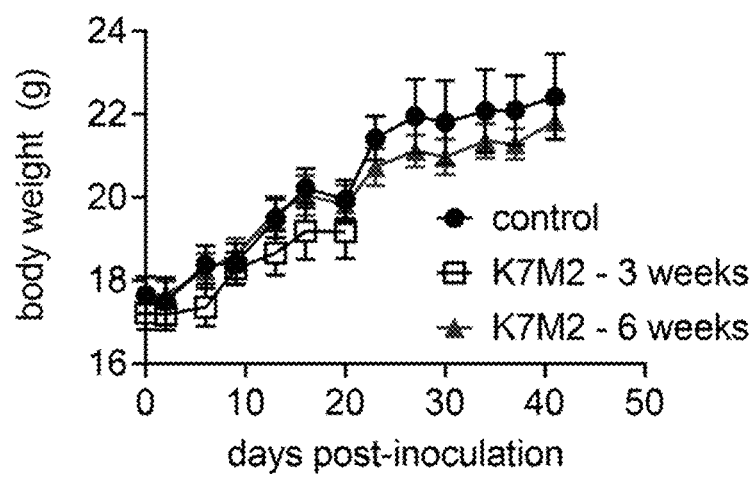
FIGS. 7A-7G depict the establishment of an in vivo osteosarcoma lung metastasis model in immunocompetent mice.
Figure 7B:
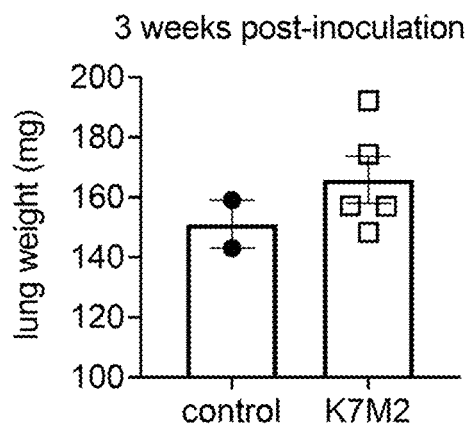
Figure 7C:
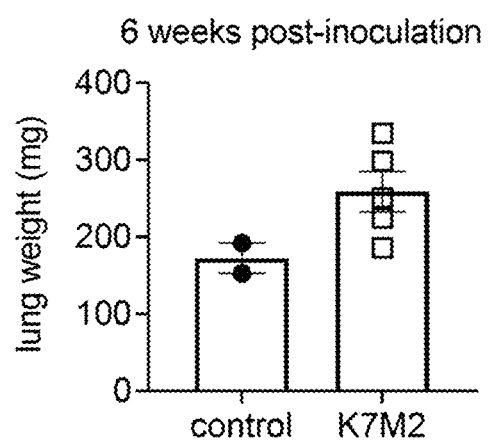
Figure 7D:
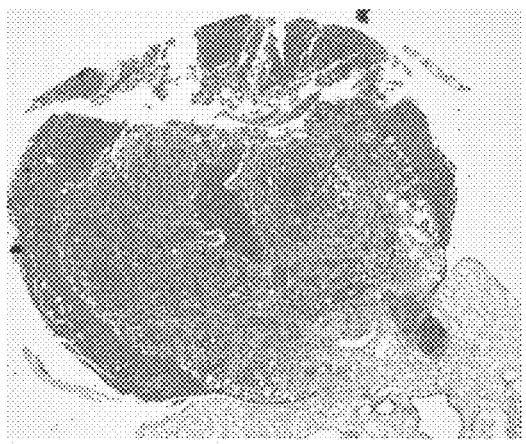
Figure 7E:
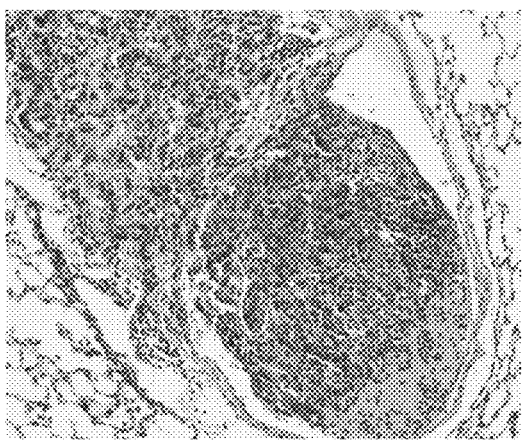
Figure 7F:
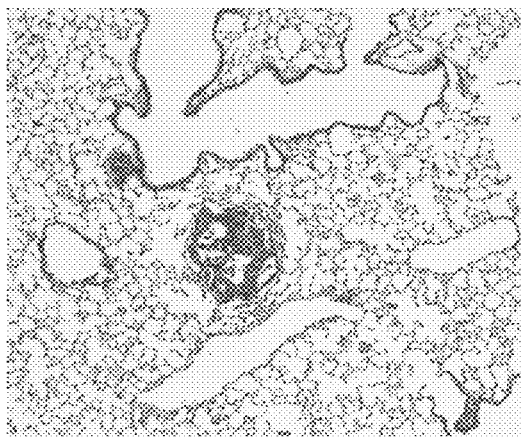
Figure 7G:
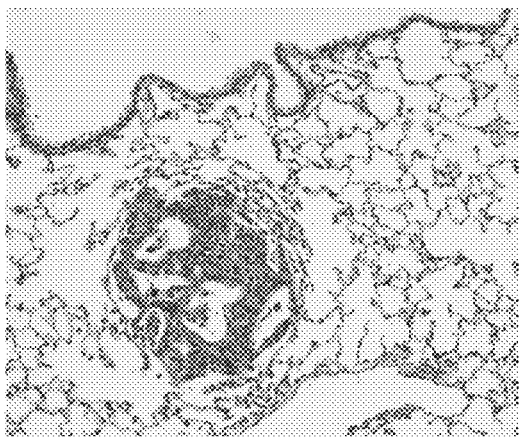

As shown in FIGS. 7A-7C, while body weight (FIG. 7A) remained relatively unchanged between the groups throughout the duration of the study, lung weights were increased in tumor recipient mice at both 3-weeks (FIG. 7B) and 6-weeks (FIG. 7C) post-inoculation of K7M2 cells. Further, histological analysis in the lungs of a K7M2 recipient 6-weeks post inoculation revealed tumor burden with signs of tumor metastasis in more than 90% of blood vessels, along with partial thrombus formation (FIGS. 7D-7G).

Taken together, these data established the K7M2 BALB/c model of osteosarcoma lung metastasis following intravenous administration of K7M2 cells with increased lung weight and positive tumor formation in the lung.

Example 8: HSV-IL12 Efficacy in an In Vivo Murine Model of Osteosarcoma

The objective of this study was, in part, to evaluate the efficacy of intratracheal administration of HSV-IL12 at inhibiting established metastatic osteosarcoma lung tumor growth. All procedures have been described above (e.g. see Example 4 above). Table 9 provides a synopsis of the experimental design.

TABLE 9

Study Design

| Grp # | Total animals | Animal # | Inoculating agent/ Route | Inoculating day | TA Name/ dose | TA total volume/ Route | TA Dosing Days | Termination | Readout |
|---|---|---|---|---|---|---|---|---|---|
| 1 | 5 | 1, 2, 3, 4, 5 | IX PBS, IV | Day 0 | — | — | Day 21 Day 28 Day 35 | Day 42 | Lung weight qPCR qRT-PCR |
| 2 | 5 | 6, 7, 8, 9, 10 | K7M2, 1.0E6 cells, IV | | Vehicle | 50 mL IT | | | Lung weight qPCR qRT-PCR |
| 3 | 5 | 11, 12, 13, 14, 15 | K7M2, 1.0E6 cells, IV | | HSV-IL12 3.73E7 pfu | | | | Lung weight qPCR qRT-PCR |
| 4 | 5 | 16, 17, 18, 19, 20 | K7M2, 1.0E6 cells, IV | | rmIL-12 0.5 mg | 50 mL, IV | | | Lung weight qPCR qRT-PCR |
| 5 | 5 | 21, 22, 23, 24, 25 | K7M2, 1.0E6 cells, IV | | IL-12 suspension 48 ng | 50 mL, IT | | | Lung weight qPCR qRT-PCR |

IT-Intratracheal; IV-Intravenous

Figure 8A:
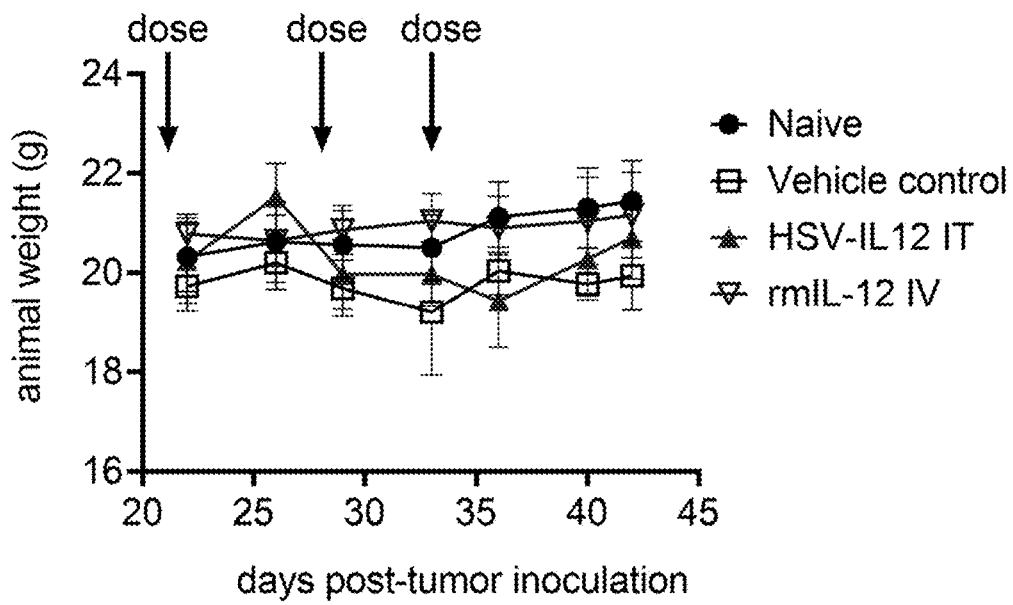
FIGS. 8A-8B depict HSV-IL12 efficacy in an in vivo murine model of osteosarcoma.
Figure 8B:
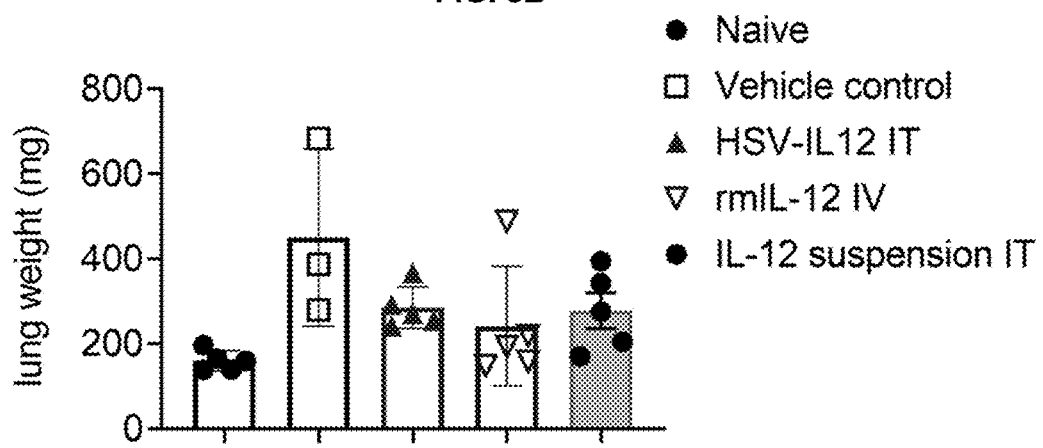

As shown in FIGS. 8A-8B, while body weight (FIG. 8A) remained relatively unchanged between the groups throughout the duration of the study, lung weights were increased in mice at 6-weeks post-inoculation of K7M2 cells (FIG. 8B). Notably, intratracheal administration of HSV-IL12 attenuated the K7M2-mediated increase in lung weights (FIG. 8B). Additionally, while all five HSV-IL12 treated animals survived to the scheduled sacrifice timepoint, two vehicle treated animals died early in the study. HSV-IL12 appeared to have comparable efficacy as recombinant protein therapy.

Taken together, these data may suggest HSV-IL12 was efficacious at inhibiting established metastatic osteosarcoma lung tumor growth.

Example 9: Intratracheal Administration and In Vivo Evaluation of Once Weekly Combinatorial HSV-IL12+HSV-GMCSF in Healthy Mice The objective of this study was, in part, to assess the toxicity of once weekly dosing with intratracheally administered, combinatorial cytokine-expressing (IL-12 and GM-CSF), non-replicating HSV-1 vectors in healthy mice. All procedures have been described above (e.g. see Example 4 above). Table 10 provides a synopsis of the experimental design.

TABLE 10

Study Design

| Grp # | Tot. Animal # | Animal # | Dose group | TA | Dose (pfu) | Volume & Route | Dosing Day | Termination | Readout |
|---|---|---|---|---|---|---|---|---|---|
| 1 | 2 | 1, 2 | Vehicle | — | — | 50 µL i.t. | Day 0 Day 7 | Day 9 | qPCR/ qRT-PCR ELISA |
| 2 | 3 | 3, 4 | | | | | | | histology |
| 3 | 3 | 5, 6, 7 | High Dose | HSV-IL12 + HSV-GMCSF | 3.73E7 1.95E7 | | | | qPCR/ qRT-PCR ELISA |
| 4 | 2 | 8, 9 | | | | | | | histology |
| 5 | 3 | 10, 11, 12 | Mid Dose | | 7.46E6 3.9E6 | | | | qPCR/ qRT-PCR ELISA |
| 6 | 2 | 13, 14 | | | | | | | histology |
| 7 | 3 | 15, 16, 17 | Recombinant protein | rIL-12 + rGM-CSF | 48 ng + 2.5 ng | | | | qPCR/ qRT-PCR ELISA |
| 8 | 2 | 18, 19 | | | | | | | histology | i.t.: intratracheal administration

Figure 9D:
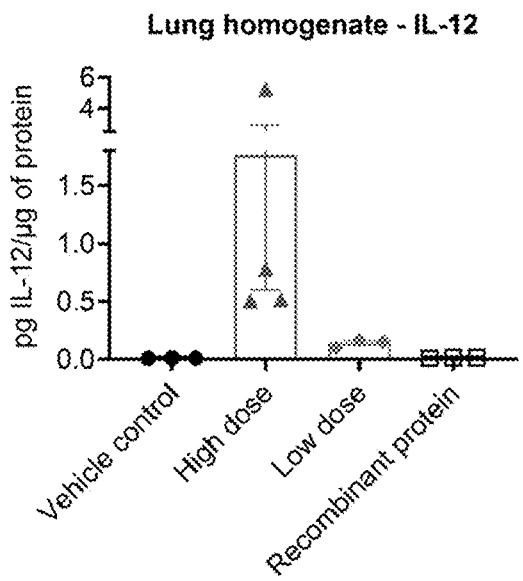
Figure 9E:
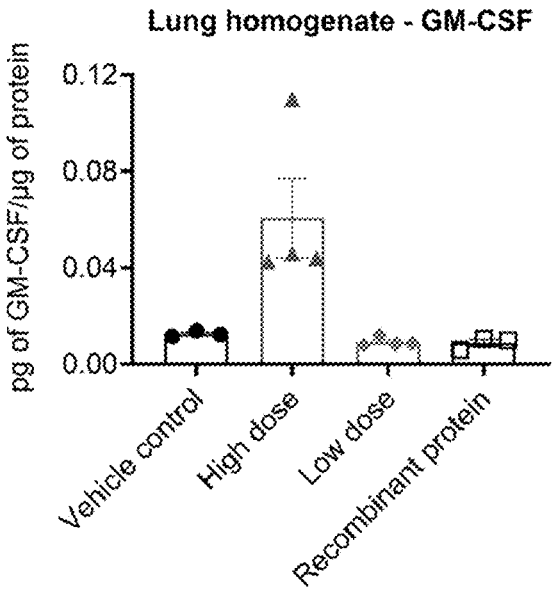
Figure 9F:
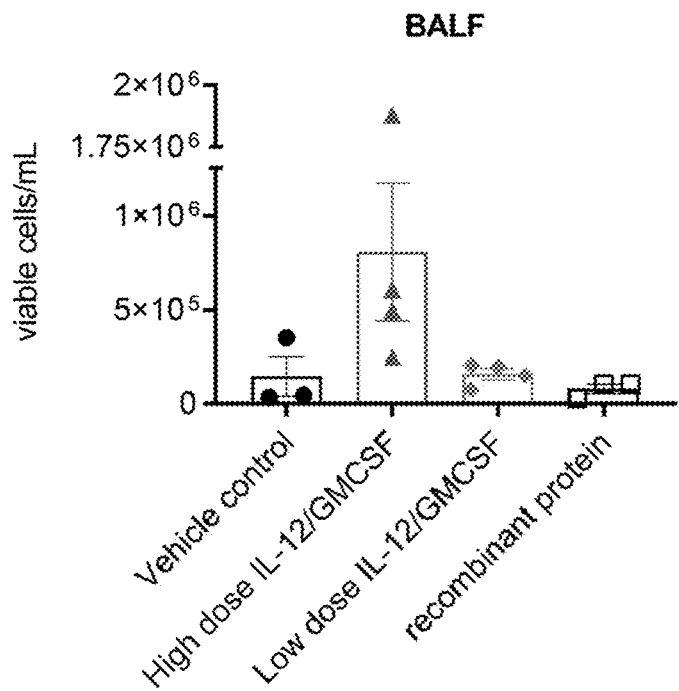

Results from this study suggested that the animals in the high dose group demonstrated somewhat dramatic weight loss following each of the weekly doses administered at 0 and 7 days (FIG. 9A). This was somewhat surprising given that each of the high doses of HSV-GMCSF and HSV-IL12 were not toxic following weekly administrations when given individually. Alternatively, animals in the mid dose group demonstrated no change in weight following treatment, indicating no toxic effect from the indicated dose. Protein analysis of IL-12 and GM-CSF expression following combinatorial treatment revealed high levels of both cytokines in the BALF (FIG. 9B-9C) and lung homogenates (FIG. 9D-9E) of animals treated with the high dose of both viruses. There was a reduction in both cytokine concentrations in each of the lung specimens from animals treated with the mid dose compared to the high dose group (FIG. 9B-9E), indicating a dose effect on transgene expression. Finally, enumeration of cellular infiltrate in the BALF indicated that the high dose treatment resulted in greater immune cell influx into the tissue (FIG. 9F), potentially contributing to the toxicity exemplified by weight loss in these animals (FIG. 9G).

Taken together, these data suggested once weekly dosing with intratracheally administered HSV-IL12+HSV-GMCSF non-replicating HSV-1 vectors resulted in expression of full-length murine IL-12 and GM-CSF which at doses of 7.46E6 and 3.9E6, respectively, are well tolerated in healthy animals.

Example 10: Combinatorial HSV-IL12 and HSV-GMCSF Efficacy in an In Vivo Murine Model of Osteosarcoma The objective of this study was, in part, to evaluate the efficacy of intratracheal administration of combinatorial HSV-IL12 and HSV-GMCSF therapy at inhibiting established metastatic osteosarcoma lung tumor growth. All procedures have been described above (e.g. see Example 4 above). Table 11 provides a synopsis of the experimental design.

TABLE 11

Study Design

| Grp # | Tot. Animal # | Animal # | Inoculation | TA | Dose | Volume & Route | Dosing Day | Termination | Readout |
|---|---|---|---|---|---|---|---|---|---|
| 1 | 5 | 1, 2, 3, 4, 5 | — | — | — | — | — | Day 42 | Body weight |
| 2 | 5 | 6, 7, 8, 9, 10 | K7M2 tumors 100 mL 1.0E6 cells | Vehicle | — | 50 mL i.t. | Day 21 Day 28 Day 35 | | Lung weight |
| 3 | 5 | 11, 12, 13, 14, 15 | i.v. day 0 | Recombinant protein | 48 ng IL-12 2.5 ng GMCSF | | | | |
| 4 | 5 | 16, 17, 18, 19, 20 | | HSV-IL12 | 7.46E6 pfu | | Day 22 Day 29 Day 36 | | |
| 5 | 5 | 21, 22, 23, 24, 25 | | HSV-GMCSF | 3.9E6 pfu | | | | |
| 6 | 5 | 26, 27, 28, 29, 30 | | HSV-IL12 + HSV-GMCSF | 7.46E6 pfu 3.9E6 pfu | | | | | i.t.: intratracheal administration; i.v.: intravenous administration

Figure 10A:
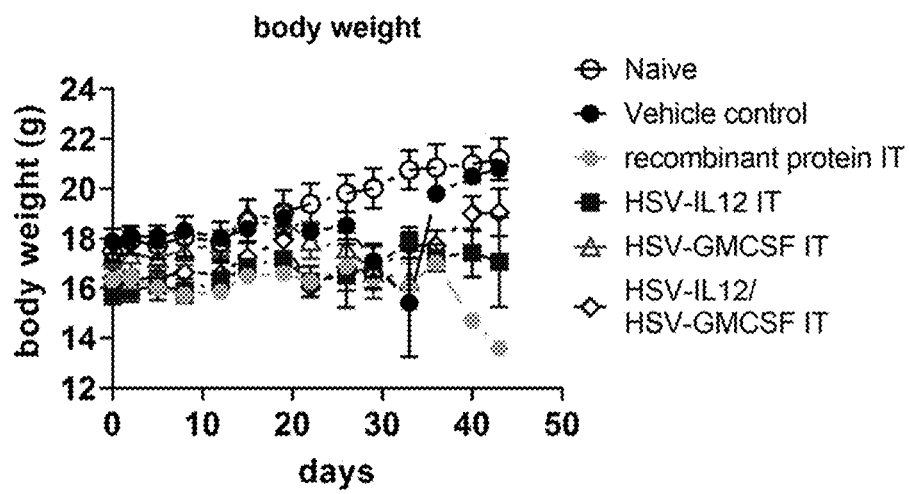
FIGS. 10A-10B depict combinatorial HSV-IL12 and HSV-GMCSF efficacy in an in vivo murine model of osteosarcoma.
Figure 10B:
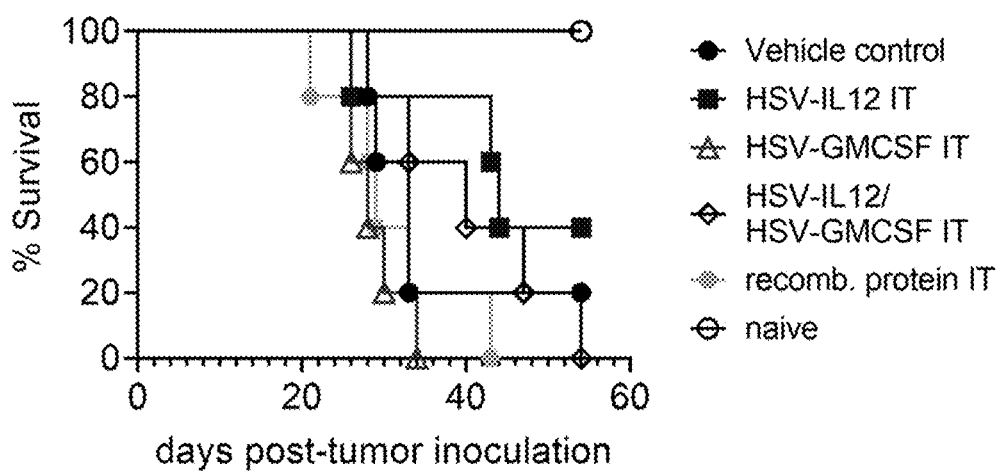

As shown in FIGS. 10A, animal body weights did show some fluctuation during the course of the study, which was indicative of animals succumbing to disease (FIG. 10A) With respect to survival, HSV-GMCSF administration to tumor-bearing mice resulted in a significant decline in the survival rate compared to all other therapies given to K7M2-inoculated animals, including vehicle alone (FIG. 10B). The results shown in FIG. 10B were surprising given the approval for human use of a replicating viral vector encoding GM-CSF for the treatment of metastatic melanoma. Further, while HSV-GMCSF therapy may not have been effective, treatment with HSV-IL12 to tumor-bearing mice enhanced survival compared to vehicle control animals, and prolonged survival of animals exposed to exogenous GM-CSF (FIG. 10B). Importantly, one animal in the HSV-IL12 treatment group was euthanized on a compassionate basis due to tumors interfering with mobility; however, when the animal was necropsied, no visible tumors were present in the lungs.

These data suggest HSV-IL12 may hold promise at limiting established metastatic lung tumor growth.

SEQUENCE LISTING

```
Sequence total quantity: 85
SEQ ID NO: 1            moltype = AA  length = 271
FEATURE                 Location/Qualifiers
source                  1..271
                        mol_type = protein
                        organism = Homo sapiens
SEQUENCE: 1
MAKVPDMFED LKNCYSENEE DSSSIDHLSL NQKSFYHVSY GPLHEGCMDQ SVSLSISETS   60
KTSKLTFKES MVVVATNGKV LKKRRLSLSQ SITDDDLEAI ANDSEEEIIK PRSAPFSFLS  120
NVKYNFMRII KYEFILNDAL NQSIIRANDQ YLTAAALHNL DEAVKFDMGA YKSSKDDAKI  180
TVILRISKTQ LYVTAQDEDQ PVLLKEMPEI PKTITGSETN LLFFWETHGT KNYFTSVAHP  240
NLFIATKQDY WVCLAGGPPS ITDFQILENQ A                                 271

SEQ ID NO: 2            moltype = AA  length = 269
FEATURE                 Location/Qualifiers
source                  1..269
                        mol_type = protein
                        organism = Homo sapiens
SEQUENCE: 2
MAEVPELASE MMAYYSGNED DLFFEADGPK QMKCSFQDLD LCPLDGGIQL RISDHHYSKG   60
FRQAASVVVA MDKLRKMLVP CPQTFQENDL STFFPFIFEE EPIFFDTWDN EAYVHDAPVR  120
SLNCTLRDSQ QKSLVMSGPY ELKALHLQGQ DMEQQVVFSM SFVQGEESND KIPVALGLKE  180
KNLYLSCVLK DDKPTLQLES VDPKNYPKKK MEKRFVFNKI EINNKLEFES AQFPNWYIST  240
SQAENMPVFL GGTKGGQDIT DFTMQFVSS                                    269

SEQ ID NO: 3            moltype = AA  length = 153
FEATURE                 Location/Qualifiers
source                  1..153
                        mol_type = protein
                        organism = Homo sapiens
SEQUENCE: 3
MYRMQLLSCI ALSLALVTNS APTSSSTKKT QLQLEHLLLD LQMILNGINN YKNPKLTRML   60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                               153

SEQ ID NO: 4            moltype = AA  length = 177
FEATURE                 Location/Qualifiers
source                  1..177
                        mol_type = protein
                        organism = Homo sapiens
SEQUENCE: 4
MFHVSFRYIF GLPPLILVLL PVASSDCDIE GKDGKQYESV LMVSIDQLLD SMKEIGSNCL   60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEH     177

SEQ ID NO: 5            moltype = AA  length = 219
FEATURE                 Location/Qualifiers
source                  1..219
                        mol_type = protein
                        organism = Homo sapiens
SEQUENCE: 5
MCPARSLLLV ATLVLLDHLS LARNLPVATP DPGMFPCLHH SQNLLRAVSN MLQKARQTLE   60
FYPCTSEEID HEDITKDKTS TVEACLPLEL TKNESCLNSR ETSFITNGSC LASRKTSFMM  120
ALCLSSIYED LKMYQVEFKT MNAKLLMDPK RQIFLDQNML AVIDELMQAL NFNSETVPQK  180
SSLEEPDFYK TKIKLCILLH AFRIRAVTID RVMSYLNAS                         219

SEQ ID NO: 6            moltype = AA  length = 328
FEATURE                 Location/Qualifiers
source                  1..328
                        mol_type = protein
                        organism = Homo sapiens
SEQUENCE: 6
MCHQQLVISW FSLVFLASPL VAIWELKKDV YVVELDWYPD APGEMVVLTC DTPEEDGITW   60
TLDQSSEVLG SGKTLTIQVK EFGDAGQYTC HKGGEVLSHS LLLLHKKEDG IWSTDILKDQ  120
```

```
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SKREKKDRVF TDKTSATVIC    300
RKNASISVRA QDRYYSSSWS EWASVPCS                                       328

SEQ ID NO: 7             moltype = AA   length = 146
FEATURE                  Location/Qualifiers
source                   1..146
                         mol_type = protein
                         organism = Homo sapiens
SEQUENCE: 7
MHPLLNPLLL ALGLMALLLT TVIALTCLGG FASPGPVPPS TALRELIEEL VNITQNQKAP     60
LCNGSMVWSI NLTAGMYCAA LESLINVSGC SAIEKTQRML SGFCPHKVSA GQFSSLHVRD    120
TKIEVAQFVK DLLLHLKKLF REGRFN                                         146

SEQ ID NO: 8             moltype = AA   length = 162
FEATURE                  Location/Qualifiers
source                   1..162
                         mol_type = protein
                         organism = Homo sapiens
SEQUENCE: 8
MRISKPHLRS ISIQCYLCLL LNSHFLTEAG IHVFILGCFS AGLPKTEANW VNVISDLKKI     60
EDLIQSMHID ATLYTESDVH PSCKVTAMKC FLLELQVISL ESGDASIHDT VENLIILANN    120
SLSSNGNVTE SGCKECEELE EKNIKEFLQS FVHIVQMFIN TS                       162

SEQ ID NO: 9             moltype = AA   length = 155
FEATURE                  Location/Qualifiers
source                   1..155
                         mol_type = protein
                         organism = Homo sapiens
SEQUENCE: 9
MTPGKTSLVS LLLLLSLEAI VKAGITIPRN PGCPNSEDKN FPRTVMVNLN IHNRNTNTNP     60
KRSSDYYNRS TSPWNLHRNE DPERYPSVIW EAKCRHLGCI NADGNVDYHM NSVPIQQEIL    120
VLRREPPHCP NSFRLEKILV SVGCTCVTPI VHHVA                               155

SEQ ID NO: 10            moltype = AA   length = 193
FEATURE                  Location/Qualifiers
source                   1..193
                         mol_type = protein
                         organism = Homo sapiens
SEQUENCE: 10
MAAEPVEDNC INFVAMKFID NTLYFIAEDD ENLESDYFGK LESKLSVIRN LNDQVLFIDQ     60
GNRPLFEDMT DSDCRDNAPR TIFIISMYKD SQPRGMAVTI SVKCEKISTL SCENKIISFK    120
EMNPPDNIKD TKSDIIFFQR SVPGHDNKMQ FESSSYEGYF LACEKERDLF KLILKKEDEL    180
GDRSIMFTVQ NED                                                       193

SEQ ID NO: 11            moltype = AA   length = 200
FEATURE                  Location/Qualifiers
source                   1..200
                         mol_type = protein
                         organism = Homo sapiens
SEQUENCE: 11
MKLDMTGDCT PVLVLMAAVL TVTGAVPVAR LHGALPDARG CHIAQFKSLS PQELQAFKRA     60
KDALEESLLL KDCRCHSRLF PRTWDLRQLQ VRERPMALEA ELALTLKVLE ATADTDPALV    120
DVLDQPLHTL HHILSQFRAC IQPQPTAGPR TRGRLHHWLY RLQEAPKKES PGCLEASVTF    180
NLFRLLTRDL NCVASGDLCV                                                200

SEQ ID NO: 12            moltype = AA   length = 196
FEATURE                  Location/Qualifiers
source                   1..196
                         mol_type = protein
                         organism = Homo sapiens
SEQUENCE: 12
MTGDCMPVLV LMAAVLTVTG AVPVARLRGA LPDARGCHIA QFKSLSPQEL QAFKRAKDAL     60
EESLLLKDCK CRSRLFPRTW DLRQLQVRER PVALEAELAL TLKVLEATAD TDPALGDVLD    120
QPLHTLHHIL SQLRACIQPQ PTAGPRTRGR LHHWLRLQE APKKESPGCL EASVTFNLFR    180
LLTRDLNCVA SGDLCV                                                    196

SEQ ID NO: 13            moltype = AA   length = 234
FEATURE                  Location/Qualifiers
source                   1..234
                         mol_type = protein
                         organism = Homo sapiens
SEQUENCE: 13
MCFPKVLSDD MKKLKARMVM LLPTSAQGLG AWVSACDTED TVGHLGPWRD KDPALWCQLC     60
LSSQHQAIER FYDKMQNAES GRGQVMSSLA ELEDDFKEGY LETVAAYYEE QHPELTPLLE    120
KERDGLRCRG NRSPVPDVED PATEEPGESF CDKVMRWFQA MLQRLQTWWH GVLAWVKEKV    180
VALVHAVQAL WKQFQSFCCS LSELFMSSFQ SYGAPRGDKE ELTPQKCSEP QSSK          234
```

| SEQ ID NO: 14 | moltype = AA length = 270 |
| --- | --- |
| FEATURE | Location/Qualifiers |
| source | 1..270 |
| | mol_type = protein |
| | organism = Homo sapiens |

SEQUENCE: 14
```
MKPKMKYSTN KISTAKWKNT ASKALCFKLG KSQQKAKEVC PMYFMKLRSG LMIKKEACYF    60
RRETTKRPSL KTGRKHKRHL VLAACQQQST VECFAFGISG VQKYTRALHD SSITGISPIT  120
EYLASLSTYN DQSITFALED ESYEIYVEDL KKDEKKDKVL LSYYESQHPS NESGDGVDGK  180
MLMVTLSPTK DFWLHANNKE HSVELHKCEK PLPDQAFFVL HNMHSNCVSF ECKTDPGVFI  240
GVKDNHLALI KVDSSENLCT ENILFKLSET                                  270
```

| SEQ ID NO: 15 | moltype = AA length = 242 |
| --- | --- |
| FEATURE | Location/Qualifiers |
| source | 1..242 |
| | mol_type = protein |
| | organism = Homo sapiens |

SEQUENCE: 15
```
MPRGFTWLRY LGIFLGVALG NEPLEMWPLT QNEECTVTGF LRDKLQYRSR LQYMKHYFPI    60
NYKISVPYEG VFRIANVTRL QRAQVSEREL RYLWVLVSLS ATESVQDVLL EGHPSWKYLQ  120
EVETLLLNVQ QGLTDVEVSP KVESVLSLLN APGPNLKLVR PKALLDNCFR VMELLYCSCC  180
KQSSVLNWQD CEVPSPQSCS PEPSLQYAAT QLYPPPPWSP SSPPHSTGSV RPVRAQGEGL  240
LP                                                                242
```

| SEQ ID NO: 16 | moltype = AA length = 233 |
| --- | --- |
| FEATURE | Location/Qualifiers |
| source | 1..233 |
| | mol_type = protein |
| | organism = Homo sapiens |

SEQUENCE: 16
```
MSTESMIRDV ELAEEALPKK TGGPQGSRRC LFLSLFSFLI VAGATTLFCL LHFGVIGPQR    60
EEFPRDLSLI SPLAQAVRSS SRTPSDKPVA HVVANPQAEG QLQWLNRRAN ALLANGVELR  120
DNQLVVPSEG LYLIYSQVLF KGQGCPSTHV LLTHTISRIA VSYQTKVNLL SAIKSPCQRE  180
TPEGAEAKPW YEPIYLGGVF QLEKGDRLSA EINRPDYLDF AESGQVYFGI IAL         233
```

| SEQ ID NO: 17 | moltype = AA length = 166 |
| --- | --- |
| FEATURE | Location/Qualifiers |
| source | 1..166 |
| | mol_type = protein |
| | organism = Homo sapiens |

SEQUENCE: 17
```
MKYTSYILAF QLCIVLGSLG CYCQDPYVKE AENLKKYFNA GHSDVADNGT LFLGILKNWK    60
EESDRKIMQS QIVSFYFKLF KNFKDDQSIQ KSVETIKEDM NVKFFNSNKK KRDDFEKLTN  120
YSVTDLNVQR KAIHELIQVM AELSPAAKTG KRKRSQMLFR GRRASQ                 166
```

| SEQ ID NO: 18 | moltype = AA length = 207 |
| --- | --- |
| FEATURE | Location/Qualifiers |
| source | 1..207 |
| | mol_type = protein |
| | organism = Homo sapiens |

SEQUENCE: 18
```
MAGPATQSPM KLMALQLLLW HSALWTVQEA TPLGPASSLP QSFLLKCLEQ VRKIQGDGAA    60
LQEKLVSECA TYKLCHPEEL VLLGHSLGIP WAPLSSCPSQ ALQLAGCLSQ LHSGLFLYQG  120
LLQALEGISP ELGPTLDTLQ LDVADFATTI WQQMEELGMA PALQPTQGAM PAFASAFQRR  180
AGGVLVASHL QSFLEVSYRV LRHLAQP                                     207
```

| SEQ ID NO: 19 | moltype = AA length = 144 |
| --- | --- |
| FEATURE | Location/Qualifiers |
| source | 1..144 |
| | mol_type = protein |
| | organism = Homo sapiens |

SEQUENCE: 19
```
MWLQSLLLLG TVACSISAPA RSPSPSTQPW EHVNAIQEAR RLLNLSRDTA AEMNETVEVI    60
SEMFDLQEPT CLQTRLELYK QGLRGSLTKL KGPLTMMASH YKQHCPPTPE TSCATQIITF  120
ESFKENLKDF LLVIPFDCWE PVQE                                        144
```

| SEQ ID NO: 20 | moltype = AA length = 107 |
| --- | --- |
| FEATURE | Location/Qualifiers |
| source | 1..107 |
| | mol_type = protein |
| | organism = Homo sapiens |

SEQUENCE: 20
```
MARAALSAAP SNPRLLRVAL LLLLLVAAGR RAAGASVATE LRCQCLQTLQ GIHPKNIQSV    60
NVKSPGPHCA QTEVIATLKN GRKACLNPAS PIVKKIIEKM LNSDKSN                107
```

| SEQ ID NO: 21 | moltype = AA length = 107 |
| --- | --- |
| FEATURE | Location/Qualifiers |
| source | 1..107 |
| | mol_type = protein |

```
                         organism = Homo sapiens
SEQUENCE: 21
MARATLSAAP SNPRLLRVAL LLLLLVAASR RAAGAPLATE LRCQCLQTLQ GIHLKNIQSV    60
KVKSPGPHCA QTEVIATLKN GQKACLNPAS PMVKKIIEKM LKNGKSN                107

SEQ ID NO: 22            moltype = AA  length = 99
FEATURE                  Location/Qualifiers
source                   1..99
                         mol_type = protein
                         organism = Homo sapiens
SEQUENCE: 22
MTSKLAVALL AAFLISAALC EGAVLPRSAK ELRCQCIKTY SKPFHPKFIK ELRVIESGPH    60
CANTEIIVKL SDGRELCLDP KENWVQRVVE KFLKRAENS                          99

SEQ ID NO: 23            moltype = AA  length = 125
FEATURE                  Location/Qualifiers
source                   1..125
                         mol_type = protein
                         organism = Homo sapiens
SEQUENCE: 23
MKKSGVLFLL GIILLVLIGV QGTPVVRKGR CSCISTNQGT IHLQSLKDLK QFAPSPSCEK    60
IEIIATLKNG VQTCLNPDSA DVKELIKKWE KQVSQKKKQK NGKKHQKKKV LKVRKSQRSR   120
QKKTT                                                              125

SEQ ID NO: 24            moltype = AA  length = 94
FEATURE                  Location/Qualifiers
source                   1..94
                         mol_type = protein
                         organism = Homo sapiens
SEQUENCE: 24
MSVKGMAIAL AVILCATVVQ GFPMFKRGRC LCIGPGVKAV KVADIEKASI MYPSNNCDKI    60
EVIITLKENK GQRCLNPKSK QARLIIKKVE RKNF                               94

SEQ ID NO: 25            moltype = AA  length = 254
FEATURE                  Location/Qualifiers
source                   1..254
                         mol_type = protein
                         organism = Homo sapiens
SEQUENCE: 25
MGRDLRPGSR VLLLLLLLL VYLTQPGNGN EGSVTGSCYC GKRISSDSPP SVQFMNRLRK     60
HLRAYHRCLY YTRFQLLSWS VCGGNKDPWV QELMSCLDLK ECGHAYSGIV AHQKHLLPTS   120
PPISQASEGA SSDIHTPAQM LLSTLQSTQR PTLPVGSLSS DKELTRPNET TIHTAGHSLA   180
AGPEAGENQK QPEKNAGPTA RTSATVPVLC LLAIIFILTA ALSYVLCKRR RGQSPQSSPD   240
LPVHYIPVAP DSNT                                                    254

SEQ ID NO: 26            moltype = AA  length = 99
FEATURE                  Location/Qualifiers
source                   1..99
                         mol_type = protein
                         organism = Homo sapiens
SEQUENCE: 26
MKVSAALLCL LLIAATFIPQ GLAQPDAINA PVTCCYNFTN RKISVQRLAS YRRITSSKCP    60
KEAVIFKTIV AKEICADPKQ KWVQDSMDHL DKQTQTPKT                          99

SEQ ID NO: 27            moltype = AA  length = 92
FEATURE                  Location/Qualifiers
source                   1..92
                         mol_type = protein
                         organism = Homo sapiens
SEQUENCE: 27
MQVSTAALAV LLCTMALCNQ FSASLAADTP TACCFSYTSR QIPQNFIADY FETSSQCSKP    60
GVIFLTKRSR QVCADPSEEW VQKYVSDLEL SA                                 92

SEQ ID NO: 28            moltype = AA  length = 92
FEATURE                  Location/Qualifiers
source                   1..92
                         mol_type = protein
                         organism = Homo sapiens
SEQUENCE: 28
MKLCVTVLSL LMLVAAFCSP ALSAPMGSDP PTACCFSYTA RKLPRNFVVD YYETSSLCSQ    60
PAVVFQTKRS KQVCADPSES WVQEYVYDLE LN                                 92

SEQ ID NO: 29            moltype = AA  length = 91
FEATURE                  Location/Qualifiers
source                   1..91
                         mol_type = protein
                         organism = Homo sapiens
SEQUENCE: 29
MKVSAAALAV ILIATALCAP ASASPYSSDT TPCCFAYIAR PLPRAHIKEY FYTSGKCSNP    60
```

```
AVVFVTRKNR QVCANPEKKW VREYINSLEM S                                91

SEQ ID NO: 30           moltype = AA   length = 97
FEATURE                 Location/Qualifiers
source                  1..97
                        mol_type = protein
                        organism = Homo sapiens
SEQUENCE: 30
MKVSAALLWL LLIAAAFSPQ GLAGPASVPT TCCFNLANRK IPLQRLESYR RITSGKCPQK   60
AVIFKTKLAK DICADPKKKW VQDSMKYLDQ KSPTPKP                            97

SEQ ID NO: 31           moltype = DNA   length = 816
FEATURE                 Location/Qualifiers
source                  1..816
                        mol_type = unassigned DNA
                        organism = Homo sapiens
SEQUENCE: 31
atggccaaag ttccagacat gtttgaagac ctgaagaact gttacagtga aaatgaagaa   60
gacagttcct ccattgatca tctgtctctg aatcagaaat ccttctatca tgtaagctat  120
ggcccactcc atgaaggctg catggatcaa tctgtgtctc tgagtatctc tgaaacctct  180
aaaacatcca agcttacctt caaggagagc atggtggtag tagcaaccaa cgggaaggtt  240
ctgaagagaa gacggttgag tttaagccaa tccatcactg atgatgacct ggaggccatc  300
gccaatgact cagaggaaga aatcatcaag cctaggtcag caccttttag cttcctgagc  360
aatgtgaaat acaactttat gaggatcatc aaatacgaat tcatcctgaa tgacgccctc  420
aatcaaagta taattcgagc caatgatcag tacctcacgg ctgctgcatt acataatctg  480
gatgaagcag tgaaatttga catgggtgct tataagtcat caaaggatga tgctaaaatt  540
accgtgattc taagaatctc aaaaaactca aattgtatgtga ctgcccaaga tgaagaccaa  600
ccagtgctgc tgaaggagat gcctgagata cccaaaacca tcacaggtag tgagaccaac  660
ctcctcttct tctgggaaac tcacggcact aagaactatt tcacatcagt tgcccatcca  720
aacttgttta ttgccacaaa gcaagactac tgggtgtgct tggcagggg gccaccctct  780
atcactgact tcagatact ggaaaaccag gcgtag                              816

SEQ ID NO: 32           moltype = DNA   length = 810
FEATURE                 Location/Qualifiers
source                  1..810
                        mol_type = unassigned DNA
                        organism = Homo sapiens
SEQUENCE: 32
atggcagaag tacctgagct cgccagtgaa atgatggctt attacagtgg caatgaggat   60
gacttgttct ttgaagctga tggccctaaa cagatgaagt gctccttcca ggacctggac  120
ctctgccctc tggatggcgg catccagcta cgaatctccg accaccacta cagcaagggc  180
ttcaggcagg ccgcgtcagt tgttgtggcc atggacaagc tgaggaagat gctggttccc  240
tgcccacaga ccttccagga gaatgacctg agcaccttct tcccttcat ctttgaagaa  300
gaacctatct tcttcgacac atgggataac gaggcttatg tgcacgatgc acctgtacga  360
tcactgaact gcacgctccg ggactcacag caaaaaagct tggtgatgtc tggtccatat  420
gaactgaaag ctctccacct ccaggacag gatatgaage aacaagtggt gttctccatg  480
tcctttgtac aaggagaaga agtaatgac aaaatactgg ccttgg cctcaaggaa  540
aagaatctgt acctgtcctg cgtgttgaaa gatgataagc ccactctaca gctgaagagt  600
gtagatccca aaaattaccc aaagaagaag atggaaaagc gatttgtctt caacaagata  660
gaaatcaata acaagctgga atttgagtct gcccagttcc ccaactggta catcagcacc  720
tctcaagcag aaaacatgcc cgtcttcctg ggagggacca aaggcggcca ggatataact  780
gacttccacca tgcaatttgt gtcttcctaa                                   810

SEQ ID NO: 33           moltype = DNA   length = 462
FEATURE                 Location/Qualifiers
source                  1..462
                        mol_type = unassigned DNA
                        organism = Homo sapiens
SEQUENCE: 33
atgtacagga tgcaactcct gtcttgcatt gcactaagtc ttgcacttgt cacaaacagt   60
gcacctactt caagttctac aaagaaaaca cagctacaac tggagcattt actgctggat  120
ttacagatga tttgaatgg aattaataat tacaagaatc ccaaactcac caggatgctc  180
acatttaagt tttacatgcc caagaaggcc acagaactga acatcttca gtgtctagaa  240
gaagaactca aacctctgga ggaagtgcta aatttagctc aaagcaaaa ctttcactta  300
agacccaggg acttaatcag caatatcaac gtaatagttc tggaactaaa gggatcctaa  360
acaacattca tgtgtgaata tgctgatgag acagcaacca ttgtagaatt tctgaacaga  420
tggattacct tttgtcaaag catcatctca cactgacttg a                      462

SEQ ID NO: 34           moltype = DNA   length = 534
FEATURE                 Location/Qualifiers
source                  1..534
                        mol_type = unassigned DNA
                        organism = Homo sapiens
SEQUENCE: 34
atgttccatg tttctttag gtatatctt ggacttcctc ccctgatcct tgttctgttg     60
ccagtagcat catctgattg tgatattgaa ggtaaagatg gcaaacaata tgagagtgtt  120
ctaatggtca gcatcgatca attattggac agcatgaaag aaattggtag caattgcctg  180
aataatgaat ttaacttttt taaagacat atctgtgatg ctaataagga aggtatgttt  240
ttattccgtg ctgctcgcaa gttgaggcaa tttcttaaaa tgaatagcac tggtgatttt  300
```

```
gatctccact tattaaaagt ttcagaaggc acaacaatac tgttgaactg cactggccag    360
gttaaaggaa gaaaccagc tgccctgggt gaagcccaac caacaaagag tttgaagaa     420
aataaatctt taaggaaca gaaaaaactg aatgacttgt gtttcctaaa gagactatta    480
caagagataa aaacttgttg gaataaaatt ttgatgggca ctaaagaaca ctga          534
```

```
SEQ ID NO: 35              moltype = DNA  length = 762
FEATURE                    Location/Qualifiers
source                     1..762
                           mol_type = unassigned DNA
                           organism = Homo sapiens
SEQUENCE: 35
atgtggcccc ctgggtcagc ctcccagcca ccgccctcac ctgccgcggc cacaggtctg    60
catccagcgg ctcgccctgt gtccctgcag tgccggctca gcatgtgtcc agcgcgcagc   120
ctcctccttg tggctaccct ggtcctcctg gaccacctca gtttggccag aaacctcccc   180
gtggccactc cagacccagg aatgttccca tgccttcacc actcccaaaa cctgctgagg   240
gccgtcagca acatgctcca gaaggccaga caaactctag aatttttaccc ttgcacttct   300
gaagagattg atcatgaaga tatcacaaaa gataaaacca gcacagtgga ggcctgttta   360
ccattggaat taaccaagaa tgagagttgc ctaaattcca gagagacctc tttcataact   420
aatgggagtt gcctgcctc cagaaagacc tcttttatga tggccctgtg ccttagtagt   480
atttatgaag acttgaagat gtaccaggtg gagttcaaga ccatgaatgc aaagcttctg   540
atggatccta agaggcagat cttttctagat caaaacatgc tggcagttat tgatgagctg   600
atgcaggccc tgaatttcaa cagtgaggact gtgccacaaa aatcctccct tgaagaaccg   660
gatttttata aaactaaaat caagctctgc ataacttcttc atgctttcag aattcgggca   720
gtgactattg atagagtgat gagctatctg aatgcttcct aa                      762
```

```
SEQ ID NO: 36              moltype = DNA  length = 987
FEATURE                    Location/Qualifiers
source                     1..987
                           mol_type = unassigned DNA
                           organism = Homo sapiens
SEQUENCE: 36
atgtgtcacc agcagttggt catctcttgg ttttccctgg tttttctggc atctccctc    60
gtggccatat gggaactgaa gaaagatgtt tatgtcgtag aattggattg gtatccggat   120
gccccctgga aaatggtggt cctcacctgt gacaccctgt aagaagatgg tatcacctgg   180
accttggacc agagcagtga ggttctaggc tctggcaaaa ccctgaccat ccaagtcaaa    240
gagtttggag atgctggcca gtacacctgt cacaaaggag gcgaggttct aagccattcg   300
ctcctgctgc ttcacaaaaa ggaagatgga atttggtcca ctgatatttt aaaggaccag   360
aaagaaccca aaataagac ctttctaaga tgcgaggcca agaattattc tggacgtttc   420
acctgctggt ggctgacgac aatcagtact gatttgacat tcagtgtcaa aagcagcaga   480
ggctcttctg accccaagg ggtgacgtgc ggagctgcta cactctctgc agagagagtc   540
agaggggaca caaggagta tgagtactca gtggagtgcc aggaggacag tgcctgccca   600
gctgctgagg agagtctgcc cattgaggtc atggtggatg ccgttcacaa gctcaagtat   660
gaaaactaca ccagcagctt cttcatcagg gacatcatca cccgaccc acccaagaac   720
ttgcagctga agccattaaa gaattctcgg caggtggagg tcagctggga gtaccctgac   780
acctggagta ctccacattc ctacttctcc ctgacattct gcgttcaggt ccagggcaag    840
agcaagagag aaaagaaaga tagagtcttc acggacaaga cctcagccac ggtcatctgc    900
cgcaaaaatg ccagcattag cgtgcgggcc caggaccgct actatagctc atcttggagc    960
gaatgggcat ctgtgccctg cagttag                                       987
```

```
SEQ ID NO: 37              moltype = DNA  length = 441
FEATURE                    Location/Qualifiers
source                     1..441
                           mol_type = unassigned DNA
                           organism = Homo sapiens
SEQUENCE: 37
atgcatccgc tcctcaatcc tctcctgttg gcactgggcc tcatggcgct tttgttgacc    60
acggtcattg ctctcacttg ccttggcggc tttgcctccc caggccctgt gcctccctct   120
acagccctca gggagctcat tgaggagctg gtcaacatca cccagaacca gaaggctccg   180
ctctgcaatg gcagcatggt atggagcatc aacctgacag ctgtgtgcagcc                240
ctggaatccc tgatcaacgt gtcaggctgc agtgccatcg agaagaccca gaggatgctg   300
agcggattct gccccgcacaa ggtctcagct gggcagtttt ccagcttgca tgtccgagac    360
accaaaatcg aggtggccca gtttgtaaag gacctgctct tacatttaaa gaaactttt    420
cgcgaggac agttcaactg a                                              441
```

```
SEQ ID NO: 38              moltype = DNA  length = 489
FEATURE                    Location/Qualifiers
source                     1..489
                           mol_type = unassigned DNA
                           organism = Homo sapiens
SEQUENCE: 38
atgagaattt cgaaaccaca tttgagaagt atttccatcc agtgctactt gtgtttactt    60
ctaaacagtc attttctaac tgaagctggc attcatgtct tcattttggg ctgtttcagt   120
gcagggcttc ctaaaacaga agccaactgg gtgaatgtaa taagtgattt gaaaaaaatt   180
gaagatctta ttcaatctat gcatattgat gctactttat atacggaaag tgatgttcac   240
cccagttgca aagtaacagc aatgaagtgc tttctcttgg agttacaagt tatttcactt   300
gagtccggag atgcaagtat tcatgataca gtagaaaatc tgatcatcct agcaaacaac   360
agtttgtctt ctaatgggaa tgtaacagaa tctggatgca aagaatgtga ggaactggag   420
gaaaaaaata ttaaagaatt tttgcagagt tttgtacata ttgtccaaat gttcatcaac   480
acttcttga                                                           489
```

```
SEQ ID NO: 39            moltype = DNA  length = 468
FEATURE                  Location/Qualifiers
source                   1..468
                         mol_type = unassigned DNA
                         organism = Homo sapiens
SEQUENCE: 39
atgactcctg ggaagacctc attggtgtca ctgctactgc tgctgagcct ggaggccata   60
gtgaaggcag gaatcacaat cccacgaaat ccaggatgcc caaattctga ggacaagaac  120
ttcccccgga ctgtgatggt caaccgtgaac atccataacc ggaataccaa taccaatccc  180
aaaaggtcct cagattacta caaccgatcc acctcacctt ggaatctcca ccgcaatgag  240
gaccctgaga gatatccctc tgtgatctgg gaggcaaagt gccgccactt gggctgcatc  300
aacgctgatg ggaacgtgga ctaccacatg aactctgtcc ccatccagca agagatcctg  360
gtcctgcgca gggagcctcc acactgcccc aactcctgcc ggctggagaa gatactggtg  420
tccgtgggct gcacctgtgt caccccgatt gtccaccatg tggcctaa              468

SEQ ID NO: 40            moltype = DNA  length = 582
FEATURE                  Location/Qualifiers
source                   1..582
                         mol_type = unassigned DNA
                         organism = Homo sapiens
SEQUENCE: 40
atggctgctg aaccagtaga agacaattgc atcaactttg tggcaatgaa atttattgac   60
aatacgcttt actttatagc tgaagatgat gaaaacctgg aatcagatta ctttggcaag  120
cttgaatcta aattatcagt cataagaaat ttgaatgacc aagttctctt cattgaccaa  180
ggaaatcggc ctctatttga agatatgact gattctgact gtagagataa tgcaccccgg  240
accatatttta ttataagtat gtataaagat agccagccta gaggtatggc tgtaactatc  300
tctgtgaagt gtgagaaaat ttcaactctc tcctgtgaga acaaaattat ttcctttaag  360
gaaatgaatc ctcctgataa catcaaggat acaaaaagtg acatcatatt ctttcagaga  420
agtgtcccag gacatgataa taagatgcaa tttgaatctt catcatacga aggatacttt  480
ctagcttgtg aaaaagagag agacctttt aaactcattt tgaaaaaaga ggatgaattg  540
ggggatagat ctataatgtt cactgttcaa aacgaagact ag                    582

SEQ ID NO: 41            moltype = DNA  length = 603
FEATURE                  Location/Qualifiers
source                   1..603
                         mol_type = unassigned DNA
                         organism = Homo sapiens
SEQUENCE: 41
atgaaactag acatgactgg ggactgcacg ccagtgctgg tgctgatggc cgcagtgctg   60
accgtgactg gagcagttcc tgtcgccagg ctccacgggg ctctcccgga tgcaaggggc  120
tgccacatag cccagttcaa gtccctgtct ccacaggagc tgcaggcctt taagagggcc  180
aaagatgcct tagaagagtc gcttctgctg aaggactgca ggtgccactc ccgcctcttc  240
cccaggacct gggacctgag gcagctgcag gtgagggagc gccccatggc tttggaggct  300
gagctggccc tgacgctgaa ggttctggag gccaccgctg acactgaccc agccctggtg  360
gacgtcttgg accagcccct tcacaccctg caccatatcc tctcccagtt ccgggcctgt  420
atccagcctc agcccacggc agggcccagg acccggggcc gcctccacca ttggctgtac  480
cggctccagg aggccccaaa aaaggagtcc cctggctgcc tcgaggcctc tgtcaccttc  540
aacctcttcc gcctcctcac gcgagacctg aattgtgttg ccagtgggga cctgtgtgtc  600
tga                                                                603

SEQ ID NO: 42            moltype = DNA  length = 603
FEATURE                  Location/Qualifiers
source                   1..603
                         mol_type = unassigned DNA
                         organism = Homo sapiens
SEQUENCE: 42
atgaaactag acatgaccgg ggactgcatg ccagtgctgg tgctgatggc cgcagtgctg   60
accgtgactg gagcagttcc tgtcgccagg ctccgcgggg ctctcccgga tgcaaggggc  120
tgccacatag cccagttcaa gtccctgtct ccacaggagc tgcaggcctt taagagggcc  180
aaagatgcct tagaagagtc gcttctgctg aaggactgca agtgccgctc ccgcctcttc  240
cccaggacct gggacctgag gcagctgcag gtgagggagc gccccgtggc tttggaggct  300
gagctggccc tgacgctgaa ggttctggag gccaccgctg acactgaccc agccctgggg  360
gatgtcttgg accagcccct tcacaccctg caccatatcc tctcccagct ccgggcctgt  420
atccagcctc agcccacggc agggcccagg acccggggcc gcctccacca ttggctgcac  480
cggctccagg aggccccaaa aaaggagtcc cctggctgcc tcgaggcctc tgtcaccttc  540
aacctcttcc gcctcctcac gcgagacctg aattgtgttg ccagcgggga cctgtgtgtc  600
tga                                                                603

SEQ ID NO: 43            moltype = DNA  length = 567
FEATURE                  Location/Qualifiers
source                   1..567
                         mol_type = unassigned DNA
                         organism = Homo sapiens
SEQUENCE: 43
atgtgcttcc cgaaggtcct ctctgatgac atgaagaagc tgaaggcccg aatgcaccag   60
gccatagaaa gatttatga taaaatgcaa atgcagaat caggacgtgg acaggtgatg  120
tcgagcctgg cagagctgga ggacgacttc aaagagggcc acctggagac agtggcggct  180
tattatgagg agcagcaccc agagctcact cctctacttg aaaaagaaag agatggatta  240
```

```
cggtgccgag gcaacagatc ccctgtcccg gatgttgagg atcccgcaac cgaggagcct  300
ggggagagct tttgtgacaa ggtcatgaga tggttccagg ccatgctgca gcggctgcag  360
acctggtggc acggggttct ggcctgggtg aaggagaagg tggtggccct ggtccatgca  420
gtgcaggccc tctggaaaca gttccagagt ttctgctgct ctctgtcaga gctcttcatg  480
tcctctttcc agtcctacgg agccccacgg ggggacaagg aggagctgac accccagaag  540
tgctctgaac cccaatcctc aaaatga                                      567
```

SEQ ID NO: 44          moltype = DNA  length = 813
FEATURE                Location/Qualifiers
source                 1..813
                       mol_type = unassigned DNA
                       organism = Homo sapiens
SEQUENCE: 44
```
atgaagccta aaatgaagta ttcaaccaac aaaatttcca cagcaaagtg gaagaacaca   60
gcaagcaaag ccttgtgttt caagctggga aaatcccaac agaaggccaa agaagtttgc  120
cccatgtact ttatgaagct ccgctctggc cttatgataa aaaaggaggc ctgttacttt  180
aggagagaaa ccaccaaaag gccttcactg aaaacaggta gaaagcacaa aagacatctg  240
gtactcgctg cctgtcaaca gcagtctact gtggagtgtc ttgcctttgg tatatcaggg  300
gtccagaaat atactagagc acttcatgat tcaagtatca caggaatttc acctattaca  360
gagtatcttg cttctctaag cacatacaat gatcaatcca ttactttgc tttggaggat   420
gaaagttatg agatatatgt tgaagacttg aaaaagatg aaaagaaaga taaggtgtta   480
ctgagttact atgagtctca acaccccta atgaatgac gtgacggtgt tgatggtaag   540
atgttaatgg taaccctgag tcctacaaaa gacttctggt tgcatgccaa caacaaggaa  600
cactctgtgg agctccataa gtgtgaaaaa ccactgccag accaggcctt cttttgtcctt 660
cataatatgc actccaactg tgtttcattt gaatgcaaga ctgatcctgg agtgtttata  720
ggtgtaaagg ataatcatct tgctctgatt aaagtagact cttctgagaa tttgtgtact  780
gaaaatatct tgtttaagct ctctgaaact tag                               813
```

SEQ ID NO: 45          moltype = DNA  length = 729
FEATURE                Location/Qualifiers
source                 1..729
                       mol_type = unassigned DNA
                       organism = Homo sapiens
SEQUENCE: 45
```
atgccccggg gcttcacctg gctgcgctat cttgggatct tccttggcgt ggccttgggg   60
aatgagcctt tggagatgtg gccccttacg cagaatgagg agtgcactgt cacgggtttt  120
ctgcgggaca gctgcagta caggagccga cttcagtaca tgaaacacta cttccccatc   180
aactacaaga tcagtgtgcc ttacgagggg gtgttcagaa tcgccaacgt caccaggctg  240
cagagggccc aggtgagcga gcgggagctg cggtatctgt gggtcttggt gagcctcagt  300
gccactgagt cggtgcagga cgtgctgctc gagggccacc atcctggaa gtacctgcag  360
gaggtggaga cgctgctgct gaatgtccag caggcctca cggatgtgga ggtcagcccc  420
aaggtggaat ccgtgttgtc cctcttgaat gccccagggc caaacctgaa gctggtgcgg  480
cccaaagccc tgctggacaa ctgcttccgg gtcatggagc tgctgtactg ctcctgctgt  540
aaacaaagct ccgtcctaaa ctggcaggac tgtgaggtgc caagtcctca gtcttgcagc  600
ccagagccct cattgcagta tgcggccacc cagctgtacc ctccgccccc gtggtccccc  660
agctcccgc tcactccac gggctcggtg aggccggtca gggcacaggg cgagggcctc  720
ttgccctga                                                          729
```

SEQ ID NO: 46          moltype = DNA  length = 702
FEATURE                Location/Qualifiers
source                 1..702
                       mol_type = unassigned DNA
                       organism = Homo sapiens
SEQUENCE: 46
```
atgagcactg aaagcatgat ccgggacgtg gagctggccg aggaggcgct cccccaagaag   60
acagggggggc cccagggctc caggcggtgc ttgttcctca gcctcttctc cttcctgatc  120
gtggcaggcg ccaccacgct cttctgcctg ctgcactttg gagtgatcgg ccccccagagg 180
gaaagagttcc ccagggacct ctctctaatc agccctctgg cccaggcagt cagatcatct  240
tctcgaaccc cgagtgacaa ggcctgtagcc catgttgagc caaacctcta gctgagggg   300
cagctccagt ggctgaaccg ccgggccaat gccctcctgg ccaatgcgt ggagctgaga  360
gataaccagc tggtggtgcc atcagagggc ctgtacctca tctactccca ggtcctcttc  420
aagggccaag gctgccctc cacccatgtg ctcctcaccc acaccatcag ccgcatcgcc  480
gtctcctacc agaccaaggt caacctcctc tctgccatca gagccctg ccagagggag   540
accccagagg gggctgaggc caagcctggg tatgagcca tcatctgggg gatgggtctc  600
cagctggaga agggtgaccg actcagcgct gagatcaatc ggccccgacta tctcgactt  660
gccgagtctg ggcaggtcta ctttgggatc attgccctgt ga                     702
```

SEQ ID NO: 47          moltype = DNA  length = 501
FEATURE                Location/Qualifiers
source                 1..501
                       mol_type = unassigned DNA
                       organism = Homo sapiens
SEQUENCE: 47
```
atgaaatata caagttatat cttggctttt cagctctgca tcgttttggg ttctcttggc   60
tgttactgcc aggacccata tgtaaaagaa gcagaaaacc ttaagaaata ttttaatgca  120
ggtcattcag atgtagcgga taatggaact ctttttctag gcattttgaa gaattggaaa  180
gaggagagtg acagaaaaat aatgcagagc caaattgtct cctttactt caaacttttt  240
aaaaacttta aagatgacca gagcatccaa aagagtgtgg agaccatcaa ggaagacatg  300
aatgtcaagt ttttcaatag caacaaaaag aaacgagatg acttcgaaaa gctgactaat  360
```

-continued

```
tattcggtaa ctgacttgaa tgtccaacgc aaagcaatac atgaactcat ccaagtgatg  420
gctgaactgt cgccagcagc taaaacaggg aagcgaaaaa ggagtcagat gctgtttcga  480
ggtcgaagag catcccagta a                                           501

SEQ ID NO: 48          moltype = DNA   length = 624
FEATURE                Location/Qualifiers
source                 1..624
                       mol_type = unassigned DNA
                       organism = Homo sapiens
SEQUENCE: 48
atggctggac ctgccaccca gagcccatg aagctgatgg ccctgcagct gctgctgtgg   60
cacagtgcac tctggacagt gcaggaagcc accccctgg gccctgccag ctccctgccc   120
cagagcttcc tgctcaagtg cttagagcaa gtgaggaaga tccagggcga tggcgcagcg   180
ctccaggaga agctggtgag tgagtgtgcc acctacaagc tgtgccaccc cgaggagctg   240
gtgctgctcg acactctct gggcatcccc tgggctcccc tgagcagctg ccccagccag   300
gccctgcagc tggcaggctg cttgagccaa ctccatagcg gccttttcct ctaccagggg   360
ctcctgcagg ccctggaagg gatctccccc gagttgggtc ccaccttgga cacactgcag   420
ctggacgtcg ccgactttgc caccaccatc tggcagcaga tggaagaact gggaatggcc   480
cctgccctgc agcccaccca gggtgccatg ccggccttcg cctctgcttt ccagcgccgg   540
gcaggagggg tcctggttgc ctcccatctg cagagcttcc tggaggtgtc gtaccgcgtt   600
ctacgccacc ttgcccagcc ctga                                         624

SEQ ID NO: 49          moltype = DNA   length = 435
FEATURE                Location/Qualifiers
source                 1..435
                       mol_type = unassigned DNA
                       organism = Homo sapiens
SEQUENCE: 49
atgtggctgc agagcctgct gctcttgggc actgtggcct gcagcatctc tgcacccgcc   60
cgctcgccca gcccagcac gcagcccctgg gagcatgtga atgccatcca ggaggcccgg   120
cgtctcctga acctgagtag agacactgct gctgagatga atgaaacagt agaagtcatc   180
tcagaaatgt tgacctcca ggagccgacc tgcctacaga cccgcctgga gctgtacaag   240
cagggcctgc ggggcagcct caccaagctc aaggggcccct tgaccatgat ggccagccac   300
tacaagcagc actgccctcc aaccccggaa acttcctgtg caacccagat tatcacctttt   360
gaaagtttca aagagaacct gaaggacttt ctgcttgtca tcccctttga ctgctgggag   420
ccagtccagg agtga                                                   435

SEQ ID NO: 50          moltype = DNA   length = 324
FEATURE                Location/Qualifiers
source                 1..324
                       mol_type = unassigned DNA
                       organism = Homo sapiens
SEQUENCE: 50
atggcccgcg ctgctctctc cgccgccccc agcaatcccc ggctcctgcg agtggcactg   60
ctgctcctgc tcctggtagc cgctggccgg cgcgcagcag gagcgtccgt ggccactgaa   120
ctgcgctgcc agtgcttgca gacccttgcag ggaattcacc ccaagaacat ccaaagtgtg   180
aacgtgaagt cccccggacc ccactgcgcc caaaccgaag tcatagccac actcaagaat   240
gggcggaaag cttgcctcaa tcctgcatcc cccatagtta agaaaatcat cgaaaagatg   300
ctgaacagtg acaaatccaa ctga                                         324

SEQ ID NO: 51          moltype = DNA   length = 324
FEATURE                Location/Qualifiers
source                 1..324
                       mol_type = unassigned DNA
                       organism = Homo sapiens
SEQUENCE: 51
atggcccgcg ccacgctctc cgccgccccc agcaatcccc ggctcctgcg ggtggcgctg   60
ctgctcctgc tcctggtggc cgccagccgg cgcgcagcag gagcgcccct ggccactgaa   120
ctgcgctgcc agtgcttgca gacccttgcag ggaattcacc tcaagaacat ccaaagtgtg   180
aaggtgaagt ccccccggacc ccactgcgcc caaaccgaag tcatagccac actcaagaat   240
gggcagaaag cttgtctcaa ccccgcatcg cccatggtta agaaaatcat cgaaaagatg   300
ctgaaaaatg gcaaatccaa ctga                                         324

SEQ ID NO: 52          moltype = DNA   length = 300
FEATURE                Location/Qualifiers
source                 1..300
                       mol_type = unassigned DNA
                       organism = Homo sapiens
SEQUENCE: 52
atgacttcca agctgccgt ggctctcttg gcagccttcc tgatttctgc agctctgtgt   60
gaaggtgcag ttttgccaag gagtgctaaa gaacttagat gtcagtgcat aaagacatac   120
tccaaacctt tccaccccaa atttatcaaa gaactgagag tgattgagag tggaccacac   180
tgcgccaaca cagaaattat tgtaaagctt tctgatggaa gagagctctg tctggacccc   240
aaggaaaact gggtgcagag ggttgtggag aagtttttga gagggctga gaattcataa   300

SEQ ID NO: 53          moltype = DNA   length = 378
FEATURE                Location/Qualifiers
source                 1..378
                       mol_type = unassigned DNA
```

```
                        organism = Homo sapiens
SEQUENCE: 53
atgaagaaaa gtggtgttct tttcctcttg ggcatcatct tgctggttct gattggagtg    60
caaggaaccc cagtagtgag aaagggtcgc tgttcctgca tcagcaccaa ccaagggact   120
atccacctac aatccttgaa agaccttaaa caatttgccc caagcccttc ctgcgagaaa   180
attgaaatca ttgctacact gaagaatgga gttcaaacat gtctaaaccc agattcagca   240
gatgtgaagg aactgattaa aaagtgggag aaacaggtca gccaaaagaa aaagcaaaag   300
aatgggaaaa aacatcaaaa aaagaaagtt ctgaaagttc gaaaatctca acgttctcgt   360
caaaagaaga ctacataa                                                 378

SEQ ID NO: 54           moltype = DNA   length = 285
FEATURE                 Location/Qualifiers
source                  1..285
                        mol_type = unassigned DNA
                        organism = Homo sapiens
SEQUENCE: 54
atgagtgtga agggcatggc tatagccttg gctgtgatat tgtgtgctac agttgttcaa    60
ggcttcccca tgttcaaaag aggacgctgt ctttgcatag gccctgggt aaaagcaggt    120
aaagtggcag atattgagaa agcctccata atgtacccaa gtaacaactg tgacaaaata   180
gaagtgatta ttaccctgaa agaaaataaa ggacaacgat gcctaaatcc caaatcgaag   240
caagcaaggc ttataatcaa aaaagttgaa agaaagaatt tttaa                   285

SEQ ID NO: 55           moltype = DNA   length = 822
FEATURE                 Location/Qualifiers
source                  1..822
                        mol_type = unassigned DNA
                        organism = Homo sapiens
SEQUENCE: 55
atgtctggga gtcagagcga ggtggctcca tccccgcaga gtccgcggag ccccgagatg    60
ggacgggact tgcggcccgg gtcccgcgtg ctcctgctcc tgcttctgct cctgctggtg   120
tacctgactc agccaggcaa tggcaacgag ggcagcgtca ctggaagttg ttattgtggt   180
aaaagaattt cttccgactc cccgccatcg gttcagttca tgaatcgtct ccggaaacac   240
ctgagagctt accatcggtg tctatactac acgaggttcc agctcctttc ctggagcgtg   300
tgtggggca acaaggaccc atgggttcag gaattgatga gctgtcttga tctcaaagaa   360
tgtggacatg cttactcggg gattgtgcc caccagaagc atttacttcc taccagcccc   420
ccaatttctc aggcctcaga gggggcatct tcagatatcc acaccctgc ccagatgctc    480
ctgtccacct tgcagtccac tcagcgcccc accctcccag taggatcact gtcctcggac   540
aaagagctca ctcgtcccaa tgaaaccacc attcacactg cgggccacag tctggcagct   600
gggcctgagg ctggggagaa ccagaagcag ccggaaaaaa atgctggtcc acagccagtg   660
acatcagcca cagtgccagt cctgtgcctc ctggccatca tcttcatcct caccgcagcc   720
cttttcctatg tgctgtgcaa gaggaggagg gggcagtcac cgcagtcctc tccagatctg   780
ccggttcatt atatacctgt ggcacctgac tctaatacct ga                      822

SEQ ID NO: 56           moltype = DNA   length = 300
FEATURE                 Location/Qualifiers
source                  1..300
                        mol_type = unassigned DNA
                        organism = Homo sapiens
SEQUENCE: 56
atgaaagtct ctgccgccct tctgtgcctg ctgctcatag cagccacctt cattcccaa     60
gggctcgctc agccagatgc aatcaatgcc ccagtcgctg ctgttataa cttcaccaag   120
aggaagatct cagtgcagag gctcgcgagc tatagaagaa tcaccagcag caagtgtccc   180
aaagaagctg tgatcttcaa gaccattgtg gccaaggaga tctgtgctga ccccaagcag   240
aagtgggttc aggattccat ggaccacctg gacaagcaaa cccaaactcc gaagacttga   300

SEQ ID NO: 57           moltype = DNA   length = 279
FEATURE                 Location/Qualifiers
source                  1..279
                        mol_type = unassigned DNA
                        organism = Homo sapiens
SEQUENCE: 57
atgcaggtct ccactgctgc ccttgctgtc tcctctgca ccatggctct ctgcaaccag      60
ttctctgcat cacttgctgc tgacacgccg accgctgct gcttcagcta cacctccgg    120
cagattccac agaatttcat agctgactac tttgagacga gcagccagtg ctccaagccc   180
ggtgtcatct tcctaaccaa gcgaagccgg caggtctgtg ctgaccccag tgaggagtgg   240
gtccagaaat atgtcagcga cctggagctg agtgcctga                          279

SEQ ID NO: 58           moltype = DNA   length = 279
FEATURE                 Location/Qualifiers
source                  1..279
                        mol_type = unassigned DNA
                        organism = Homo sapiens
SEQUENCE: 58
atgaagctct gcgtgactgt cctgtctctc ctcatgctag tagctgcctt ctgctctcca    60
gcgctctcag caccaatggg ctcagaccct cccaccgcct gctgcttttc ttacaccgcg   120
aggaagcttc ctcgcaactt tgtggtagat tactatgaga ccagcagcct ctgctcccag   180
ccagctgtga tattccaaac caaaagaagc aagcaagtct gtgctgatcc cagtgaatcc   240
tgggtccagg agtacgtgta tgacctggaa ctgaactga                          279
```

| SEQ ID NO: 59 | moltype = DNA length = 276 |
| --- | --- |
| FEATURE | Location/Qualifiers |
| source | 1..276 |
| | mol_type = unassigned DNA |
| | organism = Homo sapiens |

SEQUENCE: 59
```
atgaaggtct ccgcggcagc cctcgctgtc atcctcattg ctactgccct ctgcgctcct   60
gcatctgcct ccccatattc ctcggacacc acacctgct gctttgccta cattgcccgc  120
ccactgcccc gtgcccacat caaggagtat ttctacacca gtggcaagtg ctccaaccca  180
gcagtcgtct ttgtcacccg aaagaaccgc caagtgtgtg ccaacccaga gaagaaatgg  240
gttcgggagt acatcaactc tttggagatg agctag                            276
```

| SEQ ID NO: 60 | moltype = DNA length = 294 |
| --- | --- |
| FEATURE | Location/Qualifiers |
| source | 1..294 |
| | mol_type = unassigned DNA |
| | organism = Homo sapiens |

SEQUENCE: 60
```
atgaaggtct ccgcagcact tctgtggctg ctgctcatag cagctgcctt cagccccag   60
gggctcgctg ggccagcttc tgtcccaacc acctgctgct taacctggc caataggaag  120
ataccccttc agcgactaga gagctacagg agaatcacca gtggcaaatg tccccagaaa  180
gctgtgatct tcaagaccaa actggccaag gatatctgtg ccgaccccaa gaagaagtgg  240
gtgcaggatt ccatgaagta tctggaccaa aaatctccaa ctccaaagcc ataa        294
```

| SEQ ID NO: 61 | moltype = DNA length = 462 |
| --- | --- |
| FEATURE | Location/Qualifiers |
| misc_feature | 1..462 |
| | note = Synthetic Construct |
| source | 1..462 |
| | mol_type = other DNA |
| | organism = synthetic construct |

SEQUENCE: 61
```
atgtaccgga tgcagctgct gagctgtatc gccctgtctc tggccctggt cacaaatagc   60
gcccctacca gcagcagcac caagaaaaca cagctgcaac tggaacacct cctgctggac  120
ctgcagatga tcctgaacgg catcaacaac tacaagaacc ccaagctgac ccggatgctg  180
accttcaagt tctacatgcc caagaaggcc accgagctga agcacctcca gtgcctggaa  240
gaggaactga agccctgga gaagtgctga atctggccc agcaagaa cttccacctg      300
aggcctaggg acctgatcag caacatcaac gtgatcgtgc tggaactgaa aggcagcgag  360
acaaccttca tgtgcgagta cgccgacgag acagctacca tcgtggaatt tctgaaccgg  420
tggatcacct tctgccagag catcatcagc accctgacct ga                     462
```

| SEQ ID NO: 62 | moltype = DNA length = 762 |
| --- | --- |
| FEATURE | Location/Qualifiers |
| misc_feature | 1..762 |
| | note = Synthetic Construct |
| source | 1..762 |
| | mol_type = other DNA |
| | organism = synthetic construct |

SEQUENCE: 62
```
atgtggcctc ctggatctgc ttctcagcct cctccatctc ctgccgctgc tacaggactt   60
catcctgccg caagacccgt gtctctgcag tgcagactga gcatgtgcc cgccagatct  120
ctgctgctgg tggctacact ggtgctgctg gatcatctga gcctggccag aaacctgcca  180
gtggccacgc ctgatcctgg catgtttcct tgtctgcacc acagccagaa cctgctgaga  240
gccgtgtcca acatgctgca gaaggccaga cagaccctcg agttctaccc tgcaccagc   300
gaggaaatcg accacgagga catccaccaag gacaagacca agcgtgtga agcctgcttg  360
cctctggaac tgaccaagaa cgagagctgc ctgaacagca gagagacaag cttcatcacc  420
aacggctctt gcctggcctc cagaaagacc tccttcatga tggccctgtg cctgagcagc  480
atctacgagg acctgaagat gtaccaggtc gagttcaaga ccatgaacgc caagctgctg  540
atggacccca agcgcagat cttcctggac cagaatatgc tggccgtgat cgacgagctg  600
atgcaggccc tgaacttcaa cagcgagaca gtgcccaga agtccagcct ggagaaaccc  660
gacttctaca agaccaagat caagctgtgc atcctgctgc acgccttccg gatcagagcc  720
gtgaccatcg acagagtgat gagctacctg aacgcctcct ga                     762
```

| SEQ ID NO: 63 | moltype = DNA length = 987 |
| --- | --- |
| FEATURE | Location/Qualifiers |
| misc_feature | 1..987 |
| | note = Synthetic Construct |
| source | 1..987 |
| | mol_type = other DNA |
| | organism = synthetic construct |

SEQUENCE: 63
```
atgtgtcacc agcagctggt catcagctgg ttcagcctgg tgttcctggc ctctcctctg   60
gtggccatct gggagctgaa gaaagacgtg tacgtggtga aactggactg gtatcccgat  120
gctcctggcg agatggtggt gctgacctgc gataccccg aagaggacgg catcacctgg  180
acactggatc agtctagcga ggtgctcggc agcggcaaga ccctgaccat ccaagtgaaa  240
gagtttggcg acgccggcca gtacacctgt cacaaaggcg agaagtgct gagccacagc  300
ctgctgctgc tccacaagaa agaggatggc atttggagca ccgacatcct gaaggaccag  360
aaagagccca gaacaagac cttcctgaga tgcgaggcca gaactacag cggccggttc  420
acatgttggt ggctgaccac catcagcacc gacctgacct tcagcgtgaa gtccagcaga  480
```

```
ggcagcagtg atcctcaggg cgttacatgt ggcgccgcta cactgtctgc cgaaagagtg    540
cggggcgaca acaaagaata cgagtacagc gtggaatgcc aagaggacag cgcctgtcca    600
gccgccgaag agtctctgcc tatcgaagtg atggtggacg ccgtgcacaa gctgaagtac    660
gagaactaca cctccagctt tttcatccgg gacatcatca gcccgatcc tccaaagaac     720
ctgcagctga agcctctgaa gaacagcaga caggtgacaga tgtcctggga gtaccccgac    780
acctggtcta cacccacag ctacttcagc ctgacctttt gcgtgcaagt gcagggcaag     840
tccaagcgcg agaaaaagga ccgggtgttc accgacaaga ccagcgccac cgtgatctgc    900
agaaagaacg ccagcatcag cgtcagagcc caggaccggt actacagcag ctcttggagc    960
gaatgggcca gcgtgccatg tagctaa                                        987

SEQ ID NO: 64            moltype = DNA   length = 75
FEATURE                  Location/Qualifiers
misc_feature             1..75
                         note = Synthetic Construct
source                   1..75
                         mol_type = other DNA
                         organism = synthetic construct
SEQUENCE: 64
agggccaaga ggggcagcgg cgagggcagg ggcagcctgc tgacctgcgg cgacgtggag    60
gagaaccccg gcccc                                                     75

SEQ ID NO: 65            moltype = DNA   length = 66
FEATURE                  Location/Qualifiers
misc_feature             1..66
                         note = Synthetic Construct
source                   1..66
                         mol_type = other DNA
                         organism = synthetic construct
SEQUENCE: 65
ggaagcggag ctactaactt cagcctgctg aagcaggctg gagacgtgga ggagaaccct    60
ggacct                                                               66

SEQ ID NO: 66            moltype = DNA   length = 69
FEATURE                  Location/Qualifiers
misc_feature             1..69
                         note = Synthetic Construct
source                   1..69
                         mol_type = other DNA
                         organism = synthetic construct
SEQUENCE: 66
ggaagcggac agtgtactaa ttatgctctc ttgaaattgg ctggagatgt tgagagcaac    60
cctggacct                                                            69

SEQ ID NO: 67            moltype = DNA   length = 75
FEATURE                  Location/Qualifiers
misc_feature             1..75
                         note = Synthetic Construct
source                   1..75
                         mol_type = other DNA
                         organism = synthetic construct
SEQUENCE: 67
ggaagcggag tgaaacagac tttgaatttt gaccttctca agttggcggg agacgtggag    60
tccaaccctg gacct                                                     75

SEQ ID NO: 68            moltype = AA   length = 25
FEATURE                  Location/Qualifiers
REGION                   1..25
                         note = Synthetic Construct
source                   1..25
                         mol_type = protein
                         organism = synthetic construct
SEQUENCE: 68
RAKRGSGEGR GSLLTCGDVE ENPGP                                          25

SEQ ID NO: 69            moltype = AA   length = 22
FEATURE                  Location/Qualifiers
REGION                   1..22
                         note = Synthetic Construct
source                   1..22
                         mol_type = protein
                         organism = synthetic construct
SEQUENCE: 69
GSGATNFSLL KQAGDVEENP GP                                             22

SEQ ID NO: 70            moltype = AA   length = 23
FEATURE                  Location/Qualifiers
REGION                   1..23
                         note = Synthetic Construct
source                   1..23
```

```
                                    mol_type = protein
                                    organism = synthetic construct
SEQUENCE: 70
GSGQCTNYAL LKLAGDVESN PGP                                                    23

SEQ ID NO: 71           moltype = AA  length = 25
FEATURE                 Location/Qualifiers
REGION                  1..25
                        note = Synthetic Construct
source                  1..25
                        mol_type = protein
                        organism = synthetic construct
SEQUENCE: 71
GSGVKQTLNF DLLKLAGDVE SNPGP                                                  25

SEQ ID NO: 72           moltype = AA  length = 15
FEATURE                 Location/Qualifiers
REGION                  1..15
                        note = Synthetic Construct
source                  1..15
                        mol_type = protein
                        organism = synthetic construct
SEQUENCE: 72
GGGGSGGGGS GGGGS                                                             15

SEQ ID NO: 73           moltype = AA  length = 18
FEATURE                 Location/Qualifiers
REGION                  1..18
                        note = Synthetic Construct
source                  1..18
                        mol_type = protein
                        organism = synthetic construct
SEQUENCE: 73
GGSSRSSSSG GGGSGGGG                                                          18

SEQ ID NO: 74           moltype = AA  length = 20
FEATURE                 Location/Qualifiers
REGION                  1..20
                        note = Synthetic Construct
source                  1..20
                        mol_type = protein
                        organism = synthetic construct
SEQUENCE: 74
GGGGSGGGGS GGGGSGGGGS                                                        20

SEQ ID NO: 75           moltype = AA  length = 15
FEATURE                 Location/Qualifiers
REGION                  1..15
                        note = Synthetic Construct
source                  1..15
                        mol_type = protein
                        organism = synthetic construct
SEQUENCE: 75
CGGGSGGGGS GGGGS                                                             15

SEQ ID NO: 76           moltype = AA  length = 15
FEATURE                 Location/Qualifiers
REGION                  1..15
                        note = Synthetic Construct
source                  1..15
                        mol_type = protein
                        organism = synthetic construct
SEQUENCE: 76
SHGGHGGGGS GGGGS                                                             15

SEQ ID NO: 77           moltype = AA  length = 15
FEATURE                 Location/Qualifiers
REGION                  1..15
                        note = Synthetic Construct
source                  1..15
                        mol_type = protein
                        organism = synthetic construct
SEQUENCE: 77
MGGMSGGGGS GGGGS                                                             15

SEQ ID NO: 78           moltype = AA  length = 15
FEATURE                 Location/Qualifiers
REGION                  1..15
                        note = Synthetic Construct
```

```
source                         1..15
                               mol_type = protein
                               organism = synthetic construct
SEQUENCE: 78
YGGYSGGGGS GGGGS                                                        15

SEQ ID NO: 79                  moltype = AA  length = 15
FEATURE                        Location/Qualifiers
REGION                         1..15
                               note = Synthetic Construct
source                         1..15
                               mol_type = protein
                               organism = synthetic construct
SEQUENCE: 79
WGGYSGGGGS GGGGS                                                        15

SEQ ID NO: 80                  moltype = AA  length = 12
FEATURE                        Location/Qualifiers
REGION                         1..12
                               note = Synthetic Sequence
source                         1..12
                               mol_type = protein
                               organism = synthetic construct
SEQUENCE: 80
SVSVGMKPSP RP                                                           12

SEQ ID NO: 81                  moltype = AA  length = 12
FEATURE                        Location/Qualifiers
REGION                         1..12
                               note = Synthetic Sequence
source                         1..12
                               mol_type = protein
                               organism = synthetic construct
SEQUENCE: 81
VISNHAGSSR RL                                                           12

SEQ ID NO: 82                  moltype = AA  length = 12
FEATURE                        Location/Qualifiers
REGION                         1..12
                               note = Synthetic Construct
source                         1..12
                               mol_type = protein
                               organism = synthetic construct
SEQUENCE: 82
PWIPTPRPTF TG                                                           12

SEQ ID NO: 83                  moltype = AA  length = 11
FEATURE                        Location/Qualifiers
REGION                         1..11
                               note = Synthetic Construct
source                         1..11
                               mol_type = protein
                               organism = synthetic construct
SEQUENCE: 83
RGRGRGRGRG R                                                            11

SEQ ID NO: 84                  moltype = DNA  length = 1638
FEATURE                        Location/Qualifiers
misc_feature                   1..1638
                               note = Synthetic Construct
source                         1..1638
                               mol_type = other DNA
                               organism = synthetic construct
SEQUENCE: 84
atgtgtcacc agcagctggt catcagctgg ttcagcctgg tgttcctggc ctctcctctg        60
gtggccatct gggagctgaa gaaagacgtg tacgtggtgg aactggactg gtatcccgat       120
gctcctggcg agatggtggt gctgacctgc gataccctg aaggagacgg catcacctgg        180
acactggatc agtctagcga ggtgctcggc agcggcaaga ccctgaccat ccaagtgaaa       240
gagtttggcg acgccggcca gtacacctgt cacaaaggcg gagaagtgct gagccacagc       300
ctgctgctgc tccacaagaa agaggatggc atttggagca ccgacatcct gaaggaccag       360
aaagagccca gaacaagac cttcctgaga tgcgaggcca gaactacag cggccggttc         420
acatgttggt ggctgaccac catcagcacc gacctgacct tcagcgtgaa gtccagcaga       480
ggcagcagtg atcctcaggg cgttacatgt ggcgccgcta cactgtctgc cgaaagagtg       540
cggggcgaca acaaagaata cgagtacagc gtggaatgca aagaggacag cgcctgtcca       600
gccgccgaag agtctctgcc tatcgaagtg atggtggacg ccgtgcacaa gctgaagtac       660
gagaactaca cctccagctt tttcatccgg gacatcatca gcccgatcc tccaaagaac       720
ctgcagctga agcctctgaa gaacagcaga caggtggaag tgtcctggga gtaccccgac       780
acctggtcta caccccacag ctacttcagc ctgacctttt gcgtgcaagt cagggcaag        840
tccaagcgcg agaaaaagga ccgggtgttc accgacaaga ccagcgccac cgtgatcgc        900
```

```
agaaagaacg ccagcatcag cgtcagagcc caggaccggt actacagcag ctcttggagc   960
gaatgggcca gcgtgccatg ttctggtggc ggaggatctg gcggaggtgg aagcggcgga  1020
ggcggcagcg gaggtggtgg atctagaaat ctgccagtgg ccacgcctga tcctggcatg  1080
tttccttgtc tgcaccacag ccagaacctg ctgagagccg tgtccaacat gctgcagaag  1140
gccagacaga ccctcgagtt ctaccccctgc accagcgagg aaatcgacca cgaggacatc  1200
accaaggata agaccagcac cgtggaagcc tgcctgcctc tggaactgac caagaacgag  1260
agctgcctga acagccggga aaccagcttc atcaccaacg gctcttgcct ggccagcaga  1320
aagacctcct tcatgatggc cctgtgcctg agcagcatct acgaggacct gaagatgtac  1380
caggtcgagt tcaagaccat gaacgccaag ctgctgatgg acccaagcg gcagatcttc  1440
ctggaccaga atatgctggc cgtgatcgac gagctgatgc aggccctgaa cttcaacagc  1500
gagacagtgc cccagaagtc tagcctggaa gaacccgact tctacaagac caagatcaag  1560
ctgtgcatcc tgctgcacgc cttccggatc agagccgtga ccatcgacag agtgatgagc  1620
tacctgaacg cctcctga                                                 1638

SEQ ID NO: 85          moltype = AA  length = 545
FEATURE                Location/Qualifiers
REGION                 1..545
                       note = Synthetic Construct
source                 1..545
                       mol_type = protein
                       organism = synthetic construct
SEQUENCE: 85
MCHQQLVISW FSLVFLASPL VAIWELKKDV YVVELDWYPD APGEMVVLTC DTPEEDGITW   60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSGG GGSGGGGSGG GGSGGGGSRN LPVATPDPGM  360
FPCLHHSQNL LRAVSNMLQK ARQTLEFYPC TSEEIDHEDI TKDKTSTVEA CLPLELTKNE  420
SCLNSRETSF ITNGSCLASR KTSFMMALCL SSIYEDLKMY QVEFKTMNAK LLMDPKRQIF  480
LDQNMLAVID ELMQALNFNS ETVPQKSSLE EPDFYKTKIK LCILLHAFRI RAVTIDRVMS  540
YLNAS                                                              545
```

What is claimed is:

1. A pharmaceutical composition comprising:
   (a) a herpes simplex virus type 1 (HSV-1) comprising a recombinant HSV-1 genome, wherein the recombinant HSV-1 genome comprises a polynucleotide encoding an Interleukin (IL)-2 polypeptide and a polynucleotide encoding an IL-12 polypeptide; and
   (b) a pharmaceutically acceptable excipient,
   wherein the IL-12 polypeptide comprises an IL-12 subunit alpha polypeptide and an IL-12 subunit beta polypeptide connected by a linker polypeptide, and
   wherein the recombinant HSV-1 genome further comprises a first promoter operably linked to the polynucleotide encoding the IL-2 polypeptide and a second promoter operably linked to the polynucleotide encoding the IL-12 polypeptide.

2. The pharmaceutical composition of claim 1, wherein the recombinant HSV 1 genome comprises an inactivating mutation in an HSV 1 gene selected from the group consisting of Infected Cell Protein (ICP) 0, ICP4, ICP22, ICP27 ICP47, thymidine kinase (tk), Long Unique Region (UL) 41, and UL55.

3. The pharmaceutical composition of claim 1, wherein the recombinant HSV 1 genome comprises an inactivating mutation in one or both copies of an ICP4 gene.

4. The pharmaceutical composition of claim 1, wherein the recombinant HSV 1 genome does not comprise an inactivating mutation in one or both copies of the ICP34.5 gene.

5. The pharmaceutical composition of claim 1, wherein the recombinant HSV 1 genome does not comprise an inactivating mutation in the ICP47 gene.

6. The pharmaceutical composition of claim 1, wherein the HSV-1 is not oncolytic.

7. The pharmaceutical composition of claim 1, wherein the IL-2 polypeptide comprises an amino acid sequence having at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 3.

8. The pharmaceutical composition of claim 1, wherein the recombinant HSV 1 genome does not comprise a polynucleotide encoding a Granulocyte-Macrophage Colony-Stimulating Factor (GM-CSF) polypeptide.

9. The pharmaceutical composition of claim 1, wherein the pharmaceutical composition is suitable for topical, transdermal, subcutaneous, epicutaneous, intradermal, intranasal, intratracheal, sublingual, buccal, rectal, vaginal, intravenous, intraarterial, intramuscular, intraosseous, intracardial, intraperitoneal, transmucosal, intravitreal, subretinal, intraarticular, peri-articular, intratumoral, intrathecal, intraventricular, local, or inhaled administration.

10. The pharmaceutical composition of claim 1, wherein the pharmaceutical composition is not a vaccine.

11. The pharmaceutical composition of claim 1, wherein the recombinant HSV 1 genome does not encode an antigen.

12. The pharmaceutical composition of claim 1, wherein the IL-12 subunit alpha polypeptide comprises an amino acid sequence having at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 5.

13. The pharmaceutical composition of claim 1, wherein the IL-12 subunit beta polypeptide comprises an amino acid sequence having at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 6.

14. The pharmaceutical composition of claim 1, wherein the linker polypeptide is a cleavable linker polypeptide.

15. The pharmaceutical composition of claim 1, wherein the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs: 68-83.

16. The pharmaceutical composition of claim 1, wherein the linker polypeptide is a non-cleavable linker polypeptide.

17. A pharmaceutical composition comprising:
(a) a population of HSV-1 viruses, wherein the population of HSV-1 viruses comprises recombinant HSV 1 genomes comprising a polynucleotide encoding an IL-2 polypeptide and a polynucleotide encoding an IL-12 polypeptide; and
(b) a pharmaceutically acceptable excipient;
wherein the IL-12 polypeptide comprises an IL-12 subunit alpha polypeptide and an IL-12 subunit beta polypeptide connected by a linker polypeptide, and
wherein the recombinant HSV-1 genomes further comprise a first promoter operably linked to the polynucleotide encoding the IL-2 polypeptide and a second promoter operably linked to the polynucleotide encoding the IL-12 polypeptide.

18. The pharmaceutical composition of claim 17, wherein the population of HSV 1 viruses is either all replication defective or all replication competent.

19. The pharmaceutical composition of claim 18, wherein the population of replication competent HSV 1 viruses is not conditionally replication competent.

20. The pharmaceutical composition of claim 17, wherein the polynucleotide encoding the IL-2 polypeptide and the polynucleotide encoding the IL-12 polypeptide are comprised within the same recombinant HSV 1 genome.

21. The pharmaceutical composition of claim 17, wherein the linker polypeptide is a cleavable linker polypeptide.

22. The pharmaceutical composition of claim 17, wherein the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs: 68-83.

23. The pharmaceutical composition of claim 17, wherein the linker polypeptide is a non-cleavable linker polypeptide.

* * * * *